(12) United States Patent
Rottmann et al.

(10) Patent No.: US 7,453,025 B2
(45) Date of Patent: Nov. 18, 2008

(54) REPRODUCTIVE ABLATION CONSTRUCTS

(75) Inventors: William H. Rottmann, Summerville, SC (US); Kim H. Norris-Caneda, North Charleston, SC (US); Chunsheng Zhang, North Charleston, SC (US)

(73) Assignee: Arborgen, LLC, Summerville, SC (US)

( * ) Notice: Subject to any disclaimer, the term of this patent is extended or adjusted under 35 U.S.C. 154(b) by 299 days.

(21) Appl. No.: 10/946,622

(22) Filed: Sep. 22, 2004

(65) Prior Publication Data

US 2006/0085867 A1 Apr. 20, 2006

(51) Int. Cl.
C12N 15/82 (2006.01)
C12N 15/31 (2006.01)
C12N 15/55 (2006.01)
A01H 5/00 (2006.01)
A01H 1/02 (2006.01)

(52) U.S. Cl. ............... 800/303; 800/269; 800/287; 800/319; 800/288; 435/199; 536/23.2; 536/23.7; 536/24.1

(58) Field of Classification Search .............. None
See application file for complete search history.

(56) References Cited

U.S. PATENT DOCUMENTS

| | | | |
|---|---|---|---|
| 4,458,066 A | 7/1984 | Caruthers et al. | |
| 5,491,090 A | 2/1996 | Handley, III et al. | |
| 5,506,136 A | 4/1996 | Becwar et al. | |
| 5,565,340 A | 10/1996 | Chenchik et al. | |
| 5,681,730 A | 10/1997 | Ellis | |
| 5,759,822 A | 6/1998 | Chenchik et al. | |
| 5,856,191 A | 1/1999 | Handley, III | |
| 6,051,757 A | 4/2000 | Barton et al. | |
| 6,132,970 A | 10/2000 | Stemmer | |
| 6,187,994 B1 | 2/2001 | Baszcynski et al. | |
| 6,596,925 B1 * | 7/2003 | Perera et al. ........... | 800/278 |
| 6,682,931 B2 | 1/2004 | Becwar et al. | |
| 6,791,011 B1 * | 9/2004 | Paul et al. ............. | 800/287 |
| 7,157,620 B2 * | 1/2007 | Connett-Porceddu et al. ............. | 800/294 |
| 2002/0100083 A1 | 7/2002 | Connett-Porceddu et al. | |
| 2003/0101487 A1 | 5/2003 | Kisaka et al. | |

FOREIGN PATENT DOCUMENTS

| | | |
|---|---|---|
| EP | 0 223 399 B1 | 5/1987 |
| EP | 0 344 029 B1 | 11/1989 |
| EP | 0 120 516 B1 | 10/1991 |
| EP | 0 154 204 B1 | 1/1994 |
| EP | 0 271 988 B1 | 8/1995 |
| WO | WO 92/04449 | 3/1992 |
| WO | WO 93/19189 | 9/1993 |
| WO | WO 99/61631 | 12/1999 |
| WO | WO 00/55172 | 9/2000 |

OTHER PUBLICATIONS

Chen et al. Sexual Plant Reproduction 13(2): 85-94 (2000).*
Donald et al. The EMBO Journal 9(6): 1717-1726 (1990).*
Hofig et al. Planta 217(6): 858-867 (Oct. 2003).*
Mouradov et al. Acta Horticulturae 461: 417-423 (1998).*
U.S. Appl. No. 10/861,909, filed Jun. 7, 2004, Chang.
Beals, T. P., et al., "A Novel Cell Ablation Strategy Blocks Tobacco Anther Dehiscence," The Plant Cell, 1997, pp. 1527-1545, vol. 9.
Bergelson, J., et al., "Promiscuity in transgenic plants," Nature, 1998, pp. 25-26, vol. 395.
Busch, M. A., et al., "Activation of a Floral Homeotic Gene in Arabidopsis," Science, 1999, pp. 585-587, vol. 285.
Deyholos, M. K., et al., "Separable Whorl-Specific Expression and Negative Regulation by Enhancer Elements within the AGAMOUS Second Intron," The Plant Cell, 2000, pp. 1799-1810, vol. 12.
Hartley, R.W., Barnase and Barstar Expression of Its Cloned Inhibitor Permits Expression of a Cloned Ribonuclease, J. Mol. Biol., 1988, pp. 913-915, vol. 202.
Haseloff, J., et al., "Simple RNA enzymes with new and highly specific endoribonuclease activities," Nature, 1988, pp. 585-591, vol. 334.
Jofuku, K. D., et al., "Kunitz Trypsin Inhibitor Genes Are Differentially Expressed during the Soybean Life Cycle and in Transformed Tobacco Plants," The Plant Cell, 1989, pp. 1079-1093, vol. 1.
Kaul, M. L. H., "Male Sterility in Higher Plants," 1988.
Koltunow, A. M., et al., "Different Temporal and Spatial Gene Expression Patterns Occur during Anther Development," The Plant Cell, 1990, pp. 1201-1224, vol. 2.
Kuvshinov, V., et al., "Molecular control of transgene escape from genetically modified plants," Plant Science, 2001, pp. 517-522, vol. 160.
Leple, J. C., et al., "Transgenic poplars: expression of chimeric genes using four different constructs," Plant Cell Reports, 1992, pp. 137-141, vol. 11.
Mariani, C., et al., "Introduction of male sterility of plants by a chimaeric ribonuclease gene," Nature, 1990, pp. 737-741, vol. 347.
Mossakowska, D. E., et al., "Kinetic Characterization of the Recombinant Ribonuclease from *Bacillus amyloliquefaciens* (Barnase) and Investigation of Key Residues in Catalysis by Site-Directed Mutagenesis," American Chemical Society, 1989, pp. 3843-3850, vol. 28.
Nave, E. B., et al., "Enzymatic changes in Post-meiotic Anther Development in *Petunia hybrida*. I. Anther Ontogeny and Isozyme Analyses," J. Plant Physiol, 1986, pp. 451-465, vol. 125.
Nilsson, O., et al., "Genetic ablation of flowers in transgenic *Arabidopsis*," The Plant Journal, 1998, pp. 799-804, vol. 15(6).
Paddon, C. J., et al., "Translation and Processing of *Bacillus amyloliquefaciens* Extracellular RNase," Journal of Bacteriology, 1989, pp. 1185-1187, vol. 171. No. 2.
Rezniekova, S. A., "Histochemical Study of Reserve Nutrient Substances in Anther of *Lilum candidum*," Acad. Bulg. Sci., 1978, vol. 31, pp. 1067-1071.

(Continued)

Primary Examiner—David T Fox
(74) Attorney, Agent, or Firm—Foley & Lardner LLP

(57) ABSTRACT

The present invention relates to the regulation of reproductive development, particularly to the genetic ablation of reproductive tissues in angiosperm and gymnosperm species. Reproductive-preferred promoters, regulatory elements, and cytotoxic nucleotide sequences are disclosed herein, as are constructs and methods for genetic ablation.

15 Claims, 47 Drawing Sheets

OTHER PUBLICATIONS

Sawhney, V. K., et al., "Enzymatic changes in Post-meiotic Anther Development in *Petunia hybrida*. II. Histochemical Localization of Esterase, Peroxidase, Malate- and Alcohol dehydrogenase," J. Plant Physiol., 1986, pp. 467-473, vol. 125.

Sieburth, L. E., et al., "Molecular Dissection of the AGAMOUS Control Region Shows That cis Elements for Spatial Regulation Are Located Intragenically," The Plant Cell, 1997, pp. 355-365, vol. 9.

Strauss et al., TGERC Annual Report: Flowering Control, pp. 17-29, Aug. 1998.

Vancanneyt, G., et al., "Construction of an intron-containing marker gene: Splicing of the intron in transgenic plants and its use in monitoring early events in Agrobacterium-medicated plant transformation," Mol. Gen. Genet., 1990, pp. 245-250, vol. 220.

Verheij, H. M., et al., "Structure and Function of Phospholiphase $A_2$," Rev. Physiol. Biochem. Pharmacol., 1981, pp. 93-203, vol. 91.

Yakovlev, G. I., et al., "Mutational analysis of the active site of RNase of *Bacillus intermedius* (BINASE)," FEBS Letters, 1994, pp. 305-306, vol. 354.

Michael J. Adang et al., "The Reconstruction and Expression of a *Bacillus thuringiensis cry IIIA* gene protoplasts and potato plants", Plant Molecular Biology, Mar. 1993, vol. 21, No. 6, pp. 1131-1145.

Stephen F. Altschul et al., "Basic Local Alignment Search Tool", J. Mol. Biol., Academic Press Limited, Oct. 5, 1990, vol. 215, No. 3, pp. 403-410.

Philip V. Ammirato et al., "Crop Species", Handbook of Plant Cell Culture, vol. 2, 1984 Macmillan Publishing Co., NY, 3 pages.

Shabbir B. Bambot et al., "Efficient Total Gene Synthesis of 1.35-kb Hybrid Alpha-Lytic Protease Gene Using the Polymerase Chain Reaction", PCR Methods and Applications, Cold Spring Harbor Laboratory, Feb. 1993, vol. 2, No. 3, pp. 266-271.

S. L. Beaucage, et al., "Deoxynucleoside Phosphoramidites—A New Class of Key Intermediates for Deoxypolynucleotide Synthesis", Tetrahedron Letters, Pergamon Press Ltd., 1981, vol. 22, No. 20, pp. 1859-1862.

Michael Bevan, "Binary *Argrobacterium* Vectors for Plant Transformation", IRL Press Limited, 1984, vol. 12, No. 22, pp. 8711-8721.

E. T. Bolton et al., "A General Method for the Isolation of RNA Complementary to DNA", Biochemistry: Bolton and McCarthy, Proc. Natl. Acad. Sci., 1962, vol. 48, pp. 1390-1397.

Tom I. Bonner et al., "Reduction in the Rate of DNA Reassociation by Sequence Divergence", Journal of Molecular Biology, Mar. 15, 1973, vol. 81, pp. 123-135.

Mark D. Burow et al., "High Frequency Generation of Transgenic Tobacco Plants after Modified Leaf Disk Cocultivation with *Agrobacterium tumefaciens*", Plant Molecular Biology Reporter, Transaction Periodicals Consortium, Rutgers University, May 1990, vol. 8, No. 2, pp. 124-139.

Alan H. Christensen et al., "Ubiquitin Promoter-based Vectors for High Level Expression of Selectable and/or Screenable Marker Genes in Monocotyledonous Plants", Transgenic Research, Chapman & Hall, May 1996, vol. 5, No. 3, pp. 213-218.

Henry Daniell et al., "Containment of Herbicide Resistance Through Genetic Engineering of the Chloroplast Genome", Apr. 1998, Nature Biotechnology, vol. 16, pp. 345-348.

Datta et al., "Nucleotide sequence of a gene encoding soybean repetitive praline-rich protein 3," *Plant Molecular Biology*, 1990, pp. 285-286, vol. 14, Kluwer Academic Publishers, Belgium.

Kathleen D'Halluin et al., "Transgenic Maize Plants by Tissue Electroporation", The Plant Cell, 1992 Society of Plant Physiologists, Dec. 1992, vol. 4, pp. 1495-1505.

Patrick Dillon et al., "Use of Polymerase Chain Reaction for the Rapid Construction of Synthetic Genes", PCR Protocols: Current Methods and Applications, Methods in Molecular Biology, 1993, Humana Press Inc., vol. 15, pp. 263-268.

Robert T. Fraley et al., "Expression of Bacterial Genes in Plant Cells", Proc. Natl. Acad. Sci. USA, Monsanto Company, Aug. 1983, vol. 80, pp. 4803-4807.

Golovkin et al., "Production of transgenic maize plants by direct DNA uptake into embryogenic protoplasts,"*Plant Science*, 1993, pp. 41-52, vol. 90, Elsevier Scientific Publishers Ireland Ltd.

Diane Hatton et al., "Two Classes of CIS Sequences Contribute to Tissue-Specific Expression of a PAL2 Promoter in Transgenic Tobacco", The Plant Journal, 1995, vol. 7, No. 6, pp. 859-876.

Karl D. Hauffe et al., "Combinatorial Interactions Between Positive and Negative CIS-acting Elements Control Spatial Patterns of 4CL-1 Expression in Transgenic Tobacco", The Plant Journal, 1993, vol. 4, No. 2, pp. 235-253.

Akio Hayashimoto et al., "A Polyethylene Glycol=Mediated Protoplast Transformation System for Production of Fertile Transgenic Rice Plants", Plant Physiology, The American Society of Plant Physiologists, Jul. 1990, vol. 93, No. 3, pp. 857-863.

Luis Herrara-Estrella et al., Expression of Chimaeric Genes Transferred into Plant Cells Using a Ti-plasmid-derived Vector, Nature, International Weekly Journal of Science, Macmillan Journals Ltd., May 19-25, 1983, vol. 303, No. 5914, pp. 209-213.

Maud A. W. Hinchee et al., "Production of Transgenic Soybean Plants Using Agrobacterium-Mediated DNA Transfer", Bio/Technology, The International Monthly for Industrial Biology, Aug. 1988, vol. 6, pp. 915-922.

Eugene W. Holowachuk et al., "Efficient Gene Synthesis by Klenow Assembly / Extension—Pfu Polymerase Amplification (KAPPA) of Overlapping Oligonucleotides", PCR Methods and Applications, Cold Spring Harbor Laboratory, vol. 4, pp. 299-302, 1995.

R. B. Horsch et al., Rapid Assay of Foreign Gene Expression in Leaf Discs Transformed by *Agrobacterium tumefaciens*: Role of T-DNA Borders in the Transfer Process, Proc. Natl. Acad. Sci. USA, Jun. 1986, vol. 83, pp. 4428-4432.

R. B. Horsch et al., "A Simple and General Method for Transferring Genes into Plants", Science 227, Mar. 1985, pp. 1229-1231.

Richard A. Jefferson et al., GUS Fusions: Beta-glucuronidase as a Sensitive and Versatile Gene Fusion Marker in Higher Plants, The Embo Journal, IRL Press Limited, Dec. 20, 1987, vol. 6, No. 13, pp. 3901-3907.

Beat Keller et al., "Vascular expression of the *grp1.8* promoter is controlled by three specific regulatory elements and one unspecific activating sequence", Plant Molecular Biology, International Society for Plant Molecular Biology, Kluwer Academic Publishers, Oct. 1994, vol. 26, No. 2, pp. 747-756.

Harry J. Klee et al., "Vectors for Transformation of Higher Plants", Bio/Technology, Jul. 1985, vol. 3, pp. 637-642.

T. M. Klein et al., Factors Influencing Gene Delivery into *ZEA Mays* Cells by High-Velocity Microprojectiles, Bio/Technology, BioActive Compounds From Algae May 1988, vol. 6, pp. 559-563.

Halina Kononowicz, Subdomains of the Octopine Synthase Upstream Activating Element Direct Cell-Specific Expression in Transgenic Tobacco Plants, The Plant Cell, 1992 American Society of Plant Physiologists, Jan. 1992, vol. 4, pp. 17-27.

Eric Lacombe et al., Characterization of *cis*-elements Required for Vascular Expression of the *Cinnamoyl CoA Reductase* Gene and for Protein DNA Complex Formation, The Plant Journal, 2000 Blackwell Science Ltd., vol. 23, No. 5, pp. 663-676.

Antonio Leyva et al., "*cis*-Element Combinations Determine Phenylalanine Ammonia-Lyase Gene Tissue-Specific Expression Patterns", The Plant Cell, 1992 American Society of Plant Physiologists, Mar. 1992, vol. 4, pp. 263-271.

McCarthy et al., "The Rate of Change of DNA in Evolution," *In Evolution of Genetic Systems*, 1972, pp. 1-43, H.H. Smith (ed.), Brookhaven Symposium in Biology No. 23, Gordon and Breach, New York.

David McElroy et al., "Isolation of an Efficient Actin Promoter for Use in Rice Transformation", The Plant Cell, 1990 American Society of Plant Physiologists, Feb. 1990, vol. 2, pp. 163-171.

B. L. Miki et al., "Procedures for Introducing Foreign DNA into Plants", Methods in Plant Molecular Biology and Biotechnology, CRC Press, 1993, pp. 67-88.

David A. Neustaedter et al., " A Novel Parsley *4CL1 cis*-element is Required for Developmentally Regulated Expression and Protein DNA Complex Formation", The Plant Journal, 1999, Blackwell Science Ltd., vol. 18, No. 1, pp. 77-88.

Eun-Gyu No et al., "Sequences Upstream and Downstream of Two Xylem-Specific Pine Genes Influence Their Expression", Plant Science, 2000 Elsevier Science, vol. 160, pp. 77-86.

Patrick Paddison et al., "Short Hairpin RNAs (shRNAs) Induce Sequence-Specific Silencing in Mammalian Cells", Genes & Development, Cold Spring Laboratory Press, 2002, vol. 16, pp. 948-958.

Ingo Potrykus et al., "Direct Gene Transfer to Cells of a Graminaceous Monocot", Mol. Gen. Genet, Springer-Verlag, 1985, vol. 199, pp. 183-188.

Rogers et al., "Improved Vectors for Plant Transformation: Expression Cassette Vectors and New Selectable Markers," *Methods in Enzymology*, 1987, pp. 252-277, vol. 153, Academic Press, Inc.

Schmidhauser et al., "Regions of Broad-Host-Range Plasmid RK2 Involved in Replication and Stable Maintenance in Nine Species of Gram-Negative Bacteria," *Journal of Bateriology*, Oct. 1985, pp. 446-455, vol. 164, No. 1, American Society of Microbiology.

Sibley et al., "The Phylogeny and Classification of the Passerine Birds, Based on Comparisons of the Genetic Material, DNA," *ACTA XVIII Congressus Internationalis Ornithologici*, Aug. 16-24, 1982, pp. 83-121, vol. 1.

C.J.S. Smith et al., "Antisense RNA Inhibition of Polygalacturonase Gene Expression in Transgenic Tomatoes", Nature, Aug. 1988, vol. 334, No. 25, pp. 724-726.

Christopher J.S. Smith et al., "Inheritance and Effect on Ripening of Antisense Polygalacturonase Genes in Transgenic Tomatoes", Plant Molecular Biology, International Society for Plant Molecular Biology, Kluwer Academic Publishers, Mar. 1990, vol. 14, No. 3, pp. 369-379.

David M. Stalker et al., "Purification and Properties of a Nitrilase Specific for the Herbicide Bromoxynil and Corresponding Nucleotide Sequence Analysis of the b*xn* Gene", The Journal of Biological Chemistry, The American Society for Biochemistry and Molecular Biology, Inc., May 5, 1988, vol. 263, No. 13, pp. 6310-6314.

Joëlle Thillet et al., "Site-Directed Mutagenesis of Mouse Dihydrofolate Reductase", The Journal of Biological Chemistry, The American Society for Biochemistry and Molecular Biology, Inc., Sep. 1968, vol. 263, No. 25, pp. 12500-12508.

Vimla Vasil et al., "Regeneration of Plants From Embryogenic Suspension Culture Protoplasts of Wheat (*Triticum aestivum* L.)", Bio/Technology, May 1990, vol. 8, pp. 429-434.

Vimla Vasil et al., "Herbicide Resistant Fertile Transgenic Wheat Plants Obtained by Microprojectile Bombardment of Regenerable Embryogenic Callus", Bio/Technology, Jun. 1992, vol. 10, pp. 667-674.

Michael A. Wosnick et al., "Rapid Construction of Large Synthetic Genes: Total Chemical Synthesis of Two Different Versions of the Bovine Prochymosin Gene", Gene, Elsevier Science Publishers, vol. 60, No. 1, pp. 115-127, (1987).

* cited by examiner

Figure 1A

```
LOCUS       pWVR220      8006 bp    DNA    circular        3-JUN-2003
DEFINITION  PrMC2.400::H102E::RNS2TER.
SOURCE
  ORGANISM
COMMENT     This file is created by Vector NTI
            http://www.informaxinc.com/
COMMENT     VNTDATE|263385014|
COMMENT     VNTDBDATE|304421719|
COMMENT     VNTNAME|pWVR220|
COMMENT     VNTAUTHORNAME|Demo User|
FEATURES             Location/Qualifiers
     misc_marker     1246..2037
                     /vntifkey="22"
                     /label=npt\III\(kanR)
     misc_marker     2339..3484
                     /vntifkey="22"
                     /label=trfA
     misc_structure  complement(3940..3963)
                     /vntifkey="88"
                     /label=LEFT\BORDER
     CDS             complement(4588..5379)
                     /vntifkey="4"
                     /label=NPT\II\(kanR)
     terminator      complement(4319..4539)
                     /vntifkey="43"
                     /label=NOSTER
     promoter        complement(5380..6689)
                     /vntifkey="29"
                     /label=UBQ10\promoter
     intron          complement(5380..5683)
                     /vntifkey="15"
                     /label=INTRON
     misc_marker     744..1013
                     /vntifkey="22"
                     /label=barstar
     CDS             complement(7094..7423)
                     /vntifkey="4"
                     /label=barnaseH102E
     promoter        complement(7424..7821)
                     /vntifkey="29"
                     /label=PrMC2.400
     terminator      complement(6732..6992)
                     /vntifkey="43"
                     /label=RNS2TER
     misc_structure  complement(7874..7897)
                     /vntifkey="88"
                     /label=RIGHT\BORDER
BASE COUNT     2181 a    1845 c     2006 g      1974 t
ORIGIN
        1 cgccggcgtt gtggatacct cgcggaaaac ttggccctca ctgacagatg aggggcggac
       61 gttgacactt gaggggccga ctcacccggc gcggcgttga cagatgaggg gcaggctcga
      121 tttcggccgg cgacgtggag ctggccagcc tgcaaatcg gcgaaaacgc ctgattttac
      181 gcgagtttcc cacagatgat gtggacaagc ctggggataa gtgccctgcg gtattgacac
      241 ttgaggggcg cgactactga cagatgaggg gcgcgatcct tgacacttga ggggcagagt
      301 gctgacagat gagggcgca cctattgaca tttgaggggc tgtccacagg cagaaaatcc
      361 agcatttgca agggtttccg cccgttttc ggccaccgct aacctgtctt ttaacctgct
      421 tttaaaccaa tatttataaa ccttgttttt aaccagggct gcgccctgtg cgcgtgaccg
      481 cgcacgccga aggggggtgc ccccccttct cgaaccctcc cggcccgcta acgcgggcct
      541 cccatccccc cagggggctgc gcccctccgg cgcgaacggc ctcaccccaa aaatggcagc
      601 gctggcagtc cataattgtg gtccaatttg cagccgtccg agacaggagg acatcgtcca
      661 gctgaaaccg gggcagaatc cggccatttc tgaagagaaa aatggtaaac tgatagaata
      721 aaatcataag aaaggagccg cacatgaaaa aagcagtcat taacggggaa caaatcagaa
      781 gtatcagcga cctccaccag acattgaaaa aggagcttgc ccttccggaa tactacggtg
      841 aaaacctgga cgctttatgg gattgtctga cgctgatgggt ggagtacccg ctcgtttgg
      901 aatggaggca gtttgaacaa agcaagcagc tgactgaaaa tggcgccgag agtgtgcttc
      961 aggttttccg tgaagcgaaa gcggaaggct gcgacatcac catcatactt tcttaatacg
     1021 atcaatggga gaggaacaat atggaaacac aaaccacaat tgtggtttca aaatcggctc
     1081 cgtcgatact atgttatacg ccaactttga aaacaacttt gaaaaagctg ttttctggta
     1141 tttaaggttt tagaatgcaa ggaacagtga attggagttc gtcttgttat aattagcttc
     1201 ttggggtatc tttaaatact gtagaaaaga ggaagaaat aataaatggc taaaatgaga
     1261 atatcaccgg aattgaaaaa actgatcgaa aaataccgct gcgtaaaaga tacggaagga
     1321 atgtctcctg ctaaggtata taagctggtg ggagaaaatg aaaacctata tttaaaaatg
```

Figure 1B

```
1381 acggacagcc ggtataaagg gaccacctat gatgtggaac gggaaaagga catgatgcta
1441 tggctggaag gaaagctgcc tgttccaaag gtcctgcact ttgaacggca tgatggctgg
1501 agcaatctgc tcatgagtga ggccgatggc gtcctttgct cggaagagta tgaagatgaa
1561 caaagccctg aaaagattat cgagctgtat gcggagtgca tcaggctctt tcactccatc
1621 gacatatcgg attgtccctata cgaatagc ttagacagcc gcttagccga attggattac
1681 ttactgaata acgatctggc cgatgtggat tgcgaaaact gggaagaaga cactccattt
1741 aaagatccgc gcgagctgta tgatttttta aagacggaaa agcccgaaga ggaacttgtc
1801 ttttcccacg gcgacctggg agacagcaac atctttgtga aagatggcaa agtaagtggc
1861 tttattgatc ttgggagaag cggcagggcg gacaagtggt atgacattgc cttctgcgtc
1921 cggtcgatca gggaggatat cggggaagaa cagtatgtcg agctattttt tgacttactg
1981 gggatcaagc ctgattggga gaaaataaaa tattatattt tactggatga attgtttag
2041 tacctagatg tggcgcaacg atgccggcga caagcaggag cgcaccgact tcttccgcat
2101 caagtgtttt ggctctcagg ccgaggccca cggcaagtat ttggcaagg ggtcgctggt
2161 attcgtgcag ggcaagattc ggaataccaa gtacgagaag gacggccaga cggtctacgg
2221 gaccgacttc attgccgata aggtggatta tctggacacc aaggcaccag gccggtcaaa
2281 tcaggaataa gggcacattg cccccggcgtg agtcggggca atcccgcaag gagggtgaat
2341 gaatcggacg tttgaccgga aggcatacag gcaagaactg atcgacgcgg ggttttccgc
2401 cgaggatgcc gaaaccatcg caagccgcac cgtcatgcgt gcgccccgcg aaaccttcca
2461 gtccgtcggc tcgatggtcc agcaagctac ggccaagatc gagcgcgaca gcgtgcaact
2521 ggctcccccct gccctgcccg cgccatcggc cgccgtggag cgttcgcgtc gtctcgaaca
2581 ggaggcggca ggtttggcga agtcgatgac catcgacacg cgaggaacta tgacgaccaa
2641 gaagcgaaaa accgccggcg aggacctggc aaaacaggtc agcgaggcca agcaggccgc
2701 gttgctgaaa cacacgaagc agcagataca ggaaatgcag ctttcccttgt tcgatattgc
2761 gccgtggccg gacacgatgc gagcgatgcc aaacgacacg gcccgctctg ccctgttcac
2821 cacgcgcaac aagaaaatcc cgcgcgaggc gctgcaaaac aaggtcattt tccacgtcaa
2881 caaggacgtg aagatcacct acaccggcgt cgagctgcgg gccgacgatg acgaactggt
2941 gtggcagcag gtgttggagt acgcgaagcg cacccctatc ggcgagccga tcaccttcac
3001 gttctacgag ctttgccagg acctgggctg gtcgatcaat ggccggtatt acacgaaggc
3061 cgaggaatgc ctgtcgcgcc tacaggcgac ggcgatgggc ttcacgtccg accgcgttgg
3121 gcacctggaa tcggtgtcgc tgctgcaccg cttccgcgtc ctggaccgtg gcaagaaaac
3181 gtcccgttgc caggtcctga tcgacgagga aatcgtcgtg ctgtttgctg gcgaccacta
3241 cacgaaattc atatgggaga agtaccgcaa gctgtcgccg acggcccgac ggatgttcga
3301 ctatttcagc tcgcaccggg agccgtaccc gctcaagctg gaaaccttcc gcctcatgtg
3361 cggatcggat tccacccgcg tgaagaagtg gcgcgagcag gtcggcgaag cctgcgaaga
3421 gttgcgaggc agcggcctgg tggaacacgc ctgggtcaat gatgacctgg tgcattgcaa
3481 acgctagggc cttgtggggt cagttccggc tggggttca gcagccagcg ctttactggc
3541 atttcaggaa caagcgggca ctgctcgacg cacttgcttc gctcagtatc gctcgggacg
3601 cacggcgcgc tctacgaact gccgatagac aactgtcacg gttaagcgag aaatgaataa
3661 gaaggctgat aattcggatc tctgcgaggg agatgatatt tgatcacagg cagcaacgct
3721 ctgtcatcgt tacaatcaac atgctaccct ccgcgagatc atccgtgttt caaaccggc
3781 agcttagttg ccgttcttcc gaatagcatc ggtaacatga gcaaagtctg ccgccttaca
3841 acggctctcc cgctgacgcc gtcccggact gatgggctgc ctgtatcgag tggtgatttt
3901 gtgccgagct gccggtcggg gagctgttgg ctggctggtg gcaggatata ttgtggtgta
3961 aacaaattga cgcttagaca acttaataac acattgcgga cgtttttaat gtactggggt
4021 ggtttttctt ttcaccagtg agacgggcaa cagctgattg cccttcaccg cctggcctg
4081 agagagttgc agcaagcggt ccacgctggt ttgccccagc aggcgaaaat cctgtttgat
4141 ggtggttccg aaatcggcaa aatcccttat aaatcaaaag aatagcccga gatagggttg
4201 agtgttgttc cagtttggaa caagagtcca ctattaaaga acgtggactc caacgtcaaa
4261 gggcgaaaaa ccgtctatca gggcgatggc ccacggccgc tctagaacta gtggatcccc
4321 cctacgtgcg atctagtaac atagatgaca ccgcgcgcga taatttatcc tagtttgcgc
4381 gctatatttt gttttctatc gcgtattaaa tgtataattg cgggactcta atcataaaaa
4441 cccatctcat aaataacgtc atgcattaca tgttaattat tacatgctta acgtaattca
4501 acagaaatta tatgataatc cggcaacaga attcaatctt aagaaacttt
4561 attgccaaat gtttgaacga tccctcagaa gaactcgtca agaaggcgat agaaggcgat
4621 gcgctgcgaa tcgggagcgg cgataccgta aagcacgagg aagcggtcag cccattcgcc
4681 gccaagctct tcagcaatat cacgggtagc caacgctatg tcctgatagc ggtccgccac
4741 acccagccg ccacagtcga tgaatccaga aaagcggcca ttttccacca tgatattcgg
4801 caagcaggca tcgccatggg tcacgacgag atcctcgccg tcgggcatgc gcgccttgag
4861 cctggcgaac agttcggctg gcgcgagccc ctgatgctct tcgtccagat catcctgatc
4921 gacaagaccg gcttccatcc gagtacgtgc tcgctcgatg cgatgtttcg cttggtggtc
4981 gaatgggcag gtagccgat caagcgtatg cagccgccgc attgcatcag ccatgatgga
5041 tactttctcg gcaggagcaa ggtgagatga caggagatcc tgccccggca cttcgcccaa
5101 tagcagccag tcccttcccg cttcagtgac aacgtcgagc acagctgcgc aaggaacgcc
5161 cgtcgtggcc agccacgata gccgcgctgc ctcgtcctgg agttcattca gggcaccgga
5221 caggtcggtc ttgacaaaaa gaaccgggcg cccctgcgct gacagccgga acacggcggc
5281 atcagagcag ccgattgtct gttgtgccca gtcatagccg aatagcctct ccacccaagc
5341 ggccggagaa cctgcgtgca atccatcttg ttcaatcatc tgttaatcag aaaaactcag
5401 attaatcgac aaattcgatc gcacaaacta gaactaaca ccagatctag atagaaatca
5461 caaatcgaag agtaattatt cgacaaaact caaattattt gaacaaatcg gatgatattt
5521 atgaaaccct aatcgagaat taagatgata tctaacgatc aaacccagaa aatcgtcttc
5581 gatctaagat taacagaatc taaaccaaag aacatatacg aaattgggat cgaacgaaaa
5641 caaaatcgaa gattttgaga gaataaggaa cacagaaatt taccttgatc acggtagaga
5701 gaattgagag aaagttttta agattttgag aaattgaaat ctgaattgtg aagaagaaga
5761 gctctttggg tattgtttta tagaagaaga agaagaaaag acgaggacga ctaggtcacg
```

Figures 1C

```
5821 agaaagctaa ggcggtgaag caatagctaa taataaaatg acacgtgtat tgagcgttgt
5881 ttacacgcaa agttgttttt ggctaattgc cttatttta ggttgaggaa aagtatttgt
5941 gctttgagtt gataaacacg actcgtgtgt gccggctgca accactttga cgccgtttat
6001 tactgactcg tcgacaacca caatttctaa cggtcgtcat aagatccagc cgttgagatt
6061 taacgatcgt tacgatttat attttttag cattatcgtt ttatttttta aatatacggt
6121 ggagctgaaa attggcaata attgaaccgt gggtcccact gcattgaagc gtatttcgta
6181 ttttctagaa ttcttcgtgc tttatttctt ttccttttg tttttttg ccatttatct
6241 aatgcaagtg ggcttataaa atcagtgaat ttcttggaaa agtaacttct ttatcgtata
6301 acatattgtg aaattatcca tttctttaa tttttagtg ttattggata ttttgtatg
6361 attattgatt tgcataggat aatgactttt gtatcaagtt ggtgaacaag tctcgttaaa
6421 aaaggcaagt ggtttggtga ctcgatttat tcttgttatt taattcatat atcaatggat
6481 cttatttggg gcctggtcca tatttaacac tcgtgttcag tccaatgacc aataatattt
6541 tttcattaat aacaatgtaa caagaatgat acacaaaaca ttctttgaat aagttcgcta
6601 tgaagaaggg aacttatccg gtcctagatc atcagttcat acaaacctcc atagagttca
6661 acatcttaaa caaggatatc ctgatccgtt gacggcgcgc caagcggccg catttaaatg
6721 ggccctatct aatcgaattt tgtaaactgg tttgataagc catcaatgca tcagtcaaga
6781 atgaatcatt gcaactaagt tgatataatt caatttacca tagaactcaa atgttgatat
6841 cttcttatgg atttctgat cttctacatt attagaaaga aacttgattt accagtaatg
6901 atgatacata tccaatagaa cgaaataagc caatctttat aggttttggt agtaaagtta
6961 caacatcaga gacatgtatg tattgtctct cagaagagct cttgaccgat cagagtttga
7021 agaaaaattt attacacact ttatgtaaag ctgaaaaaaa cggcctcccg cagggaagcc
7081 gttttttcg ttatctgatt tttgtaaagg tctgatactc gtccgttgtt ttgtaaatca
7141 gccagtcgct tgagtaaaga atccggtctg aatttctgaa gcctgatgta tagttaatat
7201 ccgcttcacg ccatgttcgt ccgcttttgc ccgggagttt gccttccctg tttgagaaga
7261 tgtctccgcc gatgcttttc cccggagcga cgtctgcaag gttcccttt gatgccaccc
7321 agccgagggc ttgtgcttct gattttgtaa tgtaattatc aggtagctta tgatatgtct
7381 gaagataatc cgcaaccccg tcaaacgtgt tgataacctg tgccatgttc ccgtttgata
7441 cctgaatttt ggccattctc ataaatcttc taaaaacagc agaactgact attcaaagaa
7501 agtagaaccc acagaaagta atcaaagtag tttgattaaa tgcgttgtgt atcatcgcag
7561 cccctgctac ggatatttat aggaaaggtt tgagagcaat gtgtgcagca agttgtgtgt
7621 gaatcacctg cttccatggc ggaggataaa taatttagtc acgcatttag ttgaacgtaa
7681 ctactaactc ctctaccgct aatcattctt cttttgcccg ggcaagttca acaacaaccc
7741 cacaatcacg cttcctgtat tttgttttgt tttcaaaaca atagaattca ctttttactg
7801 ccaaaattat gttttactcg agagcccggg ctcctgcagg taccttaatt aaaagtttaa
7861 actatcagtg tttgacagga tatattggcg ggtaaaccta agagaaaaga gcgtttatta
7921 gaataatcgg atatttaaaa gggcgtgaaa aggtttatcc gttcgtccat ttgtatgtgc
7981 atgccaacca cagggttccc cagatc
```
//

Figure 2A

```
LOCUS       pWVCZ20       13001 bp    DNA    circular         20-SEP-2004
SOURCE
   ORGANISM
COMMENT     This file is created by Vector NTI
            http://www.informaxinc.com/
COMMENT     VNTDATE|350136453|
COMMENT     VNTDBDATE|350142683|
COMMENT     VNTNAME|pWVCZ20|
COMMENT     VNTAUTHORNAME|Demo User|
FEATURES             Location/Qualifiers
     promoter        6650..7957
                     /vntifkey="29"
                     /label=UBQ10\promoter
     promoter        2863..4262
                     /vntifkey="29"
                     /label=PrAG\promoter
     CDS             4263..6324
                     /vntifkey="4"
                     /label=GUS(INT)
     misc_feature    98..2841
                     /vntifkey="21"
                     /label=AtAGenh
     misc_feature    1..25
                     /vntifkey="21"
                     /label=Right\Border
     misc_feature    9374..9398
                     /vntifkey="21"
                     /label=Left\Border
     CDS             7958..9018
                     /vntifkey="4"
                     /label=NPT\II\(kanR)
     terminator      9037..9367
                     /vntifkey="43"
                     /label=Nos-T
     terminator      6331..6593
                     /vntifkey="43"
                     /label=Nos-T
BASE COUNT     3662 a    2918 c    2826 g    3595 t
ORIGIN
        1 gtttacccgc caatatatcc tgtcaaacac tgatagttta aacttttaat taaggtacct
       61 gcaggagccc gggctgcagg aattcgatat caagcttgat agggtcaaat cgaccacttg
      121 cacagttaag tgattctaat acgaaacctt aaaagcaaac atcggttctt ttgagtcaga
      181 agaaatgcaa cttaatgtga cacatgatgt gaagaaaaaa caaaagtaat ataagaaaag
      241 ggaacaatta aatagttaat aaaatatttc cttaaagttg taacaaataa agaatcattt
      301 tatgaaacaa tatgaaccct aaataaatta aaattcctct gaaaccttaa atttatcgag
      361 ctagtgattg gctgccaact gccatgctgg caaaattaga gtgacatgat tggtctgaac
      421 atgtctaggg tttcagacat gtgacatgtg tcaacaaccc attaacacat tgggtataaa
      481 tccaatagac atttgatagt attaaaattg taaccattgg attaaattta aacgtgatgg
      541 atgtaactaa atgacttgtc cgagtaacat cacaacgttc catactttcc ttatttggaa
      601 tataattaaa tttaccattt attcttttt cttgagtttc ctgtatatgt acttgtacat
      661 agatatatat gcacaaatac gtattacaat gacatattat agactttgat gtctgaactc
      721 tcaaccttct cgatggagag atcatgaccg tagattttt tggatcgtag aaggcagacc
      781 aaactcttaa actattggat ccgtactaaa aatctcactt tcctctcagt acccataatg
      841 agagagaaaa tgataaaaat ccctaacatt attctctctc tagaaaaaaa aagatacttc
      901 aaaaagaaag agaaattgca taaatctatc tacaccaaag atgttgaagc aattccaatg
      961 ctatacttct atgccaaatc tatttattca gtgatcatta atcttttac ttccaagaaa
     1021 tatgaacaat ttagtatcct tataattttt gtctctatat atgtaatatg aacattgggt
     1081 attgaccaaa tgagaaatct aatattaaat ggtcaaaagt agtaatatga tgacattttt
     1141 gaatttataa ataggttaca aattaattca ttatgacata aaaccttctt gtcagaagtc
     1201 aagaactgaa actaacaaaa ctttataata aattagtaaa aatacaaatg aaaaataaaa
     1261 agaaataata tctgagtgat gacgtgatca aagattcttt aacaaagaca acaaatcttct
     1321 cagacccaaa acctaatctt gcgctcaatt ccaacctctg aaaaaacctc aaaaatctta
     1381 taaagaaaa taaataaaga aacgaaactc tgatttcgta gagtacccat cggatatata
     1441 aaagaaatt agtaggtaaa tgaagactaa ttttgattga ctgatttaat ttgaagtcgt
     1501 tgttagcttt tcttgttttg gacatgagaa ttatatattt caggacatga gagttgacaa
     1561 ctgtaaacga ttaagaaaat tgatctttta atttttcaaac accatttaat cttgacatgt
     1621 tttatgtttt ggtggagaag aaagtaatca cgtgggactc tctactaata agtatttgga
     1681 aattgcgtgt cgaattagag attactagtt tgagtaatgt agttcgaaat gagattagtt
     1741 atttttaatt ttaaaaagag taatttttaag gaataacaaa aagagtccc cataagctaa
     1801 tttgtcttaa ttacctcctt gtttcattga ctatttgaaa tcttgaaaat tcagttgaaa
     1861 tttcaaatct atgtttcttt tgaccacttc taaactaatc ttagctcata tataatttc
     1921 caaaactaca aaaataacac taacatttaa cattctcaag agaaaacaaa aacaaaaact
     1981 tagataacca tctaaattgt cctacatgta cgtataagtt ccattatttt ctatcactca
```

Figures 2B

```
2041 tataagttaa aatttcatga aaactcaaaa atctagctag tttcaccnta ttcactctca
2101 cttaccatca catgtgtttg tatcaaatat atgatatgat ataattcatg agagagaaag
2161 agagctagag ataagaaagg aaagtaagag aaagaagaga agaaaaagag agacacagac
2221 attaacaaca atggaggatg gatgatcaca aaacagaaga tatgacctca tagtccttcc
2281 ttactctctc cccaatttgt ttcccaaaac ttactttat agtcataaaa atcaagtttt
2341 tacctattac aacaccagat ctataaaatat atctaaatct tcaagtactt gttagtaagg
2401 aaaatagaaa gatataagat tttattatta ttataataac agaaatgagt gaagaaagaa
2461 cacccaacaa agtgaatctt agttctacaa aactgaatct aaaactccac attagaaaaa
2521 accctgatgg tttcttattt cttttcattt attatctaac tctcactcag atctccttta
2581 actttgtacc atttccctca cttcatatat ctatatataa caaactctct cttttattt
2641 aagtcttaag ggaaaattaa tatacacatg aagacaagaa attagatcta caaaattgtt
2701 acaaaaaccc ccgaagtaaa taaaataaac atatcaaaca aatattccca ctaatgttag
2761 tgtgtttata tatatatgtg tgtggaatat gaaggaaaaa agtgaaaaat aatcctaccc
2821 ataagagcat tcaagaagaa gctcgagggt atcgataagc ttaaactcga cagcaaatat
2881 gatttagatt atgacctaga aataagcata gcattaaagc atatacataa caagcggtga
2941 tatactctga ctgccactgt acttgaggaa aggtagtgga ctctgctcag gtacattagt
3001 ttggtaaggt tggcttggct tctgggtaat atgagaagta aagaagtaaa aggtatttga
3061 ctctagtcaa gtacattgga ttgcctttgt cgggggcttgg atggcttggg ttcgtgtgag
3121 aagccaacaa tttataagaa atatatataaa taaaaaataa aaaaatttaa gtgttggaag
3181 tgaaaacggt ggggcagaaa tatacacaga agagtacttt aacaatgcgc aaccaaggca
3241 gattcacaac ttgatttctg gacctcgaat acgagataat ggtggtaaga aataaaggaa
3301 gagtggagcg catttgaaaa tgaatggaga gcgcacaaaa tggaggacga ataaatgaaa
3361 tataatgcaa gggtgcattt ccctattatt tccagaaatg tatatgtggg gtcggcattc
3421 tcatgggcgt cgcattcagg gggtgtcata gcggtccttt gattgcagtg tgggagttgc
3481 aacatgtacc aacaaatcca ttcatcccaa aacctaaatt tatcctctcc attactatta
3541 cctacaccta tacctagtaa atatgtcctg ccttgtaact cctccactgc ctgcacacgt
3601 cttagtcaat ccatctgcct tcaaataggc attatttgt tcttcccct ccgactgaaa
3661 ggctatcgac cgaccgaccg ctcatcttct tcttctgcgc aattttttct gctggatcat
3721 catcattacc atcatcgcca tcccaccat catcatcatg atggtatctc tatctctccc
3781 tggcaatcga ttgtagagga aaggaagagg gaaggggcat atgtattgat caacctaccc
3841 gaaaaaacaa tctgatcagc cctgctaatc ttgcttataa atctcttatc cactgttcaa
3901 tcattcaggt ttcttcccac tttcaagcaa aggcgcccgg attggccgtg ttcttagatt
3961 ttcaggtact taaatggaca atattcccca cctgaagccg ttctgaaaaa gatttgttg
4021 tagaaacaaa cgattgtaat atttgcttaa gttgagctta aggggtttgg tacctaactt
4081 gccttgtggt tatttgtttc tcagaactcg ggctgcgtcc aactgtagga acgaaccagc
4141 acaaggggtt gcagcttttg ctgttgctgt tgcgcccatt gcttttgac tggtattagt
4201 agttgcagct ttgtttttgca tacgctgtga ggatctgtgc gcggaaattt tgtgtacaaa
4261 tcatgttacg tcctgtagaa acccccaaccc gtgaaatcaa aaaactcgac ggcctgtggg
4321 cattcagtct ggatcgcgaa aactgtggaa ttggtcagcg ttggtgggaa agcgcgttac
4381 aagaaagccg ggcaattgct gtgccaggca gttttaacga tcagttcgcc gatgcagata
4441 ttcgtaatta tgcgggcaac gtctggtatc agcgcgaagt ctttataccg aaaggttggg
4501 caggccagcg tatcgtgctg cgtttcgatg cggtcactca ttacggcaaa gtgtgggtca
4561 ataatcagga agtgatggag catcagggcg gctatacgcc atttgaagcc gatgtcacgc
4621 cgtatgttat tgccgggaaa agtgtacgta agtttctgct tctacctttg atatatatat
4681 aaaattatc attaattagt agtaatataa tattttcaaat attttttca aaataaaaga
4741 atgtagtata tagcaattgc ttttctgtag tttataagtg tgtatatttt aatttataac
4801 cttctaata tatgaccaaa atttgttgat gtgcaggtat caccgtttgt gtgaacaacg
4861 aactgaactg gcagactatc ccgccgggaa tggtgattac cgacgaaaac ggcaagaaaa
4921 agcggtctta cttccatgat ttctttaact atgccggaat ccatcgcagc gtaatgctct
4981 acaccacgcc gaacacctgg gtggacgata tcaccgtggt gacgcatgtc gcgcaagact
5041 gtaaccacgc gtctgttgac tggcaggtgg tggccaatgg tgatgtcagc gttgaactgc
5101 gtgatgcgga tcaacaggtg gttgcaactg gacaaggcac tagcgggact ttgcaagtgg
5161 tgaatccgca cctctggcaa ccgggtgaag gttatctcta tgaactgtgc gtcacagcca
5221 aaagccagac agagtgtgat atctacccgc ttcgcgtcga catccgcta gtggcagtga
5281 agggcgaaca gttcctgatt aaccacaaac cgttctactt tactggcttt ggtcgtcatg
5341 aagatgcgga cttgcgtggc aaaggattcg ataacgtgct gatggtgcac gaccacgcat
5401 taatggactg gattggggcc aactcctacc gtacctcgca ttacctttac gctgaagaga
5461 tgctcgactg ggcagatgaa catggcatcg tggtgattga tgaaactgct gctgtcgcgg
5521 ttaacctctc tttaggcatt ggtttcgaag cgggcaacaa gccgaaagaa ctgtacagcg
5581 aagaggcagt caacggggaa actcagcaag cgcacttaca ggcgattaaa gagctgatag
5641 cgcgtgacaa aaaccaccca agcgtggtga tgtggagtat tgccaacgaa ccggatacca
5701 gtccgcaagg tgcacgggaa tatttcgcgc cactgggaga agcaacgcgt aaactcgacc
5761 cgacgcgtcc gatcacctgc gtcaatgtaa tgttctgcga cgctcacacc gataccatca
5821 gcgatctctt tgatgtgctg tgcctgaacc gttattacgg atggtatgtc caaagcggcg
5881 atttggaaac ggcagagaag gtactggaaa aagaacttct ggcctggcag gagaaactgc
5941 atcagccgat tatcatcacc gaatacggcg tggatacgtt agccgggctg cactcaatgt
6001 acaccgacat gtggagtgaa gcgcatgcct ggatatgtat caccgcgtct
6061 ttgatcgcgt cagcgccgtc gtcggtgaac aggtatggaa tttcgccgat tttgcgacct
6121 cgcaaggcat attgcgcgtt ggcggtaaca agaaagggat cttcactcgc gaccgcaaac
6181 cgaagtcggc ggctttcctg ctgcaaaaac gctggactgg catgaacttc ggtgaaaaac
6241 cgcagcaggg aggcaaacaa tgaatcaaca actctcctgg cgcaccatcg tcggctacag
```

Figure 2C

```
6301 cctcgggaat tgctaccgga gagagagctc gaatttcccc gatcgttcaa acatttggca
6361 ataaagtttc ttaagattga atcctgttgc cggtcttgcg atgattatca tataatttct
6421 gttgaattac gttaagcatg taattaattaa catgtaatgc atgacgttat ttatgagatg
6481 ggttttatg attagagtcc cgcaattata catttaatac gcgatagaaa acaaaatata
6541 gcgcgcaaac taggataaat tatcgcgcgc ggtgtcatct atgttactag atcgggaatt
6601 cctgcagccc gggggatcca ctagttctag agcggccgct tggcgcgccg tcaacggatc
6661 aggatatcct tgtttaagat gttgaactct atggaggttt gtatgaactg atgatctagg
6721 accggataag ttcccttctt catagcgaac ttattcaaag aatgttttgt gtatcattct 6781 tgttacattg ttattaatga aaaatatta ttggtcattg gactgaacac gagtgttaaa
6841 tatggaccag gccccaaata agatccattg atatatgaat taaataacaa gaataaatcg
6901 agtcaccaaa ccacttgcct tttttaacga gacttgttca ccaacttgat acaaaagtca
6961 ttatcctatg caaatcaata atcatacaaa aatatccaat aacactaaaa aattaaaaga
7021 aatggataat ttcacaatat gttatacgat aaagaagtta cttttccaag aaattcactg
7081 attttataag cccacttgca ttagataaat ggcaaaaaaa aacaaaaagg aaaagaaata
7141 aagcacgaag aattctagaa aatacgaaat acgcttcaat gcagtgggac ccacggttca
7201 attattgcca attttcagct ccaccgtata tttaaaaaat aaaacgataa tgctaaaaaa
7261 atataaatcg taacgatcgt taaatctcaa cggctggatc ttatgacgac cgttagaaat
7321 tgtggttgag tcagtaataa acggcgtcaa agtggttgca gccggcacac acgagtcgtg
7381 tttatcaact caaagcacaa atactttcc tcaacctaaa aataaggcaa ttagccaaaa
7441 acaactttgc gtgtaaacaa cgctcaatac acgtgtcatt ttattattag ctattgcttc
7501 accgccttag ctttctcgtg acctagtcgt cctcgtcttt tcttcttctt cttctataaa
7561 acaataccca aagagctctt cttcttcaca attcagattt caatttctca aaatcttaaa
7621 aactttctct caattctctc taccgtgatc aaggtaaatt tctgtgttcc ttattctctc
7681 aaaatcttcg attttgtttt cgttcgatcc caatttcgta tatgttcttt ggtttagatt
7741 ctgttaatct tagatcgaag acgattttct gggtttgatc gttagatatc atcttaattc
7801 tcgattaggg tttcataaat atcatccgat ttgttcaaat aatttgagtt ttgtcgaata
7861 attacttctc gattttgtgat ttctatctag atctggtgti agtttctagt ttgtgcgatc
7921 gaatttgtcg attaatctga gttttctga ttaacagatg attgaacaag atggattgca
7981 cgcaggttct ccggccgctt gggtggagag gctattcggc tatgactggg cacaacagac
8041 aatcggctgc tctgatgccg ccgtgttccg gctgtcagcg caggggcgcc cggttctttt
8101 tgtcaagacc gacctgtccg gtgccctgaa tgaactccag gacgaggcag cgcggctatc
8161 gtggctggcc acgacgggcg ttccttgcgc agctgtgctc gacgttgtca ctgaagcggg
8221 aagggactgg ctgctattgg gcgaagtgcc ggggcaggat ctcctgtcat ctcaccttgc
8281 tcctgccgag aaagtatcca tcatggctga tgcaatgcgg cggctgcata cgcttgatcc
8341 ggctacctgc ccattcgacc accaagcgaa acatcgcatc gagcgagcac gtactcggat
8401 ggaagccggt cttgtcgatc aggatgatct ggacgaagag catcagggc tcgcgccagc
8461 cgaactgttc gccaggctca aggcgcgcat gcccgacggc gaggatctcg tcgtgaccca
8521 tggcgatgcc tgcttgccga atatcatggt ggaaaatggc cgcttttctg gattcatcga
8581 ctgtggccgg ctgggtgtgg cggaccgcta tcaggacata gcgttggcta cccgtgatat
8641 tgctgaagag cttggcggcg aatgggctga ccgcttcctc gtgctttacg gtatcgccgc
8701 tcccgattcg cagcgcatcg ccttctatcg ccttcttgac gagttcttct gagggatcgt
8761 tcaaacattt ggcaataaag tttcttaaga ttgaatcctg ttgccggtct tgcgatgatt
8821 atcatataat ttctgttgaa ttacgttaag catgtaataa ttaacatgta atgcatgacg
8881 ttatttatga gatgggtttt tatgattaga gtcccgcaat tatacattta atacgcgata
8941 gaaaacaaaa tatagcgcgc aaactaggat aaattatcgc gcgcggtgtc atctatgtta
9001 ctagatcgca cgtagggggg atccactagt tctagagcgg ccgtgggcca tcgccctgat
9061 agacggtttt tcgcccttg acgttggagt ccacgttctt taatagtgga ctcttgttcc
9121 aaactggaac aacactcaac cctatctcgg gctattcttt tgatttataa gggattttgc
9181 cgatttcgga accaccatca aacaggattt tcgcctgctg gggcaaacca gcgtggaccg
9241 cttgctgcaa ctctctcagg gccaggcggt gaagggcaat cagctgttgc ccgtctcact
9301 ggtgaaaaga aaaccaccc cagtacatta aaaacgtccg caatgtgtta ttaagttgtc
9361 taagcgtcaa tttgtttaca ccacaatata tcctgccacc agccagccaa cagctccccg
9421 accggcagct cggcacaaaa tcaccactcg atacaggcag cccatcagtc cgggacggcg
9481 tcagcgggag agccgttgta aggcggcaga ctttgctcat gttaccgatg ctattcggaa
9541 gaacggcaac taagctgccg ggtttgaaac acggatgatc tcgcggaggg tagcatgttg
9601 attgtaacga tgacagagcg ttgctgcctg tgatcaaata tcatctccct cgcagagatc
9661 cgaattatca gccttcttat tcatttctcg cttaaccgtg acagttgctt atcggcagtt
9721 cgtagagcgc gccgtgcgtc ccgagcgata ctgagcgaag caagtgcgtc gagcagtgcc
9781 cgcttgttcc tgaaatgcca gtaaagcgct ggctgctgaa cccccagccg gaactgaccc
9841 cacaaggccc tagcgtttgc aatgcaccag gtcatcattg acccaggcgt gttccaccag
9901 gccgctgcct cgcaactctt cgcaggcttc tcgcgccact tcttcaccgcg
9961 ggtggaatcc gatccgcaca tgaggcggaa ggtttccagc ttgagcgggt acggctcccg
10021 gtgcgagctg aaatagtcga acatccgtcg ggccgtcggc gacagcttgc ggtacttctc
10081 ccatatgaat ttcgtgtagt ggtcgccagc aaacagcacg acgatttcct cgtcgatcag
10141 gacctggcaa cgggacgttt tcttgccacg gtccaggacg cggaagcggt gcagcagcga
10201 caccgattcc aggtgcccaa cgcggtcgga cgtgaagccc atcgccgtcg cctgtaggcg
10261 cgacaggcat tcctcggcct tcgtgtaata ccggccattg atcgaccagc ccaggtcctg
10321 gcaaagctcg tagaacgtga aggtgatcgg ctcgccgata ggggtgcgct tcgcgtactc
10381 caacacctgc tgccacacca gttcgtcatc gtcggcccgc agctcgacgc ggtgtaggt
10441 gatcttcacg tccttgttga cgtggaaaat gaccttgttt tgcagcgcct cgcgcgggat
10501 tttcttgttg cgcgtggtga acagggcaga gcgggccgtg tcgtttggca tcgctcgcat
10561 cgtgtccggc cacggcgcaa tatcgaacaa ggaaagctgc atttccttga tctgctgctt
10621 cgtgtgtttc agcaacgcgg cctgcttggc ctcgctgacc tgttttgcca ggtcctcgcc
```

Figure 2D

```
10681 ggcggttttt cgcttcttgg tcgtcatagt tcctcgcgtg tcgatggtca tcgacttcgc
10741 caaacctgcc gcctcctgtt cgagacgacg cgaacgctcc acggcggccg atggcgcggg
10801 cagggcaggg ggagccagtt gcacgctgtc gcgctcgatc ttggccgtag cttgctggac
10861 catcgagccg acggactgga aggtttcgcg gggcgcacgc atgacggtgc ggcttgcgat
10921 ggtttcggca tcctcggcgg aaaacccgc gtcgatcagt tcttgcctgt atgccttccg
10981 gtcaaacgtc cgattcattc accctccttg cgggattgcc ccgactcacg ccggggcaat
11041 gtgcccttat tcctgatttg acccgcctgg tgccttggtg tccagataat ccaccttatc
11101 ggcaatgaag tcggtcccgt agaccgtctg gccgtccttc tcgtacttgg tattccgaat
11161 cttgccctgc acgaatacca gcgacccctt gcccaaatac ttgccgtggg cctcggcctg
11221 agagccaaaa cacttgatgc ggaagaagtc ggtgcgctcc tgcttgtcgc cggcatcgtt
11281 gcgccacatc taggtactaa aacaattcat ccagtaaaat ataatatttt attttctccc
11341 aatcaggctt gatccccagt aagtcaaaaa atagctcgac atactgttct tccccgatat
11401 cctccctgat cgaccggacg cagaaggcaa tgtcatacca cttgtccgcc ctgccgcttc
11461 tcccaagatc aataaagcca cttactttgc catctttcac aaagatgttg ctgtctccca
11521 ggtcgccgtg ggaaaagaca agttcctctt cgggcttttc cgtctttaaa aaatcataca
11581 gctcgcgcgg atctttaaat ggagtgtctt cttcccagtt ttcgcaatcc acatcggcca
11641 gatcgttatt cagtaagtaa tccaattcgg ctaagcggct gtctaagcta ttcgtatagg
11701 gacaatccga tatgtcgatg gagtgaaaga gcctgatgca ctccgcatac agctcgataa
11761 tcttttcagg gctttgttca tcttcatact cttccgagca aaggacgcca tcggcctcac
11821 tcatgagcag attgctccag ccatcatgcc gttcaaagtg caggacctt ggaacaggca
11881 gctttccttc cagccatagc atcatgtcct tttcccgttc cacatcatag gtggtccctt
11941 tataccggct gtccgtcatt tttaaatata ggttttcatt ttctcccacc agcttatata
12001 ccttagcagg agacattcct tccgtatctt ttacgcagcg gtattttcg atcagttttt
12061 tcaattccgg tgatattctc attttagcca tttattattt ccttcctctt ttctacagta
12121 tttaaagata ccccaagaag ctaattataa caagacgaac tccaattcac tgttccttgc
12181 attctaaaac cttaaatacc agaaaacagc ttttttcaaag ttgttttcaa agttggcgta
12241 taacatagta tcgacggagc cgattttgaa accacaatta tggactgcca gcgctgccat
12301 ttttggggtg aggccgttcg cggccgaggg gcgcagcccc tggggggatg ggaggcccgc
12361 gttagcgggc cgggaggtt cgagaagggg gggcaccccc cttcggcgtg cgcggtcacg
12421 cgcacagggc gcagccctgg ttaaaaacaa ggtttataaa tattggttta aaagcaggtt
12481 aaaagacagg ttagcggtgg ccgaaaaacg ggcggaaacc cttgcaaatg ctggattttc
12541 tgcctgtgga cagcccctca aatgtcaata ggtgcgcccc tcatctgtca gcactctgcc
12601 cctcaagtgt caaggatcgc gcccctcatc tgtcagtagt cgcgcccctc aagtgtcaat
12661 accgcagggc acttatcccc aggcttgtcc acatcatctg tgggaaactc gcgtaaaatc
12721 aggcgttttc gccgatttgc gaggctggcc agctccacgt cgccggccga aatcgagcct
12781 gccctcatc tgtcaacgcc gcgccggtg agtcggcccc tcaagtgtca acgtccgccc
12841 ctcatctgtc agtgagggcc aagttttccg cgaggtatcc acaacgccgg cggatctggg
12901 gaaccctgtg gttggcatgc acatacaaat ggacgaacgg ataaaccttt tcacgccctt
12961 ttaaatatcc gattattcta ataaacgctc ttttctctta g
```
//

Figure 3A

```
LOCUS       pWVCZ23       8534 bp    DNA     circular              20-SEP-2004
SOURCE
  ORGANISM
COMMENT     This file is created by Vector NTI
            http://www.informaxinc.com/
COMMENT     VNTDATE|350136839|
COMMENT     VNTDBDATE|350143806|
COMMENT     VNTNAME|pWVCZ23|
COMMENT     VNTAUTHORNAME|Demo User|
FEATURES             Location/Qualifiers
     misc_feature    1..25
                     /vntifkey="21"
                     /label=Right\Border
     misc_feature    4423..4447
                     /vntifkey="21"
                     /label=Left\Border
     promoter        103..1502
                     /vntifkey="29"
                     /label=PrAG\promoter
     CDS             1503..1936
                     /vntifkey="4"
                     /label=barnaseE73G
     terminator      1943..2210
                     /vntifkey="43"
                     /label=Nos-T
     promoter        2227..2565
                     /vntifkey="30"
                     /label=Nos\Promoter CDS             2586..3479
                     /vntifkey="4"
                     /label=NPT\II\(kanR)
     terminator      3764..4066
                     /vntifkey="43"
                     /label=Nos-T
BASE COUNT      2075 a    2191 c   2113 g    2155 t
ORIGIN
        1 gtttaccegc caatatatcc tgtcaaacac tgatagttta aactttaat taaggtacct
       61 gcaggagccc gggctctcga ggtcgacggt atcgataagc ttaaactcga cagcaaatat
      121 gatttagatt atgacctaga aataagcata gcattaaagc atatacataa caagcggtga
      181 tatactctga ctgccactgt acttgaggaa aggtagtgga ctctgctcag gtacattagt
      241 ttggtaaggt tggcttggct tctgggtaat atgagaagta aagaagtaaa aggtatttga
      301 ctctagtcaa gtacattgga ttgccttgt cggggcttgg atggcttggg ttcgtgtgag
      361 aagccaacaa tttataagaa atatataaaa taaaaataa aaaatttaa gtgttggaag
      421 tgaaaacggt ggggcagaaa tatacacaga agagtacttt aacaatgcgc aaccaaggca
      481 gattcacaac ttgatttctg gacctcgaat acgagataat ggtggtaaga aataaaggaa
      541 gagtggagcg catttgaaaa tgaatggaga gcgcacaaaa tggaggacga ataaatgaaa
      601 tataatgcaa gggtgcattt ccctattatt tccagaaatg tatatgtggg gtcggcattc
      661 tcatgggcgt cgcattcagg gggtgtcata gcggtccttt gattgcagtg tgggagttgc
      721 aacatgtacc aacaaatcca ttcatcccaa aacctaaatt tatcctctcc attactatta
      781 cctacaccta tacctagtaa atatgtcctg ccttgtaact cctccactgc ctgcacacgt
      841 cttagtcaat ccatctgcct tcaaataggc attatttgt tctttcccct ccgactgaaa
      901 ggctatcgac cgaccgaccg ctcatcttct tcttctgcgc aattttttct gctggatcat
      961 catcattacc atcatcgcca tccccaccat catcatcatg atggtatctc tatctctccc
     1021 tggcaatcga ttgtagagga aaggaagagg gaagggcat atgtattgat caacctaccc
     1081 gaaaaaacaa tctgatcagc cctgctaatc ttgcttataa atctcttatc cactgttcaa
     1141 tcattcaggt ttcttcccac tttcaagcaa aggcgcccgg attggccgtg ttcttagatt
     1201 ttcaggtact taaatggaca atattcccca cctgaagccg ttctgaaaaa gatttgtttg
     1261 tagaaacaaa cgattgtaat atttgcttaa gttgagctta aggggtttgg tacctaactt
     1321 gcettgtggt tatttgtttc tcagaactcg ggctgcgtcc aactgtagga acgaaccagc
     1381 acaaggggtt gcagcttttg ctgttgctgt tgcgcccatt gcttttggac tggtattagt
     1441 agttgcagct ttgtttgca tacgctgtga ggatctgtgc gcggaaattt tgtgtacaaa
     1501 tcatggcaca ggttatcaac acgtttgacg gggttgcgga ttatcttcag acatatcata
     1561 agctacctga taattacatt acaaaatcag aagcacaagc cctcggctgg gtggcatcaa
     1621 aagggaacct tgcagacgtc gctccgggga aaagcatcgg cggagacatc ttctcaaaca
     1681 gggaaggcaa actcccgggc aaaagcggac gaacatggcg tgaagcggat attaactata
     1741 catcaggctt cagaaattca gaccggattc tttactcaag cgactggctg atttacaaaa
     1801 caacggacca ttatcagacc tctacaaaaa tcagataacg aaaaaaacgg cttccctgcg
     1861 ggaggccgtt ttttcagct ttacataaag tgtgtaataa atttttcttc aaactctgat
     1921 cggtcaattg cactttgagc tcgaattcc ccgatcgttc aaacatttgg caataaagtt
     1981 tcttaagatt gaatcctgtt gccggtcttg cgatgattat catataattt ctgttgaatt
     2041 acgttaagca tgtaataatt aacatgtaat gcatgacgtt atttatgaga tgggtttta
     2101 tgattagagt cccgcaatta tacatttaat acgcgataga aaacaaaata tagcgcgcaa
```

Figure 3B

```
2161 actaggataa attatcgcgc gcggtgtcat ctatgttact agatcgggaa ggcgcgccgc
2221 ggccgcaaca ctgatagttt aaactgaagg cgggaaacga caatctgatc atgagcggag
2281 aattaaggga gtcacgttat gaccccgcc gatgacgcgg gacaagccgt tttacgtttg
2341 gaactgacag aaccgcaacg ttgaaggagc cactcagccg cgggtttctg gagtttaatg
2401 agctaagcac atacgtcaga aaccattact gcgcgttcaa aagtcgccta aggtcactat
2461 cagctagcaa atatttcttg tcaaaaatgc tccactgacg ttccataaat tcccctcggt
2521 atccaattag agtctcatat tcactctcaa tccaaataat ctgcaccgga tctggatcgt
2581 ttcgcatgat tgaacaagat ggattgcacg caggttctcc ggccgcttgg gtggagaggc
2641 tattcggcta tgactgggca caacagacaa tcggctgtc tgatgccgcc gtgttccggc
2701 tgtcagcgca ggggcgcccg gttctttttg tcaagaccga cctgtccggt gccctgaatg
2761 aactgcagga cgaggcagcg cggctatcgt ggctggccac gacgggcgtt ccttgcgcag
2821 ctgtgctcga cgttgtcact gaagcgggaa gggactggct gctattgggc gaagtgccgg
2881 ggcaggatct cctgtcatct caccttgctc ctgccgagaa agtatccatc atggctgatg
2941 caatgcggcg gctgcatacg cttgatccgg ctacctgccc attcgaccac caagcgaaac
3001 atccgcatcga gcgagcacgt actcggatgg aagccgtct tgtcgatcag gatgatctgg
3061 acgaagagca tcaggggctc gcgccagccg aactgttcgc caggctcaag gcgcgcatgc
3121 ccgacggcga tgatctcgtc gtgacccatg gcgatgcctg cttgccgaat atcatggtgg
3181 aaaatggccg cttttctgga ttcatcgact gtggccggct gggtgtggcg gaccgctatc
3241 aggacatagc gttggctacc cgtgatattg ctgaagagct tggcggcgaa tgggctgacc
3301 gcttcctcgt gctttacggt atcgccgctc ccgattcga gcgcatcgcc ttctatcgcc
3361 ttcttgacga gttcttctga gcgggactct ggggttcgaa atgaccgacc aagcgacgcc
3421 caacctgcca tcacgagatt tcgattccac cgccgccttc tatgaaaggt tgggcttcgg
3481 aatcgttttc cgggacgccg gctggatgat cctccagcgc ggggatctca tgctggagtt
3541 cttcgcccac gggatctctg cggaacaggc ggtcgaaggt gccgatatca ttacgacagc
3601 aacggccgac aagcacaacg ccacgatcct gagcgacaat atgatcgggc ccggcgtcca
3661 catcaacggc gtcggcggcg actgccagg caagaccgag atgcaccgcg atatcttgct
3721 gcgttcggat attttcgtgg agttccgcc acagaccgg atgatcccg atcgttcaaa
3781 catttggcaa taaagtttct taagattgaa tcctgttgcc ggtcttgcga tgattatcat
3841 ataatttctg ttgaattacg ttaagcatgt aataattaac atgtaatgca tgacgttatt
3901 tatgagatgg gtttttatga ttagagtccc gcaattatac atttaatacg cgatagaaaa
3961 caaaatatag cgcgcaaact aggataaatt atcgcgcgcg gtgtcatcta tgttactaga
4021 tcgggcctcc tgtcaatgct ggcggcggct ctggtggtgg ttctggtgga tccactagtt
4081 ctagagcggc cgtgggccat cgcccttgata gacggttttt cgccctttga cgttggagtc
4141 cacgttcttt aatagtggac tcttgttcca aactgaaca acactcaacc ctatctcggg
4201 ctattctttt gatttataag ggattttgcc gatttcggaa ccaccatcaa acaggatttt
4261 cgcctgctgg ggcaaaccag cgtggaccgc ttgctgcaac tctctcaggg ccaggcggtg
4321 aagggcaatc agctgttgcc cgtctcactg gtgaaaagaa aaaccacccc agtacattaa
4381 aaacgtccgc aatgtgttat taagttgtct aagcgtcaat ttgtttacac cacaatatat
4441 cctgccacca gccagccaac agctccccga ccggcagctc ggcacaaaat caccactcga
4501 tacaggcagc catcagtcc gggacggcgt cagcgggaga gccgttgtaa ggcggcagac
4561 tttgctcatg ttaccgatgc tattcggaag aacggcaact aagctgccgg gtttgaaaca
4621 cggatgatct cgcggagggt agcatgttga ttgtaacgat gacagacgt tgctgcctgt
4681 gatcaaatat catctccctc gcagagatcc gaattatcag ccttcttatt catttctcgc
4741 ttaaccgtga cagttgtcta tcggcagttc gtagagcgcg ccgtcgtcc cgagcgatac
4801 tgagcgaagc aagtgcgtcg agcagtgccc gcttgttcct gaaatgccag taaagcgctg
4861 gctgctgaac ccccagccgg aactgacccc acaaggccct agcgtttgca atgcaccagg
4921 tcatcattga cccaggcgtg ttccaccagg ccgctgcctc gcaactcttc gcaggcttcg
4981 ccgacctgct cgcgccactt cttcacgcgg gtggaatccg atccgcacat gaggcggaag
5041 gtttccagct tgagcgggta cggctcccgg tgcgagctga aatagtcgaa catccgtcgg
5101 gccgtcggcg acagcttgcg gtacttctcc catatgaatt tcgtgtagtg gtcgccagca
5161 aacgacacga cgatttcctc gtcgatcagg acctggccaac gggacgtttt cttgccacgg
5221 tccaggacgc ggaagcggtg cagcagcgac accgattcca ggtgcccaac gcggtcggac
5281 gtgaagccca tcgccgtcgc ctgtaggcgc gacaggcatt cctcggcctt cgtgtaatac
5341 cggccattga tcgaccagcc caggtcctgg caaagctcgt agaacgtgaa ggtgatcggc
5401 tcgccgatag gggtgcgctt cgcgtactcc aacacctgct gccacaccag ttcgtcatcg
5461 tcggcccgca gtcgacgcc ggtgtaggtg atcttcacgt ccttgttgac gtggaaaatg
5521 accttgtttt gcagcgcctc gcgcgggatt ttcttgttgc gcgtggtgaa cagggcagag
5581 cgggccgtgt cgtttggcat cgctcgcatc gtgtccggcc acggcgcaat atcgaacaag
5641 gaaagctgca tttccttgat ctgctgcttc gtgtgtttca gcaacgcggc ctgcttggcc
5701 tgctgacct gttttgccag gtcctcgccg gcggttttc gcttcttggt cgtcatagtt
5761 cctcgcgtgt cgatggtcat cgacttcgcc aaacctgccg cctcctgttc gagacgacgc
5821 gaacgctcca cggcggccga tggcgcgggc agggcagggg gagccagttg cacgctgtcg
5881 cgctcgatct tggccgtagc ttgctggacc atcgagccga cggactggaa ggtttcgcgg
5941 ggcgcacgca tgacggtgcg gcttgcgatg gtttcggcat cctcggcgga aaacccccgcg
6001 tcgatcagtt cttgcctgta cggccttccgg tcaaacgtcc gattcattca ccctccttgc
6061 gggattgccc cgactcacgc cggggcaatg tgcccttatt cctgatttga cccgcctggt
6121 gccttggtgt ccagataatc caccttatcg gcaatgaagt cggtcccgta gaccgtctgg
6181 ccgtccttct cgtacttggt attccgaatc ttgccctgca cgaataccag cgaccccttg
6241 cccaaaatact tgccctgggc ctcgcctga gagccaaaac acttgatgcg gaagaagtcg
6301 gtgcgctcct gcttgtcgcc ggcatcgttg cgccacatct aggtactaaa acaattcatc
6361 cagtaaaata taatatttta ttttctccca atcaggcttg atcccagta agtcaaaaaa
6421 tagctcgaca tactgttctt ccccgatatc ctccctgatc gaccggacgc agaaggcaat
6481 gtcataccac ttgtccgccc tgccgcttct cccaagatca ataaagccac ttactttgcc
6541 atctttcaca aagatgttgc tgtctcccag gtcgccgtgg gaaaagacaa gttcctcttc
```

Figure 3C

```
6601 gggcttttcc gtctttaaaa aatcatacag ctcgcgcgga tctttaaatg gagtgtcttc
6661 ttcccagttt tcgcaatcca catcggccag atcgttattc agtaagtaat ccaattcggc
6721 taagcggctg tctaagctat tcgtataggg acaatccgat atgtcgatgg agtgaaagag
6781 cctgatgcac tccgcataca gctcgataat cttttcaggg ctttgttcat cttcatactc
6841 ttccgagcaa aggacgccat cggcctcact catgagcaga ttgctccagc catcatgccg
6901 ttcaaagtgc aggacctttg gaacaggcag cttttccttcc agccatagca tcatgtcctt
6961 ttcccgttcc acatcatagg tggtcccttt ataccggctg tccgtcattt ttaaatatag
7021 gttttcattt tctcccacca gcttatatac cttagcagga gacattcctt ccgtatcttt
7081 tacgcagcgg tattttcga tcagtttttt caattccggt gatattctca ttttagccat
7141 ttattatttc cttcctcttt tctacagtat ttaaagatac cccaagaagc taattataac
7201 aagacgaact ccaattcact gttccttgca ttctaaaacc ttaaatacca gaaaacagct
7261 ttttcaaagt tgttttcaaa gttggcgtat aacatagtat cgacggagcc gattttgaaa
7321 ccacaattat gggagagacc ataatgtggt ccaatttgca gcagccgtcc gagacaggag
7381 gacatcgtcc agctgaaacc ggggcagaat ccggccattt ctgaagagaa aaatggtaaa
7441 ctgatagaat aaaatcataa gaaaggagcc gcacatgaaa aaagcagtca ttaacgggga
7501 acaaatcaga agtatcagcg acctccacca gacattgaaa aaggagcttg cccttccgga
7561 atactacggt gaaaacctgg acgctttatg ggattgtctg accggatggg tggagtaccc
7621 gctcgttttg gaatggaggc agtttgaaca aagcaagcag ctgactgaaa atggcgccga
7681 gagtgtgctt caggttttcc gtgaagcgaa agcggaaggc tgcgacatca ccatcatact
7741 ttcttaatac gatcaatggg agatgaacaa tatgaaaca caaaccacaa ttatgtctct
7801 cagcccacaa ttatggactg ccagcgctgc catttttggg gtgaggccgt tcgcggccga
7861 ggggcgcagc ccctgggggg atgggaggcc cgcgttagcg ggccgggagg gttcgagaag
7921 gggggcacc cccttcggc gtgcgcggtc acgcgcacag ggcgcagccc tggttaaaaa
7981 caaggtttat aaatattggt ttaaaagcag gttaaaagac aggttagcgg tggccgaaaa
8041 acgggcggaa acccttgcaa atgctggatt ttctgcctgt ggacagcccc tcaaatgtca
8101 ataggtgcgc ccctcatctg tcagcactct gcccctcaag tgtcaaggat cgcgcccctc
8161 atctgtcagt agtcgcgccc ctcaagtgtc aataccgcag ggcacttatc cccaggcttg
8221 tccacatcat ctgtgggaaa ctcgcgtaaa atcaggcgtt ttcgccgatt tgcgaggctg
8281 gccagctcca cgtcgccggc cgaaatcgag cctgccctc atctgtcaac gccgcgccgg
8341 gtgagtcggc ccctcaagtg tcaacgtccg ccctcatct gtcagtgagg gccaagtttt
8401 ccgcgaggta tccacaacgc cggcggatct ggggaaccct gtggttggca tgcacataca
8461 aatggacgaa cggataaacc ttttcacgcc cttttaaata tccgattatt ctaataaacg
8521 ctcttttctc ttag
//
```

Figure 4A

```
LOCUS       pWVCZ24      11300 bp    DNA    circular           20-SEP-2004
SOURCE
  ORGANISM
COMMENT     This file is created by Vector NTI
            http://www.informaxinc.com/
COMMENT     VNTDATE|350136867|
COMMENT     VNTDBDATE|350144320|
COMMENT     VNTNAME|pWVCZ24|
COMMENT     VNTAUTHORNAME|Demo User|
FEATURES             Location/Qualifiers
     misc_feature    98..2841
                     /vntifkey="21"
                     /label=AtAGenh
     misc_feature    1..25
                     /vntifkey="21"
                     /label=Right\Border
     promoter        2869..4268
                     /vntifkey="29"
                     /label=PrAG\promoter
     CDS             4269..4702
                     /vntifkey="4"
                     /label=barnaseE73G
     terminator      4709..4976
                     /vntifkey="43"
                     /label=Nos-T
     promoter        4993..5331
                     /vntifkey="30"
                     /label=Nos\Promoter
     CDS             5352..6316
                     /vntifkey="4"
                     /label=NPT\II\(kanR)
     terminator      6531..6833
                     /vntifkey="43"
                     /label=Nos-T
     misc_feature    7189..7213
                     /vntifkey="21"
                     /label=Left\Border
BASE COUNT     3164 a     2619 c     2490 g     3027 t
ORIGIN
        1 gtttacccgc caatatatcc tgtcaaacac tgatagttta aacttttaat taaggtacct
       61 gcaggagccc gggctgcagg aattcgatat caagcttgat agggtcaaat cgaccacttg
      121 cacagttaag tgattctaat acgaaacctt aaaagcaaac atcggttctt ttgagtcaga
      181 agaaatgcaa cttaatgtga cacatgatgt gaagaaaaaa caaaagtaat ataagaaaag
      241 ggaacaatta aatagttaat aaaatatttc cttaaagttg taacaaataa agaatcattt
      301 tatgaaacaa tatgaaccct aaataaatta aaattcctct gaaaccttaa atttatcgag
      361 ctagtgattg gctgccaact gccatgctgg caaaattaga gtgacatgat tggtctgaac
      421 atgtctaggg tttcagacat gtgacatgtg tcaacaaccc attaacacat tgggtataaa
      481 tccaatagac atttgatagt attaaaattg taaccattgg attaaattta aacgtgatgg
      541 atgtaactaa atgacttgtc cgagtaacat cacaacgttc catactttcc ttatttggaa
      601 tataattaaa tttaccattt attctttttt cttgagtttc ctgtatatgt acttgtacat
      661 agatatatat gcacaaatac gtattacaat gacatattat agactttgat gtctgaactc
      721 tcaaccttct cgatggagag atcatgaccg tagattttt tggatcgtag aaggcagacc
      781 aaactcttaa actattggat ccgtactaaa aatctcactt tcctctcagt acccataatg
      841 agagagaaaa tgataaaaat ccctaacatt attctctctc tagaaaaaaa aagatacttc
      901 aaaaagaaag agaaattgca taaatctatc tacaccaaag atgttgaagc aattccaatg
      961 ctatacttct atgccaaatc tatttattca gtgatcatta atcttttac ttccaagaaa
     1021 tatgaacaat ttagtatcct tataattttt gtctctatat atgtaatatg aacattgggt
     1081 attgaccaaa tgagaaatct aatattaaat ggtcaaaagt agtaaatga tgcatttttt
     1141 gaatttataa ataggttaca aattaattca ttatgacata aaaccttctt gtcagaagtc
     1201 aagaactgaa actaacaaaa ctttataata aattagtaaa aatacaaatg aaaaataaaa
     1261 agaaataata tctgagtgat gacgtgatca aagattcttt aacaaagaca acaaatctta
     1321 cagacccaaa acctaatctt gcgctcaatt ccaacctctg aaaaaacctc aaaaatctta
     1381 taaagaaaa taaataaaga aacgaaactc tgatttcgta gagtacccat cggatatata
     1441 aaaagaaatt agtaggtaaa tgaagactaa ttttgattga ctgatttaat ttgaagtcgt
     1501 tgttagcttt tcttgttttg gacatgagaa ttatatattt caggacatga gagttgacaa
     1561 ctgtaaacga ttaagaaaat tgatcttta attttcaaac accatttaat cttgacatgt
     1621 tttatgtttt ggtggagaag aaagtaatca cgtgggactc tctactaata agtatttgga
     1681 aattgcgtgt cgaattagag attactagtt tgagtaatgt agttcgaaat gagattagtt
     1741 attttaatt ttaaaaagag taatttaag gaataacaaa aaagagtccc cataagctaa
     1801 tttgtcttaa ttacctcctt gtttcattga ctatttgaaa tcttgaaaat tcagttgaaa
     1861 tttcaaatct atgtttcttt tgaccacttc taaactaatc ttagctcata tataatttc
     1921 caaaactaca aaaataacac taacatttaa cattctcaag agaaaacaaa aacaaaaact
     1981 tagataacca tctaaattgt cctacatgta cgtataagtt ccattatttt ctatcactca
```

Figure 4B

```
2041 tataagttaa aatttcatga aaactcaaaa atctagctag tttcacctta ttcactctca
2101 cttaccatca catgtgtttg tatcaaatat atgatatgat ataattcatg agagagaaag
2161 agagctagag ataagaaagg aaagtaagag aaagaagaga agaaaaagag agacacagac
2221 attaacaaca atggaggatg gatgatcaca aaacagaaga tatgacctca tagtccttcc
2281 ttactctctc cccaatttgt ttcccaaaac ttactttat agtcataaaa atcaagtttt
2341 tacctattac aacaccagat ctataaatat atctaaatct tcaagtactt gttagtaagg
2401 aaaatagaaa gatataagat tttattatta ttataataac agaaatgagt gaagaaagaa
2461 cacccaacaa agtgaatctt agttctacaa aactgaatct aaaactccac attagaaaaa
2521 accctgatgg tttcttattt cttttcattt attatctaac tctcactcag atctccttta
2581 actttgtacc atttccctca cttcatatat ctatatataa caaactctct cttttttattt
2641 aagtcttaag ggaaaattaa tatacacatg aagacaagaa attagatcta caaaattgtt
2701 acaaaaaccc ccgaagtaaa taaaataaac atatcaaaca aatattccca ctaatgttag
2761 tgtgttata tatatatgtg tgtggaatat gaaggaaaaa agtgaaaaat aatcctaccc
2821 ataagagcat tcaagaagaa gctcgaggtc gacggtatcg ataagcttaa actcgacagc
2881 aaatatgatt tagattatga cctagaaata agcatagcat taaagcatat acataacaag
2941 cggtgatata ctctgactgc cactgtactt gaggaaaggt agtggactct gctcaggtac
3001 attagtttgg taaggttggc ttggcttctg ggtaatatga gaagtaaaga agtaaaaggt
3061 atttgactct agtcaagtac attggattgc ctttgtcggg gcttggatgg cttgggttcg
3121 tgtgagaagc caacaattta taagaaatat ataaaataaa aataaaaaa atttaagtgt
3181 tggaagtgaa aacggtgggg cagaaatata cacagaagag tactttaaca atgcgcaacc
3241 aaggcagatt cacaacttga tttctggacc tcgaatacga gataatggtg gtaagaaata
3301 aaggaagagt ggagcgcatt tgaaaatgaa tggagagcgc acaaaatgga ggacgaataa
3361 atgaaatata atgcaagggt gcatttccct attatttcca gaaatgtata tgtggggtcg
3421 gcattctcat gggcgtcgca ttcaggggt gtcatagcgg tcctttgatt gcagtgtggg
3481 agttgcaaca tgtaccaaca aatccattca aaatttatc ctctccatta
3541 ctattaccta cacctatacc tagtaaatat gtcctgcctt gtaactcctc cactgcctgc
3601 acacgtctta gtcaatccat ctgccttcaa ataggcatta ttttgttctt tcccctccga
3661 ctgaaaggct atcgaccgac cgaccgctca tcttcttctt ctgcgcaatt ttttctgctg
3721 gatcatcatc attaccatca tcgccatccc caccatcatc atcatgatgt tatctctatc
3781 tctccctggc aatcgattgt agaggaaagg aagagggaag gggcatatgt attgatcaac
3841 ctacccgaaa aaacaatctg atcagccctg ctaatcttgc ttataaatct cttatccact
3901 gttcaatcat tcaggtttct tcccactttc aagcaaaggc gcccggattg gccgtgttct
3961 tagattttca ggtacttaaa tggacaatat tccccacctg aagccgttct gaaaaagatt
4021 tgtttgtaga aacaaacgat tgtaatattt gcttaagttg agcttaaggg gtttggtacc
4081 taacttgcct tgtggttatt tgtttctcag aactcgggct gcgtccaact gtaggaacga
4141 accagcacaa ggggttgcag cttttgctgt tgctgttgcg cccattgctt ttggactggt
4201 attagtagtt gcagctttgt tttgcatacg ctgtgaggat ctgtgcgcgg aaattttgtg
4261 tacaaatcat ggcacaggtt atcaacacgt ttgacggggt tgcggattat cttcagacat
4321 atcataagct acctgataat tacattacaa aatcagaagc acaagccctc ggctgggtgg
4381 catcaaaagg gaaccttgca gacgtcgctc cggggaaaag catcggcgga gacatcttct
4441 caaacaggga aggcaaactc ccgggcaaaa gcggacgaac atggcgtgaa gcggatatta
4501 actatacatc aggcttcaga aattcagacc ggattcttta ctcaagcgac tggctgattt
4561 acaaaacaac ggaccattat cagacctcta caaaaatcag ataacgaaaa aaacggcttc
4621 cctgcgggag gccgtttttt tcagctttac ataaagtgtg taataaattt ttcttcaaac
4681 tctgatcggt caattgcact ttgagctcga atttccccga tcgttcaaac atttggcaat
4741 aaagtttctt aagattgaat cctgttgcg gtcttgcgat gattatcata taatttctgt
4801 tgaattacgt taagcatgta ataattaaca tgtaatgcat gacgttattt atgagatggg
4861 tttttatgat tagagtcccg caattataca tttaatacgc gatagaaaac aaaatatagc
4921 gcgcaaacta ggataaatta tcgcgcgcgg tgtcatctat gttactagat cgggaaggcg
4981 cgccgcgggcc gcaacactga tagtttaaac tgaaggcggg aaacgacaat tgcggatctg
5041 gcggagaatt aagggagtca cgttatgacc cccgccgatg acgcgggaca agccgtttta
5101 cgtttggaac tgacagaacc gcaacgttga aggagccact cagccgcggg tttctggagt
5161 ttaatgagct aagcacatac gtcagaaacc attattgcgc gttcaaaagt cgcctaaggt
5221 cactatcagc tagcaaatat ttcttgtcaa aaatgctcca ctgacgttcc ataaattccc
5281 ctccgtatcc aattagagtc tcatattgc tctcaatcca aataatcctgc accggatctg
5341 gatcgtttcg catgattgaa caagatggat tgcacgcagg ttctccggcc gcttgggtgg
5401 agaggctatt cggctatgac tgggcacaac agacaatcgg ctgctctgat gccgccgtgt
5461 tccggctgtc agcgcagggg cgcccggttc tttttgtcaa gaccgacctg tccggtgccc
5521 tgaatgaact gcaggacgag gcagcgcggc tatcgtggct ggccacgacg ggcgttcctt
5581 gcgcagctgt gctcgacgtt gtcactgaag cgggaaggga ctggctgcta ttgggcgaag
5641 tgccggggca ggatctcctg tcatctcacc ttgctcctgc cgagaaagta tccatcatgg
5701 ctgatgcaat gcggcggctg catacgcttg atccggctac ctgcccattc gaccaccaag
5761 cgaaacatcg catcgagcga cacgtactg gatggaagcc ggtcttgtc gatcaggatg
5821 atctggacga agagcatcag gggctcgcgc cagccgaact gttcgccagg ctcaaggcgc
5881 gcatgcccga cggcgatgat ctcgtcgtga cccatggcga tgcctgcttg ccgaatatca
5941 tggtggaaaa tggccgcttt tctggattca tcgactgtgg ccggctggt gtggcggacc
6001 gctatcagga catagcgttg gctacccgtg atattgctga agagcttggc ggcgaatggg
6061 ctgaccgctt cctcgtgctt tacggtatcg ccgctcccga ttcgcagcgc atcgccttct
6121 atcgccttct tgacgagttc ttctgagcgg gactctgggg ttcgaaatga ccgaccaagc
6181 gacgcccaac ctgccatcac gagatttcga ttccaccgcc gccttctatg aaaggttggg
6241 cttcggaatc gtttttccggg acgccggctg gatgatcctc cagcgcgggg atctcatgct
6301 ggagttcttc gcccacggga tctgcgccgg gaaggtgccg atatcattac
6361 gacagcaacg gccgacaagc acaacgccac gatcctgagc gacaatatga tcgggcccgg
6421 cgtccacatc aacggcgtcg gcggcgactg cccaggcaag accgagatgc accgcgatat
```

Figure 4C

```
 6481 cttgctgcgt tcggatattt tcgtggagtt cccgccacag acccggatga tccccgatcg
 6541 ttcaaacatt tggcaataaa gtttcttaag attgaatcct gttgccggtc ttgcgatgat
 6601 tatcatataa tttctgttga attacgttaa gcatgtaata attaacatgt aatgcatgac
 6661 gttatttatg agatgggttt ttatgattag agtcccgcaa ttatacattt aatacgcgat
 6721 agaaaacaaa atatagcgcg caaactagga taaattatcg cgcgcggtgt catctatgtt
 6781 actagatcgg gcctcctgtc aatgctggcg gcggctctgg tggtggttct ggtggatcca
 6841 ctagttctag agcggccgtg ggccatcgcc ctgatagacg gttttcgcc ctttgacgtt
 6901 ggagtccacg ttctttaata gtggactctt gttccaaact ggaacaacac tcaaccctat
 6961 ctcgggctat tcttttgatt tataagggat tttgccgatt tcggaaccac catcaaacag
 7021 gatttcgcc tgctggggca aaccagcgtg gaccgcttgc tgcaactctc tcagggccag
 7081 gcggtgaagg gcaatcagct gttgcccgtc tcactggtga aagaaaaac caccccagta
 7141 cattaaaaac gtccgcaatg tgttattaag ttgtctaagc gtcaatttgt ttacaccaca
 7201 atatatcctg ccaccagcca gccaacagct ccccgaccgg cagctcggca caaatcacc
 7261 actcgataca ggcagcccat cagtccggga cggcgtcagc gggagagccg ttgtaaggcg
 7321 gcagactttg ctcatgttac cgatgctatt cggaagaacg gcaactaagc tgccgggttt
 7381 gaaacacgga tgatctcgcg gagggtagca tgttgattgt aacgatgaca gagcgttgct
 7441 gcctgtgatc aaatatcatc tccctcgcag agatccgaat tatcagcctt cttattcatt
 7501 tctcgcttaa ccgtgacagt tgtctatcgg cagttcgtag agcgcgccgt gcgtcccgag
 7561 cgatactgag cgaagcaagt gcgtcgagca gtgcccgctt gttcctgaaa tgccagtaaa
 7621 gcgctggctg ctgaaccccc agccggaact gaccccacaa ggccctagcg tttgcaatgc
 7681 accaggtcat cattgaccca ggcgtgttcc accaggccgc tgcctcgcaa ctcttcgcag
 7741 gcttcgccga cctgctcgcg ccacttcttc acgcgggtgg aatccgatcc gcacatgagg
 7801 cggaaggttt ccagcttgag cgggtacggc tcccggtgcg agctgaaata gtcgaacatc
 7861 cgtcgggccg tcggcgacag cttgcggtac ttctcccata tgaatttcgt gtagtggtcg
 7921 ccagcaaaca gcacgacgat ttcctcgtcg atcaggaccg ggcaacggga cgttttcttg
 7981 ccacggtcca ggacgcggaa gcggtgcagc agcgacaccg attccaggtg cccaacggtg
 8041 tcggacgtga agcccatcgc cgtcgcctgt aggcgcgaca ggcattcctc ggccttcgtg
 8101 taataccggc cattgatcga ccagcccagg tcctggcaaa gctcgtagaa cgtgaaggtg
 8161 atcggctcgc cgataggggt gcgcttcgcg tactccaaca cctgctgcca caccagttcg
 8221 tcatcgtcgg cccgcagctc gacgccggtg taggtgatct tcacgtcctt gttgacgtgg
 8281 aaaatgacct tgttttgcag cgcctcgcgc gggattttct tgttgcgcgt ggtgaacagg
 8341 gcagagcggg ccgtgtcgtt tggcatcgct cgcatcgtgt ccggccacgg cgcaatatcg
 8401 aacaaggaaa gctgcatttc cttgatctgc tgcttcgtgt gtttcagcaa cgcggcctgc
 8461 ttggcctcgc tgacctgttt tgccaggtcc tcgccggcgg tttttcgctt cttggtcgtc
 8521 atagttcctc gcgtgtcgat ggtcatcgac ttcgccaaac ctgccgcctc ctgttcgaga
 8581 cgacgcgaac gctccacggc ggccgatggc gcgggcaggg caggggagc cagttgcacg
 8641 ctgtcgcgct cgatcttggc cgtagcttgc tggaccatcg agccgacgga ctggaaggtt
 8701 tcgcggggcg cacgcatgac ggtgcggctt gcgatggttt cggcatcctc ggcggaaaac
 8761 cccgcgtcga tcagttcttg cctgtatgcc ttccggtcaa acgtccgatt cattcaccct
 8821 ccttgcggga ttgccccgac tcacgccggg gcaatgtgcc cttattcctg atttgacccg
 8881 cctggtgcct tggtgtccag ataatccacc ttatcggcaa tgaagtcggt cccgtagacc
 8941 gtctggccgt ccttctcgta cttggtattc cgaatcttgc cctgcacgaa taccagcgac
 9001 cccttgccca aatacttgcc gtgggcctcg gcctgagagc caaaacactt gatgcggaag
 9061 aagtcggtgc gctcctgctt gtcgccggca tcgttgcgcc acatctaggt actaaaacaa
 9121 ttcatccagt aaaatataat attttatttt ctcccaatca ggcttgatcc ccagtaagtc
 9181 aaaaaatagc tcgacatact gttcttcccc gatatcctcc ctgatcgacc ggacgcagaa
 9241 ggcaatgtca taccacttgt ccgccctgcc gcttctccca agatcaataa agccacttac
 9301 tttgccatct ttcacaaaga tgttgctgtc tcccaggtcg ccgtgggaaa agacaagttc
 9361 ctcttcgggc ttttccgtct ttaaaaaatc atacagctcg cgcggatctt taaatggagt
 9421 gtcttcttcc cagttttcgc aatccacatc ggccagatcg ttattcagta agtaatccaa
 9481 ttcggctaag cggctgtcta agctattcgt ataggacaa tccgatatgt cgatggagtg
 9541 aaagagcctg atgcactccg catacagctc gataatcttt tcagggcttt gttcatcttc
 9601 atactcttcc gagcaaagga cgccatcggc ctcactcatg agcagattgc tccagccatc
 9661 atgccgttca aagtgcagga cctttggaac aggcagcttt ccttccagcc atagcatcat
 9721 gtccttttcc cgttccacat cataggtggt ccctttatac cggctgtccg tcattttaa
 9781 atataggttt tcattttctc ccaccagctt atataccta gcaggagaca ttccttccgt
 9841 atcttttacg cagcggtatt tttcgatcag ttttttcaat tccggtgata ttctcatttt
 9901 agccatttat tatttccttc ctctttttcta cagtatttaa agataccca agaagctaat
 9961 tataacaaga cgaactccaa ttcactgttc cttgcattct aaaaccttaa ataccagaaa
10021 acagctttt caaagttgtt ttcaaagttg gcgtataaca tagtatcgac ggagccgatt
10081 ttgaaaccac aattatggga gagaccataa tgtggtccaa tttgcagcag ccgtccgaga
10141 caggaggaca tcgtccagct gaaaccgggg cagaatccgg ccatttctga agagaaaaat
10201 ggtaaactga tagaataaaa tcataagaaa ggagccgcac atgaaaaag cagtcattaa
10261 cggggaacaa atcagaagta tcagcgacct ccaccagaca ttgaaaaagg agcttgccct
10321 tccggaatac tacggtgaaa acctggacgc tttatgggat tgtctgaccg gatgggtgga
10381 gtacccgctc gttttggaat ggaggcagtt tgaacaaagc aagcagctga ctgaaaatgg
10441 cgccgagagt gtgcttcagg ttttccgtga agcgaaagcc gaaggctgcg acatcaccat
10501 catactttct taatacgatc aatgggagat gaacaatatg gaaacacaaa ccacaattat
10561 gtctctcagc ccacaattat ggactgccag cgctgccatt tttggggtga ggccgttcgc
10621 ggccgagggg cgcagccct ggggggtcg ttagcgggcg tggaggtc
10681 gagaaggggg ggcacccccc ttcggcgtgc gcggtcacgc gcacagggcg cagcctggt
10741 taaaaacaag gtttataaat attggtttaa aagcaggtta aagacaggt tagcggtggc
10801 cgaaaaacgg gcggaaaccc ttgcaaatgc tggattttct gcctgtggac agcccctcaa
10861 atgtcaatag gtgcgcccct catctgtcag cactctgccc ctcaagtgtc aaggatcgcg
```

Figure 4D

```
10921 ccccctcatct gtcagtagtc gcgcccctca agtgtcaata ccgcagggca cttatcccca
10981 ggcttgtcca catcatctgt gggaaactcg cgtaaaatca ggcgttttcg ccgatttgcg
11041 aggctggcca gctccacgtc gccggccgaa atcgagcctg ccctcatct gtcaacgccg
11101 cgccgggtga gtcggcccct caagtgtcaa cgtccgcccc tcatctgtca gtgagggcca
11161 agttttccgc gaggtatcca caacgccggc ggatctgggg aaccctgtgg ttggcatgca
11221 catacaaatg gacgaacgga taaacctttt cacgcccttt taaatatccg attattctaa
11281 taaacgctct tttctcttag
//
```

Figure 5A

```
LOCUS       pARB599B    12631 bp    DNA    circular       20-SEP-2004
SOURCE
  ORGANISM
COMMENT     C inserted at position 10437 to match sequence analysis (multiple reads)
            ->TTTCCACCCTGG T inserted at position 10268 to match sequence analysis (multiple reads)
            ->GAAGGTTTGAG At position 9892, C substituted (inserted) for T, to match sequence
analysis (multiple reads)
            ->TTTATATCGTAT Extra A deleted from position 9575 to match sequence analysis (multiple
reads)
            ->TATTTAGTTAAAA COMMENT     This file is created by Vector NTI
            http://www.informaxinc.com/
COMMENT     ORIGDB|GenBank
COMMENT     VNTDATE|303987976|
COMMENT     VNTDBDATE|350144422|
COMMENT     VNTNAME|pARB599B|
COMMENT     VNTAUTHORNAME|D006|
FEATURES             Location/Qualifiers
     misc_marker     933..1202
                     /vntifkey="22"
                     /label=barstar
     misc_marker     1435..2226
                     /ORF
                     /vntifkey="22"
                     /label=npt\III\\\(kanR)
     misc_marker     2528..3673
                     /ORF
                     /vntifkey="22"
                     /label=trfA
     misc_feature    3897..4910
                     /vntifkey="21"
                     /label=ColE1\region
     rep_origin      4617..4617
                     /vntifkey="33"
                     /label=ColE1\origin
     misc_signal     complement(5150..5173)
                     /feature
                     /vntifkey="87"
                     /label=LEFT\BORDER
     terminator      complement(5234..5483)
                     /vntifkey="43"
                     /label=NOSTER
     CDS             complement(5497..6288)
                     /vntifkey="4"
                     /label=NPT2
     promoter        complement(6289..7602)
                     /vntifkey="29"
                     /label=UBQ10\promoter
     intron          complement(6289..6592)
                     /vntifkey="15"
                     /label=INTRON
     promoter        complement(8339..8727)
                     /vntifkey="29"
                     /label=PrMC2.400
     terminator      complement(7643..7903)
                     /vntifkey="43"
                     /label=RNS2TER
     CDS             complement(8005..8337)
                     /vntifkey="4"
                     /label=barnaseH102E
     misc_signal     complement(57..80)
                     /feature
```

Figure 5B

```
                        /vntifkey="87"
                        /label=RIGHT\BORDER
           CDS          11037..11225
                        /gene="Euc 200bp frag"
                        /product="Euc4CL RNAi 200bp fragment"
                        /vntifkey="4"
                        /label=Euc\200bp\frag
           CDS          complement(11948..12136)
                        /gene="Euc 200bp frag"
                        /product="Euc4CL RNAi 200bp fragment"
                        /vntifkey="4"
                        /label=Euc\200bp\frag
           promoter     8751..10998
                        /vntifkey="29"
                        /label=MTU4CL\promoter
           intron       11254..11876
                        /vntifkey="15"
                        /label=Y\intron
           3'UTR        12144..12360
                        /vntifkey="50"
                        /label=SUB\3'UTR
           terminator   12367..12631
                        /vntifkey="43"
                        /label=Nos
                        /note="5'"
BASE COUNT     3692 a      2640 c      2786 g      3513 t
ORIGIN
        1 ggccgcattt gggctcctgc aggtaccttg attaaaagtt taaactatca gtgtttgaca
       61 ggatatattg gcgggtaaac ctaagagaaa agagcgttta ttagaataat cggatattta
      121 aaagggcgtg aaaaggttta tccgttcgtc catttgtatg tgcatgccaa ccacagggtt
      181 ccccagatcc gccggcgttg tggataccct gcggaaaact tggccctcac tgacagatga
      241 ggggcggacg ttgacacttg aggggccgac tcacccggcg cggcgttgac agatgagggg
      301 caggctcgat ttcggccggc gacgtggagc tggccagcct cgcaaatcgg cgaaaacgcc
      361 tgattttacg cgagtttccc acagatgatg tggacaagcc tggggataag tgccctgcgg
      421 tattgacact tgaggggcgc gactactgac agatgagggg cgcgatcctt gacacttgag
      481 gggcagagtg ctgacagatg aggggcgcac ctattgacat ttgaggggct gtccacaggc
      541 agaaaatcca gcatttgcaa gggtttccgc ccgttttcg gccaccgcta acctgtcttt
      601 taacctgctt ttaaaccaat atttataaac cttgtttta accagggctg cgccctgtgc
      661 gcgtgaccgc gcacgccgaa gggggtgcc ccccttctc gaaccctccc ggcccgctaa
      721 cgcgggcctc ccatccccc aggggctgcg ccctcggcc gcgaacggcc tcacccaaa
      781 aatggcagcg ctggcagtcc ataattgtgg tccaatttgc agccgtccga gacaggagga
      841 catcgtccag ctgaaaccgg ggcagaatcc ggccatttct gaagagaaaa atggtaaact
      901 gatagaataa aatcataaga aaggagccgc acatgaaaaa agcagtcatt aacggggaac
      961 aaatcagaag tatcagcgac ctccaccaga cattgaaaaa ggagcttgcc cttccggaat
     1021 actacggtga aaacctggac gctttatggg attgtctgac cggatgggtg gagtacccgc
     1081 tcgttttgga atggaggcag tttgaacaaa gcaagcagct gactgaaaat ggcgccgaga
     1141 gtgtgcttca ggttttccgt gaagcgaaag cggaaggctg cgacatcacc atcatactt
     1201 cttaatacga tcaatgggag atgaacaata tggaaacaca aaccacaatt gtggtttcaa
     1261 aatcggctcc gtcgatacta tgttatacgc caactttgaa aacaactttg aaaaagctgt
     1321 tttctggtat ttaaggtttt agaatgcaag gacagtgaa ttggagttcg tcttgttata
     1381 attagcttct tggggtatct ttaaatactg tagaaaagag gaaggaaata ataaatggct
     1441 aaaatgagaa tatcaccgga attgaaaaaa ctgatcgaaa aataccgctg cgtaaaagat
     1501 acggaaggaa tgtctcctgc taaggtatat aagctggtgg gagaaaatga aaacctatat
     1561 ttaaaaatga cggacagccg gtataaaggg accacctatg atgtggaacg ggaaaaggac
     1621 atgatgctat ggctggaagg aaagctgcct gttccaaagg tcctgcactt tgaacggcat
     1681 gatggctgga gcaatctgct catgagtgag gccgatggcg tcctttgctc ggaagagtat
     1741 gaagatgaac aaagccctga aaagattatc gagctgtatg cggagtgcat caggctcttt
     1801 cactccatcg acatatcgga ttgtccctat acgaatagct tagacagccg cttagccgaa
     1861 ttggattact tactgaataa cgatctggcc gatgtggatt gcgaaaactg ggaagaagac
     1921 actccattta aagatccgcg cgagctgtat gatttttta agacggaaaa gcccgaagag
     1981 gaacttgtct tttcccacgg cgacctggga gacagcaaca tctttgtgaa agatggcaaa
     2041 gtaagtggct ttattgatct tgggagaagc ggcaggggcgg acaagtggta tgacattgcc
     2101 ttctgcgtcc ggtcgatcag ggaggatatc ggggaagaac agtatgtcga gctatttttt
     2161 gacttactgg ggatcaagcc tgattgggag aaaataaaat attatatttt actggatgaa
     2221 ttgttttagt acctagatgt ggcgcaacga tgccggcgac aagcaggagc gcaccgactt
     2281 cttccgcatc aagtgttttg gctctcaggc cgaggcccaa ggcaagtatt tgggcaaggg
     2341 gtcgctggta ttcgtgcagg gcaagattcg gaataccaag tacgagaagg acgccagac
     2401 ggtctacggg accgacttca ttgccgataa ggtggattat ctggacacca aggcaccagg
     2461 cgggtcaaat caggaataag ggcacattgc cccggcgtga gtcggggcaa tcccgcaagg
     2521 agggtgaatg aatcggacgt ttgaccggaa ggcatacagg caagaactga tcgacgcggg
     2581 gttttccgcc gaggatgccg aaaccatcgc aagccgcacc gtcatgcgtg cgccccgcga
     2641 aaccttccag tccgtcggct cgatggtcca gcaagctacg gccaagatcg agcgcgacag
     2701 cgtgcaactg gctccccctg ccctgcccgc gccatcggcc gccgtggagc gttcgcgtcg
     2761 tctcgaacag gaggcggcag gtttggcgaa gtcgatgacc atcgacacgc gaggaactat
```

Figure 5C

```
2821 gacgaccaag aagcgaaaaa ccgccggcga ggacctggca aaacaggtca gcgaggccaa
2881 gcaggccgcg ttgctgaaac acacgaagca gcagatcaag gaaatgcagc tttccttgtt
2941 cgatattgcg ccgtggccgg acacgatgcg agcgatgcca aacgacacgg cccgctctgc
3001 cctgttcacc acgcgcaaca agaaaatccc gcgcgaggcg ctgcaaaaca aggtcatttt
3061 ccacgtcaac aaggacgtga agatcaccta caccggcgtc gagctgcggg ccgacgatga
3121 cgaactggtg tggcagcagg tgttggagta cgcgaagcgc accctatcg gcgagccgat
3181 caccttcacg ttctacgagc tttgccagga cctgggctgg tcgatcaatg gccggtatta
3241 cacgaaggcc gaggaatgcc tgtcgcgcct acaggcgacg gcgatgggct tcacgtccga
3301 ccgcgttggg cacctggaat cggtgtcgct gctgcaccgc ttccgcgtcc tggaccgtgg
3361 caagaaaacg tcccgttgcc aggtcctgat cgacgaggaa atcgtcgtgc tgtttgctgg
3421 cgaccactac acgaaattca tatgggagaa gtaccgcaag ctgtcgccga cggcccgacg
3481 gatgttcgac tatttcagct cgcaccggga gccgtacccg ctcaagctgg aaaccttccg
3541 cctcatgtgc ggatcggatt ccacccgcgt gaagaagtgg cgcgagcagg tcggcgaagc
3601 ctgcgaagag ttgcgaggca gcggcctggt ggaacacgcc tgggtcaatg atgacctggt
3661 gcattgcaaa cgctagggcc ttgtggggtc agttccggct gggggttcag cagccagcgc
3721 tttactggca tttcaggaac aagcgggcac tgctcgacgc acttgcttcg ctcagtatcg
3781 ctcgggacgc acggcgcgct ctacgaactg ccgatagaca actgtcacgg ttaagcgaga
3841 aatgaataag aaggctgata attcggatct ctgcgaggga gatgatattt gatccggtgt
3901 gaaataccgc acagatgcgt aaggagaaaa taccgcatca ggcgctcttc cgcttcctcg
3961 ctcactgact cgctgcgctc ggtcgttcgg ctgcggcgag cggtatcagc tcactcaaag
4021 gcggtaatac ggttatccac agaatcaggg gataacgcag gaaagaacat gtgagcaaaa
4081 ggccagcaaa aggccaggaa ccgtaaaaag gccgcgttgc tggcgttttt ccataggctc
4141 cgccccctg acgagcatca caaaaatcga cgctcaagtc agaggtggcg aaacccgaca
4201 ggactataaa gataccaggc gtttccccct ggaagctccc tcgtgcgctc tcctgttccg
4261 accctgccgc ttaccggata cctgtccgcc tttctccctt cgggaagcgt ggcgctttct
4321 catagctcac gctgtaggta tctcagttcg gtgtaggtcg ttcgctccaa gctgggctgt
4381 gtgcacgaac ccccgttca gcccgaccgc tgcgccttat ccggtaacta tcgtcttgag
4441 tccaacccgg taagacacga cttatcgcca ctggcagcag ccactggtaa caggattagc
4501 agagcgaggt atgtaggcgg tgctacagag ttcttgaagt ggtggcctaa ctacggctac
4561 actagaagga cagtatttgg tatctgcgct ctgctgaagc cagttacctt cggaaaaaga
4621 gttggtagct cttgatccgg caaacaaacc accgctggta gcggtggttt ttttgtttgc
4681 aagcagcaga ttacgcgcag aaaaaaagga tcaagaag atcctttgat ctttttctacg
4741 gggtctgacg ctcagtggaa cgaaaactca cgttaaggga ttttggtcat gagattatca
4801 aaaaggatct tcacctagat cctttaaat taaaaatgaa gttttaaatc aatctaaagt
4861 atatatgagt aaacttggtc tgacagttac caatgcttca tcagtgaggc tgatcacagg
4921 cagcaacgct ctgtcatcgt tacaatcaac atgctaccct ccgcgagatc atccgtgttt
4981 caaacccggc agcttagttg ccgttcttcc gaatagcatc ggtaacatga gcaaagtctg
5041 ccgccttaca acggctctcc cgctgacgcc gtcccggact gatgggctgc ctgtatcgag
5101 tggtgatttt gtgccgagct gccggtcggg gagctgttgg ctggctggtg gcaggatata
5161 ttgtggtgta aacaaattga cgcttagaca acttaataac acaccgcggt ctagaactag
5221 tggatccccc ctacgtgcga tctagtaaca tagatgacac cgcgcgcgat aattatcct
5281 agtttgcgcg ctatattttg tttttctatcg cgtattaaat gtataattgc gggactctaa
5341 tcataaaaac ccatctcata aataacgtca tgcattacat gttaattatt acatgcttaa
5401 cgtaattcaa cagaaattat atgataatca tcgcaagacc ggcaacagga ttcaatctta
5461 agaaacttta ttgccaaatg tttgaacgat ccctcagaag aactcgtcaa gaaggcgata
5521 gaaggcgatg cgctgcgaat cgggagcggc gataccgtaa agcacgagga agcggtcagc
5581 ccattcgccg ccaagctctt cagcaatatc acgggtagcc aacgctatgt cctgatagcg
5641 gtccgccaca cccagccggc cacagtcgat gaatccagaa aagcggccat tttccaccat
5701 gatattcggc aagcaggcat cgccatgggt cacgacgaga tcctcgccgt cgggcatgcg
5761 cgccttgagc ctggcgaaca gttcggctgg cgcgagcccc tgatgctctt cgtccagatc
5821 atcctgatcg acaagaccgg cttccatccg agtacgtgct cgctcgatgc gatgtttcgc
5881 ttggtggtcg aatgggcagg tagccggatc aagcgtatgc agccgccgca ttgcatcagc
5941 catgatggat actttctcgg caggagcaag gtgagatgac aggagatcct gccccggcac
6001 ttcgcccaat agcagccagt cccttcccgc ttcagtgaca acgtcgagca cagctgcgca
6061 aggaacgccc gtcgtggcca gccacgatag ccgcgctgcc tcgtcctgga gttcattcag
6121 ggcaccggac aggtcggtct tgacaaaaag accgggcgc ccctgcgctg acagccggaa
6181 cacggcggca tcagagcgac cgattgtctg ttgtgcccag tcatagccga atagcctctc
6241 cacccaagcg gccggagaac ctgcgtgcaa tccatcttgt tcaatcatct gttaatcaga
6301 aaaactcaga ttaatcgaca aattcgatcg cacaaactag aaactaacac cagatctaga
6361 tagaaatcac aaatcgaaga gtaattattc gacaaaactc aaattatttg aacaaatcgg
6421 atgatattta tgaaacccta atcgagaatt aagatgatat ctaacgatca aacccagaaa
6481 atcgtcttcg atctaagatt aacagaatct aaaccaaaga acatatacga aattgggatc
6541 gaacgaaaac aaaatcgaag attttgagag aataaggaac acagaaattt accttgatca
6601 cggtagagag aattgagaga aagtttttaa gatttgaga aattgaaatc tgaattgtga
6661 agaagaaag ctctttgggt attgttttat agaagaagaa gaagaaaaga cgaggacgac
6721 taggtcacga gaaagctaag gcggtgaagc aatagctaat aataaaatga cacgtgtatt 6781 gagcgttgtt tacacgcaaa gttgttttttg gctaattgcc ttattttag gttgaggaaa
6841 agtatttgtg ctttgagttg ataaacacga ctcgtgtgtg ccggctgcaa ccactttgac
6901 gccgtttatt actgactcgt cgacaaccac aatttctaac ggtcgtcata agatccagcc
6961 gttgagattt aacgatcgtt acgatttata ttttttttagc attatcgttt tattttttaa
7021 atatacggtg gagctgaaaa ttggcaataa ttgaaccgtg ggtcccactg cattgaagcg
7081 tatttcgtat tttctagaat tcttcgtgct ttatttcttt tccttttgt ttttttttgc
7141 catttatcta atgcaagtgg gcttataaaa tcagtgaatt tcttggaaaa gtaacttctt
```

Figure 5D

```
7201 tatcgtataa catattgtga aattatccat ttcttttaat tttttagtgt tattggatat
7261 ttttgtatga ttattgattt gcataggata atgactttgt tatcaagttg gtgaacaagt
7321 ctcgttaaaa aaggcaagtg gtttggtgac tcgatttatt cttgttattt aattcatata
7381 tcaatggatc ttatttgggg cctggtccat atttaacact cgtgttcagt ccaatgacca
7441 ataatatttt ttcattaata acaatgtaac aagaatgata cacaaaacat tctttgaata
7501 agttcgctat gaagaaggga acttatccgg tcctagatca tcagttcata caaacctcca
7561 tagagttcaa catcttaaac aaggatatcc tgatccgttg acggcgcgcc aagcggggcc
7621 gcatttaaat gggccctatc taatcgaatt ttgtaaactg gtttgataag ccatcaatgc
7681 atcagtcaag aatgaatcat tgcaactaag ttgatataat tcaatttacc atagaactca
7741 aatgttgata tcttcttatg gattttctga tcttctacat tattagaaag aaacttgatt
7801 taccagtaat gatgatacat atccaataga acgaaataag ccaatcttta taggttttgg
7861 tagtaaagtt acaacatcag agacatgtat gtattgtctc tcagaagagc tcttgaccga
7921 tcagagtttg aagaaaaatt tattacacac tttatgtaaa gctgaaaaaa acggcctccc
7981 gcagggaagc cgttttttc gttatctgat ttttgtaaag gtctgatact cgtccgttgt
8041 tttgtaaatc agccagtcgc ttgagtaaag aatccggtct gaatttctga agcctgatgt
8101 atagttaata tccgcttcac gccatgttcg tccgcttttg cccgggagtt tgccttccct
8161 gtttgagaag atgtctccgc cgatgctttt ccccggagcg acgtctgcaa ggttcccttt
8221 tgatgccacc cagccgaggg cttgtgcttc tgattttgta atgtaattat caggtagctt
8281 atgatatgtc tgaagataat ccgcaacccc gtcaaacgtg ttgataacct gtgccatgtt
8341 cccgtttgat acctgaattt tggccattct caatactctt ctaaaaacag cagaactgac
8401 tattcaaaga aagtagaacc cacagaaagt aatcaaagta gtttgattaa atgcgttgtg
8461 tatcatcgca gcccctgcta cggatattta taggaaaggt ttgagagcaa tgtgtgcagc
8521 aagttgtgtg tgaatccacct gcttccatgg cggaggataa ataatttagt cacgcattta
8581 gttgaacgta actactaact cctctaccgc taatcattct tcttttgccc gggcaagttc
8641 aacaacaacc ccacaatcac gcttcctgta ttttgttttg ttttcaaaac aatagaattc
8701 acttttact gccaaaatta tgtttactc gagagcccaa atgcggccgc ggccgggtgg
8761 tgacatttat tcataaattc atctcaaaac aagaaggatt tacaaaaata aaagaaaaca
8821 aaatttcat ctttaacata attataattg tgttcaaaaa attcaaactt aaacccttaa
8881 tataaagaat ttctttcaac aatacacttt aatcacaact tcttcaatca caacctcctc
8941 caacaaaatt aaaatagatt aataaataaa taaacttaac tatttaaaaa aaatattat
9001 acaaaattta ttaaaacttc aaaataaaca aacttttat acaaaattca tcaaaacttt
9061 aaaataaagc taaacactga aaatgtgagt acatttaaaa ggacgctgat cacaaaaatt
9121 ttgaaaacat aaacaaactt gaaactctac cttttaagaa tgagtttgtc gtctcattaa
9181 ctcattagtt ttatagttcg aatccaatta acgtatcttt tattttatgg aataagggtg
9241 ttttaataag tgattttggg attttttag taatttattt gtgatatgtt atggagtttt
9301 taaaaatata tatatatata tatattttg ggtgagttt acttaaaatt tggaaaaggt
9361 tggtaagaac tataaattga gttgtgaatg agtgtttat ggatttttta agatgttaaa
9421 tttatatatg taattaaaat tttattttga ataacaaaaa ttataattgg ataaaaaatt
9481 gttttgttaa atttagagta aaaatttcaa aatctaaaat aattaaacac tattattttt
9541 aaaaaatttg ttggtaaatt ttatcttata tttagttaaa atttagaaaa aattaatttt
9601 aaattaataa actttttgaag tcaaaatattc caaatatttt ccaaaatatt aaatctattt
9661 tgcattcaaa atacaattta aataataaaa cttcatggaa tagattaacc aatttgtata
9721 aaaaccaaaa atctcaaata aaatttaaat tacaaaacat tatcaacatt atgatttcaa
9781 gaaagacaat aaccagtttc caataaaata aaaaacctca tggcccgtaa ttaagatctc
9841 attaattaat tcttattttt taattttttt acatagaaaa tatctttata tcgtatccaa
9901 gaaatataga atgttctcgt ccagggacta ttaatctcca aacaagtttc aaaatcatta
9961 cattaaagct catcatgtca tttgtggatt ggaaattata ttgtataaga gaaatataga
10021 atgttctcgt ctagggacta ttaatttcca aacaaatttc aaaatcatta cattaaagct
10081 catcatgtca tttgtggatt ggaaattaga caaaaaaat cccaaatctt tctctcaatc
10141 tcccaaaata tagttcgaac tccatatttt tggaaattga gaatttttt acccaataat
10201 atatttttt atacatttta gagattttcc agacatattt gctctgggat ttattggaat
10261 gaaggtttga gttataaact ttcagtaatc caagtatctt cggttttga agatactaaa
10321 tccattatat aataaaaaca catttttaaac accaatttaa tgggatttca gatttgtatc
10381 ccatgctatt ggctaaggca tttttcttat tgtaatctaa ccaattctaa tttccaccct
10441 ggtgtgaact gactgacaaa tgcggtccga aaacagcgaa tgaaatgtct gggtgatcgg
10501 tcaaacaagc ggtgggcgag agagcgcggg tgttggccta gccgggatgg gggtaggtag
10561 acggcgtatt accggcgagt tgtccgaatg gagttttcgg ggtaggtagt aacgtagacg
10621 tcaatggaaa aagtcataat ctccgtcaaa aatccaaccg ctccttcaca tcgcagagtt
10681 ggtggccacg ggaccctcca cccactcact cgatcgcctg ccgtggttgc ccattattca
10741 accatacgcc acttgactct tcaccaacaa ttccaggccg gctttctata caatgtactg
10801 cacaggaaaa tccaatataa aaagcggcc tctgcttcct tctcagtagc cccagctca
10861 ttcaattctt cccactgcag gctacatttg tcagacacgt tttccgccat ttttcgcctg
10921 tttctgcgga gaatttgatc aggttcggat tgggattgaa tcaattgaaa ggttttatt
10981 ttcagtattt cgatcgccgg atccccgggg ctgcaggaat tgggctgcag atcgatattt
11041 gattcacat gctattgtaa tgtatttatt gtttcaattc cgaattagac aaagtgctta
11101 aagctctctt ttcggatttt ttttttcatt aatgtataat aattgcggac attacaatat
11161 actgtacaac gtgatttgag cttgatgaat tacaagattg gaagaacttc gaagacaaaa
11221 aaaaaatcga tctgcaggaa ttcgtccagc agtaattcgg taccctgat cagcactgct
11281 gccaagaatg taagttttta ttctttttaa atgttcaaac agttttataa agtactataa
11341 gcttttttta gccaaaagaa atatcttaag tttagtaac caataaagaa ttattgcggc
11401 ctcctatttt aattatagta catatgtcat agtagatgtt ttttttatta ttattatttt
11461 ttattttttt atagtttttt acaaattcga cttggagacc ttatgatttg gaagatactc
11521 catttaatt tatgagttgt gtttgaaaac atattttaag actaaacacg tagagaacat
11581 tcttaacaaa tttgtaaata aataaattta actctattct ctaggattta aatattatag
```

Figure 5E

```
11641 gtatatatat aattttctaa taagtttata tcgagtcact catacgagtt gtgtagaaag
11701 ttaatcacgg gtaccaattt taaattaaaa ataagaataa ttatatgatc ttaaatttat
11761 acaactctga taaaagattg ggctttgaca tctttgaaga aaactagatt tagtaatatt
11821 ctgattaaat tgggttcaca ctttgtagtg ggcacacttt ccgggttcga aatcgaaatc
11881 tggaagctta tcgatctcga ggggcccact agtatcgatc tcgagggggcc cactagtatc
11941 gatcgatttt tttttttgtct tcgaagttct tccaatcttg taattcatca agctcaaatc
12001 acgttgtaca gtatattgta atgtccgcaa ttattataca ttaatgaaaa aaaaaatccg
12061 aaaagagagc tttaagcact ttgtctaatt cggaattgaa acaataaata cattacaata
12121 gcatgtgaaa tcaaatatcg atccgatggg tgttatttgt ggataataaa ttcgggtgat
12181 gttcagtgtt tgtcgtattt ctcacgaata aattgtgttt atgtatgtgt tagtgttgtt
12241 tgtctgtttc agaccctctt atgttatatt tttcttttcg tcggtcagtt gaagccaata
12301 ctggtgtcct ggccggcact gcaataccat ttcgtttaat ataaagactc tgttatccgt
12361 gagctcgaat ttccccgatc gttcaaacat ttggcaataa agtttcttaa gattgaatcc
12421 tgttgccggt cttgcgatga ttatcatata atttctgttg aattacgtta agcatgtaat
12481 aattaacatg taatgcatga cgttatttat gagatgggtt tttatgatta gagtcccgca
12541 attatacatt taatacgcga tagaaaacaa aatatagcgc gcaaactagg ataaattatc
12601 gcgcgcggtg tcatctatgt tactagatcg c
//
```

Figure 6A

```
LOCUS       pARB639B    16396 bp    DNA    circular         20-SEP-2004
SOURCE
  ORGANISM
COMMENT     T inserted at position 9913 to match sequence analysis (multiple reads)
            ->TTTCTTGTTCTTC Extra A deleted from position 13340 to match sequence analysis (multiple
reads)
            ->TATTTAGTTAAAA At position 13657, C substituted (inserted) for T, to match sequence
analysis (multiple reads)
            ->TTTATATCGTAT T inserted at position 14033 to match sequence analysis (multiple reads)
            ->GAAGGTTTGAG C inserted at position 14202 to match sequence analysis (multiple reads)
            ->TTTCCACCCTGG COMMENT     This file is created by Vector NTI
            http://www.informaxinc.com/
COMMENT     ORIGDB|GenBank
COMMENT     VNTDATE|307364054|
COMMENT     VNTDBDATE|350144386|
COMMENT     VNTNAME|pARB639B|
COMMENT     VNTAUTHORNAME|D006|
FEATURES            Location/Qualifiers
     primer_bind    3439..3460
                    /vntifkey="28"
                    /label=BKBT1>
     primer_bind    complement(5094..5116)
                    /vntifkey="28"
                    /label=BKBT2<
     primer_bind    5032..5052
                    /vntifkey="28"
                    /label=LFBORD1>
     primer_bind    complement(841..859)
                    /vntifkey="28"
                    /label=BARPROR1<
     primer_bind    complement(197..217)
                    /vntifkey="28"
                    /label=RTBORD1<
     primer_bind    7273..7295
                    /vntifkey="28"
                    /label=UQNPR1>
     primer_bind    6332..6354
                    /vntifkey="28"
                    /label=UQNPR3>
     primer_bind    5959..5976
                    /vntifkey="28"
                    /label=UQNPR4>
     primer_bind    5553..5572
                    /vntifkey="28"
                    /label=UQNPR5>
     primer_bind    1171..1188
                    /vntifkey="28"
                    /label=NPT3F1>
     primer_bind    6735..6753
                    /vntifkey="28"
                    /label=UQNPR7>
     primer_bind    1727..1750
                    /vntifkey="28"
                    /label=NPT3F2>
     primer_bind    2668..2687
```

Figure 6B

```
                /vntifkey="28"
                /label=TRFAF1>
primer_bind     2965..2983
                /vntifkey="28"
                /label=TRFAF2>
primer_bind     582..597
                /vntifkey="28"
                /label=ORIVF1>
primer_bind     4749..4770
                /vntifkey="28"
                /label=LFBORD2>
misc_marker     933..1202
                /vntifkey="22"
                /label=barstar
misc_marker     1435..2226
                /ORF
                /vntifkey="22"
                /label=npt\III\\\(kanR)
misc_marker     2528..3673
                /ORF
                /vntifkey="22"
                /label=trfA
misc_feature    3897..4910
                /vntifkey="21"
                /label=ColE1\region
rep_origin      4617..4617
                /vntifkey="33"
                /label=ColE1\origin
misc_signal     complement(5150..5173)
                /feature
                /vntifkey="87"
                /label=LEFT\BORDER
terminator      complement(5234..5483)
                /vntifkey="43"
                /label=NOSTER
CDS             complement(5497..6288)
                /vntifkey="4"
                /label=NPT2
promoter        complement(6289..7602)
                /vntifkey="29"
                /label=UBQ10\promoter
intron          complement(6289..6592)
                /vntifkey="15"
                /label=INTRON
promoter        complement(8319..9718)
                /vntifkey="29"
                /label=PrAG
enhancer        9719..12490
                /vntifkey="9"
                /label=AtAGenh
CDS             complement(7986..8318)
                /vntifkey="4"
                /label=BarnaseE73G
terminator      complement(7608..7878)
                /vntifkey="43"
                /label=NOSTER
misc_signal     complement(57..80)
                /feature
                /vntifkey="87"
                /label=RIGHT\BORDER
primer_bind     9746..9773
                /vntifkey="28"
                /label=AtAGIN5>
primer_bind     10047..10066
                /vntifkey="28"
                /label=AGenhseq-1>
primer_bind     10579..10600
                /vntifkey="28"
                /label=AGenhseq-2>
primer_bind     11154..11171
                /vntifkey="28"
                /label=AGenhseq-3>
primer_bind     11770..11791
                /vntifkey="28"
```

Figure 6C

```
                       /label=AGenhseq-4>
      primer_bind      complement(8095..8112)
                       /vntifkey="28"
                       /label=Barnseq2<
      primer_bind      complement(8913..8930)
                       /vntifkey="28"
                       /label=PRPseq3<
      primer_bind      8498..8517
                       /vntifkey="28"
                       /label=PrAGKpn<
      primer_bind      9388..9405
                       /vntifkey="28"
                       /label=PRPseq1>
      primer_bind      9342..9359
                       /vntifkey="28"
                       /label=PRPseq2<
      CDS              14802..14990
                       /gene="Euc 200bp frag"
                       /product="Euc4CL RNAi 200bp fragment"
                       /vntifkey="4"
                       /label=Euc\200bp\frag
      CDS              complement(15713..15901)

/gene="Euc 200bp frag"
                       /product="Euc4CL RNAi 200bp fragment"
                       /vntifkey="4"
                       /label=Euc\200bp\frag
      promoter         12516..14763
                       /vntifkey="29"
                       /label=MTU4CL\promoter
      intron           15019..15641
                       /vntifkey="15"
                       /label=Y\intron
      3'UTR            15909..16125
                       /vntifkey="50"
                       /label=SUB\3'UTR
      terminator       16132..16396
                       /vntifkey="43"
                       /label=Nos
                       /note="5'"
BASE COUNT     4852 a        3244 c       3426 g      4874 t
ORIGIN
        1 ggccgcattt gggctcctgc aggtacctta attaaaagtt taaactatca gtgtttgaca
       61 ggatatattg gcgggtaaac ctaagagaaa agagcgttta ttagaataat cggatattta
      121 aaagggcgtg aaaaggttta tccgttcgtc catttgtatg tgcatgccaa ccacagggtt
      181 ccccagatcc gccggcgttg tggatacctc gcggaaaact tggccctcac tgacagatga
      241 ggggcggacg ttgacacttg aggggccgac tcacccggcg cggcgttgac agatgagggg
      301 caggctcgat ttcggccggc gacgtggagc tggccagcct cgcaaatcgg cgaaaacgcc
      361 tgattttacg cgagtttccc acagatgatg tggacaagcc tggggataag tgccctgcgg
      421 tattgacact tgaggggcgc gactactgac agatgagggg cgcgatcctt gacacttgag
      481 gggcagagtg ctgacagatg aggggcgcac ctattgacat ttgagggggt gtccacaggc
      541 agaaaatcca gcatttgcaa gggtttccgc ccgtttttcg gccaccgcta acctgtcttt
      601 taacctgctt ttaaaccaat atttataaac cttgttttta accagggctg cgccctgtgc
      661 gcgtgaccgc gcacgccgaa gggggtgcc ccccttctc gaaccctccc ggcccgctaa
      721 cgcgggcctc ccatccccc agggggctgcg ccccctcgcc gcaacggcc tcaccccaaa
      781 aatggcagcg ctggcagtcc ataattgtgg tccaatttgc agccgtccga gacaggagga
      841 catcgtccag ctgaaaccgg ggcagaatcc ggccatttct gaagagaaaa atggtaaact
      901 gatagaataa aatcataaga aaggagccgc acatgaaaaa agcagtcatt aacggggaac
      961 aaatcagaag tatcagcgac ctccaccaga cattgaaaaa ggagcttgcc cttccggaat
     1021 actacggtga aaacctggac gctttatggg attgtctgac cggatgggtg gagtacccgc
     1081 tcgttttgga atggaggcag tttgaacaaa gcaagcagct gactgaaaat ggcgccgaga
     1141 gtgtgcttca ggttttccgt gaagcgaaag cggaaggctg cgacatcacc atcatacttt
     1201 cttaatacga tcaatgggag atgaacaata tggaaacaca aaccacaatt gtggtttcaa
     1261 aatcggctcc gtcgatacta tgttatacgc caactttgaa aacaactttg aaaaagctgt
     1321 tttctggtat ttaaggtttt agaatgcaag gaacagtgaa ttggagttcg tcttgttata
     1381 attagcttct tggggtatct ttaaatactg tagaaaagag gaaggaaata ataaatggct
     1441 aaaatgagaa tatcaccgga attgaaaaaa ctgatcgaaa ataccgctg cgtaaaagat
     1501 acggaaggaa tgtctcctgc taaggtatat aagctggtgg gagaaaatga aaacctatat
     1561 ttaaaaatga cggacagccg gtataaaggg accacctatg atgtggaacg ggaaaaggac
     1621 atgatgctat ggctggaagg aaagctgcct gttccaaagg tcctgcactt tgaacggcat
     1681 gatggctgga gcaatctgct catgagtgag gccgatggcg tcctttgctc ggaagagtat
     1741 gaagatgaac aaagcccctga aaagattatc gagctgtatg cggagtgcat caggctcttt
     1801 cactccatcg acatatcgga ttgtccctat acgaatagct tagacagccg cttagccgaa
     1861 ttggattact tactgaataa cgatctggcc gatgtggatt gcgaaaactg ggaagaagac
```

Figure 6D

```
1921 actccattta aagatccgcg cgagctgtat gatttttaa agacggaaaa gcccgaagag
1981 gaacttgtct tttcccacgg cgacctggga gacagcaaca tctttgtgaa agatggcaaa
2041 gtaagtggct ttattgatct tgggagaagc ggcagggcgg acaagtggta tgacattgcc
2101 ttctgcgtcc ggtcgatcag ggaggatatc ggggaagaac agtatgtcga gctattttt
2161 gacttactgg ggatcaagcc tgattgggag aaaataaaat attatatttt actggatgaa
2221 ttgttttagt acctagatgt ggcgcaacga tgccggcgac aagcaggagc gcaccgactt
2281 cttccgcatc aagtgttttg gctctcaggc cgaggcccac ggcaagtatt tgggcaaggg
2341 gtcgctggta ttcgtgcagg gcaagattcg gaataccaag tacgagaagg acggccagac
2401 ggtctacggg accgacttca ttgccgataa ggtggattat ctggacacca aggaccagg
2461 cgggtcaaat caggaataag ggcacattgc cccggcgtga gtcggggcaa tcccgcaagg
2521 agggtgaatg aatcggacgt ttgaccggaa ggcatacagg caagaactga tcgacgcggg
2581 gttttccgcc gaggatgccg aaaccatcgc aagccgcacc gtcatgcgtg cgccccgcga
2641 aaccttccag tccgtcggct cgatggtcca gcaagctacg gccaagatcg agcgcgacag
2701 cgtgcaactg gctcccctg ccctgccgc gccatcggcc gccgtggagc gttcgcgtcg
2761 tctcgaacag gaggcggcag gtttggcgaa gtcgatgacc atcgacacgc gaggaactat
2821 gacgaccaag aagcgaaaaa ccgccggcga ggacctggca aaacaggtca gcgaggccaa
2881 gcaggccgcg ttgctgaaac acacgaagca gcagatcaag gaaatgcagc tttccttgtt
2941 cgatattgcg ccgtggccgg acacgatgcg agcgatgcca aacgacacgg cccgctctgc
3001 cctgttcacc acgcgcaaca agaaaatccc gcgcgaggcg ctgcaaaaca aggtcatttt
3061 ccacgtcaac aaggacgtga agatcaccta caccggcgtc gagctgcggg ccgacgatga
3121 cgaactggtg tggcagcagg tgttggagta cgcgaagcgc accctatcg gcgagccgat
3181 caccttcacg ttctacgagc tttgccagga cctgggctgg tcgatcaatg gccggtatta
3241 cacgaaggcc gaggaatgcc tgtcgcgcct acaggcgacg gcgatgggct tcacgtccga
3301 ccgcgttggg cacctggaat cggtgtcgct gctgcaccgc ttccgcgtcc tggaccgtgg
3361 caagaaaacg tcccgttgcc aggtcctgat cgacgaggaa atcgtcgtgc tgtttgctgg
3421 cgaccactac acgaaattca tatgggcgaa gtaccgcaag ctgtcgccga cggcccgacg
3481 gatgttcgac tatttcagct cgcaccggga gccgtacccg ctcaagctgg aaaccttccg
3541 cctcatgtgc ggatcggatt ccacccgcgt gaagaagtgg cgcgagcagg tcggcgaagc
3601 ctgcgaagag ttgcgaggca gcggcctggt ggaacacgcc tgggtcaatg atgacctggt
3661 gcattgcaaa cgctagggcc ttgtgggtc agttccggct ggggttcag cagccagcgc
3721 tttactggca tttcaggaac aagcgggcac tgctcgacgc acttgcttcg ctcagtatcg
3781 ctcgggacgc acggcgcgct ctacgaactg ccgatagaca actgtcacgg ttaagcgaga
3841 aatgaataag aaggctgata attcggatct ctgcgaggga gatgatattt gatccggtgt
3901 gaaataccgc acagatgcgt aaggagaaaa taccgcatca ggcgctcttc cgcttcctcg
3961 ctcactgact cgctgcgctc ggtcgttcag ctgcggcgag cggtatcagc tcactcaaag
4021 gcggtaatac ggttatccac agaatcaggg gataacgcag gaaagaacat gtgagcaaaa
4081 ggccagcaaa aggccaggaa ccgtaaaaag gccgcgttgc tggcgttttt ccataggctc
4141 cgcccccctg acgagcatca caaaaatcga cgctcaagtc agaggtggcg aaacccgaca
4201 ggactataaa gataccaggc gtttccccct ggaagctccc tcgtgcgctc tcctgttccg
4261 accctgccgc ttaccggata cctgtccgcc tttctccctt cgggaagcgt ggcgctttct
4321 catagctcac gctgtaggta tctcagttcg gtgtaggtcg ttcgctccaa gctgggctgt
4381 gtgcacgaac cccccgttca gcccgaccgc tgcgccttat ccggtaacta tcgtcttgag
4441 tccaacccgg taagacacga cttatcgcca ctggcagcag ccactggtaa caggattagc
4501 agagcgaggt atgtaggcgg tgctacagag ttcttgaagt ggtggcctaa ctacggctac
4561 actagaagga cagtatttgg tatctgcgct ctgctgaagc cagttacctt cggaaaaaga
4621 gttggtagct cttgatccgg caaacaaacc accgctggta gcggtggttt ttttgtttgc
4681 aagcagcaga ttacgcgcag aaaaaaagga tatcaagaag atcctttgat cttttctacg
4741 gggtctgacg ctcagtggaa cgaaaactca cgttaaggga ttttggtcat gagattatca
4801 aaaaggatct tcacctagat cctttttaaat taaaaatgaa gttttaaatc aatctaaagt
4861 atatatgagt aaacttggtc tgacagttac caatgcttca tcagtgaggc tgatcacagg
4921 cagcaacgct ctgtcatcgt tacaatcaac atgctaccct ccgcgagatc atccgtgttt
4981 caaacccggc agcttagttg ccgttcttcc gaatagcatc ggtaacatga gcaaagtctg
5041 ccgccttaca acggctctcc cgctgacgcc gtcccgacgt gatgggctgc ctgtatcgag
5101 tggtgatttt gtgccgagct gccggtcggg gagctgttgg ctggctggtg gcaggatata
5161 ttgtggtgta aacaaattga cgcttagaca acttaataac acaccgcggt ctagaactag
5221 tggatccccc ctacgtgcga tctagtaaca tagatgacac cgcgcgcgat aatttatcct
5281 agtttgcgcg ctatattttg ttttctatcg cgtattaaat gtataattgc gggactctaa
5341 tcataaaaac ccatctcata aataacgtca tgcattacat gttaattatt acatgcttaa
5401 cgtaattcaa cagaaattat atgataatca tcgcaagacc ggcaacagga ttcaatctta
5461 agaaacttta ttgccaaatg tttgaacgat ccctcagaag aactcgtcaa gaaggcgata
5521 gaaggcgatg cgctgcgaat cggagcggc gataccgtaa agcacgagga agcggtcagc
5581 ccattcgccg ccaagctctt cagcaatatc acgggtagcc aacgctatgt cctgatagcg
5641 gtccgccaca cccagccggc cacagtcgat gaatccagaa aagcggccat tttccaccat
5701 gatattcggc aagcaggcat cgccatgggt cacgacgaga tcctcgccgt cgggcatgcg
5761 cgccttgagc ctggcgaaca gttcggctgg cgcgagcccc tgatgctctt cgtccagatc
5821 atcctgatcg acaagaccgg cttccatccg agtacgtgct cgctcgatgc gatgtttcgc
5881 ttggtggtcg aatgggcagg tagccgcgatc agccgcgatc agccgcgatc
5941 catgatggat actttctcgg caggagcaag gtgagatgac aggagatcct gccccggcac
6001 ttcgcccaat agcagccagt cccttcccgc ttcagtgaca acgtcgagca cagctgcgca
6061 aggaacgccc gtcgtggcca gccacgatag ccgcgctgcc tcgtcctgga gttcattcag
6121 ggcaccggac aggtcggtct tgacaaaaag aaccgggcgc ccctgcgctg acagccggaa
6181 cacggcggca tcagagcagc cgattgtctg ttgtgcccag tcatagccga atagcctctc
6241 cacccaagcg gccggagaac ctgcgtgcaa tccatcttgt tcaatcatct gttaatcaga
6301 aaaactcaga ttaatcgaca aattcgatcg cacaaactag aaactaacac cagatctaga
```

Figure 6E

```
 6361 tagaaatcac aaatcgaaga gtaattattc gacaaaactc aaattatttg aacaaatcgg
 6421 atgatattta tgaaaccta atcgagaatt aagatgatat ctaacgatca aacccagaaa
 6481 atcgtcttcg atctaagatt aacagaatct aaaccaaaga acatatacga aattgggatc
 6541 gaacgaaaac aaaatcgaag attttgagag aataaggaac acagaaattt accttgatca
 6601 cggtagagag aattgagaga aagtttttaa gattttgaga aattgaaatc tgaattgtga
 6661 agaagaagag ctctttgggt attgttttat agaagaagaa gaagaaaaga cgaggacgac
 6721 taggtcacga gaaagctaag gcggtgaagc aatagctaat aataaaatga cacgtgtatt
 6781 gagcgttgtt tacacgcaaa gttgtttttg gctaattgcc ttattttag gttgaggaaa
 6841 agtatttgtg ctttgagttg ataaacacga ctcgtgtgtg ccggctgcaa ccactttgac
 6901 gccgtttatt actgactcgt cgacaaccac aatttctaac ggtcgtcata agatccagcc
 6961 gttgagattt aacgatcgtt acgatttata ttttttagc attatcgttt tatttttaa
 7021 atatacggtg gagctgaaaa ttggcaataa ttgaaccgtg ggtcccactg cattgaagcg
 7081 tatttcgtat tttctagaat tcttcgtgct ttatttcttt tcctttttgt ttttttttgc
 7141 catttatcta atgcaagtgg gcttataaaa tcagtgaatt tcttggaaaa gtaacttctt
 7201 tatcgtataa catattgtga aattatccat ttctttttaat ttttttagtgt tattggatat
 7261 ttttgtatga ttattgattt gcataggata atgactttttg tatcaagttg gtgaacaagt
 7321 ctcgttaaaa aaggcaagtg gtttggtgac tcgatttatt cttgttattt aattcatata
 7381 tcaatggatc ttatttgggg cctggtccat atttaacact cgtgttcagt ccaatgacca
 7441 ataatatttt ttcattaata acaatgtaac aagaatgata cacaaaacat tctttgaata
 7501 agttcgctat gaagaaggga acttatccgg tcctagatca tcagttcata caaacctcca
 7561 tagagttcaa catcttaaac aaggatatcc tgatccgttg acggcgcgcc ttcccgatct
 7621 agtaacatag atgacaccgc gcgcgataat ttatccagt ttgcgcgcta tattttgttt
 7681 tctatcgcgt attaaatgta taattgcggg actctaatca taaaaaccca tctcataaat
 7741 aacgtcatgc attacatgtt aattattaca tgcttaacgt aattcaacag aaattatatg
 7801 ataatcatcg caagaccggc aacaggattc aatcttaaga aactttattg ccaaatgttt
 7861 gaacgatcgg ggaaattcga gctcaaagtg caattgaccg atcagagttt gaagaaaaat
 7921 ttattacaca ctttatgtaa agctgaaaaa aacggcctcc cgcagggaag ccgttttttt
 7981 cgttatctga ttttttgtaaa ggtctgataa tggtccgttg ttttgtaaat cagccagtcg
 8041 cttgagtaaa gaatccggtc tgaatttctg aagcctgatg tatagttaat atccgctcca
 8101 cgccatgttc gtccgctttt gccgggagt ttgccttccc tgtttgagaa gatgtctccg
 8161 ccgatgcttt tccccggagc gacgtctgca aggttcctt ttgatgccac ccagccgagg
 8221 gcttgtgctt ctgatttttgt aatgtaatta tcaggtagct tatgatatgt ctgaagataa
 8281 tccgcaaccc cgtcaaacgt gttgataacc tgtgccatga tttgtacaca aaatttccgc
 8341 gcacagatcc tcacagcgta tgcaaaacaa agctgcaact actaatacca gtccaaaagc
 8401 aatgggcgca acagcaacag caaaagctgc aacccctgt gctggttcgt tcctacagtt
 8461 ggacgcagcc cgagttctga gaaacaaata accacaaggc aagttaggta ccaaacccct
 8521 taagctcaac ttaagcaaat attacaatcg tttgtttcta caaacaaatc tttttcagaa
 8581 cggcttcagg tggggaatat tgtccattta agtacctgaa aatctaagaa cacggccaat
 8641 ccgggcgcct ttgcttgaaa gtgggaagaa acctgaatga ttgaacagtg gataagagat
 8701 ttataagcaa gattagcagg gctgatcaga ttgttttttc gggtaggttg atcaatacat
 8761 atgccccttc cctcttcctt tcctctacaa tcgattgcca gggagagata gagataccat
 8821 catgatgatg atggtgggga tggcgatgat ggtaatgatg atgatccagc agaaaaaatt
 8881 gcgcagaaga agaagatgag cggtcggtcg gtcgatagcc tttcagtcgg aggggaaaga
 8941 acaaaataat gccatttga aggcagatgg attgactaag acgtgtgcag gcagtggagg
 9001 agttacaagg caggacatat ttactaggta taggtgtagg taatagtaat ggagaggata
 9061 aatttaggtt ttgggatgaa tggatttgtt ggtacatgtt gcaactccca cactgcaatc
 9121 aaaggaccgc tatgacaccc cctgaatgcg acgcccatga gaatgccgac cccacatata
 9181 catttctgga aataataggg aaatgcaccc ttgcattata tttcatttat tcgtcctcca
 9241 ttttgtgcgc tctccattca ttttcaaatg cgctccactc ttcctttatt tcttaccacc
 9301 attatctcgt attcgaggtc cagaaatcaa gttgtgaatc tgccttggtt gcgcattgtt
 9361 aaagtactct tctgtgtata tttctgccc accgttttca cttccaacac ttaaattttt
 9421 ttatttttta ttttatatat ttcttataaa ttgttggctt ctcacacgaa cccaagccat
 9481 ccaagccccg acaaaggcaa tccaatgtac ttgactagag tcaaatacct tttacttctt
 9541 tacttctcat attacccaga agccaagcca accttaccaa actaatgtac ctgagcagag
 9601 tccactacct ttcctcaagt acagtggcag tcagagtata tcaccgcttg ttatgtatat
 9661 gcttaatgc tatgcttatt tctaggtcat aatctaaatc atatttgctg tcgagtttaa
 9721 gcttatcgat accgtcgacc tcgagcttct tcttgaatgc tcttatgggt aggattattt
 9781 ttcactttt tccttcatat tccacacaca tatatatata aacacactaa cattagtggg
 9841 aatatttgtt tgatatgttt attttattta cttcggggt ttttgtaaca attttgtaga
 9901 tctaatttct tgttcttcat gtgtatatta attttcccctt aagacttaaa taaaaagaga
 9961 gagtttgtta tatatagata tatgaagtga gggaaatggt acaaagttaa aggagatctg
10021 agtgagagtt agataataaa tgaaagaaa taagaaacca tcagggtttt ttctaatgtg
10081 gagttttaga ttcagttttg tagaactaag attcacttg ttgggtgttc tttcttcact
10141 catttctgtt attataataa taataaaatc ttatatcttt ctattttcct tactaacaag
10201 tacttgaaga tttagatata tttatagatc tggtgttgta ataggtaaaa acttgatttt
10261 tatgactata aaagtaagtt ttgggaaaca aattggggag agagtaagga aggactatga
10321 ggtcatatct tctgttttgt gatcatccat cctccattgt tgttaatgtc tgtgtctctc
10381 ttttcttct cttctttctc ttactttcct ttcttatctc tagctctctt tctctctcat
10441 gaattatatc atatcatata tttgatacaa acacatgtga tggtaagtga gagtgaataa
10501 ggtgaaacta gctagatttt tgagtttca tgaaatttta acttatatga gtgatagaaa
10561 ataatggaac ttatacgtac atgtaggaca atttagatgg ttatctaagt ttttgttttt
10621 gttttctctt gagaatgtta aatgttagtg ttattttttgt agttttggaa aattatatat
10681 gagctaagat tagttagaa gtggtcaaaa gaaacataga tttgaaattt caactgaatt
10741 ttcaagattt caaatagtca atgaaacaag gaggtaatta agacaaatta gcttatgggg
```

Figure 6F

```
10801 actctttttt gttattcctt aaaattactc ttttttaaaat taaaaataac taatctcatt
10861 tcgaactaca ttactcaaac tagtaatctc taattcgaca cgcaatttcc aaatacttat
10921 tagtagagag tcccacgtga ttactttctt ctccaccaaa acataaaaca tgtcaagatt
10981 aaatggtgtt tgaaaattaa aagatcaatt ttcttaatcg tttacagttg tcaactctca
11041 tgtcctgaaa tatataattc tcatgtccaa aacaagaaaa gctaacaacg acttcaaatt
11101 aaatcagtca atcaaaatta gtcttcattt acctactaat ttctttttat atatccgatg
11161 ggtactctac gaaatcagag tttcgtttct ttatttattt tcttttataa gattttgag
11221 gtttttcag aggttggaat tgagcgcaag attaggtttt gggtctgtaa gatttgttgt
11281 ctttgttaaa gaatctttga tcacgtcatc actcagatat tatttctttt tattttcat
11341 ttgtattttt actaatttat tataaagttt tgttagtttc agttcttgac ttctgacaag
11401 aaggttttat gtcataatga attaatttgt aacctattta taaattcaaa aatgtcatca
11461 tattactact tttgaccatt taatattaga tttctcatt ggtcaataacc caatgttcat
11521 attacatata tagagacaaa aattataagg atactaaatt gttcatattt cttggaagta
11581 aaaagattaa tgatcactga ataaatagat ttggcataga agtatagcat tggaattgct
11641 tcaacatctt tggtgtagat agatttatgc aatttctctt tctttttgaa gtatctttt
11701 ttttctagag agagaataat gttagggatt tttatcattt tctctctcat tatgggtact
11761 gagaggaaag tgagatttt agtacggatc caatagttta agagtttggt ctgccttcta
11821 cgatccaaaa aaatctacgg tcatgatctc tccatcgaga aggttgagag ttcagacatc
11881 aaagtctata atatgtcatt gtaatacgta tttgtgcata tatatctatg tacaagtaca
11941 tatacaggaa actcaagaaa aaagaataaa tggtaaattt aattatattc caaataagga
12001 aagtatggaa cgttgtgatg ttactcggac aagtcattta gttacatcca tcacgtttaa
12061 atttaatcca atggttacaa ttttaatact atcaaatgtc tattggattt atacccaatg
12121 tgttaatggg ttgttgacac atgtcacatg tctgaaaccc tagacatgtt cagaccaatc
12181 atgtcactct aattttgcca gcatggcagt tggcagccaa tcactagctc gataaattta
12241 aggtttcaga ggaattttaa tttatttagg gttcatattg tttcataaaa tgattcttta
12301 tttgttacaa ctttaaggaa atattttatt aactatttaa ttgttcccctt ttcttatatt
12361 actttttgttt tttcttcaca tcatgtgtca cattaagttg catttcttct gactcaaaag
12421 aaccgatgtt tgcttttaag gtttcgtatt agaatcactt aactgtgcaa gtggtcgatt
12481 tgaccctatc aagcttgata tcgaattgcg gccgcggccg ggtggtgaca tttattcata
12541 aattcatctc aaaacaagaa ggatttacaa aaataaaaga aaacaaaatt ttcatcttta
12601 acataattat aattgtgttc acaaaattca aacttaaacc cttaatataa agaatttctt
12661 tcaacaatac actttaatca caacttcttc aatcacaacc tcctccaaca aaattaaaat
12721 agattaataa ataaataaac ttaactattt aaaaaaaaat attatacaaa atttattaaa
12781 acttcaaaat aaacaaactt tttatacaaa attcatcaaa actttaaaat aaagctaaac
12841 actgaaaatg tgagtacatt taaaaggacg ctgatcacaa aaattttgaa aacataaaca
12901 aacttgaaac tctaccttt aagaatgagt ttgtcgtctc attaactcat tagtttata
12961 gttcgaatcc aattaacgta tcttttattt tatggaataa gggtgttta ataagtgatt
13021 ttgggatttt tttagtaatt tatttgtgat atgttatgga gttttaaaa atatatatat
13081 atatatatat ttttgggttg agtttactta aaatttggaa aaggttggta agaactataa
13141 attgagttgt gaatgagtgt tttatggatt ttttaagatg ttaaatttat atatgtaatt
13201 aaaattttat tttgaataac aaaaattata attggataaa aaattgttttt gttaaattta
13261 gagtaaaaat ttcaaaatct aaaataatta aacactatta tttttaaaaa atttgttggt
13321 aaattttatc ttatatttag ttaaaattta gaaaaaatta atttaaatt aataaactt
13381 tgaagtcaaa tattccaaat atttttccaaa atattaaatc tattttgcat tcaaaataca
13441 atttaaataa taaaacttca tggaatagat taaccaattt gtataaaaac caaaaatctc
13501 aaataaaatt taaattacaa aacattatca acattatgat ttcaagaaag acaataacca
13561 gtttccaata aaataaaaaa cctcatggcc cgtaattaag atctcattaa ttaattctta
13621 tttttttaatt tttttacata gaaaatatct ttatatcgta tccaagaaat atagaatgtt
13681 ctcgtccagg gactattaat ctccaaacaa gtttcaaaat cattacatta aagctcatca
13741 tgtcatttgt ggattggaaa ttatattgta taagagaaat atagaatgtt ctcgtctagg
13801 gactattaat ttccaaacaa atttcaaaat cattacatta aagctcatca tgtcatttgt
13861 ggattggaaa ttagacaaaa aaaatcccaa atatttctct caatctccca aaatatagtt
13921 cgaactccat attttttggaa attgagaatt tttttaccca ataatatatt tttttataca
13981 tttttagagat tttccagaca tatttgctct gggatttatt ggaatgaagg tttgagttat
14041 aaactttcag taatccaagt atcttcggtt tttgaagata ctaaatccat tatataataa
14101 aaacacattt taaacaccaa tttaatggga tttcagattt gtatcccatg ctattggcta
14161 aggcattttt cttattgtaa tctaacctaat tctaatttcc accctgctgt gaactgactg
14221 acaaatgcgg tccgaaaaca gcgaatgaaa tgtctgggtg atcggtcaaa caagcggtgg
14281 gcgagagagc gcgggtgttg gcctagccgg gatgggggta ggtagacggc gtattaccgg
14341 cgagttgtcc gaatggagtt ttcggggtag gtagtaacgt agacgtcaat ggaaaaagtc
14401 ataatctccg tcaaaaatcc aacgctcct tcacatcgca gagttggtgg ccacgggacc
14461 ctccacccac tcactcgatc gcctgccgtg gttgcccatt attcaaccat acgccacttg
14521 actcttcacc aacaattcca ggccggcttt ctatacaatg tactgcacag gaaaatccaa
14581 tataaaaagc cggcctctgc ttccttctca gtagccccca gctcattcaa ttcttccac
14641 tgcaggctac atttgtcaga cacgttttcc gccattttttc gcctgtttct gcggagaatt
14701 tgatcaggtt cggattggga ttgaatcaat tgaaaggttt ttattttcag tatttcgatc
14761 gccggatccc ccgggctgca ggaattgggc tgcagatcga tatttgattt cacatgctat
14821 tgtaatgtat ttattgtttc aattccgaat tagacaaagt gcttaaagct ctcttttcgg
14881 attttttttt tcattaatgt ataataattg cggacattac aatatactgt acaacgtgat
14941 ttgagcttga tgaattacaa gattggaaga acttcgaaga caaaaaaaaa atcgatctgc
15001 aggaattcgt ccagcagtaa ttcggtaccc ctgatcagca ctgctgccaa gaatgtaagt
15061 ttttattttct tttatatgtt caaacagttt tataaagtac tataagcttt ttttagccaa
15121 aagaaatatc ttaagttttta gtaaccaata aagaattatt gcggcctcct tatttaatta
15181 tagtacatat gtcatagtag atgttttttt tattattatt atttttttatt ttttttatagt
```

Figure 6G

```
15241 tttttacaaa ttcgacttgg agaccttatg atttggaaga tactccattt aattttatga
15301 gttgtgtttg aaaacatatt ttaagactaa acacgtagag aacattctta acaaatttgt
15361 aaataaataa atttaactct attctctagg atttaaatat tataggtata tatataattt
15421 tctaataagt ttatatcgag tcactcatac gagttgtgta gaaagttaat cacgggtacc
15481 aatttttaaat taaaaataag aataattata tgatcttaaa tttatacaac tctgataaaa
15541 gattgggctt tgacatcttt gaagaaaact agatttagta atattctgat taaattgggt
15601 tcacactttg tagtgggcac actttccggg ttcgaaatcg aaatctggaa gcttatcgat
15661 ctcgaggggc ccactagtat cgatctcgag gggcccacta gtatcgatcg attttttttt
15721 tgtcttcgaa gttcttccaa tcttgtaatt catcaagctc aaatcacgtt gtacagtata
15781 ttgtaatgtc cgcaattatt atacattaat gaaaaaaaaa atccgaaaag agagctttaa
15841 gcactttgtc taattcggaa ttgaaacaat aaatacatta caatagcatg tgaaatcaaa
15901 tatcgatccg atgggtgtta tttgtggata ataaattcgg gtgatgttca gtgtttgtcg
15961 tatttctcac gaataaattg tgtttatgta tgtgttagtg ttgtttgtct gtttcagacc
16021 ctcttatgtt atatttttct tttcgtcggt cagttgaagc caatactggt gtcctggccg
16081 gcactgcaat accatttcgt ttaatataaa gactctgtta tccgtgagct cgaatttccc
16141 cgatcgttca aacatttggc aataaagttt cttaagattg aatcctgttg ccggtcttgc
16201 gatgattatc atataatttc tgttgaatta cgttaagcat gtaataatta acatgtaatg
16261 catgacgtta tttatgagat gggtttttat gattagagtc ccgcaattat acatttaata
16321 cgcgatagaa aacaaaatat agcgcgcaaa ctaggataaa ttatcgcgcg cggtgtcatc
16381 tatgttacta gatcgc
//
```

Figure 7A

```
LOCUS       pAGF243       7970 bp    DNA    circular          7-JUL-2003
DEFINITION  PrMC2.400-3::H102E::RNS2TER in pWVR13.
SOURCE
  ORGANISM
COMMENT     This file is created by Vector NTI
            http://www.informaxinc.com/
COMMENT     VNTDATE|307549965|
COMMENT     VNTDBDATE|307550293|
COMMENT     VNTNAME|pAGF243|
COMMENT     VNTAUTHORNAME|khnorri|
FEATURES             Location/Qualifiers
    misc_marker      1246..2037
                     /vntifkey="22"
                     /label=npt\III\(kanR)
    misc_marker      2339..3484
                     /vntifkey="22"
                     /label=trfA
    misc_structure   complement(3940..3963)
                     /vntifkey="88"
                     /label=LEFT\BORDER
    CDS              complement(4588..5379)
                     /vntifkey="4"
                     /label=NPT\II\(kanR)
    terminator       complement(4319..4539)
                     /vntifkey="43"
                     /label=NOSTER
    promoter         complement(5380..6689)
                     /vntifkey="29"
                     /label=UBQ10\promoter
    intron           complement(5380..5683)
                     /vntifkey="15"
                     /label=INTRON
    misc_marker      744..1013
                     /vntifkey="22"
                     /label=barstar
    promoter         complement(7424..7785)
                     /vntifkey="29"
                     /label=PrMC2.400-3
    CDS              complement(7094..7423)
                     /vntifkey="4"
                     /label=H102Ebarnase
    terminator       complement(6732..6992)
                     /vntifkey="43"
                     /label=RNS2TER
    misc_structure   complement(7838..7861)
                     /vntifkey="88"
                     /label=RIGHT\BORDER
BASE COUNT      2175 a      1836 c      2000 g      1959 t
ORIGIN
        1 cgccggcgtt gtggatacct cgcggaaaac ttggccctca ctgacagatg aggggcggac
       61 gttgacactt gaggggccga ctcacccggc gcggcgttga cagatgaggg gcaggctcga
      121 tttcggccgg cgacgtggag ctggccagcc tgcaaatcg gcgaaaacgc ctgattttac
      181 gcgagtttcc cacagatgat gtggacaagc ctggggataa gtgccctgcg gtattgacac
      241 tgaggggcg cgactactga cagatgaggg gcgcgatcct tgacacttga ggggcagagt
      301 gctgacagat gaggggcgca cctattgaca tttgaggggc tgtccacagg cagaaaatcc
      361 agcatttgca agggtttccg cccgtttttc ggccaccgct aacctgtctt ttaacctgct
      421 tttaaaccaa tatttataaa ccttgttttt aaccagggct gcgccctgtg cgcgtgaccg
      481 cgcacgccga agggggggtgc ccccccttct cgaaccctcc cggcccgcta acgcgggcct
      541 cccatccccc caggggctgc gccctcggc cgcgaacggc ctcacccaa aatggcagc
      601 gctggcagtc cataattgtg gtccaatttg cagccgtccg agacaggagg acatcgtcca
      661 gctgaaaccg gggcagaatc cggccatttc tgaagagaaa aatggtaaac tgatagaata
      721 aaatcataag aaaggagccg cacatgaaaa aagcagtcat taacggggaa caaatcagaa
      781 gtatcagcga cctccaccag acattgaaaa aggagcttgc ccttccgaa tactacggtg
      841 aaaacctgga cgctttatgg gattgtctga ccggatgggt ggagtacccg ctcgttttgg
      901 aatggagca gtttgaacaa agcaagcagc tgactgaaaa tggcgccgag agtgtgcttc
      961 aggttttccg tgaagcgaaa gcggaaggct gcgacatcac catcatactt tcttaatacg
     1021 atcaatggga gaggaacaat atggaaacac aaaccacaat tgtggtttca aaatcggctc
     1081 cgtcgatact atgttatacg ccaactttga aaacaacttt gaaaagctg ttttctggta
     1141 tttaaggttt tagaatgcaa ggaacagtga attggagttc gtcttgttat aattagcttc
     1201 ttgggggtatc tttaaatact gtagaaaaga ggaaggaaat aataaatggc taaatgaga
     1261 atatcaccgg aattgaaaaa actgatcgaa aaataccgct gcgtaaaaga tacggaagga
     1321 atgtctcctg ctaaggtata taagctggtg ggagaaaatg aaaacctata tttaaaaatg
     1381 acggacagcc ggtataaagg gaccacctat gatgtggaac gggaaaagga catgatgcta
```

Figure 7B

```
1441 tggctggaag gaaagctgcc tgttccaaag gtcctgcact ttgaacggca tgatggctgg
1501 agcaatctgc tcatgagtga ggccgatggc gtcctttgct cggaagagta tgaagatgaa
1561 caaagccctg aaaagattat cgagctgtat gcggagtgca tcaggctctt tcactccatc
1621 gacatatcgg attgtcccta tacgaatagc ttagacagcc gcttagccga attggattac
1681 ttactgaata acgatctggc cgatgtggat tgcgaaaact gggaagaaga cactccattt
1741 aaagatccgc gcgagctgta tgattttta aagacggaaa agcccgaaga ggaacttgtc
1801 ttttcccacg gcgacctggg agacagcaac atctttgtga aagatggcaa agtaagtggc
1861 tttattgatc ttgggagaag cggcagggcg gacaagtggt atgacattgc cttctgcgtc
1921 cggtcgatca gggaggatat cggggaagaa cagtatgtcg agctatttt tgacttactg
1981 gggatcaagc ctgattggga gaaaataaaa tattatattt tactggatga attgttttag
2041 tacctagatg tggcgcaacg atgccggcga caagcaggag cgcaccgact tcttccgcat
2101 caagtgtttt ggctctcagg ccgaggccca cggcaagtat ttgggcaagg ggtcgctggt
2161 attcgtgcag ggcaagattc ggaataccaa gtacgagaag gacggccaga cggtctacgg
2221 gaccgacttc attgccgata aggtggatta tctgacacc aaggcaccag gcgggtcaaa
2281 tcaggaataa gggcacattg ccccggcgtg agtcgggca atcccgcaag gagggtgaat
2341 gaatcggacg tttgaccgga aggcatacag gcaagaactg atcgacgcg ggttttccgc
2401 cgaggatgcc gaaaccatcg caagccgcac cgtcatgcgt gcgccccgcg aaaccttcca
2461 gtccgtcggc tcgatggtcc agcaagctac ggccaagatc gagcgcgaca gcgtgcaact
2521 ggctccccct gccctgcccg cgccatcggc cgccgtggag cgttcgcgtc gtctcgaaca
2581 ggaggcggca ggttggcga agtcgatgac catcgacacg cgaggaacta tgacgaccaa
2641 gaagcgaaaa accgccggcg aggacctggc aaaacaggtc agcgaggcca agcaggccgc
2701 gttgctgaaa cacacgaagc agcagatcaa ggaaatgcag ctttccttgt tcgatattgc
2761 gccgtggccg gacacgatgc gagcgatgcc aaacgacacg gcccgctctg ccctgttcac
2821 cacgcgcaac aagaaaatcc cgcgcgaggc gctgcaaaac aaggtcattt tccacgtcaa
2881 caaggacgtg aagatcacct acaccggcgt cgagctgcgg gccgacgatg acgaactggt
2941 gtggcagcag gtgttggagt acgcgaagcg caccccctatc ggcgagccga tcaccttcac
3001 gttctacgag ctttgccagg acctgggctg gtcgatcaat ggccggtatt acacgaaggc
3061 cgaggaatgc ctgtcgcgcc tacaggcgac ggcgatgggc ttcacgtccg accgcgttgg
3121 gcacctggaa tcggtgtcgc tgctgcaccg cttccgcgtc ctggaccgtg gcaagaaaac
3181 gtcccgttgc caggtcctga tcgacgagga aatcgtcgtg ctgtttgctg gcgaccacta
3241 cacgaaattc atatgggaga agtaccgcaa gctgtcgccg acggcccgac ggatgttcga
3301 ctatttcagc tcgcaccggg agccgtaccc gctcaagctg gaaccttcc gcctcatgtg
3361 cggatcggat tccacccgcg tgaagaagtg gcgcgagcag gtcggcgaag cctgcgaaga
3421 gttgcgaggc agcggcctgg tggaacacgc ctgggtcaat gatgacctgg tgcattgcaa
3481 acgctagggc cttgtgggt cagttccggc tgggggttca gcagccagcg ctttactggc
3541 atttcaggaa caagcgggca ctgctcgacg cacttgcttc gctcagtatc gctcgggacg
3601 cacggcgcgc tctacgaact gccgatagac aactgtcacg gttaagcgaa aaatgaataa
3661 gaaggctgat aattcggatc tctgcgaggg agatgatatt tgatcacagg cagcaacgct
3721 ctgtcatcgt tacaatcaac atgctaccct ccgcgagatc atccgtgttt caaacccggc
3781 agcttagttg ccgttcttcc gaatagcatc ggtaacatga gcaaagtctg ccgccttaca
3841 acggctctcc cgctgacgcc gtcccggact gatggcctgc ctgtatcgag tggtgatttt
3901 gtgccgagct gccggtcggg gagctgttgg ctggctggtg gcaggatata ttgtggtgta
3961 aacaaattga cgcttagaca acttaataac acattgcgga cgttttaat gtactgggt
4021 ggttttctt ttcaccagtg agacgggcaa cagctgattg cccttcaccg cctggccctg
4081 agagagttgc agcaagcggt ccacgctggt ttgccccage aggcgaaaat cctgtttgat
4141 ggtggttccg aaatcggcaa aatcccttat aaatcaaaag aatagcccga gatagggttg
4201 agtgttgttc cagtttggaa caagagtcca ctattaaaga acgtggactc caacgtcaaa
4261 gggcgaaaaa ccgtctatca gggcgatggc ccacggccgc tctagaacta gtggatcccc
4321 cctacgtgcg atctagtaac atagatgaca ccgcgcgcga taatttatcc tagtttgcgc
4381 gctatatttt gttttctatc gcgtattaaa tgtataattg cgggactcta atcataaaaa
4441 cccatctcat aaataacgtc atgcattaca tgttaattat tacatgctta acgtaattca
4501 acagaaatta tatgataatc atcgcaagac cggcaacagg attcaatctt aagaaacttt
4561 attgccaaat gtttgaacga tccctcagaa gaactcgtca agaaggcgat agaaggcgat
4621 gcgctgcgaa tcgggagcgg cgataccgta aagcacgagg aagcggtcag cccattcgcc
4681 gccaagctct tcagcaatat cacgggtagc caacgctatg tcctgatagc ggtccgccac
4741 acccagccgg ccacagtcga tgaatccaga aaagcggcca ttttccacca tgatattcgg
4801 caagcaggca tcgccatggg tcacgacgag atcctcgccg tcgggcatgc gcgccttgag
4861 cctggcgaac agttcggctg gcgcgagccc ctgatgctct tcgtccagat catcctgatc
4921 gacaagaccg gcttccatcc gagtacgtgc tcgctcgatg cgatgtttcg cttggtggtc
4981 gaatgggcag gtagccggat caagcgtatg cagccgccgc attgcatcag ccatgatgga
5041 tactttctcg gcaggagcaa ggtgagatga caggagatcc tgcccggca cttcgcccaa
5101 tagcagccag tcccttcccg cttcagtgac acagtcgcgc acggcgtcgc aaggaacgcc
5161 cgtcgtggcc agccacgata gccgcgctgc ctcgtcctgg agttcattca gggcaccgga
5221 caggtcggtc ttgacaaaaa gaaccgggcg cccctgcgct gacagccgga acacggcggc
5281 atcagagcag ccgattgtct gttgtgccca gtcatagccg aatagcctct ccacccaagc
5341 ggccggagaa cctgcgtgca atccatcttg ttcaatcatc tgttaatcag aaaaactcag
5401 attaatcgac aaattcgatc gcacaaacta gaaactaaca ccagatctag atagaaatca
5461 caaatcgaag agtaattatt cgacaaaact caaattattt gaacaaatcg gatgatattt
5521 atgaaccct aatcgagaat taagatgata tctaacgatc aaaccagaa atcgtcttc
5581 gatctaagat taacagaatc taaaccaaag aacatatacg aaatttgggat cgaacgaaaa
5641 caaaatcgaa gattttgaga gaataaggaa cacagaaatt taccttgatc acggtagaga
5701 gaattgagag aaagttttta agattttgag aaattgaaat ctgaattgtg aagaagaaga
5761 gctctttggg tattgtttta tagaagaaga agaagaaaag acgaggacga ctaggtcacg
5821 agaaagctaa ggcggtgaag caatagctaa taataaaatg acacgtgtat tgagcgttgt
```

Figure 7C

```
5881 ttacacgcaa agttgttttt ggctaattgc cttatttta ggttgaggaa aagtatttgt
5941 gctttgagtt gataaacacg actcgtgtgt gccggctgca accactttga cgccgtttat
6001 tactgactcg tcgacaacca caatttctaa cggtcgtcat aagatccagc cgttgagatt
6061 taacgatcgt tacgatttat attttttag cattatcgtt ttatttta aatatacggt
6121 ggagctgaaa attggcaata attgaaccgt gggtcccact gcattgaagc gtatttcgta
6181 ttttctagaa ttcttcgtgc tttatttctt ttcctttttg tttttttg ccatttatct
6241 aatgcaagtg ggcttataaa atcagtgaat ttcttggaaa agtaacttct ttatcgtata
6301 acatattgtg aaattatcca tttcttttaa tttttagtg ttattggata tttttgtatg
6361 attattgatt tgcataggat aatgactttt gtatcaagtt ggtgaacaag tctcgttaaa
6421 aaaggcaagt ggtttggtga ctcgatttat tcttgttatt taattcatat atcaatggat
6481 cttatttggg gcctggtcca tatttaacac tcgtgttcag tccaatgacc aataatattt
6541 tttcattaat aacaatgtaa caagaatgat acacaaaaca ttctttgaat aagttcgcta
6601 tgaagaaggg aacttatccg gtcctagatc atcagttcat acaaacctcc atagagttca
6661 acatcttaaa caaggatatc ctgatccgtt gacggcgcgc caagcggccg catttaaatg
6721 ggccctatct aatcgaattt tgtaaactgg tttgataagc catcaatgca tcagtcaaga
6781 atgaatcatt gcaactaagt tgatataatt caatttacca tagaactcaa atgttgatat
6841 cttcttatgg attttctgat cttctacatt attagaaaga aacttgattt accagtaatg
6901 atgatacata tccaatagaa cgaaataagc caatctttat aggttttggt agtaaagtta
6961 caacatcaga gacatgtatg tattgtctct cagaagagct cttgaccgat cagagtttga
7021 agaaaaattt attacacact ttatgtaaag ctgaaaaaaa cggcctcccg cagggaagcc
7081 gttttttttcg ttatctgatt tttgtaaagg tctgatactc gtccgttgtt ttgtaaatca
7141 gccagtcgct tgagtaaaga atccggtctg aatttctgaa gcctgatgta tagttaatat
7201 ccgcttcacg ccatgttcgt ccgctttgc ccgggagttt gccttccctg tttgagaaga
7261 tgtctccgcc gatgcttttc cccggagcga cgtctgcaag gttcccttt gatgccaccc
7321 agccgagggc ttgtgcttct gatttgtaa tgtaattatc aggtagctta tgatatgtct
7381 gaagataatc cgcaacccg tcaaacgtgt tgataacctg tgccataaat cttctaaaaa
7441 cagcagaact gactattcaa agaaagtaga acccacagaa agtaatcaaa gtagtttgat
7501 taaatgcgtt gtgtatcatc gcagcccctg ctacggatat ttataggaaa ggtttgagag
7561 caatgtgtgc agcaagttgt gtgtgaatca cctgcttcca tggcggagga taaataattt
7621 agtcacgcat ttagttgaac gtaactacta actcctctac cgctaatcat tcttcttttg
7681 cccgggcaag ttcaacaaca accccacaat cacgcttcct gtatttgtt ttgtttcaa
7741 aacaatagaa ttcacttttt actgccaaaa ttatgttta ctcgagagcc cggctcctg
7801 caggtacctt aattaaaaagt ttaaactatc agtgtttgac aggatatatt ggcgggtaaa
7861 cctaagagaa aagagcgttt attagaataa tcggatattt aaaagggcgt gaaaaggttt
7921 atccgttcgt ccatttgtat gtgcatgcca accacagggt tccccagatc
//
```

Figure 8A

```
LOCUS       pABDP010    10312 bp   DNA     circular          20-SEP-2004
DEFINITION  Complementary copy of CZ28-bstar + UBQ10::NPTII::E9/LPAG1d4::bstar::NOST.
SOURCE
  ORGANISM
COMMENT     This file is created by Vector NTI
            http://www.informaxinc.com/
COMMENT     VNTDATE|350147921|
COMMENT     VNTDBDATE|350147921|
COMMENT     VNTNAME|pABDP010|
COMMENT     VNTAUTHORNAME|dlpetri|
COMMENT     Vector_NTI_Display_Data_(Do_Not_Edit!)
COMMENT     (SXF FEATURES             Location/Qualifiers
     misc_marker     complement(8611..9402)
                     /vntifkey="22"
                     /label=NPTIII
     misc_marker     complement(7164..8309)
                     /vntifkey="22"
                     /label=trfA
     misc_signal     6685..6709
                     /vntifkey="87"
                     /label=LB
     terminator      4318..4963
                     /vntifkey="43"
                     /label=E9
     CDS             5730..6059
                     /vntifkey="4"
                     /label=barstar terminator      6065..6332
                     /vntifkey="43"
                     /label=NOS-T
                     /note="Added BamHI and XhoI sites to 3' end"
     promoter        4964..5729
                     /vntifkey="29"
                     /label=LPAG1d4
     CDS             3522..4317
                     /vntifkey="4"
                     /label=NPTII
     misc_signal     4314..4316
                     /vntifkey="87"
                     /label=TGA
     promoter        2212..3521
                     /vntifkey="29"
                     /label=UBQ10\promoter
     intron          3218..3521
                     /vntifkey="15"
                     /label=INTRON
     misc_signal     1..25
                     /vntifkey="87"
                     /label=RB
                     /note="Right Border of T-DNA"
     misc_signal     1474..1476
                     /vntifkey="87"
                     /label=ATG
                     /note="ATG of Barnase E73G"
     CDS             1474..1912
                     /vntifkey="4"
                     /label=Barnase\E73G
     terminator      1920..2178
                     /vntifkey="43"
                     /label=NOS-T
     promoter        82..1473
                     /vntifkey="29"
                     /label=LPAG1-P
                     /note="LPAG1 promoter- still determining exact location of 5'
end"
BASE COUNT     2628 a    2467 c    2322 g    2895 t
ORIGIN
        1 gtttacccgc caatatatcc tgtcaaacac tgatagttta aacttttaat taaggtacct
       61 gcaggagccc gggctctcga gcagcaaata tgatttagat tatgacctag aaataagcat
      121 agcattaaag catatacaaa acaagcggtg atatactctg actgccactg tacttgagga
```

Figure 8B

```
 181 aaggtagtgg actctgctca ggtacattag tttggtaagg ttggcttggc ttctgggtaa
 241 tatgagaagt aaagaagtaa aaggtatttg actctagtca agtacattgg attgccttcg
 301 tcggggcttg gatggcttgg gttcgtgtga gaagccaaca atttataaaa aaatatattg
 361 aaaaaaaaaa aaatcgtcta agtgttggaa gtgaaaacgg tgggacataa atatacacag
 421 aagagtactt taacaatgcg caaccaaggc agattcacaa cttgatttct ggacctcgaa
 481 tacgagataa tggtggtaag aaataaagga agagtggagt gcatttgaaa atgaatggag
 541 agcgcacaaa atggaggacg aataaatgaa atataatgca agagtgcatt tccctattat
 601 ttccagaaat gtatatgtgg ggtcggcatt cacatgggcg tcgcattcag ggggtgtcat
 661 agcggtcctt tgattgcagt gtgggagttg caacatgtac caacaaattc attcatccca
 721 aaacctaaat ttatcctctc cattactatt acctacacct ataccagta aatatgtcct
 781 gccttgtaac tcctccactg cctgcacacg tcttagtcaa tccatctgcc ttcaaatagg
 841 cattattttg ttcttccc tccgactgaa aggctatcga ccgaccgacc gctcatcttc
 901 ttcttctgcg caattttttc tgctggatca tcatcattac catcatcgcc atccccacca
 961 tcatcatcat gatggtatct ctatctctcc ctggcaatcg attgtagagg aaaggaagag
1021 ggaaggggca tatgtattga tcaacctacc cgaaaaaaca atctgatcag ccctgctaat
1081 cttgcttata aatctcttat ccactgttca atcattcagg tttcttccca cttccaagca
1141 aaggcgcccg gattggccgt gttcttagat tttcaggtac ttaaatggac aatattcccc
1201 acctgaagcc gttctgaaaa agatttgttt gtagaaacaa acgattgtaa tatttgctta
1261 agttgagctt aagggtttg gtacctaact tgccttgtgg ttatttgttt ctcagaactc
1321 gggctgcgtc caactgtagg aacgaaccag cacaaggggt tgcagctttt gctgttgctg
1381 ttgcgcccat tgcttttgga ctggtattag tagttgcagc tttgtttgc atacgctgtg
1441 aggatctgtg cgcggaaatt ttgtgtacaa atcatggcac aggttatcaa cacgtttgac
1501 ggggttgcgg attatcttca gacatatcat aagctacctg ataattcat tacaaaatca
1561 gaagcacaag ccctcggctg ggtggcatca aaagggaacc ttgcagacgt cgctccgggg
1621 aaaagcatcg gcggagacat cttctcaaac agggaaggca aactcccggg caaaagcgga
1681 cgaacatggc gtggagcgga tattaactat acatcaggct tcagaaattc agaccggatt
1741 ctttactcaa gcgactggct gatttacaaa acaacgacc attatcagac ctttacaaaa
1801 atcagataac gaaaaaaacg gcttccctgc gggaggccgt tttttcagc tttacataaa
1861 gtgtgtaata aattttctt caaactctga tcggtcaatt gcactttgag ctcgaatttc
1921 cccgatcgtt caaacatttg gcaataaagt ttcttaagat tgaatcctgt tgccggtctt
1981 gcgatgatta tcatataatt tctgttgaat tacgttaagc atgtaataat taacatgtaa
2041 tgcatgacgt tatttatgag atgggttttt atgattagag tcccgcaatt atacatttaa
2101 tacgcgatag aaaacaaaat atagcgcgca aactaggata aattatcgcg cgcggtgtca
2161 tctatgttac tagatcggga aggcgcgccg cggccgcttg gcgcgccgtc aacggatcag
2221 gatatccttg tttaagatgt tgaactctat ggaggtttgt atgaactgat gatctaggac
2281 cggataagtt cccttcttca tagcgaactt attcaaagaa tgttttgtgt atcattcttg
2341 ttacattgtt attaatgaaa aaatattatt ggtcattgga ctgaacacga gtgttaaata
2401 tggaccaggc cccaaataag atccattgat atatgaatta aataacaaga ataaatcgag
2461 tcaccaaacc acttgccttt tttaacgaga cttgttcacc aacttgatac aaaagtcatt
2521 atcctatgca aatcaataat catacaaaaa tatccaataa cactaaaaaa ttaaaagaaa
2581 tggataattt cacaatatgt tatacgataa agaagttact tttccaagaa attcactgat
2641 tttataagcc cacttgcatt agataaatgg caaaaaaaaa caaaaaggaa agaaataaa
2701 gcacgaagaa ttctagaaaa tacgaaatac gcttcaatgc agtgggaccc acggttcaat
2761 tattgccaat tttcagctcc accgtatatt taaaaaataa aacgataatg ctaaaaaaat
2821 ataaatcgta acgatcgtta aatctcaacg gctggatctt atgacgaccg ttagaaattg
2881 tggttgtcga cgagtcagta ataaacggcg tcaaagtggt tgcagccggc acacacgagt
2941 cgtgtttatc aactcaaagc acaaatactt ttcctcaacc taaaaataag gcaattagcc
3001 aaaaacaact ttgcgtgtaa acaacgctca atacacgtgt catttatta ttagctattg
3061 cttcaccgcc ttagctttct cgtgacctag tcgtcctcgt cttttcttct tcttcttcta
3121 taaaacaata cccaaagagc tcttcttctt cacaattcag atttcaattt ctcaaaatct
3181 taaaaacttt ctctcaattc tctctaccgt gatcaaggta aatttctgtg ttccttattc
3241 tctcaaaatc ttcgattttg ttttcgttcg atcccaattt cgtatatgtt ctttggttta
3301 gattctgtta atcttagatc gaagacgatt ttctgggttt gatcgttaga tatcatctta
3361 attctcgatt agggtttcat aaatatcatc cgatttgttc aaataatttg agttttgtcg
3421 aataattact cttcgatttg tgatttctat ctagatctgg tgttagtttc tagtttgtgc
3481 gatcgaattt gtcgattaat ctgagttttt ctgattaaca gatgattgaa caagatggat
3541 tgcacgcagg ttctccggcc gcttggtgg agaggctatt cggctatgac tgggcacaac
3601 agacaatcgg ctgctctgat gccgccgtgt tccggctgtc agcgcagggg cgcccggttc
3661 tttttgtcaa gaccgacctg tccggtgccc tgaatgaact ccaggacgag gcagcgcggc
3721 tatcgtggct ggccacgacg ggcgttcctt gcgcagctgt gctcgacgtt gtcactgaag 3781 cgggaaggga ctggctgcta ttgggcgaag tgccggggca ggatctcctg tcatctcacc
3841 ttgctcctgc cgagaaagta tccatcatgg ctgatgcaat gcggcggctg catacgcttg
3901 atccggctac ctgcccattc gaccaccaag cgaaacatcg catcgagcga gcacgtactc
3961 ggatggaagc cggtcttgtc gatcaggatg atctggacga agagcatcag ggctcgcgc
4021 cagccgaact gttcgccagg ctcaaggcgc gcatgcccga cggcgaggat ctcgtcgtga
4081 cccatggcga tgcctgcttg ccgaatatca tggtggaaaa tggccgcttt tctggattca
4141 tcgactgtgg ccggctgggt gtggcggacc gctatcagga catagcgttg gctacccgtg
4201 atattgctga agagcttggc ggcgaatggg ctgaccgctt cctcgtgctt tacggtatcg
4261 ccgctcccga ttcgcagcgc atcgccttct atcgccttct tgacgagttc ttctgagaat
4321 tcagctttcg ttcgtatcat cggtttcgac aacgttcgtc aagttcaatg catcagtttc
4381 attgcgcaca caccagaatc ctactgagtt cgagtattat ggcattggga aaactgtttt
4441 tcttgtacca tttgttgtgc ttgtaattta ctgtgttttt tattcggttt tcgctatcga
4501 actgtgaaat ggaaatggat ggagaagagt taatgaatga tatggtcctt ttgttcattc
```

Figure 8C

```
4561 tcaaattaat attatttgtt ttttctctta tttgttgtgt gttgaatttg aaattataag
4621 agatatgcaa acattttgtt ttgagtaaaa atgtgtcaaa tcgtggcctc taatgaccga
4681 agttaatatg aggagtaaaa cacttgtagt tgtaccatta tgcttattca ctaggcaaca
4741 aatatatttt cagacctaga aaagctgcaa atgttactga atacaagtat gtcctcttgt
4801 gttttagaca tttatgaact ttcctttatg taattttcca gaatccttgt cagattctaa
4861 tcattgcttt ataattatag ttatactcat ggatttgtag ttgagtatga aaatattttt
4921 taatgcattt tatgacttgc caattgattg acaacgcaag cttttcattc atcccaaaac
4981 ctaaatttat cctctccatt actattacct acacctatac ctagtaaata tgtcctgcct
5041 tgtaactcct ccactgcctg cacacgtctt agtcaatcca tctgccttca aataggcatt
5101 attttgttct ttcccctccg actgaaaggc tatcgaccga ccgaccgctc atcttcttct
5161 tctgcgcaat tttttctgct ggatcatcat cattaccatc atcgccatcc ccaccatcat
5221 catcatgatg gtatctctat ctctccctgg caatcgattg tagaggaaag gaagaggaa
5281 gggcatatg tattgatcaa cctacccgaa aaacaatct gatcagccct gctaatcttg
5341 cttataaatc tcttatccac tgttcaatca ttcaggtttc ttcccacttc caagcaaagg
5401 cgcccggatt ggccgtgttc ttagattttc aggtacttaa atggacaata ttccccacct
5461 gaagccgttc tgaaaaagat ttgtttgtag aaacaaacga ttgtaatatt tgcttaagtt
5521 gagcttaagg ggtttggtac ctaacttgcc ttgtggttat ttgtttctca gaactcgggc
5581 tgcgtccaac tgtaggaacg aaccagcaca aggggttgca gcttttgctg ttgctgttgc
5641 gcccattgct tttggactgg tattagtagt tgcagctttg ttttgcatac gctgtgagga
5701 tctgtgcgcg gaaattttgt gtacaaatca tgaaaaaagc agtcattaac ggggaacaaa
5761 tcagaagtat cagcgacctc caccagacat tgaaaaagga gcttgcccctt ccggaatact
5821 acggtgaaaa cctgacgct ttatgggatt gtctgaccgg atgggtggag tacccgctcg
5881 ttttggaatg gaggcagttt gaacaaagca agcagctgac tgaaaatggc gccgagagtg 5941 tgcttcaggt tttccgtgaa gcgaaagcgg aaggctgcga catcaccatc atactttctt
6001 aatacgatca atgggagatg aacaatatgg aaacacaaac cacaattatg tctctcagcg
6061 agctcgaatt tccccgatcg ttcaaacatt tggcaataaa gtttcttaag attgaatcct
6121 gttgccggtc ttgcgatgat tatcatataa tttctgttga attacgttaa gcatgtaata
6181 attaacatgt aatgcatgac gttatttatg agatgggttt ttatgattag agtcccgcaa
6241 ttatacattt aatacgcgat agaaaacaaa atatagcgcg caaactagga taaattatcg
6301 cgcgcggtgt catctatgtt actagatcgg ggatccacta gttctagagc ggcgtgggcc
6361 atcgccctga tagacggttt ttcgcccttt gacgttggag tccacgttct ttaatagtgg
6421 actcttgttc caaactggaa caacactcaa ccctatctcg ggctattctt ttgatttata
6481 agggattttg ccgatttcgg aaccaccatc aaacaggatt ttcgcctgct ggggcaaacc
6541 agcgtggacc gcttgctgca actctctcag ggccaggcgg tgaagggcaa tcagctgttg
6601 cccgtctcac tggtgaaaag aaaaaccacc ccagtacatt aaaaacgtcc gcaatgtgtt
6661 attaagttgt ctaagcgtca atttgtttac accacaatat atcctgccac cagccagcca
6721 acagctcccc gaccggcagc tcggcacaaa atcaccactc gatacaggca gcccatcagt
6781 ccgggacggc gtcagcggga gagccgttgt aaggcggcag actttgctca tgttaccgat
6841 gctattcgga agaacggcaa ctaagctgcc gggtttgaaa cacggatgat ctcgcggagg
6901 gtagcatgtt gattgtaacg atgacgaagc gttgctgcct gtgatcaaat atcatctccc
6961 tcgcagagat ccgaattatc agccttctta ttcatttctc gcttaaccgt gacagttgtc
7021 tatcggcagt tcgtagagcg cgccgtgcgt cccgagcgat actgagcgaa gcaagtgcgt
7081 cgagcagtgc ccgcttgttc ctgaaatgcc agtaaagcgc tggctgctga acccccagcc
7141 ggaactgacc ccacaaggcc ctagcgtttg caatgcacca ggtcatcatt gaccaggcg
7201 tgttccacca ggccgctgcc tcgcaactct tcgcaggctt cgccgacctg ctcgcgccac
7261 ttcttcacgc gggtggaatc cgatccgcac atgaggcgga aggtttccag cttgagcggg
7321 tacggctccc ggtgcgagct gaaatagtcg aacatccgtc gggccgtcgg cgacagcttg
7381 cggtacttct cccatatgaa tttcgtgtag tggtcgcag caaacagcac gacgatttcc
7441 tcgtcgatca ggacctggca acgggacgtt ttcttgccac ggtccaggac gcggaagcgg
7501 tgcagcagcg acaccgattc caggtgccca acgcggtcgg acgtgaagcc catcgccgtc
7561 gcctgtaggc gcgacaggca ttcctcggcc ttcgtgtaat accggccatt gatcgaccag
7621 cccaggtcct ggcaaagctc gtagaacgtg aaggtgatcg gctcgccgat aggggtgcgc
7681 ttcgcgtact ccaacacctg ctgccacacc agttcgtcat cgtcggcccg cagctcgacg
7741 ccggtgtagg tgatcttcac gtccttgttg acgtggaaaa tgaccttgtt ttgcagcgcc
7801 tcgcgcggga ttttcttgtt gcgcgtggtg aacagggcag agcgggccgt gtcgtttggc
7861 atcgctcgca tcgtgtccgg ccacggcgca atatcgaaca aggaaagctg catttccttg
7921 atctgctgct tcgtgtgttt cagcaacgcg gcctgcttgg cctcgctgac ctgttttgcc
7981 aggtcctcgc cggcggtttt tcgcttcttg gtcgtcatag ttcctcgcgt gtcgatggtc
8041 atcgacttcg ccaaacctgc cgcctcctgt tcgagacgac gcgaacgctc cacggcggcc
8101 gatggcgcgg gcagggcagg gggagccagt tgcacgctgt cgcgctcgat cttggccgta
8161 ccttgctgga ccatcgagcc gacggactgg aaggtttcgc ggggcgcacg catgacggtg
8221 cggcttgcga tggtttcggc atcctcggcg gaaaaccccg cgtcgatcag ttcttgcctg
8281 tatgccttcc ggtcaaacgt ccgattcatt caccctcctt gcgggattgc cccgactcac
8341 gccggggcaa tgtgcccttaa ttcctgatttt gacccgcctg gtgccttggt gtccagataa
8401 tccaccttat cggcaatgaa gtcggtcccg tagaccgtct ggccgtcctt ctcgtacttg
8461 gtattccgaa tcttgccctg cacgaatacc agcgacccct tgcccaaata cttgccgtgg
8521 gcctcggcct gagagccaaa acacttgatg cggaagaagt cggtgcgctc ctgcttgtcg
8581 ccggcatcgt tgcgccacat ctaggtacta aaacaattca tccagtaaaa tataatattt
8641 tatttctctc caatcaggct tgatccccag taagtcaaaa aatagctcga catactgttc
8701 ttccccgata tcctcccctga tcgaccggac gcagaaggca atgtcatacc acttgtccgc
8761 cctgccgctt ctcccaagat caataaagcc acttacttgg ccatctttca caaagatgtt
8821 gctgtctccc aggtcgccgt gggaaaagac aagttcctct tcgggctttt ccgtctttaa
```

Figure 8D

```
 8881 aaaatcatac agctcgcgcg gatctttaaa tggagtgtct tcttcccagt tttcgcaatc
 8941 cacatcggcc agatcgttat tcagtaagta atccaattcg gctaagcggc tgtctaagct
 9001 attcgtatag ggacaatccg atatgtcgat ggagtgaaag agcctgatgc actccgcata
 9061 cagctcgata atcttttcag ggctttgttc atcttcatac tcttccgagc aaaggacgcc
 9121 atcggcctca ctcatgagca gattgctcca gccatcatgc cgttcaaagt gcaggacctt
 9181 tggaacaggc agctttcctt ccagccatag catcatgtcc ttttcccgtt ccacatcata
 9241 ggtggtccct ttataccggc tgtccgtcat ttttaaatat aggttttcat tttctcccac
 9301 cagcttatat accttagcag gagacattcc ttccgtatct tttacgcagc ggtattttc
 9361 gatcagtttt ttcaattccg gtgatattct cattttagcc atttattatt tccttcctct
 9421 tttctacagt atttaaagat accccaagaa gctaattata acaagacgaa ctccaattca
 9481 ctgttccttg cattctaaaa cctaaatac cagaaaacag cttttttcaaa gttgttttca
 9541 aagttggcgt ataacatagt atcgacggag ccgattttga aaccacaatt atggactgcc
 9601 agcgctgcca ttttggggt gaggccgttc gcggccgagg ggcgcagccc ctgggggat
 9661 gggaggcccg cgttagcggg ccgggagggt tcgagaaggg ggggcacccc ccttcggcgt
 9721 gcgcggtcac gcgcacaggg cgcagccctg gttaaaaaca aggtttataa atattggttt
 9781 aaaagcaggt taaaagacag gttagcggtg gccgaaaaac gggcggaaac ccttgcaaat
 9841 gctggatttt ctgcctgtgg acagcccctc aaatgtcaat aggtgcgccc ctcatctgtc
 9901 agcactctgc ccctcaagtg tcaaggatcg cgcccctcat ctgtcagtag tcgcgccct
 9961 caagtgtcaa taccgcaggg cacttatccc caggcttgtc cacatcatct gtgggaaact
10021 cgcgtaaaat caggcgtttt cgccgatttg cgaggctggc cagctccacg tcgccggccg
10081 aaatcgagcc tgccctcat ctgtcaacgc cgcgcccggt gagtcgccc ctcaagtgtc
10141 aacgtccgcc cctcatctgt cagtgagggc caagttttcc gcgaggtatc cacaacgccg
10201 gcggatctgg ggaaccctgt ggttggcatg cacatacaaa tggacgaacg gataaaccttt
10261 ttcacgccct tttaaatatc cgattattct aataaacgct cttttctctt ag
//
```

Figure 9A

```
LOCUS        pABDP04      10312 bp    DNA    circular           20-SEP-2004
DEFINITION   Complementary copy of CZ28-bstar + UBQ10::NPTII::E9/LPAG1d4::bstar::NOST.
SOURCE
  ORGANISM
COMMENT      This file is created by Vector NTI
             http://www.informaxinc.com/
COMMENT      VNTDATE|350150026|
COMMENT      VNTDBDATE|350150026|
COMMENT      VNTNAME|pABDP04|
COMMENT      VNTAUTHORNAME|dlpetri|
COMMENT      Vector_NTI_Display_Data_(Do_Not_Edit!)
COMMENT      (SXF FEATURES             Location/Qualifiers
     misc_marker     complement(8611..9402)

/vntifkey="22"
                     /label=NPTIII
     misc_marker     complement(7164..8309)
                     /vntifkey="22"
                     /label=trfA
     misc_signal     6685..6709
                     /vntifkey="87"
                     /label=LB
     terminator      4318..4963
                     /vntifkey="43"
                     /label=E9
     CDS             5730..6059
                     /vntifkey="4"
                     /label=barstar
     terminator      6065..6332
                     /vntifkey="43"
                     /label=NOS-T
                     /note="Added BamHI and XhoI sites to 3' end"
     promoter        4964..5729
                     /vntifkey="29"
                     /label=LPAG1d4
     CDS             3522..4317
                     /vntifkey="4"
                     /label=NPTII
     misc_signal     4314..4316
                     /vntifkey="87"
                     /label=TGA
     promoter        2212..3521
                     /vntifkey="29"
                     /label=UBQ10\promoter
     intron          3218..3521
                     /vntifkey="15"
                     /label=INTRON
     misc_signal     1..25
                     /vntifkey="87"
                     /label=RB
                     /note="Right Border of T-DNA"
     misc_signal     1474..1476
                     /vntifkey="87"
                     /label=ATG
                     /note="ATG of Barnase E73G"
     CDS             1474..1912
                     /vntifkey="4"
                     /label=Barnase\F106S
     terminator      1920..2178
                     /vntifkey="43"
                     /label=NOS-T
     promoter        82..1473
                     /vntifkey="29"

/label=LPAG1-P
                     /note="LPAG1 promoter- still determining exact location of 5'
end"
BASE COUNT    2629 a    2468 c    2321 g    2894 t
ORIGIN
        1 gtttacccgc caatatatcc tgtcaaacac tgatagttta aacttttaat taaggtacct
       61 gcaggagccc gggctctcga gcagcaaata tgatttagat tatgacctag aaataagcat
```

Figure 9B

```
 121 agcattaaag catatacaaa acaagcggtg atatactctg actgccactg tacttgagga
 181 aaggtagtgg actctgctca ggtacattag tttggtaagg ttggcttggc ttctgggtaa 241 tatgagaagt aaagaagtaa aaggtatttg actctagtca agtacattgg attgccttcg
 301 tcggggcttg gatggcttgg gttcgtgtga gaagccaaca atttataaaa aaatatattg
 361 aaaaaaaaaa aaatcgtcta agtgttggaa gtgaaaacgg tgggacataa atatacacag
 421 aagagtactt taacaatgcg caaccaaggc agattcacaa cttgatttct ggacctcgaa
 481 tacgagataa tggtggtaag aaataaagga agagtggagt gcatttgaaa atgaatggag
 541 agcgcacaaa atggaggacg aataaatgaa atataatgca agagtgcatt tccctattat
 601 ttccagaaat gtatatgtgg ggtcggcatt cacatgggcg tcgcattcag ggggtgtcat
 661 agcggtcctt tgattgcagt gtgggagttg caacatgtac caacaaattc attcatccca
 721 aaacctaaat ttatcctctc cattactatt acctacacct atacctagta aatatgtcct
 781 gccttgtaac tcctccactg cctgcacacg tcttagtcaa tccatctgcc ttcaaatagg
 841 cattattttg ttctttcccc tccgactgaa aggctatcga ccgaccgacc gctcatcttc
 901 ttcttctgcg caattttttc tgctggatca tcatcattac catcatcgcc atccccacca
 961 tcatcatcat gatggtatct ctatctctcc ctggcaatcg attgtagagg aaaggaagag
1021 ggaagggca tatgtattga tcaacctacc cgaaaaaaca atctgatcag ccctgctaat
1081 cttgcttata aatctcttat ccactgttca atcattcagg tttcttccca cttccaagca
1141 aaggcgcccg gattggccgt gttcttagat tttcaggtac ttaaatggac aatattcccc
1201 acctgaagcc gttctgaaaa agatttgttt gtagaaacaa acgattgtaa tatttgctta
1261 agttgagctt aaggggtttg gtacctaact tgccttgtgg ttatttgttt ctcagaactc
1321 gggctgcgtc caactgtagg aacgaaccag cacaagggt tgcagctttt gctgttgctg
1381 ttgcgcccat tgcttttgga ctggtattag tagttgcagc tttgttttgc atacgctgtg
1441 aggatctgtg cgcggaaatt ttgtgtacaa atcatggcac aggttatcaa cacgtttgac
1501 ggggttgcgg attatcttca gacatatcat aagctacctg ataattacat tacaaaatca
1561 gaagcacaag ccctcggctg ggtggcatca aaagggaacc ttgcagacgt cgctccgggg
1621 aaaagcatcg gcggagacat cttctcaaac agggaaggca aactcccggg caaaagcgga
1681 cgaacatggc gtgaagcgga tattaactat acatcaggct tcagaaattc agaccggatt
1741 ctttactcaa gcgactggct gatttacaaa acaacgaacc attatcagac ctctacaaaa
1801 atcagataac gaaaaaaacg gcttccctgc gggaggccgt ttttttcagc tttacataaa
1861 gtgtgtaata aatttttctt caaactctga tcggtcaatt gcactttgag ctcgaatttc
1921 cccgatcgtt caaacatttg gcaataaagt ttcttaagat tgaatcctgt tgccggtctt
1981 gcgatgatta tcatataatt tctgttgaat tacgttaagc atgtaataat taacatgtaa
2041 tgcatgacgt tatttatgag atgggttttt atgattagag tcccgcaatt atacatttaa
2101 tacgcgatag aaaacaaaat atagcgcgca aactaggata aattatcgcg cgcggtgtca
2161 tctatgttac tagatcggga aggcgcgccg cggccgcttg gcgcgccgtc aacggatcag
2221 gatatccttg tttaagatgt tgaactctat ggaggtttgt atgaactgat gatctaggac
2281 cggataagtt cccttcttca tagcgaactt attcaaagaa tgttttgtgt atcattcttg
2341 ttacattgtt attaatgaaa aaatattatt ggtcattgga ctgaacacga gtgttaaata
2401 tggaccaggc cccaaataag atccattgat atatgaatta aataacaaga ataaatcgag
2461 tcaccaaacc acttgccttt tttaacgaga cttgttcacc aacttgatac aaaagtcatt
2521 atcctatgca aatcaataat catacaaaaa tatccaataa cactaaaaaa ttaaaagaaa
2581 tggataattt cacaatatgt tatacgataa agaagttact tttccaagaa attcactgat
2641 tttataagcc cacttgcatt agataaatgg caaaaaaaaa caaaaaggaa aagaaataaa
2701 gcacgaagaa ttctagaaaa tacgaaatac gcttcaatgc agtgggacc acggttcaat
2761 tattgccaat tttcagctcc accgtatatt taaaaaataa aacgataatg ctaaaaaaat
2821 ataaatcgta acgatcgtta aatctcaacg gctggatctt atgacgaccg ttagaaattg
2881 tggttgtcga cgagtcagta ataaacggcg tcaaagtggt tgcagccggc acacacgagt
2941 cgtgtttatc aactcaaagc acaaatactt ttcctcaacc taaaaataag gcaattagcc
3001 aaaaacaact ttgcgtgtaa acaacgctca atacacgtgt cattttatta ttagctattg
3061 cttcaccgcc ttagctttct cgtgacctag tcgtcctcgt ctttttcttct tcttcttcta
3121 taaaacaata cccaaagaac tcttcttctt cacaattcag atttcaattt ctcaaaatct
3181 taaaaacttt ctctcaattc tctctaccgt gatcaaggta aatttctgtg ttccttattc
3241 tctcaaaatc ttcgattttg ttttcgttcg atcccaattt cgtatatgtt ctttggttta
3301 gattctgtta atcttagatc gaagacgatt ttctgggttt gatcgttaga tatcatctta
3361 attctcgatt agggtttcat aaatatcatc cgatttgttc aaataatttg agttttgtcg
3421 aataattact cttcgatttg tgatttctat ctagatctgg tgttagtttc tagtttgtgc
3481 gatcgaattt gtcgattaat ctgagttttt ctgattaaca gatgattgaa caagatggat
3541 tgcacgcagg ttctccggcc gcttgggtgg agaggctatt cggctatgac tgggcacaac
3601 agacaatcgg ctgctctgat gccgccgtgt tccggctgtc agcgcagggg cgcccggttc
3661 ttttttgtcaa gaccgacctg tccggtgccc tgaatgaact ccaggacgag gcagcgcggc
3721 tatcgtggct ggccacgacg ggcgttcctt gcgcagctgt gctcgacgtt gtcactgaag
3781 cgggaaggga ctggctgcta ttgggcgaag tgccggggca ggatctcctg tcatctcacc
3841 ttgctcctgc cgagaaagta tccatcatgg ctgatgcaat gcggcggctg catacgcttg
3901 atccggctac ctgcccattc gaccaccaag cgaaacatcg catcgagcga gcacgtactc
3961 ggatggaagc cggtcttgtc gatcaggatg atctggacga agagcatcag ggctcgcgc
4021 cagccgaact gttcgccagg ctcaaggcgc gcatgcccga cggcgaggat ctcgtcgtga
4081 cccatggcga tgcctgcttg ccgaatatca tggtggaaaa tggccgcttt tctggattca
4141 tcgactgtgg ccggctgggt gtggcggacc gctatcagga catagcgttg gctacccgtg
4201 atattgctga gagcttggcg gcgaatggg ctgaccgctt cctcgtgctt tacggtatcg
4261 ccgctcccga ttcgcagcgc atcgccttct atcgccttct tgacgagttc ttctgagaat
4321 tcagctttcg ttcgtatcat cggtttcgac aacgttcgtc aagttcaatg catcagtttc 4381 attgcgcaca caccagaatc ctactgagtt cgagtattat ggcattggga aaactgtttt
```

Figure 9C

```
4441 tcttgtacca tttgttgtgc ttgtaattta ctgtgttttt tattcggttt tcgctatcga
4501 actgtgaaat ggaaatggat ggagaagagt taatgaatga tatggtcctt ttgttcattc
4561 tcaaattaat attatttgtt ttttctctta tttgttgtgt gttgaatttg aaattataag
4621 agatatgcaa acattttgtt ttgagtaaaa atgtgtcaaa tcgtggcctc taatgaccga
4681 agttaatatg aggagtaaaa cacttgtagt tgtaccatta tgcttattca ctaggcaaca
4741 aatatatttt cagacctaga aaagctgcaa atgttactga atacaagtat gtcctcttgt
4801 gttttagaca tttatgaact ttcctttatg taattttcca gaatccttgt cagattctaa
4861 tcattgcttt ataattatag ttatactcat ggatttgtag ttgagtatga aaatattttt
4921 taatgcattt tatgacttgc caattgattg acaacgcaag cttttcattc atcccaaaac
4981 ctaaatttat cctctccatt actattacct acacctatac ctagtaaata tgtcctgcct
5041 tgtaactcct ccactgcctg cacacgtctt agtcaatcca tctgccttca aataggcatt
5101 attttgttct ttcccctccg actgaaaggc tatcgaccga ccgaccgctc atcttcttct
5161 tctgcgcaat ttttctgct ggatcatcat cattaccatc atcgccatcc ccaccatcat
5221 catcatgatg gtatctctat ctctccctgg caatcgattg tagaggaaag gaagagggaa
5281 ggggcatatg tattgatcaa cctacccgaa aaacaatct gatcagccct gctaatcttg
5341 cttataaatc tcttatccac tgttcaatca ttcaggtttc ttcccacttc caagcaaagg
5401 cgcccggatt ggccgtgttc ttagattttc aggtacttaa atggacaata ttccccacct
5461 gaagccgttc tgaaaaagat ttgtttgtag aaacaaacga ttgtaatatt tgcttaagtt
5521 gagcttaagg ggtttggtac ctaacttgcc ttgtggttat ttgtttctca gaactcgggc
5581 tgcgtccaac tgtaggaacg aaccagcaca aggggttgca gcttttgctg ttgctgttgc
5641 gcccattgct tttggactgg tattagtagt tgcagctttg ttttgcatac gctgtgagga
5701 tctgtgcgcg gaaattttgt gtacaaatca tgaaaaaagc agtcattaac ggggaacaaa
5761 tcagaagtat cagcgacctc caccagacat tgaaaaagga gcttgcccct ccggaatact
5821 acggtgaaaa cctgacgct ttatgggatt gtctgaccgg atgggtggag tacccgctcg
5881 ttttggaatg gaggcagttt gaacaaagca agcagctgac tgaaaatggc gccgagagtg
5941 tgcttcaggt tttccgtgaa gcgaaagcgg aaggctgcga catccaccatc atactttctt
6001 aatacgatca atgggagatg aacaatatgg aaacacaaac cacaattatg tctctcagcg
6061 agctcgaatt tccccgatcg ttcaaacatt tggcaataaa gttcttaag attgaatcct
6121 gttgccggtc ttgcgatgat tatcatataa tttctgttga attacgttaa gcatgtaata
6181 attaacatgt aatgcatgac gttatttatg agatgggttt ttatgattag agtcccgcaa
6241 ttatacattt aatacgcgat agaaaacaaa atatagcgcg caaactagga taaattatcg
6301 cgcgcggtgt catctatgtt actagatcgg ggatccacta gttctagagc ggcgtgggcc
6361 atcgccctga tagacggttt ttcgcccttt gacgttggag tccacgttct ttaatagtgg
6421 actcttgttc caaactggaa caacactcaa ccctatctcg ggctattctt ttgatttata
6481 agggattttg ccgatttcgg aaccaccatc aaacaggatt ttcgcctgct ggggcaaacc 6541 agcgtggacc gcttgctgca actctctcag ggccaggcgg tgaagggcaa tcagctgttg
6601 cccgtctcac tggtgaaaag aaaaaccacc ccagtacatt aaaaacgtcc gcaatgtgtt
6661 attaagttgt ctaagcgtca atttgtttac accacaatat atcctgccac cagccagcca
6721 acagctcccc gaccggcagc tcggcacaaa atcaccactc gatacaggca gccccatcagt
6781 ccgggacggc gtcagcggga gagccgttgt aaggcggcag actttgctca tgttaccgat
6841 gctattcgga agaacggcaa ctaagctgcc gggtttgaaa cacggatgat ctcgcggagg
6901 gtagcatgtt gattgtaacg atgacagagc gttgctgcct gtgatcaaat atcatctccc
6961 tgcagagat ccgaattatc agccttctta ttcatttctc gcttaaccgt gacagttgtc
7021 tatcggcagt tcgtagagcg cgccgtgcgt cccgagcgat actgagcgaa gcaagtgcgt
7081 cgagcagtgc ccgcttgttc ctgaaatgcc agtaaagcgc tggctgctga accccagcc
7141 ggaactgacc ccacaaggcc ctagcgtttg caatgcacca ggtcatcatt gacccaggcg
7201 tgttccacca ggccgctgcc tcgcaactct cgcgactctt cgccgacctg ctcgcgccac
7261 ttcttcacgc gggtggaatc cgatccgcac atgaggcgga aggtttccag cttgagcggg
7321 tacggctccc ggtgcgagct gaaatagtcg aacatccgtc gggccgtcgg cgacagcttg
7381 cggtacttct cccatatgaa tttcgtgtag tggtcgccag caaacagcac gacgatttcc
7441 tcgtcgatca ggacctggca acgggacgtt ttcttgccac ggtccaggac gcggaagcgg
7501 tgcagcagcg acaccgattc caggtgccca acgcggtcgg acgtgaagcc catcgccgtc
7561 gcctgtaggc gcgacaggca ttcctcggcc ttcgtgtaat accggccatt gatcgaccag
7621 cccaggtcct ggcaaagctc gtagaacgtg aaggtgatcg gctcgccgat aggggtgcgc
7681 ttcgcgtact ccaacacctg ctgccacacc agttcgtcat cgtcggccga cagctcgacg
7741 ccggtgtagg tgatcttcac gtccttgttg acgtggaaaa tgaccttgtt ttgcagcgcc
7801 tcgcgcggga ttttcttgtt gcgcgtggtg aacagggcag agcgggccgt gtcgtttggc
7861 atcgctcgca tcgtgtccgg ccacggcgca atatcgaaca aggaaagctg catttccttg
7921 atctgctgct tcgtgtgttt cagcaacgcg gcctgcttgg cctcgctgac ctgttttgcc
7981 aggtcctcgc cggcggtttt tcgcttcttg gtcgtcatag ttcctcgcgt gtcgatggtc
8041 atcgacttcg ccaaacctgc cgcctcctgt tcgagacgac gcgaacgctc cacggcggcc
8101 gatggcgcgg gcagggcagg gggagccagt tgcacgctgt cgcgctcgat cttggccgta
8161 gcttgctgga ccatcgagcc gacggactgg aagtttcgc ggggcgcacg catgacggtg
8221 cggcttgcga tggtttcggc atcctcggcg gaaaaccccg cgtcgatcag ttcttgcctg
8281 tatgccttcc ggtcaaacgt ccgattcatt caccctcctt gcgggattgc ccgactcac
8341 gccggggcaa tgtgccctta ttcctgattt gacccgcctg gtgccttggt gtccagataa
8401 tccaccttat cggcaatgaa gtcggtccg tagaccgtct ggccgtcctt ctcgtacttg
8461 gtattccgaa tcttgccctg cacgaatacc agcgaccct tgcccaaata cttgccgtgg
8521 gcctcggcct gagagccaaa acacttgatg cggaagaagt cggtgcgctc ctgcttgtcg
8581 ccggcatcgt tgcgccacat ctaggtacta aaacaattca tccagtaaaa tataatatttt
8641 tattttctcc caatcaggct tgatcccag taagtcaaaa aatagctcga catactgttc
8701 ttccccgata tcctccctga tcgaccggac gcagaaggca atgtcatacc acttgtccgc
8761 cctgccgctt ctcccaagat caataaagcc acttactttg ccatctttca caaagatgtt
```

Figure 9D

```
 8821 gctgtctccc aggtcgccgt gggaaaagac aagttcctct tcgggctttt ccgtctttaa
 8881 aaaatcatac agctcgcgcg gatctttaaa tggagtgtct tcttcccagt tttcgcaatc
 8941 cacatcggcc agatcgttat tcagtaagta atccaattcg gctaagcggc tgtctaagct
 9001 attcgtatag ggacaatccg atatgtcgat ggagtgaaag agcctgatgc actccgcata
 9061 cagctcgata atctttcag ggctttgttc atcttcatac tcttccgagc aaaggacgcc
 9121 atcggcctca ctcatgagca gattgctcca gccatcatgc cgttcaaagt gcaggacctt
 9181 tggaacaggc agctttcctt ccagccatag catcatgtcc ttttcccgtt ccacatcata
 9241 ggtggtccct ttataccggc tgtccgtcat ttttaaatat aggttttcat tttctcccac
 9301 cagcttatat accttagcag gagacattcc ttccgtatct tttacgcagc ggtattttc
 9361 gatcagtttt ttcaattccg gtgatattct cattttagcc atttattatt tccttcctct
 9421 tttctacagt atttaaagat accccaagaa gctaattata acaagacgaa ctccaattca
 9481 ctgttccttg cattctaaaa ccttaaatac cagaaaacag cttttcaaa gttgttttca
 9541 aagttggcgt ataacatagt atcgacggag ccgattttga aaccacaatt atggactgcc
 9601 agcgctgcca tttttggggt gaggccgttc gcggccgagg ggcgcagccc ctgggggat
 9661 gggaggcccg cgttagcggg ccgggagggt tcgagaaggg ggggcacccc ccttcggcgt
 9721 gcgcggtcac gcgcacaggg cgcagccctg gttaaaaaca aggtttataa atattggttt
 9781 aaaagcaggt taaaagacag gttagcggtg gccgaaaaac gggcggaaac ccttgcaaat
 9841 gctggatttt ctgcctgtgg acagccctc aaatgtcaat aggtgcgccc ctcatctgtc
 9901 agcactctgc ccctcaagtg tcaaggatcg cgccctcat ctgtcagtag tcgcgcccct
 9961 caagtgtcaa taccgcaggg cacttatccc caggcttgtc cacatcatct gtgggaaact
10021 cgcgtaaaat caggcgtttt cgccgatttg cgaggctggc cagctccacg tcgccggccg
10081 aaatcgagcc tgccctcat ctgtcaacgc cgcgccgggt gagtcggccc ctcaagtgtc
10141 aacgtccgcc cctcatctgt cagtgagggc caagttttcc gcgaggtatc cacaacgccg
10201 gcggatctgg ggaaccctgt ggttggcatg cacatacaaa tggacgaacg gataaaccctt
10261 ttcacgccct tttaaatatc cgattattct aataaacgct cttttctctt ag
//
```

REPRODUCTIVE ABLATION CONSTRUCTS

FIELD OF INVENTION

The present invention relates to the regulation of reproductive development. In particular, this invention relates to the genetic ablation of reproductive tissues in angiosperm and gymnosperm species. Reproductive-preferred promoters, regulatory elements, and cytotoxic nucleotide sequences are provided. Constructs and methods for genetic ablation are also included in the invention.

BACKGROUND OF THE INVENTION

With the advent of plant genetic engineering technology, the ecological implications of genetically modified crops are of great concern, particularly when there are no inherent barriers to the spread of transgenes through sexual reproduction. Specifically, concerns have arisen in cases when transgenes can spread from a transgenic plant to a weedy species through hybridization, or when the crop species itself exists in weedy forms. Bergelson et al. *Nature* 395: 25 (1998). One way to address such concerns is by genetically engineering sterility in a plant through complete ablation of reproductive structures.

Recently, there has been significant interest in using an ablation system for controlling reproductive development in plants. Reproductive control has been achieved in several plant species by genetic ablation, which entails linking a reproductive-preferred promoter with a cytotoxic gene to ablate reproductive cells. For example, barnase, an extracellular ribonuclease from *Bacillus amyloliquifaciens* has been employed for inducing male sterility. Paddon et al. *J. Bacteriol.* 171:1185-1187 (1989). European Patent No. 344,029 describes a system for producing a male sterile plant by transforming a plant with a DNA encoding barnase under the control of a tapetum-specific promoter. Transformation of tobacco and oilseed rape plants with such a promoter-gene construct prevented the plants from producing fertile pollen. Mariani et al., *Nature* 347: 737-741(1990). Flowers of transgenic *Arabidopsis thaliana* plants expressing a fusion construct of the APETALA3 (AP3) promoter and the diphtheria toxin A chain (DTA) gene lack petals and stamens, suggesting that transgene expression ablated petal and stamen cells. Transgenic *Arabidopsis* expressing the DTA gene under control of the LEAFY promoter produced no flowers. Tobacco plants transformed with a tobacco stigma-specific promoter driving the barnase gene lacked the stigmatic secretory zone and were female sterile.

Although genetic ablation has been effective, the promoters generally used for ablation are not well-suited for tissue-specific expression. As a consequence, leaky gene expression can significantly reduce and damage plant vegetative growth. Depending on the plant species, ablation can reduce vegetative growth by 80%. Strauss, S. H. and Meilan, R. TGERC Annual Report (1998). For genetic ablation to be commercially useful in the forestry industry, the amount of damage to vegetative tissues must be minimized to nominal levels.

While numerous patents and patent application publications disclose genetic ablation using a variety of promoters and cytotoxic genes, there is little disclosure addressing the effects of ablation on a plant's vegetative growth and development. The LFY promoter from *Arabidopsis*, which is expressed strongly in floral meristems and weakly in developing leaves, has been used for producing plants with ablated flowers. Nilsson et al., *Plant J.* 15:799-804 (1998). However, very few plants transformed with LFY had ablated flowers and uncompromised vegetative development. Therefore, it would be impractical to use a similar approach for reproductive ablation in a tree species, since it would take years to produce, grow, and test many transgenic trees to identify those few trees that have sterility and normal vegetative growth.

The genetic ablation of a reproductive organ requires a delicate balance between promoter activity and ablation gene toxicity. While the barnase gene is widely used for ablation in plants, barnase-induced toxicity frequently causes detrimental effects on plant growth and development. Thus, it may be desirable to reduce the toxicity of barnase, such that reproductive ablation occurs without deleterious and unrecoverable damages to a plant's vegetative growth.

Concurrent with the production of a mutant barnase having reduced toxicity, it may also be desirable to minimize leaky expression of a reproductive ablation construct in a plant's vegetative tissues. By minimizing leaky or ectopic expression of a reproductive ablation construct in a plant, expression of a mutant barnase gene in the vegetative tissues may be better tolerated by the plant due to attenuated ablation, which depends on promoter activity and RNase activity of a barnase mutant.

Accordingly, there exists a need for a reproductive ablation system having reduced barnase-induced toxicity and minimal leaky expression in a plant's vegetative tissues.

SUMMARY OF THE INVENTION

The present invention provides an isolated polynucleotide selected from the group consisting of SEQ ID NOs: 1-8 and 13-17, as well as a plasmid comprising the sequence depicted in any one of SEQ ID NOs. 18-27.

The present invention also provides a plasmid comprising the sequence depicted in any one of FIG. 1 (i.e., SEQ ID NO. 18), FIG. 2 (i.e., SEQ ID NO. 19), FIG. 3 (i.e., SEQ ID NO. 20), FIG. 4 (i.e., SEQ ID NO. 21), FIG. 5 (i.e., SEQ ID NO. 22), FIG. 6 (i.e., SEQ ID NO. 23), FIG. 7 (i.e., SEQ ID NO. 24), FIG. 8 (i.e., SEQ ID NO. 25), FIG. 9 (i.e., SEQ ID NO. 26), or FIG. 19.

Also provided is an isolated polynucleotide that confers reproductive-preferred gene expression in a plant cell, wherein the polynucleotide comprises the sequence depicted in any one of SEQ ID NOs. 1, 2, 3, 4, or 16.

In one embodiment, the polynucleotide confers male-preferred gene expression in a plant cell.

Also provided is a promoter comprising the sequence depicted in any one of SEQ ID NOs. 1, 2, 3, 4, or 16.

In one embodiment, the polynucleotide of SEQ ID NOs. 1-8 is expressed or is active in a pre-male or pre-female reproductive structure.

Also provided is an isolated polynucleotide that has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to any one of SEQ ID NOs: 1, 2, 3, 4, or 16.

In another embodiment, a polynucleotide is provided that has a sequence selected from the group consisting of (i) sequences that are complementary to a polynucleotide of any one of SEQ ID NOs. 1-8 and 16-17, (ii) sequences that are reverse sequences of a polynucleotide of any one of SEQ ID NOs. 1-8 and 16-17, and (iii) sequences that are reverse complements of a polynucleotide of any one of SEQ ID NOs. 1-8 and 16-17.

Also provided is an isolated polynucleotide that hybridizes under stringent conditions to a polynucleotide of claim 1, wherein said isolated polynucleotide hybridizes over its fulllength sequence to a polynucleotide of any of one of SEQ ID NOs. 1-26.

Also provided is an isolated polynucleotide comprising the sequence depicted in SEQ ID NO. 17.

In one embodiment, a polynucleotide is provided that has the sequence of any one of SEQ ID NOs. 1-4 and 16 which is capable of at least one of (i) binding to a nucleic acid molecule or (ii) regulating expression of an operably-linked gene in a dicotyledonous plant.

In another embodiment, a polynucleotide is provided that has the sequence of any one of SEQ ID NOs. 1-4 and 16 which is capable of at least one of (i) binding to a nucleic acid molecule or (ii) regulating expression of an operably-linked gene in a gymnosperm.

In one embodiment, a polynucleotide is provided that has the sequence of any one of SEQ ID NOs. 1-4 and 16 which is capable of upregulating or downregulating the expression of an operably-linked gene in a plant.

In one aspect of the present invention, a construct is provided that comprises an isolated polynucleotide selected from any one of SEQ ID NO: 1, 2, 3, 4, or 16 and functional variants thereof operably linked to a desired nucleic acid, wherein said promoter regulates the expression of said desired nucleic acid in a plant cell transformed with the construct. In one embodiment, the polynucleotide upregulates or downregulates expression of said desired nucleic acid. In another embodiment, the desired nucleic acid encodes an expression product that is capable of disrupting reproductive development in a plant.

The present invention provides a plant transformed with any of the constructs disclosed herein. In one embodiment, the phenotype of such a transformed plant expresses a difference in reproductive development compared with a plant of the same species that is not transformed with said construct. In one embodiment, the difference in reproductive development occurs in a male reproductive structure. In another embodiment, the difference in reproductive development occurs in any one of anther, filament, tapetum, pollen, microsporophyll, or staminate cone. In an alternative embodiment, the difference in reproductive development occurs in a female reproductive structure. In that case, in one embodiment, the difference in reproductive development occurs in any one of stigma, style, ovary, megaspore, ovuliferous cone. In yet another embodiment, the difference in reproductive development occurs in a pre-male or pre-female reproductive structure.

In one aspect, a desired nucleic acid may produce an RNA transcript, which, in one embodiment, may comprise an antisense sequence of a gene that is endogenous to the plant cell. In one embodiment, the RNA transcript induces RNA interference of a gene that is normally expressed in the plant cell.

Also provided is a plant cell comprising a construct comprising (i) a polynucleotide having the sequence of any one of SEQ ID NOs: 1, 2, 3, 4, or 16 or functional variants thereof and (ii) a desired nucleic acid, wherein said polynucleotide is operably linked to said desired nucleic acid. A transgenic plant comprising such a plant cell is also provided.

In one aspect, the present invention provides a method for producing a transgenic plant, comprising (a) transforming a plant cell with a construct that comprises (i) at least one polynucleotide having the sequence of any one of SEQ ID NOs. 1, 2, 3, 4, or 16 or functional variants thereof and (ii) a desired nucleic acid, wherein said polynucleotide regulates the activity of said desired sequence; (b) culturing said transformed plant cell under conditions that promote growth of a plant, wherein said plant is a transgenic plant that exhibits a phenotype that is different from a plant of the same species that does not contain said construct.

In one embodiment, the phenotype of the transformed plant is characterized by a difference in reproductive development compared with a plant of the same species that does not contain the construct. In another embodiment, the phenotype of the transformed plant is characterized by a difference in male reproductive development compared with a plant of the same species that does not contain the construct. Alternatively, the phenotype of the transformed plant is characterized by a difference in female reproductive development compared with a plant of the same species that does not contain the construct. In yet another embodiment, the phenotype of the transformed plant is characterized by a difference in a pre-male or pre-female reproductive structure compared with a plant of the same species that does not contain the construct.

In another aspect, a method for conferring reproductive sterility in a plant is provided, comprising (a) introducing into a plant cell a construct comprising (i) a promoter having the sequence of any one of SEQ ID NOs: 1, 2, 3, 4, or 16 or functional variants thereof and (ii) a nucleic acid encoding a gene that is capable of ablating reproductive development, wherein said nucleic acid is sense relative to said promoter and wherein said promoter regulates the expression of said gene; (b) culturing said transformed plant cell under conditions that promote growth of a plant, wherein said plant is a transgenic plant that exhibits a phenotype that is different from a plant of the same species that does not contain said construct; and (c) selecting a plant that is reproductive-sterile.

In another aspect is a method for ablating a reproductive structure in a plant, comprising (a) introducing into a plant cell a construct comprising (i) a promoter having the sequence of any one of SEQ ID NOs: 1, 2, 3, 4, or 16 or functional variants thereof and (ii) a nucleic acid encoding a gene that is capable of ablating reproductive development, wherein said promoter regulates the expression of said gene; (b) culturing said transformed plant cell under conditions that promote growth of a plant, wherein said plant is a transgenic plant that exhibits a phenotype that is different from a plant of the same species that does not contain said construct; and (c) selecting a plant having an ablated reproductive structure. In one embodiment, the plant is selected from an angiosperm or gymnosperm species.

Also provided is a method for altering pollen fertility, comprising (a) introducing into a plant cell of a woody plant a construct comprising (i) a promoter having the sequence of any one of SEQ ID NOs: 1, 2, 3, 4, or 16 or functional variants thereof and (ii) and a desired nucleic acid, wherein said promoter regulates the expression of said desired nucleic acid; (b) culturing said transformed plant cell under conditions that promote growth of a plant; and (c) obtaining a plant having altered pollen fertility. In one embodiment, the woody plant is selected from a species of *Eucalyptus* or *Pinus*.

Also provided herein is an isolated polynucleotide selected from any one of SEQ ID NO: 5-8 and variants thereof. In one embodiment, any one of these polynucleotides encods a mutant barnase enzyme. In one embodiment, such a polynucleotide encodes a mutant barnase enzyme having attenuated activity compared with a wild-type barnase enzyme. In one embodiment, the variant has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to any one of SEQ ID NOs: 5-8.

Also provided is an isolated polynucleotide having a sequence selected from (i) sequences that are complementary to a polynucleotide of any one of SEQ ID NOs: 5-8, (ii) sequences that are reverse sequences of a polynucleotide of any one of SEQ ID NOs: 5-8, and (iii) sequences that are reverse complements of a polynucleotide of any one of SEQ ID NOs: 5-8.

In another embodiment, an isolated polynucleotide that hybridizes under stringent conditions to a polynucleotide of any one of SEQ ID NOs: 5-8, wherein the isolated polynucleotide hybridizes over its full-length sequence to a polynucleotide of any one of SEQ ID NO: 5-8.

In another aspect, a method for conferring reproductive sterility in a plant without disturbing vegetative growth is provided, comprising (a) introducing into a plant cell a construct comprising (i) a promoter having reproductive-preferred activity; (ii) a nucleic acid encoding a gene that is capable of ablating reproductive development, wherein said promoter regulates the expression of said gene; (b) culturing said transformed plant cell under conditions that promote growth of a plant, wherein said plant is a transgenic plant that exhibits a phenotype that is different from a plant of the same species that does not contain said construct; and (c) selecting a plant having reproductive-sterility and undisturbed vegetative growth.

Also provided is a method for ablating reproductive development in a plant without disturbing vegetative growth, comprising (a) introducing into a plant cell a construct comprising (i) a promoter having the sequence of any one of SEQ ID NOs: 1, 2, 3, 4, or 16 or functional variants thereof; (ii) a nucleic acid encoding a gene that is capable of ablating reproductive development, wherein said promoter regulates the expression of said gene; (b) culturing said transformed plant cell under conditions that promote growth of a plant, wherein said plant is a transgenic plant that exhibits a phenotype that is different from a plant of the same species that does not contain said construct; and (c) selecting a plant having ablated reproductive development and undisturbed vegetative growth.

Also provided is a method for conferring male-sterility in a plant without disturbing vegetative growth, comprising (a) introducing into a plant cell a construct comprising (i) a promoter having reproductive-preferred expression; (ii) a nucleic acid encoding a mutant barnase, wherein said mutant barnase has attenuated activity compared with wild-type barnase; (b) culturing said transformed plant cell under conditions that promote growth of a plant, wherein said plant is a transgenic plant that exhibits a reproductive phenotype that is different from a plant of the same species that does not contain said construct; and (c) selecting a plant having male-sterility and undisturbed vegetative growth. In one embodiment, the promoter has a sequence selected from the group consisting of SEQ ID NOs: 1, 2, 3, 4, and 16. In another embodiment, the promoter is a functional variant of any one of the sequences selected from the group consisting of SEQ ID NOs: 1, 2, 3, 4, and 16.

In one embodiment, the nucleic acid of (ii) above has the sequence of any of one of SEQ ID NOs: 5-8.

The present invention also provides in one embodiment, a plant having ablated reproductive development and unaffected vegetative growth.

The present invention also provides in another embodiment, a woody plant having ablated reproductive development and normal vegetative growth.

In a further aspect, a method for obtaining wood is provided, comprising (a) introducing into a plant cell of a woody plant a construct comprising (i) a promoter having the sequence of any one of SEQ ID NOs: 1, 2, 3, 4, or 16 or functional variants thereof and (ii) and a desired nucleic acid, wherein said promoter regulates the expression of said desired nucleic acid; (b) culturing said transformed plant cell under conditions that promote growth of a plant; and (c) obtaining wood from said plant.

In another aspect is a method for obtaining wood pulp, comprising (a) introducing into a plant cell of a woody plant a construct comprising (i) a promoter having the sequence of any one of SEQ ID NOs: 1, 2, 3, 4, or 16 or functional variants thereof and (ii) and a desired nucleic acid, wherein said promoter regulates the expression of said desired nucleic acid; (b) culturing said transformed plant cell under conditions that promote growth of a plant; and (c) obtaining wood pulp from said plant.

Also provided is a method for ablating a reproductive structure in a plant, comprising (a) introducing into a plant cell a plasmid selected from the group consisting of SEQ ID NO 13-15; (b) culturing said transformed plant cell under conditions that promote growth of a plant, wherein said plant is a transgenic plant that exhibits a phenotype that is different from a plant of the same species that does not contain said plasmid; and (c) selecting a plant having an ablated reproductive structure. In another embodiment, a plasmid selected from the group consisting of SEQ ID NO 18-26 may be introduced into the plant cell in step (a) above.

Also provided is a method for conferring reproductive sterility in a plant, comprising (a) introducing into a plant cell a plasmid selected from the group consisting of SEQ ID NO 13-15; (b) culturing said transformed plant cell under conditions that promote growth of a plant, wherein said plant is a transgenic plant that exhibits a phenotype that is different from a plant of the same species that does not contain said plasmid; and (c) selecting a plant having an ablated reproductive structure. In another embodiment, a plasmid selected from the group consisting of SEQ ID NO 18-26 may be introduced into the plant cell in step (a) above.

In another embodiment, a plant is provided that is stably transformed with any of the plasmids disclosed herein. In one embodiment the plasmid that is stably introduced into the plant has the sequence of any one of SEQ ID NOs. 13-15 or 18-26.

The present invention also provides a method for conferring reproductive sterility in a transgenic plant, comprising (a) transforming a plant cell with a construct having a reproductive-preferred promoter operably linked to a cytotoxic gene and a non-reproductive-preferred promoter operably linked to a gene encoding a protein that inhibits said cytotoxic gene; wherein said reproductive-preferred promoter is active in an angiosperm or gymnosperm reproductive structure and said non-reproductive-preferred promoter is not active in an angiosperm or gymnosperm reproductive structure; (b) culturing said transformed plant cell under conditions that promote growth of a plant; and (c) selecting a transgenic plant having an ablated reproductive structure. In one embodiment, the reproductive-preferred promoters are selected from the group consisting of SEQ ID NOs: 1, 2, 3, 4, or 16. In another embodiment, the non-reproductive-preferred promoters are selected from the group consisting of SEQ ID NO. 17.

Also provided is a polypeptide comprising the amino acid sequence depicted in any one of SEQ ID NOs.: 9-12 or variant thereof. In one embodiment, the variant of the polypeptide has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to any one of SEQ ID NOs: 9-12.

The present invention also contemplates a construct, comprising a promoter comprising the sequence of either of SEQ ID NOs. 1 or 2 operably linked to a polynucleotide comprising the sequence of any one of SEQ ID NOs 5-8. In one embodiment, the polynucleotide comprises the sequence depicted in SEQ ID NO. 5. In one embodiment, the polynucleotide comprises the sequence depicted in SEQ ID NO. 6. In another embodiment, the polynucleotide comprises the sequence depicted in SEQ ID NO. 7. In another embodiment, the polynucleotide comprises the sequence depicted in SEQ ID NO. 8. Also provided is a plant transformed with this construct.

Also provided is a construct comprising a promoter comprising the sequence of either of SEQ ID NOs. 1 or 2 operably linked to a polynucleotide that encodes a polypeptide comprising the amino acid sequence depicted in any one of SEQ ID NOs. 9-12. Also provided is a plant transformed with this construct.

In one embodiment, one of these constructs may also comprise a non-reproductive preferred promoter operably linked to a barstar gene.

The non-reproductive preferred promoter disclosed herein may comprise the sequence depicted in SEQ ID NO. 17.

Also provided is a method of inducing formation of strobili in *Pinus* comprising (a) obtaining a hybrid progeny plant from the cross of pitch pine *P. rigida* with a loblolly pine *P. taeda*, (b) transforming the hybrid plant with a desired polynucleotide that is operably linked to a reproductive tissue preferred promoter, (c) regenerating a transgenic hybrid plant from the transformed hybrid plant, and (d) recovering strobili. In one embodiment, the reproductive tissue preferred promoter comprises the sequence depicted in any one of SEQ ID NOs. 1, 2, 3, 4, or 16. In another embodiment, the hybrid plant is transformed by *Agrobacterium* or biolistics-mediated transformation. In one embodiment, the strobili are male or female. In another embodiment, the strobili are produced by the transgenic hybrid plant within 1-3 years of transformation.

In another aspect, a method of testing a candidate promoter for activity in a gymnosperm reproductive tissue is provided, comprising (a) obtaining a candidate promoter sequence, (b) operably linking the candidate promoter to a reporter gene, (c) introducing the candidate promoter that is operably linked to the reporter gene into a plant material, and (d) identifying expression of the reporter gene in the plant material. In this method, the reporter gene is GUS. In one embodiment, the plant material is a plant explant or plant cell. In another embodiment, the plant material in which the reporter gene expression is identified is selected from the group consisting of petals, stamens, carpels, shoot tips, anthers, tapetum, callus, and embryo.

The present invention also provides a hybrid progeny plant, comprising a reproductive tissue preferred promoter operably linked to a desired polynucleotide, wherein the hybrid progeny plant is obtained from the cross of pitch pine *P. rigida* with loblolly pine *P. taeda*. In one embodiment, the reproductive tissue preferred promoter comprises the sequence depicted in any one of SEQ ID NOs. 1, 2, 3, 4, or 16. In one embodiment, the desired polynucleotide comprises the sequence depicted in any one of SEQ ID NOs. 5-8. In another embodiment, the desired polynucleotide encodes a polypeptide that comprises the amino acid sequence depicted in any one of SEQ ID NOs. 9-12. Also provided is a hybrid progeny plant transformed with a construct comprising the sequence of any of SEQ ID NOs. 13-15, wherein the hybrid progeny plant is obtained from the cross of pitch pine *P. rigida* with loblolly pine *P. taeda*.

The present invention also provides a method of testing putative flowering control constructs for activity in delaying reproduction in gymnosperms, comprising (i) transforming a somatic embryogenic culture of a hybrid of *P. rigida* and *P. taeda* with a promoter operably linked to a desired polynucleotide, (ii) selecting transgenic cells from the transformed culture, (iii) culturing the transgenic cells to obtain at least one somatic embryo, (iv) germinating the embryo to obtain a transgenic plant, (v) growing the plant, and (vi) examining the plant for formation of strobili. In one embodiment, the promoter is a polynucleotide that is selected for testing promoter activity in a plant reproductive tissue. In another embodiment, the culture is transformed via *Agrobacterium*-mediated- or biolistic transformation. In a further embodiment, the desired polynucleotide is a reporter gene or an ablation construct. In this respect, in one embodiment, the ablation construct has the nucleic acid sequence depicted in any one of SEQ ID NOs. 13-15. In another embodiment, the construct may comprise the sequence depicted in any one of SEQ ID NOs. 18-26. In one embodiment, the plant of step (v) above is grown for 1 to 3 years.

Generally, a desired nucleic acid or desired polynucleotide of the present invention that is operably linked to a promoter or is incorporated into a plasmid or construct disclosed herein may comprise the sequence of any one of SEQ ID NOs. 5-8. In one embodiment, the desired nucleic acid or desired polynucleotide is a mutated barnase gene sequence. In a preferred embodiment, a reproductive-preferred promoter is operably linked to a polynucleotide that promote the genetic ablation of reproductive tissues in angiosperm and gymnosperm species. In a preferred embodiment, the polynucleotide is a mutant barnase gene. In one embodiment, the promoter comprises the sequence depicted in any one of SEQ ID NOs. 1-4 or 16. In another embodiment, the barnase gene has the sequence depicted in any one of SEQ ID NOs. 5-8 or encodes a polypeptide that comprises the sequence depicted in any one of SEQ ID NOs. 9-12. Any construct may comprise such a promoter-desired polynucleotide expression cassette.

BRIEF DESCRIPTION OF THE DRAWINGS

FIG. 1[A-C]—pWVR220 [PrMC2.400::barnaseH102E] (SEQ ID NO. 18)

FIG. 2[A-D]—pWVCZ20 [(AtAGenh)PrAG::GUS(intron)] (SEQ ID NO.19)

FIG. 3[A-C]—pWVCZ23 [PrAG::barnaseE73G] (SEQ ID NO. 20)

FIG. 4[A-D]—pWVCZ24 [(AtAGenh)PrAG::barnaseE73G] (SEQ ID NO. 21)

FIG. 5[A-E]—pARB599B [PrMC2::barnaseH102E] (SEQ ID NO. 22). Short nucleotide sequences disclosed are residues 10431-10442, 10261-10271, 9885-9896, and 9569-9581 of SEO ID NO: 22, respectively in order of appearance.

FIG. 6[A-G]—pARB639B [(AtAGenh)PrAG::barnaseE73G] (SEQ ID NO. 23). Short nucleotide sequences disclosed are residues 9906-9918, 13334-13346, 13650-13661, 14026-14036, and 14196-14207 of SEO ID NO: 23, respectively in order of appearance.

FIG. 7[A-C]—pAGF243 [PrMC2.400-3::barnaseH102E] (SEQ ID NO. 24)

FIG. 8[A-D]—pABDP010 [complementary copy of CZ28-bstar+UBQ10:: NPTII::E9/ LPAG1d4:: bstar::NOST] (SEQ ID NO. 25)

FIG. 9[A-D]—pABDP04 [complementary copy of CZ28-bstar+UBQ10:: NPTII::E9/ LPAG1d4:: bstar::NOST] (SEQ ID NO. 26)

DETAILED DESCRIPTION OF THE EMBODIMENTS

Figure 10:
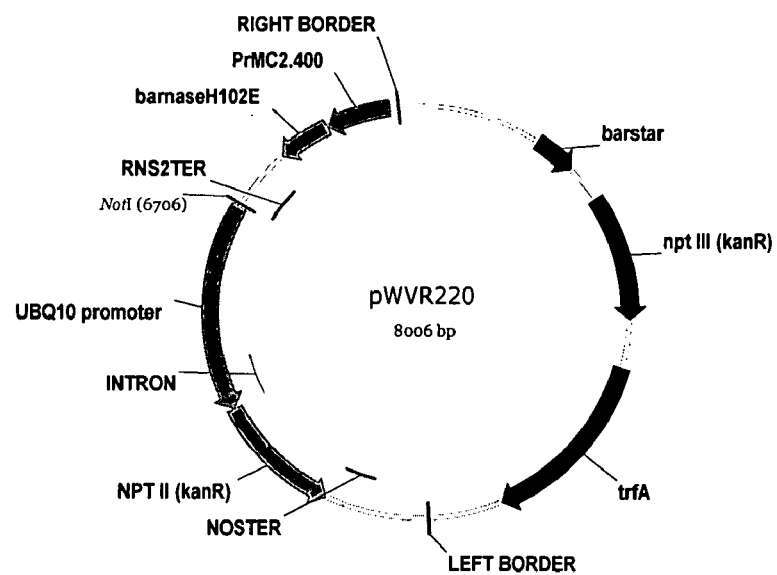
FIG. 10—plasmid map for pWVR220
Figure 11:
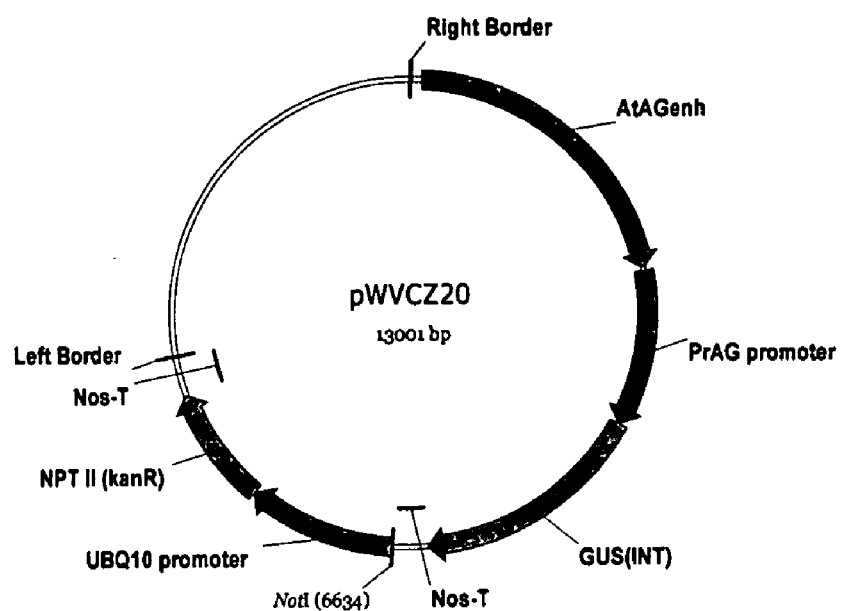
FIG. 11—plasmid map for pWVCZ20
Figure 12:
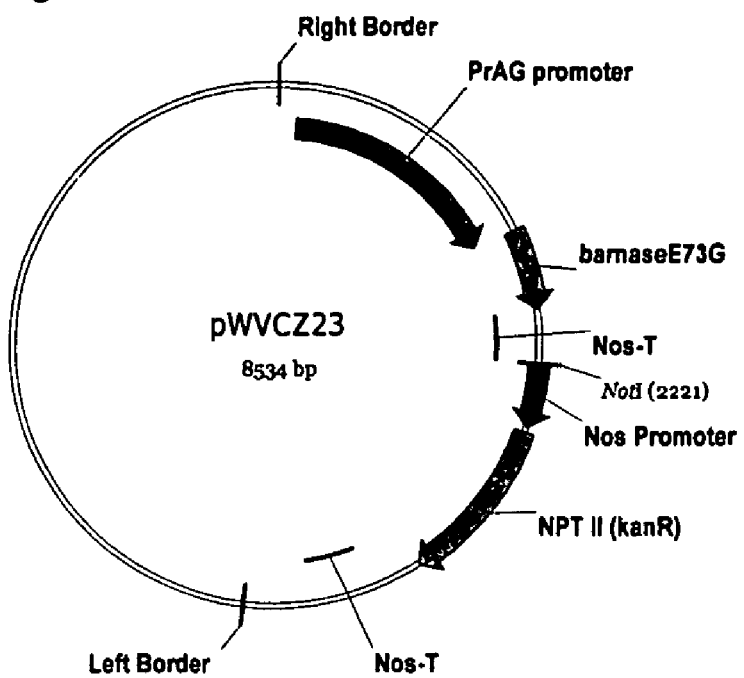
FIG. 12—plasmid map for pWVCZ23
Figure 13:
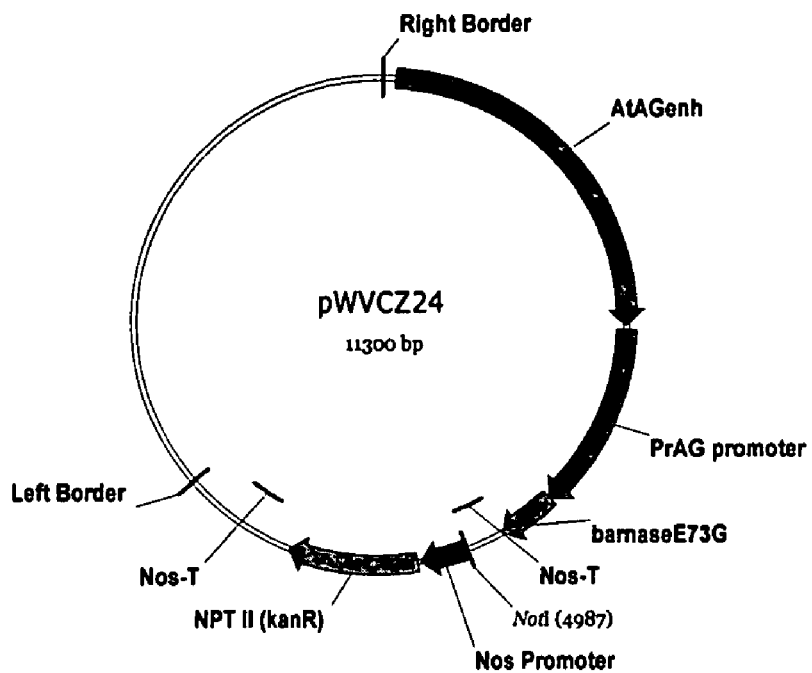
FIG. 13—plasmid map for pWVCZ24
Figure 14:
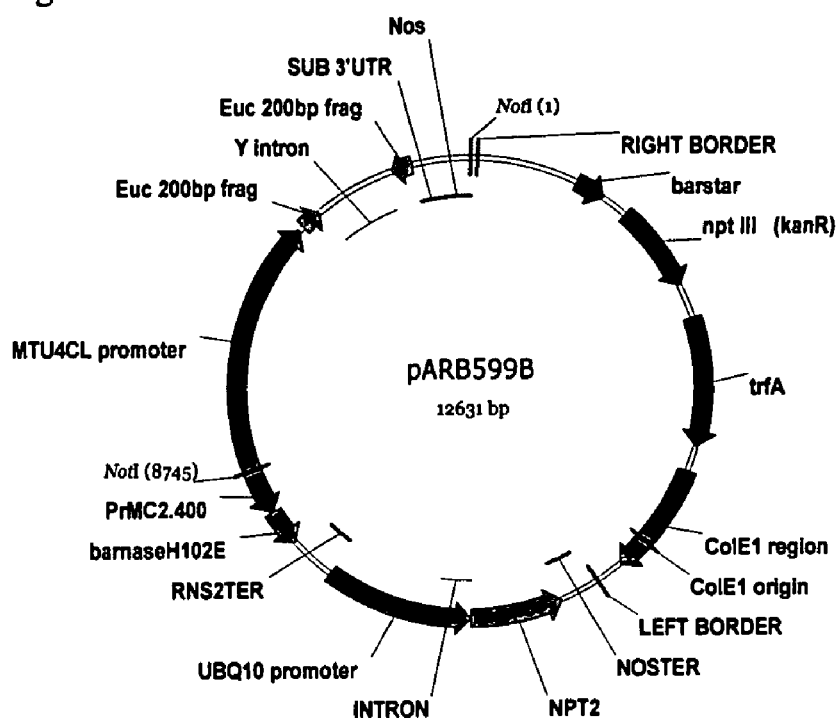
FIG. 14—plasmid map for pARB599B
Figure 15:
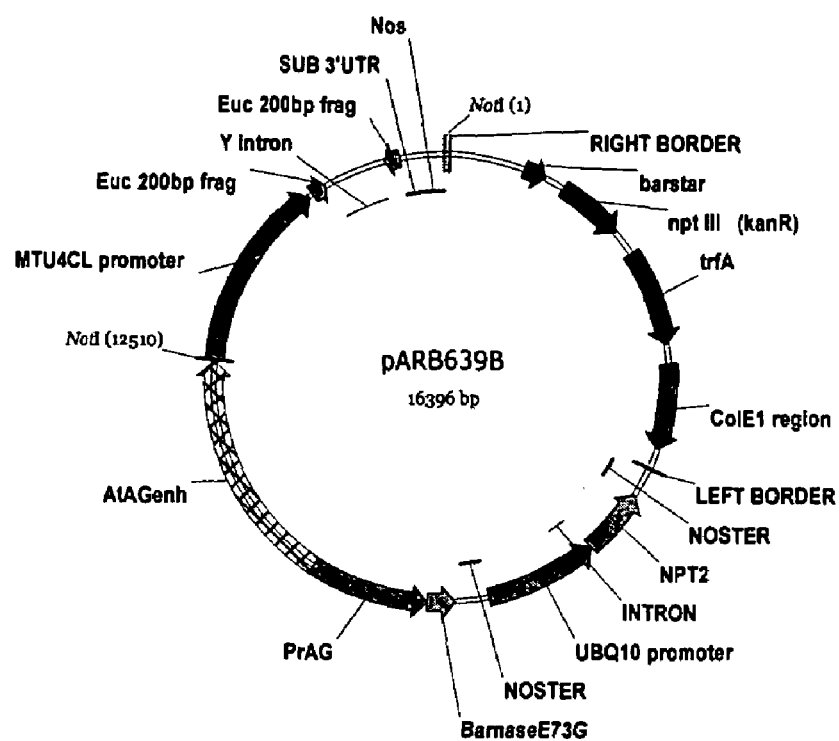
FIG. 15—plasmid map for pARB639B
Figure 16:
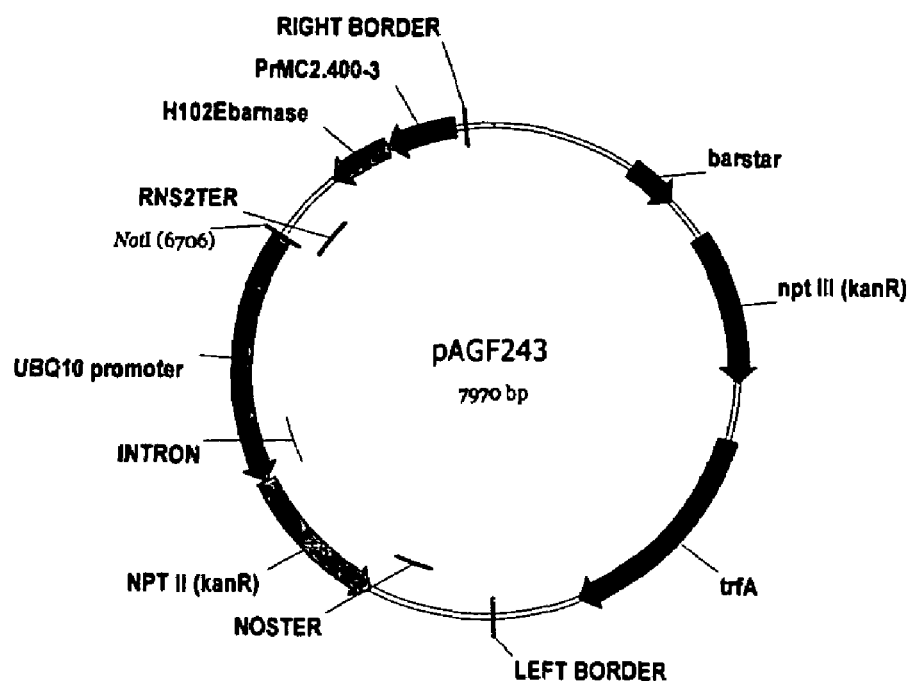
FIG. 16—plasmid map for pAGF243
Figure 17:
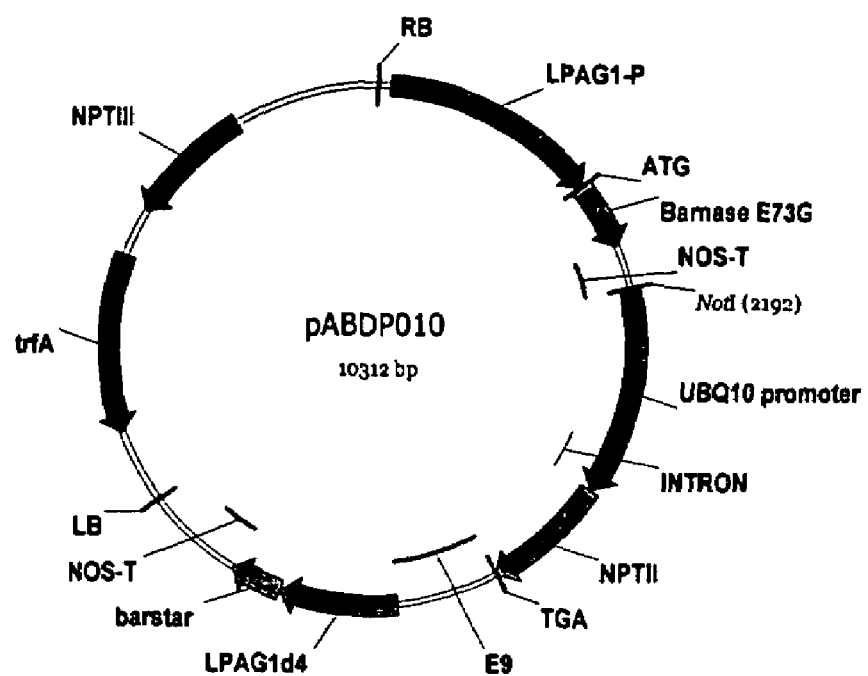
FIG. 17—plasmid map for pABDP010
Figure 18:
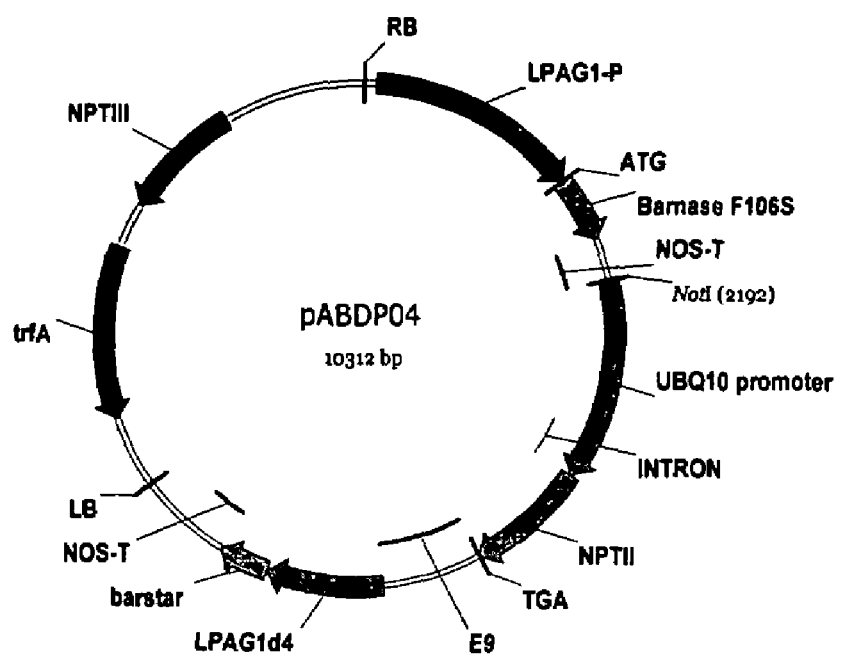
FIG. 18—plasmid map for pABDP04

The present invention relates to an isolated nucleic molecule comprising a polynucleotide having at least 95% sequence identity to a sequence selected from the group consisting of any of the polynucleotide sequences set forth below, i.e., SEQ ID NOs. 1-26 as well as those depicted in FIGS. 1-9 and portions thereof. The invention also provides functional fragments of the polynucleotide sequences disclosed herein. The invention further provides complementary nucleic acids, or fragments thereof, to any of the polynucleotide sequences disclosed herein, as well as a nucleic acid, comprising at least 15 contiguous bases, which hybridizes to any of the polynucleotide sequences disclosed herein.

The present invention also relates to an isolated polypeptide sequence comprising a polypeptide having a sequence selected from sequences set forth herein, such as those sequences depicted in SEQ ID NOs 9-12.

The present invention uses terms and phrases that are well known to those practicing the art. Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described herein are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology. See, e.g., Sambrook & Russel, MOLECULAR CLONING: A LABORATORY MANUAL, $3^{rd}$ ed., Cold Spring Harbor Laboratory Press, Cold Spring Harbor, N.Y., 2001.

*Agrobacterium*: as is well known in the field, Agrobacteria that are used for transforming plant cells are disarmed and virulent derivatives of, usually, *Agrobacterium tumefaciens* or *Agrobacterium rhizogenes* that contain a vector. The vector typically contains a desired polynucleotide that is located between the borders of a T-DNA.

Angiosperm: vascular plants having seeds enclosed in an ovary. Angiosperms are seed plants that produce flowers that bear fruits. Angiosperms are divided into dicotyledonous and monocotyledonous plants.

Angiosperm Reproductive Structure: includes the male and female tissues that comprise a flower. Typically, angiosperm flowers have four different floral organs: sepals (calyx), petals (corolla), stamens (androcecium), and pistils (gynoecium).

Angiosperm reproductive structure also embraces pre-male and pre-female reproductive structures. Pre-male and pre-female reproductive structures embrace cells and tissues that form before development and differentiation of male and female tissues.

Desired Polynucleotide: a desired polynucleotide of the present invention is a genetic element, such as a promoter, enhancer, or terminator, or gene or polynucleotide that is to be transcribed and/or translated in a transformed cell that comprises the desired polynucleotide in its genome. If the desired polynucleotide comprises a sequence encoding a protein product, the coding region may be operably linked to regulatory elements, such as to a promoter and a terminator, that bring about expression of an associated messenger RNA transcript and/or a protein product encoded by the desired polynucleotide. Thus, a "desired polynucleotide" may comprise a gene that is operably linked in the 5'- to 3'- orientation, a promoter, a gene that encodes a protein, and a terminator. Alternatively, the desired polynucleotide may comprise a gene or fragment thereof in an "antisense" orientation, the transcription of which produces nucleic acids that may form secondary structures that affect expression of an endogenous gene in the plant cell. A desired polynucleotide may also yield a double-stranded RNA product upon transcription that initiates RNA interference of a gene to which the desired polynucleotide is associated. A desired polynucleotide of the present invention may be positioned within a T-DNA, such that the left and right T-DNA border sequences flank or are on either side of the desired polynucleotide. The present invention envisions the stable integration of one or more desired polynucleotides into the genome of at least one plant cell. A desired polynucleotide may be mutated or may be a variant of its wild-type sequence. It is understood that all or part of the desired polynucleotide can be integrated into the genome of a plant. It also is understood that the term "desired polynucleotide" encompasses one or more of such polynucleotides. Thus, a T-DNA of the present invention may comprise one, two, three, four, five, six, seven, eight, nine, ten, or more desired polynucleotides.

Dicotyledonous plant (dicot): a flowering plant whose embryos have two seed halves or cotyledons, branching leaf veins, and flower parts in multiples of four or five. Examples of dicots include but are not limited to, *Eucalyptus, Populus, Liquidambar, Acacia*, teak, mahogany, cotton, tobacco, *Arabidopsis*, tomato, potato sugar beet, broccoli, cassava, sweet potato, pepper, poinsettia, bean, alfalfa, soybean, carrot, strawberry, lettuce, oak, maple, walnut, rose, mint, squash, daisy, geranium, avocado, cactus, and *Dichondra*.

Endogenous: refers to a gene that is native to a plant genome.

Female reproductive tissues: include, for example, stigma, style, ovary, megaspore, female cones (ovuliferous cones), female gamete, female zygote, megasporocyte, and pre-female reproductive structures.

Female-Sterility Gene: refers to a nucleic acid molecule encoding an RNA, protein, or polypeptide that disrupts growth and development of a female gametophyte, female gamete, female zygote, seed, ovuliferous cone, or pre-female reproductive structure. A plant expressing a female-sterility gene produces no viable seed. There are many different mutations that can lead to female-sterility, involving all stages of development of a specific tissue of the female reproductive organ or pre-female reproductive structure.

Examples of female-sterility genes include, but in no way limiting, encode enzymes which catalyze the synthesis of phytohormones, such as: isopentenyl transferase which is an enzyme that catalyzes the first step in cytokinin biosynthesis and is encoded by gene 4 of *Agrobacterium* T-DNA; or one or both of the enzymes involved in the synthesis of auxin and encoded by gene 1 and gene 2 of *Agrobacterium* T-DNA. Yet other examples of female-sterility genes encode: glucanases; lipases such as phospholipase $A_2$ (Verheij et al. *Rev. Blochem. Pharmacol.* 91:92-203 (1981)); lipid peroxidases; or plant cell wall inhibitors. Still other examples of female-sterility genes encode proteins toxic to plants cells, such as a bacterial toxin (e.g., the A-fragment of diphtheria toxin or botulin).

Still another example of a female-sterility gene is an antisense nucleic acid, or RNA involved in RNA interference (RNAi) such as small interfering RNA (siRNA), which can be useful for inhibiting or completely blocking the expression of a targeted gene. For example, an antisense or RNAi molecule of the invention encodes a nucleic acid strand complementary to a strand that is naturally transcribed in a plant's reproductive cells under the control of an endogenous promoter as described, for example, in European Patent Publication 0,223,399. Such an antisense nucleic acid or RNAi molecule may be capable of binding to the coding and/or non-coding portion of an RNA, naturally produced in the reproductive cell, so as to inhibit the translation of the naturally produced RNA. In one embodiment, an antisense nucleic acid and RNAi molecule of the invention can be expressed in flower, ovuliferous cone, seed, embryo, female gamete, female gametophyte, megasporocyte, and pre-female reproductive structures of the plant under the control of the endogenous promoter of the complementary endogenous DNA strand (or gene) of the plant.

Examples of such an antisense nucleic acid are the antisense DNA sequences of: the STMG-type genes, such as STMG07, STMG08, STMG4B12, and STMG3C9 genes. Jofiku and Goldberg. *The Plant Cell* 1:1079-1093 (1989). The use of RNAi inhibition of gene expression is described generally in Paddison et al., *Genes & Dev.* 16: 948-958 (2002), and the use of RNAi to inhibit gene expression in plants is specifically described in WO 99/61631, both of which are herein incorporated by reference.

A further example of a female-sterility gene encodes a specific RNA enzyme (i.e., a "ribozyme"), capable of highly specific cleavage against a given target sequence as described by Haseloff and Gerlach et al. *Nature* 334, 585-591 (1998).

Fiber composition: as used herein, fiber composition refers to a trait that can be modified to change the structure, appearance, or use of fiber. Traits that determine fiber composition include but are not limited to fiber length, coarseness, strength, color, cross-sectional, width, and fiber density. For example, it is known that fiber length imparts strength, whereas fiber coarseness determines texture and flexibility.

In angiosperms, Floral Meristems initiate a floral structure having four different types of floral organs: sepals (calyx), petals (corolla), stamens (androecium), and pistils (gynoecium). Each floral organ is initated as a whorl, comprising concentric rings around the flanks of a floral meristem. The floral structure is supported by a pedicel or peduncle.

Flowering plants produce meiospores that are either microspores (male) or megaspores (female).

Foreign: "foreign," with respect to a nucleic acid, means that that nucleic acid is derived from non-plant organisms, or derived from a plant that is not the same species as the plant to be transformed or is not derived from a plant that is not interfertile with the plant to be transformed, or does not belong to the species of the target plant. According to the present invention, foreign DNA or RNA may include nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product.

Gene: A gene is a segment of a DNA molecule that contains all the information required for synthesis of a product, polypeptide chain or RNA molecule, and includes both coding and non-coding sequences.

Genetic element: a "genetic element" is any discreet nucleotide sequence including, but not limited to, a promoter, a gene, a terminator, an intron, an enhancer, a spacer, a 5'-untranslated region, a 3'-untranslated region, or a recombinase recognition site.

Genetic modification: stable introduction of DNA into the genome of certain organisms by applying methods in molecular and cell biology.

Gymnosperm: as used herein, refers to a seed plant that bears seed without ovaries. Examples of gymnosperrns include conifers, cycads, ginkgos, and ephedras. In gymnosperms, reproductive shoot primordia develop into either male cones (staminate cones) or female cones (ovulate cones).

Gymnosperm Reproductive Structure: includes the male tissues that comprise male pollen cones (staminate cones) and female tissues that comprise female cones (ovulate cones). Gymnosperm reproductive structure also embraces pre-male and pre-female reproductive structures. Pre-male and pre-female reproductive structures embrace cells and tissues that form before development and differentiation of male and female tissues.

Introduction: as used herein, refers to the insertion of a nucleic acid sequence into a cell, by methods including infection, transfection, transformation or transduction.

Lignin: as used herein, refers to a polymeric composition composed of phenylpropanoid units, including polymerized derivatives of monolignols coniferyl, coumaryl, and sinapyl alcohol. Lignin quality refers to the ability of a lignin composition to impart strength to cell wall matrices, assist in the transport of water, and/or impede degradation of cell wall polysaccharides. Lignin composition or lignin structure may be changed by altering the relative amounts of each of monolignols or by altering the type of lignin. For example, guaiacyl lignins (derived from ferulic acid) are prominent in softwood species, whereas guaiacyl-syringyl lignins (derived from ferulic acid and sinapic acid) are characteristic of hardwood species. The degradation of lignin from softwoods, such as pine, requires substantially more alkali and longer incubations, compared with the removal of lignin from hardwoods. Lignin composition may be regulated by either up-regulation or down-regulation of enzymes involved lignin biosynthesis. For example, key lignin biosynthsesis enzymes include, but are not limited to, 4-coumaric acid: coenzyme A ligase (4CL), Cinnamyl Alcohol dehydrogenase (CAD), and Sinapyl Alcohol Dehydrogenase (SAD).

In angiosperms, male gametophytes or pollen grains develop in anthers, and the anthers are borne on stamens. Anther development occurs in two stages that correlate with pollen development. During phase I, sporogenic cells in the anther undergo microsporogenesis; nonsporogenic cells form the epidermis and tapetum. The tapetum is a tissue that surrounds sporogenic cells and provides nutritional materials for developing pollen. Additionally, the tapetum secretes the enzyme callase. During phase II, the anther enlarges and the filament elongates. At this time, pollen grains form, dehiscence occurs, and pollen grains are released.

In gymnosperms, such as conifers, a male pollen cone consists of an axis bearing a series of scales and two pollen sacs on the undersurface of each scale. Male cones consist of numerous microsporophylls that are tightly clustered in a spiral arrangement on a fertile shoot axis. Each microsporophyll bears two microsporangia, also called pollen sacs, on its lower, abaxial side. Within each microsporangium, sporangenous tissue lies. The sporangenous tissue consists of numerous diploid cells, called microsporocytes, which undergo meiosis. Around the periphery of each microsporangium lies the tapetum. Within the microsporangia, the microspores undergo mitosis and following two mitotic divisions, a four-celled male gametophyte is produced. The pollen grain comprises the microspore wall and the contained male gametophyte.

In gymnosperms, a female cone is formed by the fusion of numerous highly modified fertile shoots. In pines, for example, the female cone is comprised of individual units attached to a single, central axis. The individual units are made of an ovuliferous scale (ovule-bearing) and a subtending bract that is almost completely fused to the ovuliferous scale above it. Each ovuliferous scale is formed by the fusion of megasporophylls and other fertile shoot components. On the upper, adaxial surface of each ovuliferous scale are two ovules. The ovules are oriented with their micropyles toward the central cone axis and are partially imbedded in the tissues of the ovuliferous scale. Each ovule has an integument (one multicellular layer) that, except for the micropyles, completely surrounds the megasporangium. The integument or nucellus functions as the nutritive tissue and each nucellus has a single megasporocyte. The megasporocyte is the diploid cell that undergoes meiosis. The micropylar chamber is located within each ovule between the nucellus and the micropyle.

Male reproductive tissues: include, for example, pollen grains, tapetum, anther, filament, pollen mother cells, microspores, microsporocyte, male pollen cones (staminate cones), pollen sacs, and pre-male reproductive structures.

Male-Sterility Gene: refers to a nucleic acid molecule encoding an RNA, protein, or polypeptide that disturbs the proper metabolism, functioning and/or development of any reproductive cell in which the male-sterility gene is expressed, thereby leading to the death and/or destruction of any such reproductive cell. There are many different mutations that can lead to male-sterility, involving all stages of development of a specific tissue of the male reproductive organ or pre-male reproductive structure.

The expression of a male-sterility gene, for example, renders a plant incapable of producing fertile pollen. The expression of a male-sterility gene in a transformed plant may result in a plant producing pollen, though the pollen may be aberrant and non-functional for fertilization. For example, a non-functional pollen may fail to germinate a pollen tube. While by no means limiting, examples of male-sterility genes encode: RNases such as RNase T1 (which degrades RNA molecules by hydrolyzing the bond after any guanine residue) and Barnase; DNases such as an endonuclease (e.g., EcoRI); or proteases such as a papain (e.g., papain zymogen and papain active protein).

Other male-sterility genes encode enzymes which catalyze the synthesis of phytohormones. For example, isopentenyl transferase, an enzyme that catalyzes the first step in cytokinin biosynthesis, and enzymes involved in the synthesis of auxin may be used for inducing male-sterility. Other male-sterility genes encode glucanases; lipases such as phospholipase $A_2$ (Verheij et al. *Rev. Biochem. Pharmacol.* 91: 92-203 (1981)); lipid peroxidases; or plant cell wall inhibitors. Still other examples of male-sterility genes encode proteins toxic to a plants cell, such as a bacterial toxin (e.g., the B-fragment of diphtheria toxin or botulin).

Still another example of a male-sterility gene is an antisense nucleic acid, or RNA involved in RNA interference (RNAi) such as small interfering RNA (siRNA), which can be useful for inhibiting or completely blocking the expression of a targeted gene. For example, an antisense or RNAi molecule of the invention encodes a nucleic acid strand complementary to a strand that is naturally transcribed in a plant's reproductive cells under the control of an endogenous promoter as described, for example, in European Patent Publication 0,223,399. Such an antisense nucleic acid or RNAi molecule may be capable of binding to the coding and/or non-coding portion of an RNA, naturally produced in the reproductive cell, so as to inhibit the translation of the naturally produced RNA. In one embodiment, an antisense nucleic acid and RNAi molecule of the invention can be expressed in pollen grains, tapetum, anther, filament, pollen mother cells, microspores, microsporocyte, male pollen cones (staminate cones), pollen sacs, and pre-male reproductive structures.

Microsporogenesis is the process by which a diploid cell, the microsporocyte, undergoes meiotic division to produce four, haploid microspores (microspore tetrad). The microspore tetrad is encased in a callose cell wall.

In angiosperms, microsporogenesis occurs in the stamens, the male reproductive tissues of a flower. Each stamen has a filament and an anther. Each anther has one to four chambers, called pollen sacs or anther sacs. Each anther sac produces numerous microsporocytes, also called pollen mother cells.

In gymnosperms, microsporogenesis occurs in the microsporangia or pollen sacs of the microsporophyll. Within the microsporangia, the microspores undergo mitosis and produce a four-celled male gametophyte. A gymnosperm pollen grain comprises the microspore wall and the contained male gametophyte.

Monocotyledonous plant (monocot): a flowering plant having embryos with one cotyledon or seed leaf, parallel leaf veins, and flower parts in multiples of three. Examples of monocots include, but are not limited to, turfgrass, maize, rice, oat, wheat, barley, sorghum, orchid, iris, lily, onion, and palm. Examples of turfgrass include, but are not limited to, *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra commutata* (fine fescue), *Cynodon dactylon* (common bermudagrass varieties including Tifgreen, Tifway II, and Santa Ana, as well as hybrids thereof); *Pennisetum clandestinum* (kikuyugrass), *Stenotaphrum secundatum* (st. augustinegrass), *Zoysiajaponica japonica* (zoysiagrass), and *Dichondra micrantha*.

Operably linked: combining two or more molecules in such a fashion that in combination they fuiction properly in a plant cell. For instance, a promoter is operably linked to a structural gene when the promoter controls transcription of the structural gene.

Phenotype: phenotype is a distinguishing feature or characteristic of a plant, which may be altered according to the present invention by integrating one or more "desired polynucleotides" and/or screenable/selectable markers into the genome of at least one plant cell of a transformed plant. The "desired polynucleotide(s)" and/or markers may confer a change in the phenotype of a tranformed plant by modifying any one of a number of genetic, molecular, biochemical, physiological, morphological, or agronomic characteristics or properties of the transformed plant cell or plant as a whole. Thus, expression of one or more, stably integrated desired polynucleotide(s) in a plant genome may yield a phenotype selected from the group consisting of, for example, increased drought tolerance, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved vigor, improved taste, improved texture, decreased phosphate content, increased germination, increased micronutrient uptake, improved starch composition, and improved flower longevity.

Plant tissue: a "plant" is any of various photosynthetic, eukaryotic, multicellular organisms of the kingdom Plantae characteristically producing embryos, containing chloroplasts, and having cellulose cell walls. A part of a plant, i.e., a "plant tissue" may be transformed according to the methods of the present invention to produce a transgenic plant. Many suitable plant tissues can be transformed according to the present invention and include, but are not limited to, somatic embryos, pollen, leaves, stems, calli, stolons, microtubers, and shoots. Thus, the present invention envisions the transformation of angiosperm and gymnosperm plants such as turfgrass, wheat, maize, rice, barley, oat, sugar beet, potato, tomato, tobacco, alfalfa, lettuce, carrot, strawberry, cassava, sweet potato, geranium, soybean, oak, apple, grape, pine, fir, acacia, eucalyptus, walnut, and palm. According to the present invention "plant tissue" also encompasses plant cells. Plant cells include suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, propagule whether generated sexually or asexually, and descendents of any of these, such as cuttings or seed. Of particular interest are conifers such as pine, fir, and spruce, monocots such as Kentucky bluegrass, creeping bentgrass, maize, and wheat, and dicots such as cotton, tomato, lettuce, *Arabidopsis*, tobacco, apple and geranium.

Plant transformation and cell culture: broadly refers to the process by which plant cells are genetically modified and transferred to an appropriate plant culture medium for maintenance, further growth, and/or further development. Such methods are well known to the skilled artisan.

Pollen refers to the microspores of seeds plants and the powdery mass of microspores shed from anthers and staminate pollen cones.

Pre-female reproductive structures: refers to cells and tissues that form before development and differentiation of female tissues in angiosperm and gymnosperm species.

Pre-male reproductive structures: refers to cells and tissues that form before development and differentiation of male tissues in angiosperm and gymnosperm species.

Progeny: a "progeny" of the present invention, such as the progeny of a transgenic plant, is one that is born of, begotten by, or derived from a plant or the transgenic plant. Thus, a "progeny" plant, i.e., an "F1" generation plant is an offspring or a descendant of the transgenic plant produced by the inventive methods. A progeny of a transgenic plant may contain in at least one, some, or all of its cell genomes, the desired polynucleotide that was integrated into a cell of the parent transgenic plant by the methods described herein. Thus, the desired polynucleotide is "transmitted" or "inherited" by the progeny plant. The desired polynucleotide that is so inherited in the progeny plant may reside within a T-DNA construct, which also is inherited by the progeny plant from its parent. The term "progeny" as used herein also may be considered to be the offspring or descendants of a group of plants.

Promoter: is intended to mean a nucleic acid, preferably DNA, that binds RNA polymerase and/or other transcription regulatory elements. As with any promoter, the promoter sequences of the current present invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule.

A promoter, as used herein, may also include regulatory elements. Conversely, a regulatory element may also be separate from a promoter. Regulatory elements confer a number of important characteristics upon a promoter region. Some elements bind transcription factors that enhance the rate of transcription of the operably linked nucleic acid. Other elements bind repressors that inhibit transcription activity. The effect of transcription factors on promoter activity may determine whether the promoter activity is high or low, i.e. whether the promoter is "strong" or "weak."

A plant promoter is a promoter capable of initiating transcription in plant cells, whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as tapetum, xylem, leaves, roots, or seeds. Such promoters are referred to as tissue preferred promoters. Promoters which initiate transcription only in certain tissues are referred to as tissue specific promoters. A cell type specific promoter primarily drives expression in certain cell types in one or more organs, for example, vascular cells in roots or leaves. An inducible or repressible promoter is a promoter which is under environmental control. Examples of environmental conditions that may effect transcription by inducible promoters include anaerobic conditions, heat, or the presence of light. Tissue specific, tissue preferred, cell type specific, and inducible promoters constitute the class of non-constitutive promoters. A constitutive promoter is a promoter which is active under most environmental conditions, and in most plant parts.

Polynucleotide is a nucleotide sequence comprising a gene coding sequence or a fragment thereof (comprising at least 15 consecutive nucleotides, at least 30 consecutive nucleotides, or at least 50 consecutive nucleotides), a promoter, an intron, an enhancer region, a polyadenylation site, a translation initiation site, 5' or 3' untranslated regions, a reporter gene, a selectable marker or the like. The polynucleotide may comprise single stranded or double stranded DNA or RNA. The polynucleotide may comprise modified bases or a modified backbone. The polynucleotide may be genomic, an RNA transcript (such as an mRNA) or a processed nucleotide sequence (such as a cDNA). The polynucleotide may comprise a sequence in either sense or antisense orientations.

An isolated polynucleotide is a polynucleotide sequence that is not in its native state, e.g., the polynucleotide is comprised of a nucleotide sequence not found in nature, or the polynucleotide is separated from nucleotide sequences to which it typically is in proximity, or is in proximity to nucleotide sequences with which it typically is not in proximity.

Regenerability: as used herein, refers to the ability of a plant to redifferentiate from a de-differentiated tissue.

Reproductive-preferred promoter refers to a promoter preferentially expressed in a plant's reproductive tissue. Reproductive plant tissue includes both male and female portions of the reproductive structure, as well as pre-male and pre-female reproductive structures. Male reproductive tissues include, for example, pollen grains, tapetum, anther, filament, pollen mother cells, microspores, male pollen cones (staminate cones), and pre-male reproductive structures. Female reproductive tissues include, for example, stigma, style, ovary, megaspores, ovuliferous scale, bract, female pollen cones (ovuliferous cones), and pre-female reproductive structures. Accordingly, a reproductive-preferred promoter may be preferentially expressed in any angiosperm reproductive structure or gymnosperm reproductive structure.

Seed: a "seed" may be regarded as a ripened plant ovule containing an embryo, and a propagative part of a plant, as a tuber or spore. Seed may be incubated prior to *Agrobacterium*-mediated transformation, in the dark, for instance, to facilitate germination. Seed also may be sterilized prior to incubation, such as by brief treatment with bleach. The resultant seedling can then be exposed to a desired strain of *Agrobacterium*.

Selectable/screenable marker: a gene that, if expressed in plants or plant tissues, makes it possible to distinguish them from other plants or plant tissues that do not express that gene. Screening procedures may require assays for expression of proteins encoded by the screenable marker gene. Examples of such markers include the beta glucuronidase (GUS) gene and the luciferase (LUX) gene. Examples of selectable markers include the neomycin phosphotransferase (NPTII) gene encoding kanamycin and geneticin resistance, the hygromycin phosphotransferase (HPT or APHIV) gene encoding resistance to hygromycin, acetolactate synthase (als) genes encoding resistance to sulfonylurea-type herbicides, genes (BAR and/or PAT) coding for resistance to herbicides which act to inhibit the action of glutamine synthase such as phosphinothricin (Liberty or Basta), or other similar genes known in the art.

Sequence identity: as used herein, "sequence identity" or "identity" in the context of two nucleic acid or polypeptide sequences includes reference to the residues in the two sequences which are the same when aligned for maximum correspondence over a specified region.

As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Stamen: refers to the organ of the flower that produces the male gamete and includes an anther and filament.

Tapetum: refers to a layer of cells surrounding microsporogenous cells in the anther of an angiosperm or the microsporangeous cells within a staminate cone of a gymnosperm. Given its close proximity to the developing microspores, the tapetum likely provides nutrients, such as reducing sugars, amino acids and lipids to the developing microspores. Reznickova, C. R., Acad. *Bulg. Sci.* 31:1067 (1978). Nave, et al., *J. Plant Physiol.* 125:451 (1986). Sawhney, et al., *J. Plant Physiol* 125:467 (1986). Tapetal cells also produce beta(1,3) glucanase (callase) which promotes microspore release by digesting the callose cell wall. Therefore, a fragile relationship exists between the tapetum and the microsporogenous cells, and any disruption of tapetal function is likely to result in non-functional pollen grains. It has been shown, for example, lesions in tapetal biogenesis result in male sterility mutants (Kaul, "Male Sterility in Higher Plants" in Monographs on Theoretical and Applied Genetics; Frankel et al. eds.; Springer Verlag; Vol. 10; pp. 15-95; (1988)). Therefore, a gene encoding callase can be used for disrupting male reproductive development. Thus, a failure of the microspores to develop into mature pollen grains can be induced using, for example, a recombinant DNA molecule that comprises a gene capable of disrupting tapetal fuiction under the control of tapetum-specific regulatory sequences.

Transcription factor: Transcription factor refers to a polypeptide sequence that regulates the expression of a gene or genes by either directly binding to one or more nucleotide sequences associated with a gene coding sequence or indirectly affecting the activity of another polypeptide(s) that bind directly to one or more nucleotide sequences associated with a gene coding sequence. A transcription factor may activate (up-regulate) or repress (down-regulate) expression of a gene or genes. A transcription factor may contain a DNA binding domain, an activation domain, or a domain for protein-protein interactions. In the present invention, a transcription factor is capable of at least one of (1) binding to a nucleic acid sequence or (2) regulating expression of a gene in a plant.

Transcription and translation terminators: The expression DNA constructs of the present invention typically have a transcriptional termination region at the opposite end from the transcription initiation regulatory element. The transcriptional termination region may be selected, for stability of the mRNA to enhance expression and/or for the addition of polyadenylation tails added to the gene transcription product.

Transfer DNA (T-DNA): an *Agrobacterium* T-DNA is a genetic element that is well-known as an element capable of integrating a nucleotide sequence contained within its borders into another genome. In this respect, a T-DNA is flanked, typically, by two "border" sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleic acids, like promoter and terminator regulatory elements that facilitate its expression, i.e., transcription and/or translation of the DNA sequence encoded by the desired polynucleotide or selectable marker.

Transformation of plant cells: A process by which a nucleic acid is stably inserted into the genome of a plant cell. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, microinjection, polyethylene glycol-treatment, heat shock, lipofection and particle bombardment.

Transgenic plant: a transgenic plant of the present invention is one that comprises at least one cell genome in which an exogenous nucleic acid has been stably integrated. According to the present invention, a transgenic plant is a plant that may comprise only one genetically modified cell and cell genome, or it may comprise several or many genetically modified cells, or all of the cells may be genetically modified. A transgenic plant of the present invention may be one in which expression of the desired polynucleotide, i.e., the exogenous nucleic acid, occurs in only certain parts of the plant. Thus, a transgenic plant may contain only genetically modified cells in certain parts of its structure.

Variant: a "variant," as used herein, is understood to mean a nucleotide sequence that deviates from the reference (i.e., native, standard, or given) nucleotide sequence of a particular gene. The terms, "isoform," "isotype," and "analog" also refer to "variant" forms of a nucleotide sequence.

Variant may also refer to a "shuffled gene" such as those described in Maxygen-assigned patents. For instance, a variant of the present invention may include variants of sequences and desired polynucleotides that are modified according to the methods and rationale disclosed in U.S. Pat. No. 6,132,970, which is incorporated herein by reference.

Vegetative growth: this well-accepted term of art refers to the general, overall development of a plant. To elaborate, after reproduction, meristem cells differentiate into apical-, lateral meristems that ultimately develop into roots and shoots and, later, into leaves and flowers, for instance. Shoot and root architecture, branching patterns, development of stems, axillary buds, and primordial cells into leaves, petals, flowers, and fruit etc. are all considered "vegetative" and part of the "vegetative growth" cycle of a plant. The rate of development of such features depends on a variety of factors, such as the species of the plant, photosynthesis, availability of nutrients, and the general environment in which the plant is growing.

Genetics also plays an important literal and figurative role in shaping a plant's development. For instance, the "simple" or "compound" shape of a leaf, i.e., whether it is characterized by smooth-edges, deep lobes, individual leaflets, or tendrils can be dictated by gene expression. The "LEAFY" gene, for example, plays a role in compound leaf development and is essential for the transition from vegetative to reproductive development. LEAFY was identified in *Arabidopsis* and snapdragon, and has homologues in other angiosperms. The pea homologue, *Unifoliata*, has a mutant phenotype in which compound leaves are reduced to simple leaves, which may indicate a regulatory relationship between shoots and compound leaves.

Similarly, the acacia mutant, "tl," converts tendrils to leaflets, whilst the mutation, afilia, "af," converts leaflet to tendrils. The "af tl" double mutant has a complex architecture, resembling a parsley leaf. Likewise, other genes, which are expressed throughout such "vegetative" plant cells and tissues, coordinate and connote developmental, physiological, and structural characteristics to other discreet parts of the plant. Thus, there are many "vegetative-specific" genes that are expressed, either specifically or predominantly, in all vegetative tissues, such as roots, shoots, stems, and leaves, or which are vegetative-tissue specific. The promoters of such genes are, therefore, useful in directing the expression of a desired gene, endogenous or foreign, to a particular vegetative tissue. Thus, it is possible to preferentially express a gene product in one or more vegetative tissues, whilst avoiding expression of that same product in non-vegetative tissues, such as in reproductive tissue cells.

Wood composition: refers to a trait that can be modified to change the structure, appearance, or use of wood. While not limiting, traits that determine wood composition include cell wall thickness, cell length, cell size, lumen size, cell density, microfibril angle, tensile strength, tear strength, wood color, and length and frequency of cell division.

Wood pulp: refers to fiber generated from wood having varying degrees of purification. Wood pulp can be used for producing paper, paper board, and chemical products.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

Nucleic Acids

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vitro RNA transcripts of the DNA molecules of the present invention. Isolated nucleic acid molecules, according to the present invention, further include such molecules produced synthetically.

Nucleic acid molecules of the present invention may be in the form of RNA, such as mRNA, or in the form of DNA, including, for instance, cDNA and genomic DNA obtained by cloning or produced synthetically. The DNA or RNA may be double-stranded or single-stranded. Single-stranded DNA may be the coding strand, also known as the sense strand, or it may be the non-coding strand, also referred to as the antisense strand.

Unless otherwise indicated, all nucleotide sequences determined by sequencing a DNA molecule herein were determined using an automated DNA sequencer (such as the Model 3700 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

The present invention is also directed to fragments of the isolated nucleic acid molecules described herein. By a fragment of an isolated DNA molecule having the nucleotide sequences disclosed herein is intended DNA fragments at least 15 nucleotides, at least 20 nucleotides, at least 30 nucleotides in length, which are useful as diagnostic probes and primers is discussed in more detail below. Of course larger nucleic acid fragments of up to the entire length of the nucleic acid molecules of the present invention are also useful diagnostically as probes, according to conventional hybridization techniques, or as primers for amplification of a target sequence by the polymerase chain reaction (PCR), as described, for instance, in Molecular Cloning, A Laboratory Manual, 3rd. edition, edited by Sambrook, J and Russel, D. W., (2001), Cold Spring Harbor Laboratory Press, Cold Spring Harbor, N.Y., the entire disclosure of which is hereby incorporated herein by reference.

By a fragment at least 20 nucleotides in length, for example, is intended fragments which include 20 or more contiguous bases from the nucleotide sequence of the as disclosed herein, i.e., SEQ ID NOs. 1-26. Nucleic acids comprising the nucleotide sequences disclosed herein can be generated using conventional methods of DNA synthesis which will be routine to the skilled artisan. For example, restriction endonuclease cleavage or shearing by sonication could easily be used to generate fragments of various sizes. Alternatively, the DNA fragments of the present invention could be generated synthetically according to known techniques.

In another aspect, the invention provides an isolated nucleic acid molecule comprising a polynucleotide which hybridizes under stringent hybridization conditions to a portion of the polynucleotide in a nucleic acid molecule of the invention described above. By a polynucleotide which hybridizes to a "portion" of a polynucleotide is intended a polynucleotide (either DNA or RNA) hybridizing to at least about 15 nucleotides, at least about 20 nucleotides, at least about 30 nucleotides, and more than 30 nucleotides of the reference polynucleotide. These fragments that hybridize to the reference fragments are useful as diagnostic probes and primers. A probe, as used herein is defined as at least about 50 contiguous bases of one of the nucleic acids disclosed herein, i.e., SEQ ID NOs. 1-8 and 13-26. For the purpose of the invention, two sequences hybridize when they form a double-stranded complex in a hybridization solution of 6×SSC, 0.5% SDS, 5×Denhardt's solution and 100 µg of non-specific carrier DNA. See Ausubel et al., section 2.9, supplement 27 (1994). Sequences may hybridize at "moderate stringency," which is defined as a temperature of 60° C. in a hybridization solution of 6×SSC, 0.5% SDS, 5×Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to 68° C. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

As mentioned previously, the present application is directed to such nucleic acid molecules which are at least 90%, 95%, 96%, 97%, 98%, 99% or 100% identical to a nucleic acid sequence described above. One embodiment encompasses nucleic acid molecules which are at least 95%, 96%, 97%, 98%, 99% or 100% identical to the nucleic acid sequence shown in SEQ ID NOs. 1-8 and 13-26. By a polynucleotide having a nucleotide sequence at least, for example, 95% "identical" to a reference nucleotide sequence, is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference nucleotide sequence refers to a comparison made between two molecules using standard algorithms well known in the art. Although any sequence algorithm can be used to define sequence identity, for clarity, the present invention defines identity with reference to the Basis Local Alignment Search Tool (BLAST) algorithm (Altschul et al., *J. Mol. Biol.* 215:403-410 (1990)), where a promoter sequence set forth in the disclosure is used as the reference sequence to define the percentage identity of polynucleotide homologs over its length. The choice of parameter values for matches, mismatches, and inserts or deletions is arbitrary, although some parameter values have been found to yield more biologically realistic results than others.

When using BLAST or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Relatedness between two polynucleotides also may be described by reference to their ability to hybridize to form double-stranded complexes by the formation of complementary base pairs. Hybridization conditions have been described previously herein. An increase in temperature can be used to break apart these complexes. The more structurally identical two sequences are, the higher the temperature required to break them apart or "melt" them. The temperature required to melt a double-stranded complex is called the "$T_m$." The relationship between the Tm and other hybridization parameters is given by:

$$T_m(°\text{C.})=81.5+16.6(\log_{10}[\text{Na}^+])+0.41(\text{fraction } G+C)-0.63 (\% \text{ formamide})-(600/\text{l}),$$

where $T_m$ is the melting temperature of a DNA duplex consisting of the probe and its target; and l=the length of the hybrid in base pairs, provided l>100 base pairs. Bolton et al., *Proc. Natl. Acad. Sci.* 48:1390 (1962). Generally, a change of 1° C. in the melting point represents from 0.7% to 3.2% difference in DNA sequence similarity. Bonner et al., *Journal of Molecular Biology* 81:123-35 (1973); McCarthy et al., In EVOLUTION OF GENETIC SYSTEMS, H. H. Smith (ed.), Brookhaven Symposium in Biology No. 23, Gordon and Breach, New York, pp. 1-43 (1972). The formation of a stable DNA duplex at 60° C. typically requires at least an 80% sequence identity between sequences. Sibley et al., ACTA 1: 83-121 (Proceedings of the 18th International Ornithological Congress, Moscow, Aug. 16-24, 1982, Academy of Sciences of the USSR).

In one embodiment, the nucleic acids of the present invention confer preferential expression of polypeptides or proteins in the reproductive tissues of angiosperm and gymnosperm plants. The nucleic acids of the present invention can also preferentially direct the expression of antisense RNA, or RNA involved in RNA interference (RNAi) such as small interfering RNA (siRNA), in the reproductive tissue of plants, which can be useful for inhibiting or completely blocking the expression of targeted genes.

Reproductive plant tissue includes both male and female portions of reproductive organs. Male tissues include, for example, pollen, tapetum, anther, filament, pollen mother cells, microspores, male pollen cones (staminate cones), and pre-male reproductive structures. Female reproductive tissues include, for example, stigma, style, ovary, megaspores, female cones (ovuliferous cones), and pre-female reproductive structures.

Reproductive-preferred promoter refers to a promoter preferentially expressed in a plant's reproductive tissue. Reproductive plant tissue includes both male and female portions of the reproductive structure, as well promoters expressed in pre-male and pre-female reproductive structures. Male reproductive tissues include, for example, pollen grains, tapetum, anther, filament, pollen mother cells, microspores, and pollen cones. Female reproductive tissues include, for example, stigma, style, ovary, megaspores, and ovuliferous cones. Accordingly, a reproductive-preferred promoter may be preferentially expressed in any reproductive structure of any angiosperm or gymnosperm species, in addition to expression in any pre-male or pre-female tissue of gymnosperm and angiosperm species.

In one embodiment, a reproductive-preferred promoter confers expression of a gene in a male-reproductive tissue. In one embodiment, a reproductive-preferred promoter confers gene expression in the anther, pollen or filament cells of an angiosperm species. In a further embodiment, the reproductive-preferred promoter confers gene expression in the tapetum or anther epidermal cells. In another embodiment, a reproductive-preferred promoter confers gene expression in a male pollen cone, tapetum, microsporophyll, or any other male reproductive tissue present in a gymnosperm. For both angiosperm and gymnosperm species, a reproductive-preferred promoter confers gene expression in a pre-male or pre-female reproductive structure.

A reproductive-preferred promoter can be used for example, to render a plant male-sterile. For example, a reproductive-preferred promoter can be operably linked to a cytotoxic gene, such that expression of the cytotoxic gene in a male reproductive tissue renders the plant incapable of producing fertile male gametes. In another embodiment, a reproductive-preferred promoter may be selected and isolated such that the promoter does not express an operably-linked gene in a non-reproductive tissue, such as a vegetative tissue.

In one embodiment, a reproductive-preferred promoter confers expression of a gene in a female-reproductive tissue. In one embodiment, a reproductive-preferred promoter confers gene expression in the stigma, style, or ovary of an angiosperm species. In another embodiment, a reproductive-preferred promoter confers gene expression in a female cone (ovuliferous cone), megasporophyll, or any other female reproductive tissue present in a gymnosperm species. For both angiosperm and gymnosperm species, a reproductive-preferred promoter confers gene expression in a pre-male or pre-female reproductive structure.

A reproductive-preferred promoter can be used for example, to render a plant female-sterile. In one embodiment, a reproductive-preferred promoter can be operably linked to a cytotoxic gene, such that expression of the cytotoxic gene in a female reproductive tissue renders the plant incapable of producing fertile female gametes, female zygote, and/or seed. In another embodiment, a reproductive-preferred promoter may be selected and isolated such that the promoter does not express an operably-linked gene in a non-reproductive tissue, such as a vegetative tissue.

For example, a reproductive-preferred promoter may be identified by searching for an mRNA which is only present during reproductive development. Additionally, a reproductive-preferred promoter may be present in pre-male and pre-female reproductive tissues. In one embodiment, a reproductive-preferred promoter is identified from mRNA present during development of a plant's male reproductive tissues, including, for example, anthers, pollen, filament, male staminate cones, and pre-male reproductive tissues. In one embodiment, a reproductive-preferred promoter is identified from mRNA present during development of a plant's female reproductive tissues, including, for example, stigma, style, ovary, ovuliferous cones, and pre-female reproductive tissues. Following identification and isolation of a reproductive-preferred mRNA, cDNA is prepared from this reproductive-preferred mRNA. The resultant cDNA may be used as a probe to identify the regions in a plant genome containing DNA coding for a reproductive-preferred mRNA. Once a DNA has been identified, the sequence upstream (i.e., 5') from the DNA coding for a reproductive-preferred promoter may be isolated.

As used herein, promoter is intended to mean a nucleic acid, preferably DNA, that binds RNA polymerase and/or other transcription regulatory elements. As with any promoter, the promoters of the current invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule. As used herein, "operably linked" refers to the chemical fusion, ligation, or synthesis of DNA such that a promoter-nucleic acid sequence combination is formed in a proper orientation for the nucleic acid sequence to be transcribed into an RNA segment. The promoters of the current invention may also contain some or all of the 5' untranslated region (5' UTR) of the resulting mRNA transcript. On the other hand, the promoters of the current invention do not necessarily need to possess any of the 5' UTR.

A promoter, as used herein, may also include regulatory elements. Conversely, a regulatory element may also be separate from a promoter. Regulatory elements confer a number of important characteristics upon a promoter region. Some elements bind transcription factors that enhance the rate of transcription of the operably linked nucleic acid. Other elements bind repressors that inhibit transcription activity. The integrated effect of transcription factors on promoter activity may determine whether the promoter activity is high or low, i.e. whether the promoter is "strong" or "weak." Transcription factors that bind regulatory elements may themselves be regulated by the interaction with other bound proteins or by covalent modification, e.g. phosphorylation, in response to extracellular stimuli. The activity of some transcription factors is modulated by signaling molecules, such as intracellular metabolites or chemicals exogenous to the organism that communicate with the cellular nucleus. Promoters that are unaffected by changes in the cellular environment are referred to as constitutive promoters.

In another embodiment, the nucleic acids of the invention encode expression products that disrupt the metabolism, function, and/or development of the cell in which the nucleic acid is expressed. In one embodiment, the nucleic acids of the invention encode a cytotoxic expression product. In one embodiment, the nucleic acids of the invention embrace barnase. In a further embodiment, the barnase may be mutated by methods known in the art for increasing and/or decreasing barnase activity. In one embodiment, a mutated barnase may have attenuated cytotoxic activity.

The present invention also provides vectors comprising the isolated nucleic acid molecules and polypeptides of the invention. In one embodiment, the vectors of the present invention are Ti-plasmids derived from the *A. tumefaciens*.

In developing the constructs of this invention, the various components of the construct or fragments thereof will normally be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. to tailor the components of the desired sequence. Once the construct has been completed, it may then be transferred to an appropriate vector for further manipulation in accordance with the manner of transformation of the host cell.

A recombinant DNA molecule of the invention typically includes a selectable marker so that transformed cells can be easily identified and selected from non-transformed cells. Examples of such markers include, but are not limited to, a neomycin phosphotransferase (nptII) gene, which confers kanamycin resistance. Potrykus et al., *Mol. Gen. Genet.* 199: 183-188 (1985). Cells expressing the nptII gene can be selected using an appropriate antibiotic such as kanamycin or G418. Other commonly used selectable markers include the bar gene, which confers bialaphos resistance; a mutant EPSP synthase gene (Hinchee et al., Bio/Technology 6:915-922 (1988)), which confers glyphosate resistance; a nitrilase gene, which confers resistance to bromoxynil (Stalker et al. *J. Biol. Chem.* 263:6310-6314 (1988)); a mutant acetolactate synthase gene (ALS), which confers imidazolinone or sulphonylurea resistance (European Patent Application 154,204, 1985); and a methotrexate resistant DHFR gene (Thillet et al. *J. Biol. Chem.* 263:12500-12508 (1988)).

Additionally, vectors may include an origin of replication (replicons) for a particular host cell. Various prokaryotic replicons are known to those skilled in the art, and function to direct autonomous replication and maintenance of a recombinant molecule in a prokaryotic host cell.

The vectors will preferably contain selectable markers. Numerous selectable markers for use in selecting transfected plant cells including, but not limited to, kanamycin, glyphosate resistance genes, and tetracycline or ampicillin resistance for culturing in *E. coli, A. tumefaciens* and other bacteria.

A plasmid vector suitable for the introduction of nucleic acid of the current invention into monocots using microprojectile bombardment is composed of the following: the promoter of choice; an intron that provides a splice site to facilitate expression of the gene, such as the Hsp70 intron (PCT Publication WO 93/19189); and a 3' polyadenylation sequence such as the nopaline synthase 3' sequence (NOS 3'). Fraley et al. *Proc Natl Acad Sci USA* 80: 4803-4807 (1983). This expression cassette may be assembled on high copy replicons suitable for the production of large quantities of DNA.

A particularly useful *Agrobacterium*-based plant transformation vector for use in transformation of dicotyledonous plants is plasmid vector pMON530 (Rogers et al. (1987) Improved vectors for plant transformation: expression cassette vectors and new selectable markers. In Methods in Enzymology. Edited by R. Wu and L. Grossman. p 253-277. San Diego: Academic Press). Plasmid pMON530 is a derivative of pMON505 prepared by transferring the 2.3 kb StuI-HindIII fragment of pMON316 (Rogers et al. (1987) Improved vectors for plant transformation: expression cassette vectors and new selectable markers. In Methods in Enzymology. Edited by R. Wu and L. Grossman. p 253-277. San Diego: Academic Press) into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 (Rogers et al., 1987) in which the Ti plasmid homology region, LIH, has been replaced with a 3.8 kb HindIII to SmaI segment of the mini RK2 plasmid, pTJS75 (Schmidhauser and Helinski. *J. Bacteriol.* 164-155 (1985). This segment contains the RK2 origin of replication, oriV, and the origin of transfer, oriT, for conjugation into *Agrobacterium* using the tri-parental mating procedure (Horsch and Klee *Proc. Natl. Acad. Sci. USA* 83:4428-4432 (1986). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in *E. coli* and *A. tumefaciens*, an intact nopaline synthase gene for facile scoring of transformants and inheritance in progeny, and a pBR322 origin of replication for ease in making large amounts of the vector in *E. coli*. Plasmid pMON505 contains a single T-DNA border derived from the right end of the pTiT37 nopaline-type T-DNA. Southern blot analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON17227. This vector is described in PCT Publication WO 92/04449 and contains a gene encoding an enzyme conferring glyphosate resistance (denominated CP4), which is an excellent selection marker gene for many plants, including potato and tomato. The gene is fused to the Arabidopsis EPSPS chloroplast transit peptide (CTP2), and expression is driven by the promoter of choice.

For secretion of the translated protein into the lumen of the endoplasmic reticulum, the periplasmic space or into the extracellular environment, appropriate secretion signals may be incorporated into the expressed polypeptide. The signals may be endogenous to the polypeptide or they may be heterologous signals.

In one embodiment, the vectors of the current invention are designed in a manner such that the nucleic acids described herein are tissue-specific promoters which are operably linked to DNA encoding a polypeptide of interest. In another embodiment, the polypeptide of interest is a protein involved in an aspect of reproductive development or regulating reproductive development. Polynucleotides encoding many of the proteins involved in reproductive development include, but are not limited to, AGAMOUS (AG), APETALA1 (AP1), APETAL3 (AP3), PISTILLATA (PI), LEAFY (LFY), and LEUNIG (LUG).

In another embodiment, the coding sequence operably linked to a promoter may code for a gene product that inhibits the expression or activity of proteins involved in reproductive development. For example, a gene encoding the enzyme callase, which digests the callose cell wall surrounding the developing pollen grains, could be operably linked to a tapetum-preferred promoter and expressed before pollen maturation, thereby disrupting pollen development.

In another embodiment, the coding sequence operably linked to a promoter may encode a cytotoxic gene product. For instance, a gene encoding barnase may be operably linked to a reproductive-preferred promoter and expressed in a reproductive tissue. In a further embodiment, standard molecular biology methods may be used for mutating barnase activity. In one embodiment, a mutated barnase has reduced RNase activity compared with a wild type barnase protein. In a further embodiment, a mutated barnase having reduced RNase activity is operably linked to a reproductive-preferred promoter and expressed in a reproductive tissue. In a further embodiment, the expression of a mutated barnase having reduced RNase activity in a reproductive tissue does not compromise vegetative growth and development.

In a further embodiment, the vectors of the current invention are designed such that the nucleic acids of the current invention are operably linked to a nucleic acid encoding an antisense RNA or interfering RNA, which corresponds to a gene that code for a polypeptide of interest, resulting in a decreased expression of a targeted gene product. In one embodiment, the gene products targeted for suppression are proteins involved in reproductive development. The use of RNAi inhibition of gene expression is described generally in Paddison et al., *Genes & Dev.* 16: 948-958 (2002), and the use of RNAi to inhibit gene expression in plants is specifically described in WO 99/61631, both of which are herein incorporated by reference.

The use of antisense technology to reduce or inhibit the expression of specific plant genes has been described, for example in European Patent Publication No. 271,988. Reduction of gene expression led to a change in the phenotype of the plant, either at the level of gross visible phenotypic difference, for example a lack of lycopene synthesis in the fruit of tomato leading to the production of yellow rather than red fruit, or at a more subtle biochemical level, for example, a change in the amount of polygalacturonase and reduction in depolymerisation of pectins during tomato fruit ripening. Smith et. al., *Nature*, 334:724-726 (1988). Smith et. al., *Plant Mol. Biol.*, 14:369-379 (1990). Thus, antisense RNA has been demonstrated to be useful in achieving reduction of gene expression in plants.

In one embodiment of the method of making a plant of the invention, an exogenous DNA capable of being transcribed inside a plant to yield an antisense RNA transcript is introduced into the plant, e.g., into a plant cell. The exogenous DNA can be prepared, for example, by reversing the orientation of a gene sequence with respect to its promoter. Transcription of the exogenous DNA in the plant cell generates an intracellular RNA transcript that is "antisense" with respect to that gene.

The invention also provides host cells which comprise the vectors of the current invention. As used herein, a host cell refers to the cell in which the coding product is ultimately expressed. Accordingly, a host cell can be an individual cell, a cell culture or cells as part of an organism. The host cell can also be a portion of an embryo, endosperm, sperm or egg cell, or a fertilized egg.

The vectors of the current invention are introduced into the host cells by standard procedures known in the art for introducing recombinant vector DNA into the target host cell. Such procedures include, but are not limited to, transfection, infection, transformation, natural uptake, electroporation, biolistics and *Agrobacterium*. Methods for introducing foreign genes into plants are known in the art and can be used to insert a gene construct of the invention into a plant host, including, biological and physical plant transformation protocols. See, for example, Miki et al., 1993, "Procedure for Introducing Foreign DNA Into Plants", In: Methods in Plant Molecular Biology and Biotechnology, Glick and Thompson, eds., CRC Press, Inc., Boca Raton, pages 67-88. The methods chosen vary with the host plant, and include chemical transfection methods such as calcium phosphate, microorganism-mediated gene transfer such as *Agrobacterium* (Horsch et al., *Science* 227:1229-31, (1985)), electroporation, micro-injection, and biolistic bombardment.

Accordingly, the present invention also provides plants or plant cells, comprising the vectors of the current invention. In one embodiment, the plants are angiosperms or gymnosperms. In another embodiment, the plants are selected from *Eucalyptus* and its hybrids, and *Pinus* species. Alternatively, the plant may be selected from *Pinus banksiana, Pinus brutia, Pinus caribaea, Pinus clasusa, Pinus contorta, Pinus coulteri, Pinus echinata, Pinus eldarica, Pinus ellioti, Pinusjeffreyi, Pinus lambertiana, Pinus massoniana, Pinus monticola, Pinus nigra, Pinuspalustrus, pinus pinaster, Pinus ponderosa, Pinus radiata, Pinus resinosa, Pinus rigida, Pinus serotina, Pinus strobus, Pinus sylvestris, Pinus taeda, Pinus virginiana, Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Juniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata, Eucalyptus alba, Eucalyptus bancroftii, Eucalyptus botryoides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus grandis, Eucalyptus globulus, Eucalyptus gompho-*

*cephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-angelica, Eucalyptus obliqua, Eucalyptus occidentalisEucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo,* and *Eucalyptus youmanni.* In particular, the transgenic plant may be of the species *Eucalyptus grandis, Pinus radiata, Pinus taeda* L (loblolly pine), *Populus nigra, Populus deltoides, Tectona grandis,* or *Acacia mangium.*

Beyond the ordinary meaning of plant, the term "plants" is also intended to mean the fruit, seeds, flower, strobilus etc. of the plant. The plant of the current invention may be a direct transfectant, meaning that the vector was introduced directly into the plant, such as through *Agrobacterium*, or the plant may be the progeny of a transfected plant. The second or subsequent generation plant may or may not be produced by sexual reproduction, i.e., fertilization. Furthermore, the plant can be a gametophyte (haploid stage) or a sporophyte (diploid stage).

The present invention also provides a method for controlling reproductive development in a plant comprising cultivating a plant or seed comprising the vectors of the current invention. Proper cultivation to induce or sustain the growth or germination of the plants or seeds of the current invention is species-specific, and within the level of ordinary skill in the art. The setting for cultivation may be anywhere which fosters the growth or germination of the plant or seed. Furthermore, cultivation can also include steps such as, but not limited to, providing a stress treatment, (e.g., nitrogen deprivation, heat shock, low temperatures, sucrose deprivation) which can induce embyrogenesis.

The invention further provides isolated regulatory elements that bind transcription factors and are capable of regulating tissue-preferred or tissue-specific expression. The degree of regulation conferred by the regulatory elements may be complete, meaning that transcription is not detectable without the transcription factors, or partial, meaning that transcription is enhanced in the presence of the transcription factors. In one embodiment, at least one regulatory element is operably linked to a heterologous promoter to provide a composite promoter. The composite promoter is expressed preferentially or specifically in reproductive tissue. As used herein, heterologous promoters is a phrase whose meaning term that is relative to the regulatory elements. If a regulatory element and a promoter do not associate with one another in a natural setting, the promoter would be considered heterologous to the regulatory element. Typically, the precise orientation of a regulatory element within a promoter region will not affect its activity. Furthermore, regulatory elements can function normally when inserted into heterologous promoter regions. Thus, for example, reproductive-preferred regulatory elements can be removed from their endogenous promoter and can be inserted into heterologous promoter regions to confer reproductive-specificity or preference. The heterologous promoter may be, for example, a minimal CaMV 35S promoter. Promoters that direct expression in plant cells which are suitable for modification to minimal promoters include the cauliflower virus (CaMV) 35S promoter (Jefferson et al., *EMBO J.,* 6: 3901-07 (1987)), the rice actin promoter (McElroy et al., *Plant Cell,* 2: 163-71 (1990)), the maize ubiquitin-1 promoter (Christensen et al., *Transgenic Research,* 5: 213-18 (1996)), and the nopaline synthase promoter (Kononowics et al., *Plant Cell* 4: 17-27 (1992)).

To prepare the nucleic acids of the invention, genomic libraries were made from *Pinus radiata* and *Pinus taeda*, using a variety of restriction endonucleases to digest the genome into discrete fragments. Genomic libraries can be similarly constructed from any plant species from which it is desirable to obtain tissue-selective promoters. An adaptor was ligated to each of these genomic sequences, according to the procedure provided by Clontech for use of its Genome Walker™ Systems (Clontech, Palo Alto, Calif.). Promoter sequences then were PCR-amplified using adaptor-specific primers and "gene-specific primers." Alternatively, this PCR amplification step optionally may be conducted by the methodology described in U.S. Pat. Nos. 5,565,340 and 5,759,822, herein incorporated by reference, to yield reaction products of long length and minimal background. Using this general PCR amplification methodology, the identification of the promoter of the invention and its identification as a tissue-selective promoter, is governed by the choice of the "gene-specific primer."

A gene-specific primer is any transcribed sequence that is expressed at high levels in a tissue of interest. In the present invention, the gene-specific primer is a fragment of, or is complementary to, an mRNA that is expressed at high levels in reproductive tissue. In one embodiment, the gene-specific primer is selected by its homology to genes that are known to be expressed specifically in a particular reproductive tissue type. Genes of particular interest are those that are expressed in a particular reproductive tissue at high levels, which typically is an indicator of reproductive-preferred activity of the corresponding promoter.

Expressed sequence tags (ESTs) provide another source of gene-specific primers. An EST is a cDNA fragment of a corresponding mRNA that is present in a given library. Any plant EST database may be searched electronically to find ESTs that share identity to segments of genes that are known to be expressed specifically in a desired tissue type ("in silico screening"). These ESTs thus will provide gene-specific primers for the amplification of the promoter of the corresponding gene in a given genomic library. The amplified gene promoter need not be from the same species from which the EST database was obtained. All that is required is that the EST bears sufficient sequence similarity to the gene promoter of interest to act as a primer for PCR amplification of the target segment of the gene.

An alternative methodology to identify tissue-specific promoters rests on detection of mRNAs that are expressed in one tissue type, but not in another, implying that they are transcribed from a tissue-specific promoter. Populations of mRNAs can be distinguished on this basis by subtractive hybridization, for example. One such suitable subtractive hybridization technique is the PCR-Select™ described by Clontech.

Alternatively, a tissue-specific mRNA distribution can be determined by in situ hybridization of thin slices of plant tissue with radiolabeled probes. Probes that radioactively stain a particular tissue type are then used to detect the promoter associated with the mRNA by Southern analysis of genomic libraries, using the methodologies described below. All of the aforementioned techniques require the preparation of mRNA libraries from the tissue of interest, in this case, reproductive tissue. cDNA libraries may be made from reproductive tissues isolated from woody plant species. For example, male and female buds were isolated from *P. radiata* and *P. taeda*. Briefly, total RNA is isolated using standard techniques, and poly(A) RNA then is isolated and reverse transcribed to construct a reproductive-preferred tissue cDNA library. The cDNA library may be constructed in the λZAP-XR vector, employing Strategene cDNA synthesis and GigapakII Gold™ packaging kits. Reproductive-specific promoters can, in turn, be isolated from such cDNA libraries by PCR using a gene-specific probe and a primer that recognizes a sequence at the 5' end of the promoter. A gene-specific probe can be obtained by the in silico approach described above, or by designing a specific probe based on the sequence of the mRNA, if known. Furthermore, a primer can be synthesized which is complementary to the 5' UTR of the desired target gene. Alternatively, the primer can be designed from a partial amino acid sequence of the encoded protein, as a so-called degenerate primer.

Following isolation of the promoter of interest, various methods can be used to characterize its tissue-specific expression pattern and promoter strength. One commonly employed method is to operably link the promoter to a readily assayed reporter gene. For example, a reproductive-preferred promoter has been operably linked to the gene encoding β-glucuronidase (GUS). Lacombe et al., *Plant J.* 23: 663-76 (2000). Suitable expression constructs can be made using well-known methodologies.

Transformation of plants can be accomplished by any one of many suitable techniques, including *Agrobacterium*-mediated transformation, as described in U.S. Pat. No. 6,051,757. Other methods for transforming trees are known in the art, as exemplified by U.S. Pat. No. 5,681,730, which discloses an accelerated particle transformation method of gymnosperm somatic embryos. Other transformation methods include micro-projectile bombardment (Klein et al., *Biotechnology* 6: 559-63 (1988)), electroporation (Dhalluin et al., *Plant Cell* 4: 1495-1505 (1992)), and polyethylene glycol treatment (Golovkin et al., *Plant Sci.* 90: 41-52 (1993)). Further, U.S. Pat. No. 6,187,994 discloses a recombinase-assisted insertion of the expression construct into a specific, selected site within a plant genome. All of the aforementioned patents and publications are herein incorporated by reference.

A DNA molecule of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella et al. *Nature* 303:209 (1983), Bevan *Nucleic Acids Res.* 12 (22): 8711-8721 (1984), Klee et al. *Bio/Technology* 3(7): 637-642 (1985) and European Patent publication 120,516. In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen. DNA may also be inserted into the chloroplast genome (Daniell et al. *Nature Biotechnology* 16:345-348 (1998)).

When adequate numbers of cells (or protoplasts) containing the nucleic acid of interest are obtained, the cells (or protoplasts) are regenerated into whole plants. Choice of methodology for the regeneration step is not critical, with suitable protocols being available for hosts from *Leguminosae* (alfalfa, soybean, clover, etc.), *Umbelliferae* (carrot, celery, parsnip), *Cruciferae* (cabbage, radish, canola/rapeseed, etc.), *Cucurbitaceae* (melons and cucumber), *Gramineae* (wheat, barley, rice, maize, etc.), *Solanaceae* (potato, tobacco, tomato, peppers), various reproductive crops, such as sunflower, and nut-bearing trees, such as almonds, cashews, walnuts, and pecans. See, e.g., Ammirato et al. (1984) Handbook of Plant Cell Culture-Crop Species. Macmillan Publ. Co.; Fromm, M., (1990) UCLA Symposium on Molecular Strategies for Crop Improvement, Apr. 16-22, 1990. Keystone, CO.; Vasil et al. *Bio/Technology* 8:429-434 (1990); Vasil et al. *Bio/Technology* 10:667-674 (1992); Hayashimoto et al. *Plant Physiol.* 93:857-863 (1990); and Datta et al. (1990).

The vector comprising the promoter and reporter gene includes a mechanism to select those plant cells successfully transformed with the vector, which may be, for example, kanamycin resistant. The presence of the GUS gene in transformants may be confirmed by a PCR approach, using GUS-specific PCR primers (Clontech, Palo Alto). Segregation of kanamycin resistance in the progeny of the transformed plant cells can be used in conjunction with Southern analysis to determine the number of loci harboring the stably inserted vector. The temporal and spatial pattern of promoter expression is then inferred from a quantification of the reporter gene expression, as described in Jefferson et al., *EMBO J.* 6: 3901-07 (1987). Generally, GUS expression is determined histochemically in thin slices of plant tissues that are fixed first in 90% acetone and then in a buffered solution containing a GUS substrate, 5-bromo-4-chloro-3-indoyl-β-D-glucuronic acid (X-Gluc). The presence of the GUS expression product is indicated by a calorimetric reaction with the X-Gluc.

Reproductive-specific expression, for example, can be conferred by the presence of regulatory elements that specifically bind transcription factors in reproductive tissue. The interaction between reproductive-specific regulatory elements and reproductive-preferred transcription factors depends on the alignment between a subset of base pairs of the regulatory element with amino acid residues of the transcription factor. Likewise, tapetum-specific expression, for example, can be conferred by the presence of regulatory elements that specifically bind transcription factors in tapetal tissue. Base pairs that do not interact with the bound transcription factor may be substituted with other base pairs, while maintaining the overall ability of the regulatory element to bind specifically the tissue-specific transcription factor.

Various methodologies can be used to identify and characterize regulatory elements that affect tissue-preferred or tissue-specific promoter activity, once a promoter is identified as tissue-preferred or specific. In one methodology, the promoter region is sequentially truncated at the 5' end and the series of truncated promoters are each operably linked to a reporter gene. When a regulatory element is deleted, the effect on the promoter activity is inferred by the loss of tissue-specific expression of the reporter gene. Alternatively, a putative regulatory element can be inserted into an expression construct containing a minimal promoter, such as the CaMV 35S minimal promoter (Keller et al., Plant Mol. Biol. 26: 747-56) to ascertain if the putative regulatory element confers tissue-specific expression. A minimal promoter contains only those elements absolutely required for promoter activity, such as a RNA polymerase binding site. Additional examples for elucidating putative regulatory elements are provided by studies of tissue-specific regulatory elements that coordinately regulate transcription of the genes encoding L-phenylalanine ammonia-lyase (PAL) and 4-coumarate CoA ligase (4CL). Hatton et al., *Plant J.* 7: 859-76 (1995); Leyva et al., *Plant Cell* 4: 263-71 (1992); Hauffe et al., *Plant J.* 4: 235-53 (1993); Neustaedter et al., *Plant J.* 18: 77-88 (1999), all of which are incorporated herein by reference.

Functional Variants or Fragments of the Promoters of the Invention

Additional variants or fragments of the promoters of the invention are those with modifications interspersed throughout the sequence. Functional variants or fragments, as used herein, are nucleic acids that have a nucleic acid sequence at least about 70% identical to the reference nucleic acid, but still confer tissue-specific expression of coding products. The tissue-specificity or preference of the functional variant must be towards the same tissue as the reference nucleic acid. However, even if the fimctional variant is not as preferential or as specific as the reference nucleic acid, the variant is still considered a functional variant as used herein. In one embodiment, the sequence of the functional variant or fragment is at least about 75% identical to the reference nucleic acid. In other embodiments, the sequence of the functional variant or fragment is at least about 80%, 85%, 86%, 87%,. 88%, 89%, 90%, 91%, 92%, 93%, 94%, 95%, 96%, 97%, 98% or 99%.

Modifications that can produce functional variants may be made by sequential deletion of residues from the 5' end or the deletion of 5' UTR sequences from the 3' end. Alternatively, internal residues may be modified. Modifications that do not affect the function of the promoter regions most likely will be those that do not affect the binding of transcription factors. The modifications encompassed by the invention also include those that occur naturally in the form of allelic variants of the promoters of the invention.

Methods of Making the Nucleic Acids of the Present Invention

The nucleic acids of the invention can be obtained by using well-known synthetic techniques, standard recombinant methods, purification techniques, or combinations thereof. For example, the isolated polynucleotides of the present invention can be prepared by direct chemical synthesis using the solid phase phosphoramidite triester method (Beaucage et al., *Tetra. Letts.* 22: 1859-1862 (1981)), an automated synthesizer (Van Devanter et al., *Nucleic Acids Res.* 12: 6159-6168 (1984)), or the solid support method of U.S. Pat. No. 4,458,066. Chemical synthesis generally produces a single stranded oligonucleotide, which can be converted into double stranded oligonucleotides by hybridization with a complementary sequence, or by polymerization, using the single strand as a template. Also, longer sequences may be obtained by the ligation of shorter sequences.

Alternatively, the nucleic acids of the present invention can be obtained by recombinant methods using mutually priming oligonucleotides. See e.g Ausubel et al., (eds.), CURRENT PROTOCOLS IN MOLECULAR BIOLOGY (John Wiley & Sons, Inc. 1990). Also, see Wosnick et al., *Gene* 60: 115 (1987); and Ausubel et al. (eds.), SHORT PROTOCOLS IN MOLECULAR BIOLOGY, 3$^{rd}$ ed., (John Wiley & Sons, Inc. 1995). Established techniques using the polymerase chain reaction provide the ability to synthesize polynucleotides at least 2 kilobases in length. Adang et al., *Plant Mol. Biol.* 21: 1131 (1993); Bambot et al, *PCR Methods and Applications* 2: 266(1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993); Holowachuk et al., *PCR Methods Appl.* 4: 299 (1995).

Methods of Using the Nucleic Acids of the Invention

The nucleic acids of the current invention are useful for altering characteristics of a plant. The nucleic acids may be operably linked to a gene of interest to increase the levels of a molecule found in the reproductive tissue. Alternatively, the gene of interest may inhibit reproductive development, thereby conferring sterility to a plant.

One of the primary targets of such manipulated expression is reproductive development. For the reasons set forth above, there is considerable interest in regulating reproductive development, accomplished through genetic ablation. For example, a cytotoxic barnase molecule under the control of a tapetum-preferred promoter has been used for regulating reproductive development. European Patent Publication 344, 029.

For example, a mutant barnase gene having reduced RNase activity may be used for regulating reproductive development. In one embodiment, the mutant barnase gene may be operably linked to a promoter such that expression of the barnase gene could impose little or no damage to vegetative tissues, yet the mutant barnase may provide adequate RNase activity for reproductive ablation.

The present invention, thus generally described, will be understood more readily by reference to the following examples, which are provided by way of illustration and are not intended to be limiting of the present invention.

EXAMPLES

Example 1

Isolation of Reproductive-Preferred Promoters

Reproductive-preferred plant promoters can be isolated from genomic and cDNA libraries. Using the sequence of a reproductive-preferred promoter as a probe, putative reproductive-preferred promoter sequences can be isolated. For example, an AGAMOUS (AG) promoter from *P. radiata* may be used as a probe for identifying other reproductive-preferred promoter sequences.

For example, genomic DNA was isolated from a male-bud from loblolly pine. Following isolation of the male-bud DNA, the *P. radiata* AG1 sequence was used as a probe for screening the male-bud genomic DNA isolated. Using a PCR-based screening approach, two putative loblolly pine AG promoter sequences were isolated, denoted LPAG1 (SEQ ID NO: 1) and LPAG2 (SEQ ID NO: 2). Each cloned LPAG promoter is about 1400 bp, including 600 bp of 5' untranslated region, which contains the first intron of 139 bp of LPAG1 or LPAG2 gene.

The promoters were cloned using a "Genome Walker" kit (Clontech, Palo Alto, Calif.). This is a PCR-based method, which requires four PCR primers to be constructed, two of which must be gene-specific. The gene specific primers are designed generally within the 5' UTR of the gene. The fragment is amplified and then cloned into a T-tailed vector in front of the GUS reporter gene.

Example 2

Methodology to Determine the Tissue Specificity of a Promoter

Following the identification and cloning of a promoter as described in Example 1, the promoter is operably linked with a reporter gene to determine those tissue types in which the promoter is active. To this end, a construct containing an inventive promoter is transformed into *Agrobacterium tume-*

*faciens* by electroporation. Briefly, 40 μl of diluted AgL-1 competent cells are placed on ice and are contacted with about 10 ng of pART27 vector containing the promoter sequence. Electroporation is conducted under the following parameters:

Resistance=129 ohm

Charging voltage=1.44 kV

Field strength=14.4 kV/cm

Pulse duration=5.0 ms

Following electroporation, 400 μl of YEP liquid media is added and the cells are allowed to recover for one hour at room temperature. Cells then are centrifuged at 6000 rpm for 3 min and are resuspended in ~50 μl YEP. Cell samples are spread over the surface of a YEP Kan50/ Rif50 plate, sealed with parafilm, and incubated at 29° C. for 2 days for colony growth.

Tobacco (*Nicotiana tabacum*) plants are transformed with constructs of interest by *Agrobacterium*-mediated leaf tissue transformation (Burow et al., *Plant Mol. Biol. Rep.* 8:124-139, 1990).

Successfully transformed plants are then assayed for the expression of the operably linked reporter gene. Leaf, stem, root and reproductive regions are immersed in a staining solution (50 mM NaPO$_4$, pH 7.2, 0.5% Triton X-100, 1 mM X-Glucuronide, cycloheximide salt (Ducheffa). A vacuum is applied twice for 5 min to infiltrate the tissue with the staining solution. The tissue is then left shaking overnight at 37° C. for color development. Tissues are checked at three or four timepoints to check stain development, and if samples show early development, a piece of tissue is destained in 70% ethanol.

The GUS localization, as shown in Table 1, demonstrate that the disclosed isolated nucleotide sequences confer reporter gene expression preferentially in reproductive tissues, such as the tapetum.

As shown in Example 6, expression of a reproductive-preferred promoter is expected in vegetative tips in the presence of the primary inflorescence when the vegetative growth of axilliary buds is suppressed and the transition from vegetative buds and reproductive buds is fast.

TABLE 1

In planta GUS reproductive expression

| SEQ ID NO | | No. of Plants GUS + | % GUS Expression | GUS Reproductive Localization in Tobacco | GUS Reproductive Localization in Pine |
|---|---|---|---|---|---|
| 1 | LPAG1 | 15 Tobacco 17 Pine | 93 Tobacco 70 Pine | Petals, Stamens, Carpels, Vegetative Shoot Tip | Embryogenic calli and regenerated embryo |
| 2 | LPAG2 | 7 Tobacco 6 Pine | 64 Tobacco 40 Pine | Petals, Stamens, Carpels, Vegetative Shoot Tip | Embryogenic calli and regenerated embryo |
| 3 | PrAG | 1 Tobacco 28 Pine | 5.2 Tobacco 78 Pine | NO GUS staining | Embryogenic calli and regenerated embryo |
| 4 | PrMC2 400-1 | 24 Tobacco | 100 Tobacco | Anthers, Tapetum | No GUS staining in Embryogenic calli and re-generated embryo |
| 16 | PrMC2 400-3 | 11 (Tobacco) | 91 (Tobacco) | Anthers, Tapetum | No GUS staining in Embryogenic |

TABLE 1-continued

In planta GUS reproductive expression

| SEQ ID NO | No. of Plants GUS + | % GUS Expression | GUS Reproductive Localization in Tobacco | GUS Reproductive Localization in Pine |
|---|---|---|---|---|
| | 2 (Pine) | 12.5 (Pine) | | calli and re-generated embryo |

As described in more detail below, the "PRMC2" promoter constructs comprise a reproductive-preferred promoter from *P. radiata* operably linked to a barnase mutant, specifically H102E for PrMC2.400-1 and PrMC2.400-3. GUS expression has not been observed in anthers of tobacco transformed with the PrMC2.400 promoter. Accordingly, an in-frame PrMC2.400 promoter was cloned for use in an ablation construct and used in the experiments described above.

Example 3

Methods of Using a Reproductive-specific Promoter

Once a promoter having an appropriate tissue-specific and developmental pattern of expression is found, this promoter can be used to regulate a desired characteristic in a transgenic plant. In one embodiment, a tapetum-preferred promoter is used for regulating reproductive development in a plant. In this example, a tapetum-preferred promoter of the invention is operably linked to a gene encoding a cytotoxic protein. For example, a tapetum-preferred promoter may be operably linked to a gene encoding barnase. Expression of barnase in a reproductive-preferred tissue, such as the tapetum, may result in pollen ablation. European Patent Publication 344,1990.

To construct a transgenic plant having ablated male reproductive development, a fragment of barnase cDNA is operably linked in proper orientation to a reproductive-specific promoter of the invention and a nopaline synthase 3' terminator. The entire construct is inserted as a restriction fragment into the binary vector pBI 101.1 (Clontech, Palo Alto, Calif.). Vectors are electroporated into *A. tumefaciens* strain LBA4404 or C58pMP90, for tobacco or poplar transformations, respectively. See generally, No et al., *Plant Science* 160: 77-86 (2000). A tobacco leaf disc, as described above, or a poplar stem section, is dipped into the *Agrobacterium* culture as described above, according to the procedure of Leple et al., *Plant Cell Rep.* 11: 137-141 (1992). Kanamycin-resistant transformants are tested for activity, transgene copy number is determined by Southern analysis, and suitable transformants are rooted and transferred to a greenhouse.

Example 4

Method for Producing and Selecting an Attenuated Cytotoxic Enzyme

Synthesis of Barnase E73G and Barnase F106S

The barnase mutants F106S and E73G were obtained by random PCR mutagenesis. The PrAG promoter was operably linked to wild-type barnase coding region and three PCR reactions were performed such that the PrAG translation start codon ATG was replaced by barnase translation codon. In the first PCR, the 5' primer, PrAGKpn (5'-GGTTTGGTAC-CTAACTTGCC-3', SEQ ID NO: 27), anneals to the −199 to −179 positions of the PrAG promoter in reference to its translation starting ATG position, while the 3'primer, PrAG-7:

SEQ ID NO: 28
(5'-CGTGTTGATAACCTGTGCCATGATTTGTACACAAAATTTCCG-3'), anneals to the −21 to +3 positions including the translation starting ATG. The PrAG-7 primer has extra 18 bases which is complementary to the 5' of the barnase coding region. The PCR mixture contains 50 ng of the template DNA (pWVCZ3 DNA), 200 □M of dNTPs, 1.5 mM of MgCl₂, and 0.5 □l of Taq DNA polymerase (Perkin Elmer). The DNA is denatured at 95° C. for 20 seconds, reannealed at 55° C. for 30 seconds, and incubated at 72° C. for 60 seconds. This PCR cycle was repeated 25 times. Following PCR, a 220 bp product was gel-purified.

In the second PCR, the 5' primer, PrAG-8:

SEQ ID NO: 29
(5'-CGGAAATTTTGTGTACAAATCATGGCACAGGTTATCAACACG-3'), anneals to the 5' of the barnase coding region, and this primer has 21 extra bases which are complementary to the 3' of the PrAG promoter. The 3' primer, 3Barn (GGTTCTC-GAGTTTCACGTTAACTGGCTAG, SEQ ID NO: 30), anneals to the 3' of the barnase DNA and carries a Sac I site for cloning. The PCR mixture contains 50 ng of the template DNA (pWVR14), 200 µM of dNTPs, 1.5 mM of MgC12, and 0.5 µl of Taq DNA polymerase (Perkin Elmer). The DNA is denatured at 95° C. for 20 seconds, reannealed at 55° C. for 30 seconds, and incubated at 72° C. for 60 seconds. This PCR cycle was repeated 25 times. Following PCR, a 462 bp product is gel-purified.

In the third PCR, the 5' primer is the PrAGKpn and the 3' primer is 3Barn, and the DNA template is the mixture of the equal amount of the first and the second PCR products (~40 ng each). The amplified product of the third PCR is 640 bp which is the fusion between the 3' of the PrAG promoter and the barnase coding region. After the third PCR, the PCR fragment was digested with Kpn I and Sac I and ligated to the plasmid (pUC 19) which already carries the PrAG promoter so that after the ligation the barnase is driven by the full-length of the PrAG promoter.

The ligation mixture was introduced into *E. coli* by electroporation and transformed colonies were grown on LB agar containing 75 ug/ml ampicillin. Plasmids were extracted from two colonies and restriction enzyme digestion confirmed the presence of PrAG::barnase inserts. The plasmid DNAs were sequenced to confirm that they all have a mutation in the barnase coding region.

It was realized that all of the colonies growing on the LB plates contain mutant forms of barnase, and most of the mutations abolished barnase activity. However, some of the mutations decreased barnase activity, as indicated by the smaller sizes of colonies on the LB plates. About 100 colonies were selected and inoculated into 1 ml of LB liquid containing 75 ug/mL ampicillin. Following overnight culture at 37° C., the cell densities of the cultures were compared, and five cultures with significantly lower cell densities were selected. Low cell density indicates that the barnase is active, but much less toxic. The plasmids were purified from the five *E. coli* cultures and reintroduced into *E. coli* to confirm that the introduced plasmids, indeed, cause the smaller size of colonies on the LB agar plates, suggesting attenuated barnase activity carried by the plasmids. The reintroduction of the plasmids into *E.coli* was repeated three times. The confirmed plasmids were sequenced, and the results showed that the plasmid extracted from *E. coli* culture 29-S contained a single nucleotide substitution (A→G) in the codon for glutamate at position 73 of the barnase coding region, leading to the change of the glutamate for glycine. This barnase mutant was named barnase E73G (SEQ ID NO. 5). The plasmid extracted from *E. coli* culture 43-S also contained a single nucleotide substitution (T→C) in the codon for phenylalanine at position 106 of the barnase coding region, leading to the change of phenylalanine for serine. This barnase mutant was named barnase F106S (SEQ ID NO. 6).

Barnase F106S Assay

To assay F106S toxicity, tobacco plants were transformed, as described above in Example 2, with a construct having the PrAG promoter operably linked to a gene encoding mutant barnase F106S. No viable tobacco transformants were produced, as expression of mutant barnase F 106S was lethal. These results indicate that there is a need for an attenuated barnase that, for example, can induce male-sterility, without adversely affecting vegetative growth.

Barnase E73G Assay

The barnase mutant E73G was selected for reproductive ablation based on the results of toxicity screening in *E. coli*. Expression of barnase E73G in *E. coli* resulted in a low level of toxicity. Specifically, barnase E73G inhibited *E. coli* growth in LB liquid medium and on LB solid plates. Although the value of reduced RNase activity (toxicity) of the barnase mutants can not be obtained from this biological screen, these results suggest that E73G has attenuated RNase activity.

Further evidence for attenuated barnase activity in barnase E73G may be found in a comparison study between barnase E73G and F106S. In a comparison, barnase F 106S caused significantly more *E. coli* toxicity than barnase E73G. These results suggest that barnase F106S has higher RNase activity than barnase E73G.

Barnase H102E

The barnase H102E mutation was selected based upon a report that the corresponding mutation in a related enzyme, binase, had approximately 2% of the activity of the native enzyme. Yakovlev et al. *FEBS Lett.* 354: 305-306 (1994). As described below in Example 5, barnase H102E has attenuated activity. In this mutant, the codon for histidine 102 was substituted by a glutamate codon.

Directed mutagenesis of the barnase segment made use of an existing plasmid, pWVR14, that comprised the wild-type barnase coding region. This prior cloning of barnase used primers BAR5NCO (5'-TGACAACCATGGCACAGGT-TATCAACACGTTTGAC-3', SEQ ID NO: 31) and BAR3MFE (5'-AAAGTGCAATTGACCGATCA-GAGTTTGAAG-3', SEQ ID NO: 32) to amplify the entire coding region from the barnase cassette of plasmid pMT416. Hartley, R. W. *J. Mol. Biol.* 202: 913-915 (1988). The amplified fragment was digested with NcoI and cloned into a prepared vector with one NcoI end and one blunt end. The resulting plasmid, pWVR14, put the barnase segment adjacent to the promoter and 5'-UTR of the SEPALLATA1 gene (SEP1, previously called AGL2) and the mutagenesis procedure made use of the promoter sequence. Primers AGL2PB (5'-TTTCACAACCTCCACACACTT-3', SEQ ID NO: 33) and BARH2E (5'-GTAAAGGTCTGATACTCGTCCGTTG-3',SEQ ID NO: 34) were used to amplify the 5' portion of the coding region plus a segment of the adjoining promoter. Primers BAR5NCO and BAR3MFE were used to amplify the wild-type barnase cassette. After amplification, the fragments were purified away from the primers and PCR reagents using gel electrophoresis and the QIAEX gel purification kit (QIAGEN). Approximately 100 ng of each fragment was combined with 1×Perkin Elmer Taq buffer, 1.6 mM MgCl$_2$, 0.10 mM each dNTP and 0.5 µl Perkin Elmer Taq DNA polymerase in a 50 µl reaction, and the mixture was repeatedly denatured at 95° C., reannealed at 50° C. and incubated at 72° C. (five cycles) in order to allow extension of the 0.75 kb fragment comprising a portion of the SEP1 promoter and the complete barnase coding region. The 0.75 kb fragment was further amplified by adding 10 µl of the extension reaction to a 50 µl mixture containing 20 pmol each of primers AGL2PB and BAR3MFE, 1×PCR buffer, 1.6 mM MgCl$_2$, 0.250 mM each dNTP and 0.5 µl Taq DNA polymerase, and running seven more cycles. The fragment was digested with NcoI, and the barnase segment was gel purified and ligated into a vector with NcoI and blunt ends. The correct mutation was verified by sequence analysis. For subsequent work, such as assembly of pWVR220, the full-length barnase H102E fragment was amplified using primers BAR5NCO and BAR3SAC (5'-GAAGAAGAGCTCTTGACCGATCA-GAGTTTGAAG-3', SEO ID NO: 35), digested with NcoI and SacI, and purified. Because of the desire to have an NcoI site at the translation initation codon, an extra Alanine codon immediately after the ATG was included in primer BAR5NCO. This resulted in the His to Glu mutation actually being at codon 103 in the final coding region.

Barnase K27A

The barnase K27A mutation was selected based upon a report that the corresponding mutation in a related enzyme, binase, had approximately 20% of the activity of the native enzyme. Yakovlev et al. *FEBS Lett.* 354: 305-306 (1994). Another report suggests that barnase K27A mutant has reduced activity compared with native enzyme. Mossakowska et al. *Biochemishy* 28: 3843-3850 (1989). The barnase coding region was altered so that the codon for lysine 27 was substituted by an alanine codon. Simultaneous amplification and directed mutagenesis of the barnase segment was accomplished using PCR. Primers BAR5NCO (5'-TGA-CAACCATGGCACAGGTTATCAACACGTTTGAC-3', SEQ ID NO: 31) and BARK27AR (5'-TGCTTCTGATGCT-GTAATGTAATTATCAG-3',SEQ ID NO: 36) were used to amplify the 5' portion of the coding region and primers BARK27AF (5'-AATTACATTACAGCATCAGAAGCA-CAAG-3', SEQ ID NO: 37) and BAR3SAC (5'-GAAGAA-GAGCTCTTGACCGATCAGAGTTTGAAG-3', SEQ ID NO: 35) were used to amplify the 3' portion of the coding region from the barnase cassette of plasmid pMT416. After amplification, the fragments were purified away from the primers and PCR reagents, and then were combined. Approximately 100 ng of each fragment was combined with 1×Stratagene High Salt Buffer, 0.175 mM each dNTP and 0.25 µl TaqPlusLong in a 25 µl reaction, and the mixture was repeatedly denatured at 95° C., reannealed at 50° C. and incubated at 72° C. (five cycles) in order to allow extension of the complete coding region. The full barnase K27A fragment was further amplified by adding the extension reaction to a 75 µl mixture containing 20 pmol each of primers BAR5NCO and BAR3SAC, 1×Stratagene High Salt Buffer, 0.175 mM each dNTP and 0.75 µl TaqPlusLong, and running fifteen more cycles. The resulting full-length fragment was digested with NcoI and SacI and purified. The mutated coding sequence is set forth in SEQ ID NO: 8. As noted above, an extra Alanine codon was included immediately after the ATG in primer BAR5NCO. This resulted in the Lys to Ala mutation actually being at codon 28 in the final coding region.

Example 5

Assay for Toxicity of Barnase Mutants in *E. coli*

Barnase DNA was fused at the 3' end of PrAG promoter by PCR, and the resulting PCR fragment was cloned into pUC19 and introduced into *E. coli*. After growing at 37 degrees C. overnight (~16 hours) on LB agar supplied with 80 ug/ml ampicillin, single colonies were selected and inoculated into 1 ml of LB liquid containing ampicillin. After overnight incubation, the slow-growing *E. coli* cultures were selected and plasmids were extracted. The purified plasmids were reintroduced into *E. coli*, and single colonies were obtained on LB agar after overnight incubation at 37 degrees C. The diameters of the colonies were measured and compared with the control (pUC19 carrying the insert of barnase H102Y driven by PrAG promoter). The diameter of a single colony carrying a barnase mutant is the average of three independent experiments repeated from the step of introducing the plasmid into *E. coli*.

The toxicity of the barnase mutants was determined by comparing the diameter of the single colonies with control colonies. As shown below in Table 2, a large diameter colony indicates no toxicity, while a small diameter suggests strong toxicity.

TABLE 2

Toxicity of Barnase Mutants in *E. coli*

| Barnase Mutant Construct | Number of Colonies on Plate | Colony Diameter (mm) | Percentage of Colonies having calculated Diameter | Toxicity Level |
|---|---|---|---|---|
| Control (*Barnase H102Y) | 245 | 0.8-1.0 | 85 | None |
| Barnase H102E | <300 | 0.9-1.1 | 85 | None |
| Barnase E73G | 180 | 0.5-0.8 | 85 | Medium |
| Barnase F106S | 320 | 0.2-0.5 | 95 | High |

*Barnase H102Y has no biological RNase activity reported.

Example 6A

Tissue-Preferred Expression of LPAG Promoter

Following the identification and cloning of a promoter by the procedure outlined above in Example 1, a promoter is operably linked with a reporter gene to determine those tissue types in which a promoter is active. To determine the tissue specificity of the LPAG1 and LPAG2 promoters, each promoter was operably linked to the GUS reporter gene and the resulting constructs were introduced into tobacco plants, as described in Example 2.

GUS Analysis of Sepals and Petals

Briefly, to analyze GUS expression of LPAG1 promoter activity in tobacco, sepals and petals were removed from unopened, young flowers that are about 2 to 5 mm in height. The carpels were cut vertically in the middle using a razor blade and the resulting half carpels (attached by 2-3 young stamens) were stained for GUS activity at 37° C. for 16 hours. Three individual flowers from each transgenic line were stained, and the destaining was carried out in 70% and then 95% ethanol.

GUS Analysis of Young Leaves

Young leaves adjacent to flowers were analyzed for GUS expression. For each transgenic line, three young leaves were cut into small squares (9 mm$^2$) and stained for GUS activity at 37° C. for 16 hours, and then destained, as described above for the sepals and petals.

GUS Analysis of Vegetative Shoot Tips

Young shoot tips were collected from individual plants at two different stages of growth. Analysis of the first growth stage encompassed collecting shoot tips from tobacco plants in which 30% of the flowers on the primary terminal inflorescence were already open. This first growth stage analyzed the shoot tips with primary terminal inflorescences. The shoot tips with primary terminal inflorescences represent the axillary shoot tips growing out from the intersection of the primary stems and the primary leaves. Each shoot tip having a primary terminal inflorescence is about 10 to 15 mm long.

Analysis of the second growth stage encompasses collecting shoot tips 6 days post removal of the primary terminal inflorescence. These shoot tips do not have primary terminal inflorescence and represent the axillary shoot tips growing out from the intersection of the primary stems and the primary leaves. Each collected shoot tip without a primary terminal inflorescence is about 25 to 40 mm long.

Most of young leaves surrounding the shoot tips were removed and only one to three leaves were attached to the shoot tips. The dissected shoot tips were cut vertically in the middle and the resulting half tips (still attached by 1-3 leaves) were stained for GUS activity at 37° C. for 16 hours. Three shoot tips were collected and stained from each transgenic line.

As shown below in Table 3, LPAG1 promoter is preferentially active in the stamens and carpels (reproductive tissues) and shows no activity in leaves (vegetative tissues).

TABLE 3

GUS Expression Analysis of LPAG1 Activity in Transgenic Tobacco

| Line No. | Stamens and Carpels | Young Leaves | Analysis of vegetative shoot tips when primary terminal inflorescence is present | Analysis of vegetative shoot tips when primary terminal inflorescence is absent |
|---|---|---|---|---|
| 1 | NO | NO | Not tested | Not tested |
| 2 | YES-Medium Expression | NO | YES-Medium Expression | NO |
| 4 | YES-Strong Expression | NO | YES-Strong Expression | YES-Weak Expression |
| 5 | YES-Medium Expression | NO | YES-Medium Expression | NO |
| 6 | YES-Medium Expression | NO | YES-Medium Expression | NO |
| 7 | YES-Medium Expression | NO | YES-Medium Expression | NO |
| 8 | YES-Medium Expression | NO | YES-Medium Expression | NO |
| 9 | YES-Strong Expression | NO | YES-Strong Expression | YES-Medium Expression |
| 11 | YES-Weak Expression | NO | NO | NO |
| 12 | YES-Medium Expression | NO | YES-Medium Expression | YES-Weak Expression |
| 13 | YES-Medium Expression | NO | YES-Weak Expression | NO |
| 14 | YES-Strong Expression | NO | YES-Strong Expression | YES-Medium Expression |
| 15 | YES-Weak Expression | NO | YES-Weak Expression | NO |
| 16 | YES-Strong Expression | NO | YES-Medium Expression | NO |
| 17 | YES-Weak Expression | NO | YES-Weak Expression | NO |
| 18 | YES-Weak Expression | NO | YES-Weak Expression | NO |

As shown above in Table 3, LPAG1 promoter activity decreases in shoot tips following removal of the primary terminal inflorescence. In the presence of the primary inflorescence, the vegetative growth of axillary buds is suppressed, and the transition from vegetative buds to reproductive buds is very fast. In some cases, the floral buds emerged when the axillary shoots are only 10 mm in length. During reproductive growth in tobacco, nutrient acquisition and hormone production induce floral gene expression in the axillary shoots. Removal of the primary terminal inflorescence resets the tobacco plants back to vegetative growth, and the growth of axillary buds is no longer subject to the suppression imposed by the terminal flowers.

It was observed that after the removal of the primary terminal inflorescence the axillary buds grow fast and the floral buds are not present when the axillary shoots are 40 mm long. So, in the presence of the terminal flowers, the meristems of axillary shoots are already converted to floral meristems or half way towards floral meristems in which the expression of floral genes, such as LEAFY and AGAMOUS, is turned on, and LPAG1 promoter is also turned on. The removal of the terminal flowers resets the axillary buds back to vegetative growth and the expression of floral genes in the axillary shoot meristems is turned off, and so LPAG1 promoter activity is probably also turned off.

Example 6B

Deletion Analysis of LPAG1 Promoter

Promoter deletion analysis can be used to determine the minimal promoter and regulatory elements within a promoter sequence. Each promoter deletion is operably linked to a reporter gene and the expression profile of the promoter-reporter gene construct is analyzed.

For example, LPAG1 promoter (SEQ ID NO. 1) was serially deleted. Briefly, five serial deletions were made from the 5'-end of the LPAG1 promoter sequence. Each serial deletion deletes approximately 160 bp, for a total of a 800 bp deletion. The following is a summary of preliminary results of LPAG1 promoter deletion. The five serial deletion constructs (dentoted LPAG1d1-LPAG1d5) were introduced into pine and tobacco. Because the deletions are made from the 5'-end of the LPAG1 promoter sequence, it was estimated that the LPAG1d5 deletion construct should cut into the 5' untranslated region of LPAG1 gene and therefore, the LPAG1 promoter sequence should be absent from the LPAG1d5 construct.

Following transformation of pine and tobacco plants with the promoter-deletion constructs, as described in Example 2, transformed calli were analyzed for LPAG1 promoter activity. GUS expression analysis was determined as outlined in Example 5. The results of the LPAG1 promoter deletion experiments are summarized below in Table 4.

TABLE 4

Promoter deletion analysis of LPAG1

| Construct | Promoter Length | Relative Activity in Pine calli | Relative Activity in Tobacco Flowers |
|---|---|---|---|
| LPAG1 | 1400 | Strong | Strong |
| LPAG1 d1 | 1240 | Same as full-length promoter | Same as full-length promoter |
| LPAG1 d2 | 1080 | Same as full-length promoter | Same as full-length promoter |
| LPAG1 d3 | 920 | Same as full-length promoter | Same as full-length promoter |
| LPAG1 d4 | 760 | Same as full-length promoter | Very low GUS activity detected |
| LPAG1 d5 | 600 | NO GUS staining activity detected | NO GUS staining activity detected |

Based on the GUS expression profiles displayed in Table 4, the results clearly suggest that the nucleotide sequences (~150 bp) which are present in LPAG1d3 but absent in LPAG1d4 are essential for the LPAG1 promoter to be active in the stamens and carpels of tobacco flowers, but the same sequences are not essential for the LPAG1 promoter to be active in pine calli since LPAG1d4 still have similar GUS activities in the calli as indicated by GUS staining and MUG assays.

Example 7

Method for Ablating Pine Male and Female Cones Using a Construct Having LPAG1 and PrAG Promoters Based on the results shown in Example 6, Table 4, the LPAG1 and PrAG promoters and its promoter deletions can be used for ablating male and female cones in Pine trees.

For example, an ablation construct could have the LPAG1 promoter operably linked to a gene encoding barnase, while the PrAG or LPAG1d4 promoter is operably linked to a gene encoding barstar (barnase inhibitor). As shown above in Example 6, LPAG1 promoter is active in pine cones and embryos while the PrAG or LPAGd4 promoter is active only in pine embryos. By placing the gene encoding barstar under a promoter (PrAG) that shows little activity in a pine cone, barnase toxicity produced by the other promoter (LPAG) can effectively ablate male and female cones. On the other hand, similar levels of activities of the two promoters in pine embryos produce similar amounts of barnase and barstar, and so the barnase toxicity in the embryos is effectively neutralized, leading to transformation and regeneration of pine embryogenic calli and enbryos. Following the transformation protocols described in Example 2, pine calli are analyzed for LPAG1 expression.

Example 8

Analysis of AGAMOUS Promoter from P. radiata

As described in Example 1, a reproductive-preferred promoter can be identified and cloned from a tree species, such as P. radiata or E. grandis. The PrAG promoter is an AGAMOUS promoter from P. radiata. The PrAG promoter has a length of about 1400 bp, including a 5'-untranslated region. The PrAG promoter is disclosed in WO 00/55172, which is incorporated herein by reference.

To determine whether PrAG confers reproductive-preferred expression, the PrAG promoter was operably linked to a GUS reporter gene having an intron. The resultant PrAG-GUS promoter construct was introduced into tobacco plants, as described in Example 2. Tobacco tissues were analyzed for GUS expression and Table 5 summarizes PrAG promoter activity.

TABLE 5

GUS analysis of PrAG promoter activity

| Tobacco Tissue Sample | GUS Expression Level |
|---|---|
| Leaf | None |
| Petal | Yes |
| Stamen | Yes |
| Carpel | Yes |

Although GUS expression in leaf, petal, stamen, and carpel tissue was not detectable by enzymatic assay, GUS expression in petal, stamen, and carpel tissue was detectable using a more sensitive method, such as RNase Protection Assay with poly(A$^+$) RNA.

Example 9

Floral Specific Enhancer Increases PrAG Promoter Activity

As illustrated in Example 8, the PrAG promoter confers very weak reproductive-preferred promoter expression in tobacco. It has been shown that the *Arabidopsis* AGAMOUS gene contains a floral-specific enhancer (AtAGenh) that resides in the second intron of the AG gene. Sieburth, L. E., and Meyerowitz, E. M. *The Plant Cell* 9, 355-365 (1997). Busch, M. A., Bomblies, K., and Weigel, D. *Science* 285, 585-587 (1999). Deyholos, M. K., and Sieburth, L. E. *The Plant Cell* 12:1799-1810 (2000). It is possible that the AtAGenh enhancer element may upregulate PrAG promoter activity preferentially in the reproductive tissues of angiosperm flowers.

To determine whether AtAGenh enhances PrAG promoter activity in reproductive tissues, the second intron of Arabidopsis AG (2750 bp) was isolated and fused to the 5' end of the PrAG promoter operably linked to the GUS reporter gene having an intron ((AtAGenh)PrAG::GUSIN), and the resulting construct (pWVCZ20, See FIG. 2) was introduced into tobacco.

Following tobacco transformation, tobacco tissues were collected and analyzed for GUS expression. As indicated in Table 6 below, GUS staining revealed that, indeed, the AtAGenh enhances PrAG promoter activity primarily in the stamen and carpel, and some increase was also observed in the petal. No GUS staining was observed in sepal, leaf, and the vegetative shoot tip.

TABLE 6

AtAGenh Enhances PrAG promoter Activity

| Tobacco Tissue Sample | GUS Expression PrAG::GUSIN | GUS Expression (AtAGenh)PrAG::GUSIN |
|---|---|---|
| Stamen | Weak Expression | Enhanced GUS Expression |
| Carpel | Weak Expression | Enhanced GUS Expression |
| Petal | Weak Expression | Enhanced GUS Expression |
| Sepal | NO GUS Expression | NO GUS Expression |
| Leaf | NO GUS Expression | NO GUS Expression |
| Vegetative Shoot | NO GUS Expression | NO GUS Expression |

Example 10

Use of a Reproductive-Preferred Promoter:: Mutant Barnase Construct for Reproductive Ablation without Disturbing Vegetative Growth As described above in Example 4, various methodologies may be used to produce mutant cytotoxic genes having attenuated cytotoxic effects. By reducing the toxic effect of a barnase enzyme, barnase may be used for reproductive ablation, without compromising a plant's vegetative growth. Moreover, the combination of a reproductive-preferred promoter operably linked to an attenuated barnase provides a means for reproductive ablation, without vegetative destruction. For example, mutant barnase E73G was fused with PrAG to create pWVCZ23 (FIG. 3) and (AtAGenh)PrAG to create pWVCZ24 (FIG. 4), respectively, and the resulting constructs were introduced into tobacco. Following transformation, the tobacco plants were analyzed and the results are shown below in Table 7.

TABLE 7

| Transformation Construct | Flower Phenotype | Percentage of total transgenic plants recovered that do not produce pollen. (%) | Percentage of total transgenic plants recovered that do not produce seed. (%) | Negative Effects on Vegetative Growth |
|---|---|---|---|---|
| (AtAGenh)PrAG::E73G | Degenerated stamen and carpel; retarded petal; normal sepal | 68 | 68 | NO |
| PrAG::E73G | Normal | 10 | 10 | NO |

As shown in Table 7, 68% of tobacco plants transformed with (AtAGenh)PrAG::E73G have a sterile reproductive phenotype, i.e., many transformed plants produced neither viable pollen nor viable seeds. Likewise, 10% of plants transformed with PrAG::E73G produced no viable pollen and seeds. Interestingly, transformation with either construct does not compromise vegetative growth. The above results clearly demonstrate that the ablation cassette, (AtAGenh)PrAG::barnaseE73G, can produce male- and female-sterile tobacco, and this cassette may be able to produce similar ablation effects on other angiosperm plants, including angiosperm and gymnosperm species.

Example 11

Use of a Temperature-Sensitive Barnase for Ablating Reproductive Primordia without Disturbing Vegetative Growth Barnase is a well-characterized enzyme, and numerous mutants have been identified. In particular, barnase mutants having altered stability and/or toxicity have been identified. A temperature-sensitive barnase may be desirable for ablating reproductive primordia without affecting vegetative growth.

For example, a heat-sensitive barnase could be used for reproductive ablation. Expression of a heat-sensitive barnase, for example, may have little toxic effect during the summer (high temperature) when the majority of vegetative growth occurs, but may be toxic during the winter or low temperature production of reproductive buds. A reproductive-preferred promoter, such as PrMC2 (SEQ ID NOs 4 or 16) could be used for minimizing expression of a heat-sensitive barnase in vegetative tissues.

Example 12

Barstar Neutralizes Barnase Toxicity in Transgenic Pine Calli and Regenerated Embryos Barstar is a natural inhibitor of barnase, and it has been used for protecting non-targeted tissues from barnase toxicity and for restoring plant fertility. Beals T. P. and Goldberg R. B. *Plant Cell.* 9:9:1527-45 (1997). Kuvshinov V et al. *Plant Sci.* 160:3:517-522 (2001). Previous experiments demonstrate that three promoters, LPAG1, PrAG, and LPAG1d4, have similar activities in pine calli and regenerated embryos. While LPAG1 promoter has high activity in tobacco flowers, the PrAG and LPAG1d4 promoters showed no or trace activities in the tobacco flowers, suggesting that PrAG and LPAG1d4 promoters may not be active in angiosperm or gymnosperm reproductive tissues. Thus, the PrAG and LPAG1d4 promoters could be operably linked to a gene that neutralizes the cytotoxic effects of barnase, such as barstar, and the promoter::barstar construct would target non-reproductive tissues. Such a promoter::barstar construct, for example PrAG::barstar, would protect vegetative tissues from deleterious barnase expression.

Moreover, it may be beneficial to create an ablation construct having a reproductive-preferred promoter operably linked to barnase and a non-reproductive-preferred promoter operably linked to barstar. For example, a pine cone ablation construct could have the LPAG1 promoter driving barnase while the PrAG or LPAG1d4 promoter drives barstar (such as LPAG1 :: barnase E73G/ PrAG::barstar or LPAG1::barnase E73G/LPAG1d4:: barstar), with both cassettes in one backbone. During pine transformation, the toxicity of barnase due to LPAG1 activity in pine calli and regenerated embryos will be effectively neutralized by the barstar produced by the activity of PrAG or LPAG1d4 promoter, and thus the transformation can proceed smoothly. However, in the mature transgenic pine trees, the presence of barnase in the pine-cone buds, due to LPAG1 promoter activity, will effectively kill the cones because of barnase toxicity and the lack of the barstar in the pine-cone buds.

Example 13

Cloning of In-frame PrMC2.400 Promoter Fragments

The PrMC2.400 promoter sequence was identified and isolated at described in U.S. Patent Application Publication 20030101487, which is incorporated by reference. The PrMC2.400 sequence has an ATG that is not in-frame with the ATG used in pWVR220 and other PrMC2 constructs. Although previous tests in *Arabidopsis* clearly showed that GUS is expressed from the PrMC2.400 promoter, GUS expression has not been observed in anthers of tobacco transformed with the PrMC2.400 promoter. Accordingly, an in-frame PrMC2.400 promoter was cloned for use in an ablation construct.

Using the PCR primers below, two different PrMC2.400 promoter sequences were isolated. As described below, the two PrMC2.400 promoters were cloned into expression vectors to ensure that the sequences are in-frame with an operably linked gene.

There are several in-frame ATGs in the PrMC2.400 promoter sequence, particularly at positions 361, 367, and 397. Using the reverse primers described, two different PrMC2.400 products were produced: PrMC2.400-1 contains all three ATGs; PrMC2.400-3 contains only the first ATG. The reverse primers were phoshorylated at the 5' end so they could be blunt-ligated to the appropriate sites in a cloning vector. The PrMC2-XG primer contains an XhoI site. PCR was performed using a high fidelity Taq polymerase blend (TaqPlus Long, Stratagene). After PCR, the amplification products were gel purified and then digested with XhoI using standard procedures. Each product was cloned into an intermediate vector and sequenced. Sequencing indicated that the PrMC2.400-1 sequence differed by one nucleotide from the original sequence, there is an insertion of a 'T' residue at position 35.

The cloning of the PrMC2.400-1 and PrMC2.400-3 sequences into expression vectors has ensured that all ATG sites remain in-frame with a gene of interest.

PrMC2-XG (for):
5'-GAAGAACTCGAGTAAAACATAATTTTGGCAGTAAAAAGTGA-3'

PrMC2-R1 (rev):
5'-CATGTTCCCGTTTGATACCTGAATTTTG-3'

PrMC2-R3 (rev):
5'-CATAAATCTTCTAAAAACAGCAGAACTGAC-3'

PrMC2-XG +PrMC2-R1: produced a 3966(KNC) bp product designated PrMC2.400-1 (SEQ ID NO: 4)

PrMC2-XG +PrMC2-R3: produced a 3603(KNC) bp product designated PrMC2.400-3 (SEQ ID NO: 16)

Example 14

Cloning In-frame PrMC2.400-1::Mutant Barnase into Binary Vectors

As described in Example 17, the in-frame promoters PrMC2.400-1 and PrMC2.400-3 may be operably linked to a gene of interest for genetic ablation. For example, the in-frame PrMC2.400-1 promoter may be operably linked to an attenuated barnase sequence for reproductive ablation.

K27A

As described in Example 4, the K27A mutant barnase was previously cloned into a high copy vector, pWVR63. The PCR generated fragment PrMC2.400-1 was cloned into pWVR63 previously digested with NcoI, Mung bean nuclease treated to generate a blunt-end, followed by an XhoI digest and gel purification to isolate the vector fragment. The subsequent intermediate plasmid, pWVR205, now contained the ablation cassette PrMC2.400-1::K27Abarnase::RNS2TER. This cassette was then subcloned into a binary vector using KpnI and ApaI to generate pWVR216.

H102E

As indicated in Example 4, the H102E mutant barnase was previously cloned into a high copy vector, pWVR15. In order to have more convenient restriction enzyme ends for cloning, H102E was generated using PCR primers from pWVR15 template. The mutant barnase H102E was generated using PCR primers:

```
                                         (SEQ ID NO: 33)
Agl2-PB:  5'-TTTCACAACCTCCACACACTT-3'

(SEQ ID NO: 35)
Bar3Sac:  5'-GAAGAAGAGCTCTTGACCGATCAGAGTTTGAAG-3'
```

PCR was performed using a high fidelity Taq polymerase blend (TaqPlus Long, Strategene). Standard three-step PCR methodology was used. The PCR reaction was gel purified and subsequently digested with NcoI and SacI. The restriction digest was gel purified and the fragment isolated and concentrated. This purified PCR fragment was cloned into an intermediate vector previously digested with NcoI and SacI, producing the construct pWVR218. This construct was sequenced to ensure correct mutant barnase sequence. The PCR generated fragment PrMC2.400-1 was then cloned into pWVR218 previously digested with NcoI, Mung bean nuclease treated to generate a blunt-end, followed by an XhoI digest and gel purification to isolate the vector fragment. The subsequent plasmid, pWVR219, now contained the ablation cassette PrMC2.400-1 ::Hi02Ebarnase::RNS2TER. This construct was sequenced to ensure correct promoter sequence and promoter:gene junction. This cassette was then subcloned into a binary vector using KpnI and ApaI to generate pWVR220.

E73G

E73G mutant barnase was previously cloned into a high copy vector, as indicated in Example 4. In order to have more convenient restriction enzyme ends for cloning, E73G sequence was generated using PCR primers from a plasmid template. The mutant barnase E73G was generated using PCR primers:

```
Bar5Nco:                                  (SEQ ID NO: 31)
5'-TGACAACCATGGCACAGGTTATCAACACGTTTGAC-3'

Bar3Sac:                                  (SEQ ID NO: 35)
5'-GAAGAAGAGCTCTTGACCGATCAGAGTTTGAAG-3'
```

PCR was performed using a high fidelity Taq polymerase blend (TaqPlus Long, Strategene). Standard three-step PCR methodology was used. The PCR reaction was gel purified and subsequently digested with NcoI and SacI The restriction digest was gel purified and the fragment isolated and concentrated. This purified PCR fragment was cloned into an intermediate vector previously digested with NcoI and SacIproducing the construct pWVR230. This construct was sequenced to ensure correct mutant barnase sequence. The PCR generated fragment PrMC2.400-1 was then cloned into pWVR230, previously digested with NcoI , Mung bean nuclease treated to generate a blunt-end, followed by an XhoI digest and gel purification to isolate the vector fragment. The subsequent plasmid, pWVR231, now contained the ablation cassette PrMC2.400-1::E73Gbarnase::RNS2TER. This construct was sequenced to ensure correct promoter sequence and promoter:gene junction. This cassette was then subcloned into a binary vector using KpnI and ApaI to generate pAGF232.

GUS Control

Although previous tests in *Arabidopsis* demonstrated that GUS is expressed from the original PrMC2.400 promoter, no staining has been observed in transformed tobacco anthers. A new reporter cassette (see below) was synthesized so that it matches the frame of the ablation constructs.

The PCR generated fragment PrMC2.400-1 was cloned into pWVR52, previously digested with NcoI , Mung bean nuclease treated to generate a blunt-end, followed by an XhoI digest and gel purification to isolate the vector fragment. The subsequent plasmid, pWVR233, now contained the cassette PrMC2.400-1 ::GUS::RNS2TER. This construct was sequenced to ensure correct promoter sequence and promoter:gene junction. This cassette was then subcloned into a binary vector using-KpnI and ApaI to generate pAGF234.

Example 15

In Planta Expression of PrMC2.400-1: Barnase

*Agrobacterium tumefaciens* strain GV2260 was transformed via electroporation with binary vector pWVR216 or pWVR220 or pAGF232 or pAGF234.

Transgenic plants were produced by *Agrobacterium*-mediated transformation of tobacco (*Nicotiana tabacum*). Transformants were selected on a medium containing kanamycin. Positive transformants were identified by PCR, transferred to soil, and grown under standard greenhouse conditions. Plants were analyzed for overall vegetative growth rate, time of flowering and male-sterility.

Plants expressing the mutant barnase genes driven by the PrMC2.400-1 promoter displayed a male-sterile phenotype. Specifically, the transgenic plants did not produce pollen grains. This was confirmed microscopically, by observing anthers under a compound light microscope. Further, the pollenless plants did not produce fruit capsules and seeds. However, when the plants were cross-pollinated with wt tobacco pollen, normal seed set occurred, indicating that female fertility was unaffected. Additionally, offspring from these cross-pollinations produced a pollenless phenotype, indicating that the transgenes were inherited and the presence of the transgene in the progeny produced male sterile plants.

It was noted that tobacco lines expressing the mutant barnase gene driven by the PrMC2.400-1 promoter had a reduced stamen height, relative to the carpel. Flowering time was also delayed. A reduction in vegetative growth was readily observed for tobacco lines expressing K27A and E73G, relative to the control lines. This reduction in vegetative growth resulted in shorter plants with slower development. Lines expressing H102E showed minimal signs of vegetative effects and were very similar to controls in overall growth. The reduction in vegetative growth could be an indication of 'leakiness' of the expression of the PrMC2.400 promoter in tobacco tissue.

To assay PrMC2.400 promoter activity in vegetative tissues, young leaf tissue, roots, and vegetative shoot tips from lines transformed with PrMC2.400-1::GUS lines were tested for GUS activity. GUS activity was assayed histochemically using the chromogenic substrate X-Gluc. Tissues were vacuum-infiltrated in X-Gluc at room temperature for 1 hour then incubated at 37° C. for 16 hours. Following incubation, the tissues were destained in 100% methanol and then 95% ethanol. These tissues displayed no GUS expression. It is possible that the level of GUS expression is so low that it cannot be detected by this assay.

Additional experiments using PrMC2.400-1 linked to GUS were performed to further understand temporal and spatial expression patterns during anther development in tobacco. Tobacco flower development can be divided into 12 stages to provide reference points for the expression of genes in floral organ systems. Koltunow, et al. *The Plant Cell* 2:1201-1224 (1990). Flower buds were removed at each stage, dissected, stained for GUS activity, and observed microscopically. GUS activity was assayed histochemically using the chromogenic substrate X-Gluc. Floral buds were vacuum-infiltrated in X-Gluc at room temperature for 1 hour then incubated at 37° C. for 16 hours. Tissue was destained in 100% methanol and then 95% ethanol. The results indicate that the PrMC2.400-1 promoter is expressed in only in the anther, and PrMC2.400-1 expression is limited to those developmental stages in which the tapetum is present. The tapetum layer plays a major role in pollen formation. Therefore, expression of a cytotoxic gene in the tapetum layer could prevent pollen production.

Example 16

Cloning PrMC2.400-3::Mutant Barnase into Binary Vectors

H102E

PrMC2.400-3 was generated using primers PrMC2-XG and PrMC2-R3, as described above in Example 13. Template used to amplify this fragment was the binary vector, pWVR220. This purified PCR fragment was cloned into an intermediate vector previously digested with NcoI and SacI, producing the construct pWVR242, which now contained the ablation cassette PrMC2.400-3::H102Ebarnase::RNS2TER. This construct was sequenced to ensure correct promoter sequence and promoter:gene junction. This cassette was then subcloned into a binary vector using KpnI and ApaI to generate pWVR243.

GUS Control

The PCR generated fragment PrMC2.400-3 was cloned into pWVR52 previously digested with NcoI, Mung bean nuclease treated to generate a blunt-end, followed by an XhoI digest and gel purification to isolate the vector fragment. The subsequent plasmid, pWVR244, now contained the cassette PrMC2.400-3::GUS::RNS2TER. This construct was sequenced to ensure correct promoter sequence and promoter:gene junction. This cassette was then subcloned into a binary vector using KpnI and ApaI to generate pWVR245.

Example 17

In Planta Expression of PrMC2.400-3: Barnase

*Agrobacterium tumefaciens* strain GV2260 was transformed via electroporation with binary vector pAGF243 or pAGF245.

Transgenic plants were produced by *Agrobacterium*-mediated transformation of tobacco (*Nicotiana tabacum*). Transformants were selected on a medium containing kanamycin. Positive transformants were identified by PCR, transferred to soil, and grown under standard greenhouse conditions. Plants were observed for overall vegetative growth rate, time of flowering and male-sterility. Transgenic tobacco lines displayed a male-sterile phenotype. Specifically, the plants did not produce pollen grains. Additonally, the PrMC2.400-1 ::H102E lines had reduced stamen height, relative to carpel height, and flowering time was delayed.

Lines containing PrMC2.400-3 linked to the reporter gene GUS were compared with PrMC2.400-1 ::GUS lines. The intensity of GUS staining in floral buds, specifically anther tissue, was comparable to the PrMC2.400-1::GUS lines.

Example 18

Construction of Precursor Plasmids with Flowering Control Cassettes

Next, the ColE1 replication origin and surrounding region were amplified from pART27 (Gleave, 1992) using PCR with the primer pair, ColE1-F4 (5'-GAGAGAGGATCCGGTGT-GAAATACCGCACAG-3', SEQ ID NO: 41) and ColE1-R4 (5'-GAGAGATGATCAGCCTCACTGATTAAG-CATTGGTAACTG-3', SEQ ID NO: 42). The 1.0 kb ColE1 fragment was digested with BamHI and BclI, then was purified and ligated into the BclI site of pARB310B, between the end of the trfA gene and the left border (LB) of the T-DNA. This generated pAGF50, which acted as a high copy number plasmid in *E coli*, but still replicated in *Agrobacterium*.

pAGF50 was digested with AscI and NcoI to remove the UBQ3 promoter plus most of the NPTII coding region, and the resulting 5.7 kb fragment was gel purified. The 1.9 kb fragment with UBQ10 promoter linked to the 5'-end of the NPTII coding region was released from pWVR3 by AscI and NcoI digestion, gel purified, and ligated into the pAGF50 fragment to generate pARB1000. This plasmid was further modified by the addition of a SUBIN::GUSIN::NOSTER reporter cassette. SUBIN indicates a ubiquitin promoter from *P. radiata*, which included genomic DNA coding the 5'-UTR and an intron; GUSIN indicates the β-glucuronidase coding region plus an intron from the potato tuberin gene (Vancanneyt et al., 1990). The reporter cassette was removed from pARB494 by DraI digestion and ligated into the SmaI site of pARB1000 to generate pARB1001. In addition to being able to serve as a transformation control, pARB1001 was used as the direct precursor to the flowering control plasmids because it had two NotI sites flanking the reporter gene, which could be used to switch it with other genes of interest.

The male-specific flowering control gene, PrMC2.400:: barnaseH102E::RNS2TER, was present in pWVR219, with an unwanted NotI site near the 3'-end. The plasmid was digested with NotI, and then the site was destroyed by treating with T4 DNA polymerase in the presence of dNTPs and religating the vector. The PrMC2.400::barnaseH102E:: RNS2TER cassette was excised from the altered pWVR219 with AscI and XhoI, and the 1.1 kb fragment was gel purified. pARB1001 was prepared by partial digestion with XhoI to linearize the plasmid, followed by complete digestion with AscI . The PrMC2.400::barnaseH102E::RNS2TER cassette was ligated to the prepared pARB1001 vector to generate pARB1002. The structure of the plasmid was verified with single-pass sequencing.

Figure 19:
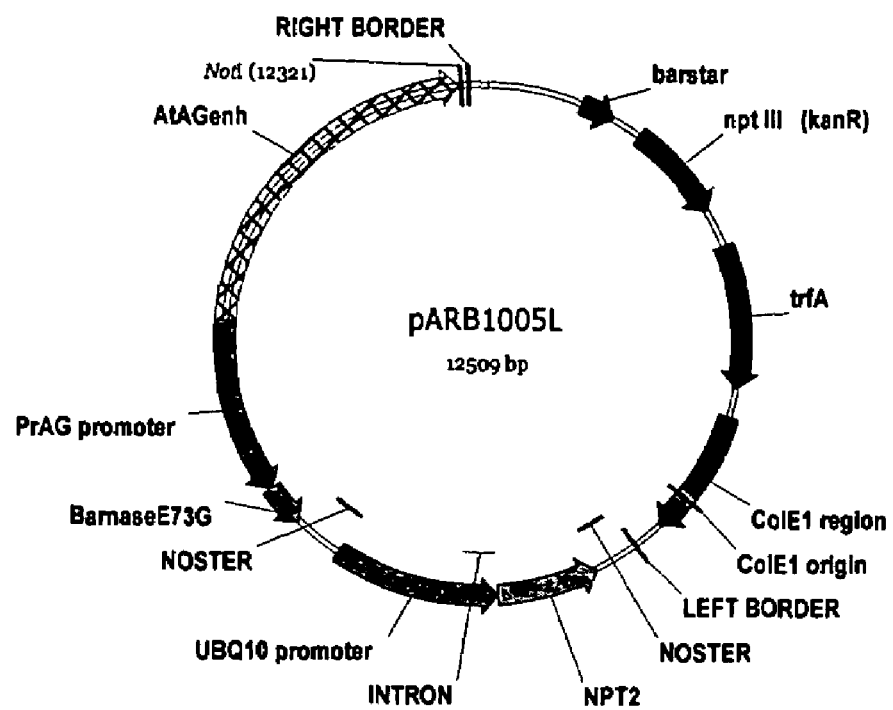
FIG. 19—pARB1005L [(AtAGenh)PrAG::barnaseE73G]

The (AtAGenh)PrAG::barnaseE73G::NOSTER cassette was removed from pWVCZ24 by EcoRI and AscI digestion. A NotI adapter comprising the oligonucleotides, EcoNot1 (5'-AATGCGGCCGCAGAGA-3') and EcoNot2 (5'-TCTCT-GCGGCCGC-3'), was ligated to the EcoRI site and digested with NotI, and then the 4.9 kb fragment was purified. The plasmid pARB1001 was digested with NotI and AscI and the 7.6 kb vector fragment was gel purified. The above cassette was ligated into these sites to generate pARB1005L (FIG. 19). The structure of the plasmid was verified with single-pass sequencing.

Example 19

Transformation of Early Flowering *Eucalyptus occidentalis*

This example details the infection and transformation of early flowering *Eucalyptus occidentalis*. In order to test flowering control constructs. *Eucalyptus occidentalis* seedlings were tested for early flowering in glasshouse growing conditions, and clones were selected on the basis of flowering within six months. These clones were introduced into sterile tissue culture for transformation with ablation constructs of the instant invention and control GUS constructs. Leaf explants were harvested and pre-cultured for 4 days and then separate explants were infected with *Agrobacterium* strain GV2260 harboring p35SGUSINT (35S::GUSINT, NOS:: NPTII) or the constructs of the instant invention, as shown in the table below, according to the method of U.S. patent application Ser. No. 10/861,909, which is incorporated herein by reference. Following eradication of the *Agrobacterium*, explants were transplanted to selection medium, which consisted of regular regeneration medium as described in that same patent application, with 30 mg/l Geneticin. Regenerated shoots of the transformants and were rooted and grown in containers on soil in a glasshouse for testing the *Eucalyptus* transformed with ablation constructs for flowering time relative to controls.

Constructs of the instant invention were also transformed into clones of *Eucalyptus camaldulensis* and commercial clones of *Eucalyptus urophylla* and *Eucalyptus grandis* using the method of U.S. patent application Ser. No. 10/861,909. Regenerated shoots of the transformants were rooted, transferred to soil and acclimated in a glasshouse, then transferred to field planting sites in Florida and South Carolina under notifications to the US Agricultural Plant Health Inspection Service. Plants are monitored regularly for the development of floral buds. No flowering has been observed to date.

TABLE 8

| Name of Construct | Flowering Control Promoter | Attenuated Barnase Gene (for example, H102E) | Euc species and clone | Approx date into transformation (or planned to transform) | Any effects noted in tissue culture suggesting leakiness of the promoter driving the attenuated barnase gene |
|---|---|---|---|---|---|
| pARB598 | PrMC2 | H102E | E. occidentalis clones 129 and 208 | December 03 | None |
| pAGF243 | PrMC2.400-3 | H102E | E. occidentalis clone 129 | March 04 | |
| pARB598 | PrMC2 | H102E | E. urophylla clone IPB1 | June 03 | None |
| pARB599 | PrMC2 | H102E | E. urophylla clone IPB1 | June 03 | Reduced transformation efficiency relative to control |
| pARB675 | PrMC2 | H102E | E. urophylla clone IPB1 | April 04 | |
| pARB639 | PrAG | E73G | E. urophylla clone IPB1 | June 03 | Could not recover lines with all T-DNA components. |
| pWVCZ24 | PrAG | E73G | E. camaldulensis clone C9 | March 03 | None |
| pWVCZ101 | PrAG | E73G | E. camaldulensis clone C10 | March 03 | None |
| pWVCZ24 | PrAG | E73G | E. grandis clone IP1 | April 03 | None |
| pWVCZ101 | PrAG | E73G | E. grandis clone IP1 | April 03 | None |
| pWVR220 | PrMC2 | H102E | E. grandis clone IP1 | April 03 | None |
| pAGF232 | PrMC2 | E73G | E. grandis clone IP1 | April 03 | None |

Example 20

Hybrid Pine

Hybrid pine (P. taeda×P. rigida) and loblolly pine (P. taeda) embryogenic cell lines were initiated from zygotic embryos of individual immature megagametophytes using the procedures described in U.S. Pat. No. 5,856,191, and maintained using the procedures described in U.S. Pat. No. 5,506,136.

After one to three months of culture on maintenance medium, the tissue cultures were cryopreserved, stored for periods of up to several years, and then retrieved using the methods of U.S. Pat. No. 6,682,931. Those skilled in the art of plant tissue culture will recognize that other cryopreservation and recovery protocols would be applicable to the present method and that the detail in this example may not be construed to limit the application of the method.

Uniform suspension cultures from two genetically different hybrid pine tissue culture lines and multiple P. taeda lines were established by inoculating a 250 ml Nephelo sidearm flask (Kontes Chemistry and Life Sciences Products) with 1 g of tissue each according to the method of U.S. Pat. No. 5,491,090. The flasks containing the cells in liquid medium were placed on a gyrotory shaker at 100 rpm in a dark culture room at a temperature of 23° C.±2° C. One week later, the liquid in each flask was brought to 35 ml by pouring 15 ml fresh medium into the culture flask and swirling to evenly distribute the cells. Cell growth was measured in the sidearm by decanting cells and medium into the sidearm portion of the flasks, allowing the cells to settle for 30 minutes and then measuring the settled cell volume (SCV). When the SCV was greater than or equal to half the maximal SCV (50% of the volume of the flask was occupied by plant cells), each culture was transferred to a 500 ml sidearm flask containing a total of 80 ml cells and medium and the transferred culture was maintained under the same conditions.

To prepare for gene transfer, polyester membrane supports were sterilized by autoclaving and placed in separate sterile Buchner funnels, and for each of six replicate plates per cell line, one to three milliliters of pine embryogenic suspension was pipetted onto each support such that the embryogenic tissue was evenly distributed. The liquid medium was suctioned from the tissues and each support bearing the embryogenic tissue was placed on gelled preparation medium for Agrobacterium inoculation according to the methods described in U.S. Patent Publication No. 20020100083. Binary reporter gene constructs were introduced into different isolates Agrobacterium tumefaciens by techniques well known to those skilled in the art, and virulence was induced with administration of acetosyringone by commonly used techniques whereupon each of the induced Agrobacterium isolates was co-mingled with separate replicates of the plant material. The cells were co-cultivated in the dark at 22°±2° C. for approximately 72 hours.

Following co-cultivation, Agrobacterium was eradicated from the cultures according to the methods described in U.S. Patent Publication No. 20020100083. Cells borne on polyester membrane supports were then transferred onto fresh selection media at intervals of 2 weeks. Active growth on the selection medium occurred in a number of isolated sectors on many of the petri dishes. Such active growth in the presence of selection agent is normally an indication that the growing tissues have integrated the selection gene into their chromosomes and are stably transformed. These areas of active growth are treated as independent transformation events and are henceforth referred to as putative transgenic sublines. The putatively transgenic embryogenic tissue was multiplied by transferring growing transgenic sectors to fresh semi-solid maintenance medium supplemented with the respective selection agent.

Putatively transformed sublines, after reaching approximately 2 g, were chosen for polymerase chain reaction (PCR) amplification for verification of the presence of transgenes using standard techniques.

TABLE 9

Primer Pairs for PCR

| | | | Product size |
|---|---|---|---|
| virD2 | GAA GAA AGC CGA AAT AAA GAG G | (SEQ ID NO: 45) | 560 |
| virD2 | TTG AAC GTA TAG TCG CCG ATA G<br>These primers were used to check contamination by *Agrobacterium* | (SEQ ID NO: 46) | |
| NptII | AAG GAG ATA TAA CAA TGA TTG AAC AAG ATG GAT TGC | (SEQ ID NO: 47) | 800 |
| NptII | TCA GAA GAA CTC GTC AAG AAG G | (SEQ ID NO: 48) | 800 |
| uid(gus) | CGA AAA CGG CAA GAA AAA GCA G | (SEQ ID NO: 49) | 450 |
| uid(gus) | ACG ACC AAA GCC AGT AAA GTA G | (SEQ ID NO: 50) | |
| Pal | AAT GGG AAG CCT GAG TTT ACA | (SEQ ID NO: 51) | 700 |
| Pal | GGC CAG CAT GTT TTC CTC CAG<br>These primers, for the PAL gene, were used as a positive control | (SEQ ID NO: 52) | |

Material from each subline also was sacrificed for GUS staining and microscopic examination. For GUS staining, an inserted uidA gene, encoding a β-glucuronidase enzyme expressing in tissue culture cells, was detected by deep blue staining of cells from each of the transgenic lines upon exposure to a colorigenic glucuronidase enzyme substrate, "X-gluc," commercially available from Inalco, according to techniques well known in the art of plant transformation. Microscopic examination demonstrates that cell division has resumed and that transient expression of the uidA transgene displays the normal frequency for these bombardments.

Germinable embryos were produced as follows. After the cell masses that had been cultured on selection medium proliferated to at least one gram, each was separately resuspended in liquid medium again. When the cell suspensions were brought to uniform (half-maximal) SCV, equivalent amounts of suspension culture cells were pipetted onto sterile membrane supports for placement on development/maturation medium as described in U.S. Pat. No. 5,506,136 to develop high quality harvestable stage 3 (cotyledonary) embryos. Dishes were incubated in a dark growth chamber at 23±2° C. The membrane supports were transferred to new petri dishes containing fresh medium every 3 weeks. At week 9, stage 3 (cotyledonary) embryos were visually analyzed for germination quality and harvested onto fabric supports on medium as described in U.S. Pat. No. 5,506,136, and incubated for about four weeks in the dark at a temperature of 4° C.±2° C. Next, embryos on their fabric supports were incubated above water in sealed containers for about three weeks in the dark at a temperature of 25° C.±2° C. Following the above two treatments, embryos on their fabric supports were transferred to medium germination medium and incubated for about three days in the dark at a temperature of 25° C.±2° C. Embryos were then removed from their fabric supports and placed onto the surface of fresh germination medium. Germination was conducted in the light at a temperature of 25° C.±2° C. Germination plates were examined weekly, over a period of about four weeks, and germinating embryos were transferred to MAGENTA® boxes containing 100 ml of germination medium for conversion to plantlets. MAGENTA® boxes containing developing plantlets were incubated in the light at 25° C.±2° C. for about eight to twelve weeks.

When the plantlets formed epicotyls (newly formed shoots of approximately two to four cm), they were transferred to containers filled with a potting mix [2:1:2 peat:perlite:vermiculite, containing 602 g/m$^3$ OSMOCOTE fertilizer (18-6-12), 340 g/m$^3$ dolomitic lime and 78 g/m$^3$ MICRO-MAX micronutrient mixture (Sierra Chemical Co.)]. The plantlets were grown in a shaded greenhouse and misted infrequently for a period of about two weeks. They were removed from mist for acclimatization in the greenhouse for about four weeks. Plantlets were then transferred to outdoor shade for about six weeks for final acclimatization before moving to full-sun conditions. They were then grown in containers until conditions were ready for field planting.

Plants regenerated from loblolly pine (*P. taeda*) lines were also planted into the same field sites and no strobilus production has been observed in the field sites as long as six years after planting. However, unexpectedly, the transgenic hybrid pine lines produced strobili three years after planting. At that point the hybrid trees were approximately one meter in height, much smaller than the adjacent transgenic loblolly pine trees.

Table 10 below shows the results of a second planting that included the non-transgenic hybrid pine origin line as a control from somatic embryogenesis, a variety of seedling genotypes with the same parents that present a control that did not pass through tissue culture, and a total of 24 different transgenic lines generated from the 97LP0006 somatic embryogenic line using two different vectors, some transformed using biolistics and some using *Agrobacterium*, with multiple replicates of most lines for a total of over 250 plants, produced some strobili two years after planting and significant numbers of strobili within three years after planting. Tests were terminated following these observations.

TABLE 10

| Reporter construct | Transformation method | Transgenic line number | #trees in planting from this line | No strobili | Female strobili | Male strobili | Both male and female | % trees showing no strobili | % trees showing female strobili | % trees showing male strobili | % trees showing both male and female strobili |
|---|---|---|---|---|---|---|---|---|---|---|---|
| Act2::GUS | Agrobacterium | 28 | 9 | 6 | 3 | 1 | 1 | 67% | 33% | 11% | 11% |
| Act2::GUS | Agrobacterium | 29 | 10 | 9 | 1 | 1 | 1 | 90% | 10% | 10% | 10% |
| Act2::GUS | Agrobacterium | 31 | 8 | 0 | 7 | 2 | 1 | 0% | 88% | 25% | 13% |
| Act2::GUS | Agrobacterium | 32 | 10 | 0 | 10 | 2 | 2 | 0% | 100% | 20% | 20% |
| Act2::GUS | Agrobacterium | 34 | 10 | 2 | 8 | 1 | 1 | 0% | 80% | 10% | 10% |
| Act2::GUS | Agrobacterium | 36 | 10 | 0 | 10 | 2 | 2 | 0% | 100% | 20% | 20% |
| Act2::GUS | Agrobacterium | 38 | 10 | 0 | 10 | 3 | 3 | 0% | 100% | 30% | 30% |
| Act2::GUS | Agrobacterium | 39 | 3 | 3 | 0 | 0 | 0 | 100% | 0% | 0% | 0% |
| Act2::GUS | Agrobacterium | 53 | 9 | 1 | 8 | 3 | 3 | 11% | 89% | 33% | 33% |
| Act2::GUS | Biolistics | 64 | 8 | 1 | 5 | 4 | 2 | 20% | 100% | 80% | 40% |
| UBQ3::GUS | Agrobacterium | 117 | 9 | 1 | 8 | 3 | 3 | 11% | 89% | 33% | 33% |
| UBQ3::GUS | Agrobacterium | 118 | 9 | 0 | 9 | 2 | 2 | 0% | 100% | 22% | 22% |
| UBQ3::GUS | Agrobacterium | 119 | 10 | 1 | 9 | 5 | 5 | 10% | 90% | 50% | 50% |
| UBQ3::GUS | Agrobacterium | 120 | 10 | 0 | 10 | 0 | 0 | 0% | 100% | 0% | 0% |
| UBQ3::GUS | Agrobacterium | 122 | 8 | 0 | 8 | 0 | 0 | 0% | 100% | 0% | 0% |
| UBQ3::GUS | Agrobacterium | 125 | 10 | 0 | 10 | 2 | 2 | 0% | 100% | 20% | 20% |
| UBQ3::GUS | Agrobacterium | 127 | 10 | 0 | 10 | 3 | 3 | 0% | 100% | 30% | 30% |
| UBQ3::GUS | Agrobacterium | 128 | 10 | 1 | 9 | 2 | 2 | 10% | 90% | 20% | 20% |
| n.a. | Non-transgenic somatic embryogenesis control | 97LP0006 | 7 | 2 | 5 | 0 | 0 | 29% | 71% | 0% | 0% |
| n.a. | Non-transgenic zygotic plant control | pitch × loblolly seedlings | 46 | 27 | 15 | 7 | 3 | 59% | 33% | 15% | 7% |

The results shown in table 10 suggest that passage through tissue culture and transformation is necessary to achieving the inventive early strobili production result, as the SE control did not produce strobili, and few of the non tissue-cultured genotypes did. However, nearly all Qf the transgenics produced either male or female strobili or both at very high frequency. Only one of 18 transgenic lines did not produce strobili within three years. The result was independent of the transformation used and independent of the transformation vector used. This suggests that best mode is to use transgenic controls, e.g. transformed with reporter gene constructs, for comparisons intended to show the efficacy of reproduction control constructs such as the inventive ablation constructs.

The trees were, at the time the strobili were produced, approximately 1.2 meters average height, easily harvestable by a person of average height without specialised equipment.

This system was then used to test the reproduction control constructs of the instant application for their utility in gymnosperms, a test that would otherwise be impossible to carry out. The embryogenic callus provides an opportunity to test whether or not the promoters being tested are leaky in a gymnosperm and whether the attenuated barnase genes are detrimental when expressed in a leaky fashion (see column 4 in the table). Once the trees are regenerated and planted in the field, effects on date of strobilus formation relative to GUS-transformed controls can be measured within three years, upon which time the field test can be terminated. This will further allow for a faster rotation of expensive production forestry land for these field tests.

TABLE 11

| Name of Construct | Promoter | Gene | What effects noted in pine callus | Plants to field planting | Approx date into pine transformation | SE lines transformed |
|---|---|---|---|---|---|---|
| pWVR216 | PrMC2.400 | barnaseK27A | None | No | Jul. 1, 2002 | 92AA0033 |
| pWVR217 | PrMC2.400 | LPRNase1 | None | No | Jul. 1, 2002 | 92AA0033 |
| pAGF234 | PrMC2.400-1 | GUS | NA | Yes | Dec. 6, 2002 | 97LP0033 |
| pWVR220 | PrMC2.400-1 | barnaseH102E | None | Yes | Dec. 6, 2002 | 97LP0033 |
| pWVR216 | PrMC2.400-1 | barnaseK27A | detrimental | No | Dec. 6, 2002 | 97LP0033 |
| pAGF232 | PrMC2.400-1 | barnaseE73G | detrimental | No | Dec. 6, 2002 | 97LP0033 |
| pAGF245 | PrMC2.400-3 | GUS | NA | No | Dec. 2, 2003 | 97LP0033 |
| pAGF243 | PrMC2.400-3 | barnaseH102E | None | Yes | Dec. 2, 2003 | 97LP0033 |

Example 21

Method for Ablating Pine Male and Female Cones Using a Construct Having LPAG1 and LPAG1d4 Promoters Based on the results shown in Example 6, Table 4, the LPAG1 and LPAG1d4 promoters can be used for ablating male and female cones of pine trees. For example, an ablation construct could have the LPAG1 promoter operably linked to a gene encoding barnase, while the LPAG1d4 promoter is operably linked to a gene encoding barstar (barnase inhibitor). As shown above in Example 6, LPAG1 promoter is active in pine cones and embryos while the LPAG1d4 promoter is active only in pine embryos. This assumption is made based on the observation that LPAG1 has high activities in tobacco flowers while LPAG1d4 has little activities in tobacco flowers. By placing the gene encoding barstar under the control of LPAG1d4 promoter that may have little activity in a pine cone, barnase toxicity produced by the other promoter (LPAG1) can effectively ablate male and female cones. On the other hand, similar levels of activities of the two promoters in pine embryos produce similar amounts of barnase and barstar, and so the barnase toxicity in the embryos is effectively neutralized, leading to transformation and regeneration of pine embryogenic calli and embryos.

DESCRIPTION OF SEQUENCE IDENTIFIERS

SEQ ID NO. 1—LPAG1
SEQ ID NO. 2—LPAG2
SEQ ID NO. 3—PrAG-ATenh
SEQ ID NO. 4—PrMC2.400-1
SEQ ID NO. 5—barnase mutant E73G (DNA)
SEQ ID NO. 6—barnase mutant F106S (DNA)
SEQ ID NO. 7—barnase mutant H102E (DNA)
SEQ ID NO. 8—barnase mutant K27A (DNA)
SEQ ID NO. 9—barnase mutant E73G (AA)
SEQ ID NO. 10—barnase mutant F106S (AA)
SEQ ID NO. 11—barnase mutant H102E (AA)
SEQ ID NO. 12—barnase mutant K27A (AA)
SEQ ID NO. 13—PrMC2 +barnase mutant H102E
SEQ ID NO. 14—PrMC2 +barnase mutant K27A
SEQ ID NO. 15—PrMC2 +barnase mutant E73G
SEQ ID NO. 16—PrMC2.400-3
SEQ ID NO. 17—LPAG1d4
SEQ ID NO. 18—pWVR220 [PrMC2.400::barnaseH102E] (FIG. 1)
SEQ ID NO. 19—pWVCZ20 [(AtAGenh)PrAG::GUS(intron)] (FIG. 2)
SEQ ID NO. 20—pWVCZ23 [PrAG::barnaseE73G] (FIG. 3)
SEQ ID NO. 21—pWVCZ24 [(AtAGenh)PrAG::barnaseE73G] (FIG. 4)
SEQ ID NO. 22—pARB599B [PrMC2::barnaseH102E] (FIG. 5)
SEQ ID NO. 23—pARB639B [(AtAGenh)PrAG::barnaseE73G] (FIG. 6)
SEQ ID NO. 24—pAGF243 [PrMC2.400-3::barnaseH102E] (FIG. 7)
SEQ ID NO. 25—pABDP010 [complementary copy of CZ28-bstar+UBQ10::NPTII::E9/ LPAG1d4::bstar::NOST] (FIG. 8)
SEQ ID NO. 26—pABDP04 [complementary copy of CZ28-bstar+UBQ10::NPTII::E9/ LPAG1d4::bstar: :NOST] (FIG. 9)

Sequences follow below.

SEQ ID NO. 1

LPAG1

```
CAGCAAATATGATTTAGATTATGACCTAGAAATAAGCATAGCATTAAAGCATATACAAAACAAGCGGTG

ATATACTCTGACTGCCACTGTACTTGAGGAAAGGTAGTGGACTCTGCTCAGGTACATTAGTTTGGTAAG

GTTGGCTTGGCTTCTGGGTAATATGAGAAGTAAAGAAGTAAAAGGTATTTGACTCTAGTCAAGTACATT

GGATTGCCTTCGTCGGGGCTTGGATGGCTTGGGTTCGTGTGAGAAGCCAACAATTTATAAAAAAATATA

TTGAAAAAAAAAAAATCGTCTAAGTGTTGGAAGTGAAAACGGTGGGACATAAATATACACAGAAGAGT

ACTTTAACAATGCGCAACCAAGGCAGATTCACAACTTGATTTCTGGACCTCGAATACGAGATAATGGTG

GTAAGAAATAAAGGAAGAGTGGAGTGCATTTGAAAATGAATGGAGAGCGCACAAAATGGAGGACGAATA

AATGAAATATAATGCAAGAGTGCATTTCCCTATTATTTCCAGAAATGTATATGTGGGGTCGGCATTCAC

ATGGGCGTCGCATTCAGGGGGTGTCATAGCGGTCCTTTGATTGCAGTGTGGGAGTTGCAACATGTACCA

ACAAATTCATTCATCCCAAAACCTAAATTTATCCTCTCCATTACTATTACCTACACCTATACCTAGTAA

ATATGTCCTGCCTTGTAACTCCTCCACTGCCTGCACACGTCTTAGTCAATCCATCTGCCTTCAAATAGG

CATTATTTTGTTCTTTCCCCTCCGACTGAAAGGCTATCGACCGACCGACCGCTCATCTTCTTCTTCTGC

GCAATTTTTTCTGCTGGATCATCATCATTACCATCATCGCCATCCCCACCATCATCATCATGATGGTAT

CTCTATCTCTCCCTGGCAATCGATTGTAGAGGAAAGGAAGAGGGAAGGGGCATATGTATTGATCAACCT

ACCCGAAAAAACAATCTGATCAGCCCTGCTAATCTTGCTTATAAATCTCTTATCCACTGTTCAATCATT

CAGGTTTCTTCCCACTTCCAAGCAAAGGCGCCCGGATTGGCCGTGTTCTTAGATTTTCAGGTACTTAAA

TGGACAATATTCCCCACCTGAAGCCGTTCTGAAAAAGATTTGTTTGTAGAAACAAACGATTGTAATATT

TGCTTAAGTTGAGCTTAAGGGGTTTGGTACCTAACTTGCCTTGTGGTTATTTGTTTCTCAGAACTCGGG

CTGCGTCCAACTGTAGGAACGAACCAGCACAAGGGGTTGCAGCTTTTGCTGTTGCTGTTGCGCCCATTG

CTTTTGGACTGGTATTAGTAGTTGCAGCTTTGTTTTGCATACGCTGTGAGGATCTGTGCGCGGAAATTT
```

-continued

TGTGTACAAATCATG

SEQ ID NO. 2

LPAG2
CAGCAAATATGATTTAGATTATGACCTAGAAATAAGCATAGCATTAAAGCATATACATAACAAGCGGTG

ATATACTCTGACTGCCACTGTACTTGATGAAAGGTAGTGGACTCTGCTCAGGTACATTAGTTTGGTAAG

GTTGGCTTGGCTTCTGGGTAATATGAGAAGTAAAGAAGTAAAAGGTATTTGACTCTAGTCAAGTACATT

GGATTGCCTTTGTCGGGGCTTGGATGGCTTGGGTTCGTGTGAGAAGCCAACAATTTATAATAAAAATAA

AATAAAAAATCGAAGTGTTGGAAGTGAAAACGGTGGGGCATAAATATACACAGAAGAGTACTTTAACAA

TGCGCAACCAAGGCAGATTCACAACTTGATTTCTGGACCTCGAATACGAGATAATGGTGGTAAGAAATA

AAGGAAGAGTGGAGTGCATTTGAAAATGAATGGAGAGCGCACAAAATGGAGGACGAATAAATGAAATAT

AATGCAAGAGTGCATTTCCCTATTATTTCCAGAAATGTATATGTGGGGTCGGCATTCACATGGGCGTCG

CATTCAGGGGGTGTCATAGCGGTCCTTTGATTGCAGTGTGGGAGTTGCAACATGTACCAACAAATTCAT

TCATCCCAAACCTAAATTTATCCTCTCCATTACTATTACCTACACCTATACCTAGTAAATATGTCCTG

CCTTGTAACTCCTCCACTGCCTGCACACGTCTTAGTCAATCCATCTGCCTTCAAATAGGCATTATTTTG

TTCTTTCCCCTCCGACTGAAAGGCTATCGACCGACCGACCGCTCATCTTCTTCTTCTGCGCAATTTTTT

CTGCTGGATCATCATCATTACCATCATCGCCATCCCCACCATCATCATCATGATGGTATCTCTATCTCT

CCCTGGCAATCGATTGTAGAGGAAAGGAAGAGGGAAGGGGCATATGTATTGATCAACCTACCCGAAAAA

ACAATCTGATCAGCCCTGCTAATCTTGCTTATAAATCTCTTATCCACTGTTCAATCATTCAGGTTTCTT

CCCACTTTCAAGCAAAGGCGCCCGGATTGGCCGTGTTCTTAGATTTTCAGGTACTTAAATGGACAATAT

TCCCCACCTGAAGCCGTTCTGAAAAAGATTTGTTTGTAGAAACAAACGATTGTAATATTTGCTTAAGTT

GAGCTTAAGGGGTTTGGTACCTAACTTGCCTTGTGGTTATTTGTTTCTCAGAACTCGGGCTGCGTCCAA

CTGTAGGAACGAACCAGCACAAGGGGTTGCAGCTTTTGCTGTTGCTGTTGCGCCCATTGCTTTTGGACT

GGTATTAGTAGTTGCAGCTTTGTTTTGCATACGCTGTGAGGATCTGTGCGCGGAAATTTTGTGTACAAA

TCATG

SEQ ID NO. 3

PrAG-ATenh
GATAGGGTCAAATCGACCACTTGCACAGTTAAGTGATTCTAATACGAAACCTTAAAAGCAAACATCGGT

TCTTTTGAGTCAGAAGAAATGCAACTTAATGTGACACATGATGTGAAGAAAAACAAAAGTAATATAAG

AAAAGGGAACAATTAAATAGTTAATAAAATATTTCCTTAAAGTTGTAACAAATAAAGAATCATTTTATG

AAACAATATGAACCCTAAATAAATTAAAATTCCTCTGAAACCTTAAATTTATCGAGCTAGTGATTGGCT

GCCAACTGCCATGCTGGCAAAATTAGAGTGACATGATTGGTCTGAACATGTCTAGGGTTTCAGACATGT

GACATGTGTCAACAACCCATTAACACATTGGGTATAAATCCAATAGACATTTGATAGTATTAAAATTGT

AACCATTGGATTAAATTTAAACGTGATGGATGTAACTAAATGACTTGTCCGAGTAACATCACAACGTTC

CATACTTTCCTTATTTGGAATATAATTAAATTTACCATTTATTCTTTTTTCTTGAGTTTCCTGTATATG

TACTTGTACATAGATATATATGCACAAATACGTATTACAATGACATATTATAGACTTTGATGTCTGAAC

TCTCAACCTTCTCGATGGAGAGATCATGACCGTAGATTTTTTGGATCGTAGAAGGCAGACCAAACTCT

TAAACTATTGGATCCGGACTAAAAATCTCACTTTCCTCTCAGTACCCATAATGAGAGAGAAAATGATAA

AAATCCCTAACATTATTCTCTCTAGAAAAAAAAAGATACTTCAAAAAGAAAGAGAAATTGCATAAAT

CTATCTACACCAAAGATGTTGAAGCAATTCCAATGCTATACTTCTATGCCAAATCTATTTATTCAGTGA

TCATTAATCTTTTTACTTCCAAGAAATATGAACAATTTAGTATCCTTATAATTTTGTCTCTATATATG

TAATATGAACATTGGGTATTGACCAAATGAGAAATCTAATATTAAATGGTCAAAAGTAGTAATATGATG

ACATTTTTGAATTTATAAATAGGTTACAAATTAATTCATTATGACATAAAACCTTCTTGTCAGAAGTCA

-continued

```
AGAACTGAAACTAACAAAACTTTATAATAAATTAGTAAAAATACAAATGAAAATAAAAAGAAATAATA

TCTGAGTGATGACGTGATCAAAGATTCTTTAACAAAGACAACAAATCTTACAGACCCAAAACCTAATCT

TGCGCTCAATTCCAACCTCTGAAAAAACCTCAAAAATCTTATAAAAGAAAATAAATAAAGAAACGAAAC

TCTGATTTCGTAGAGTACCCATCGGATATATAAAAAGAAATTAGTAGGTAAATGAAGACTAATTTTGAT

TGACTGATTTAATTTGAAGTCGTTGTTAGCTTTTCTTGTTTTGGACATGAGAATTATATATTTCAGGAC

ATGAGAGTTGACAACTGTAAACGATTAAGAAAATTGATCTTTTAATTTTCAAACACCATTTAATCTTGA

CATGTTTTATGTTTTGGTGGAGAAGAAAGTAATCACGTGGGACTCTCTACTAATAAGTATTTGGAAATT

GCGTGTCGAATTAGAGATTACTAGTTTGAGTAATGTAGTTCGAAATGAGATTAGTTATTTTTAATTTTA

AAAAGAGTAATTTTAAGGAATAACAAAAAAGAGTCCCCATAAGCTAATTTGTCTTAATTACCTCCTTGT

TTCATTGACTATTTGAAATCTTGAAAATTCAGTTGAAATTTCAAATCTATGTTTCTTTTGACCACTTCT

AAACTAATCTTAGCTCATATATAATTTTCCAAAACTACAAAAATAACACTAACATTTAACATTCTCAAG

AGAAAACAAAAACAAAAACTTAGATAACCATCTAAATTGTCCTACATGTACGTATAAGTTCCATTATTT

TCTATCACTCATATAAGTTAAAATTTCATGAAAACTCAAAAATCTAGCTAGTTTCACCTTATTCACTCT

CACTTACCATCACATGTGTTTGTATCAAATATATGATATGATATAATTCATGAGAGAGAAAGAGAGCTA

GAGATAAGAAAGGAAAGTAAGAGAAAGAAGAGAAGAAAAAGAGAGACACAGACATTAACAACAATGGAG

GATGGATGATCACAAAACAGAAGATATGACCTCATAGTCCTTCCTTACTCTCTCCCCAATTTGTTTCCC

AAAACTTACTTTTATAGTCATAAAAATCAAGTTTTTACCTATTACAACACCAGATCTATAAATATATCT

AAATCTTCAAGTACTTGTTAGTAAGGAAAATAGAAAGATATAAGATTTTATTATTATTATAATAACAGA

AATGAGTGAAGAAGAACACCCAACAAAGTGAATCTTAGTTCTACAAAACTGAATCTAAAACTCCACAT

TAGAAAAAACCCTGATGGTTTCTTATTTCTTTTCATTTATTATCTAACTCTCACTCAGATCTCCTTTAA

CTTTGTACCATTTCCCTCACTTCATATATCTATATATAACAAACTCTCTCTTTTTATTTAAGTCTTAAG

GGAAAATTAATATACACATGAAGAACAAGAAATTAGATCTACAAAATTGTTACAAAAACCCCCGAAGTA

AATAAAATAAACATATCAAACAAATATTCCCACTAATGTTAGTGTGTTTATATATATATGTGTGTGGAA

TATGAAGGAAAAAGTGAAAAATAATCCTACCCATAAGAGCATTCAAGAAGAAGCTCGAGGTCGACGGT

ATCGATAAGCTTAAACTCGACAGCAAATATGATTTAGATTATGACCTAGAAATAAGCATAGCATTAAAG

CATATACATAACAAGCGGTGATATACTCTGACTGCCACTGTACTTGAGGAAAGGTAGTGGACTCTGCTC

AGGTACATTAGTTTGGTAAGGTTGGCTTGGCTTCTGGGTAATATGAGAAGTAAAGAAGTAAAAGGTATT

TGACTCTAGTCAAGTACATTGGATTGCCTTTGTCGGGGCTTGGATGGCTTGGGTTCGTGTGAGAAGCCA

ACAATTTATAAGAAATATATAAAATAAAAAATAAAAAAATTTAAGTGTTGGAAGTGAAAACGGTGGGGC

AGAAATATACACAGAAGAGTACTTTAACAATGCGCAACCAAGGCAGATTCACAACTTGATTTCTGGACC

TCGAATACGAGATAATGGTGGTAAGAAATAAAGGAAGAGTGGAGCGCATTTGAAAATGAATGGAGAGCG

CACAAAATGGAGGACGAATAAATGAAATATAATGCAAGGGTGCATTTCCCTATTATTTCCAGAAATGTA

TATGTGGGGTCGGCATTCTCATGGGCGTCGCATTCAGGGGGTGTCATAGCGGTCCTTTGATTGCAGTGT

GGGAGTTGCAACATGTACCAACAAATCCATTCATCCCAAAACCTAAATTTATCCTCTCCATTACTATTA

CCTACACCTATACCTAGTAAATATGTCCTGCCTTGTAACTCCTCCACTGCCTGCACACGTCTTAGTCAA

TCCATCTGCCTTCAAATAGGCATTATTTTGTTCTTTCCCCTCCGACTGAAAGGCTATCGACCGACCGAC

CGCTCATCTTCTTCTTCTGCGCAATTTTTTCTGCTGGATCATCATCATTACCATCATCGCCATCCCCAC

CATCATCATCATGATGGTATCTCTATCTCTCCCTGGCAATCGATTGTAGAGGAAAGGAAGAGGGAAGGG

GCATATGTATTGATCAACCTACCCGAAAAAACAATCTGATCAGCCCTGCTAATCTTGCTTATAAATCTC

TTATCCACTGTTCAATCATTCAGGTTTCTTCCCACTTTCAAGCAAAGGCGCCCGGATTGGCCGTGTTCT
```

-continued

TAGATTTTCAGGTACTTAAATGGACAATATTCCCCACCTGAAGCCGTTCTGAAAAAGATTTGTTTGTAG

AAACAAACGATTGTAATATTTGCTTAAGTTGAGCTTAAGGGGTTTGGTACCTAACTTGCCTTGTGGTTA

TTTGTTTCTCAGAACTCGGGCTGCGTCCAACTGTAGGAACGAACCAGCACAAGGGGTTGCAGCTTTTGC

TGTTGCTGTTGCGCCCATTGCTTTTGGACTGGTATTAGTAGTTGCAGCTTTGTTTTGCATACGCTGTGA

GGATCTGTGCGCGGAAATTTTGTGTACAAATC

SEQ ID NO. 4
PrMC2-400.1
CTCGAGTAAAACATAATTTTGGCAGTAAAAAGTGAATTCTATTGTTTTGAAAACAAAACAAAATACAGG

AAGCGTGATTGTGGGGTTGTTGTTGAACTTGCCCGGGCAAAAGAAGAATGATTAGCGGTAGAGGAGTTA

GTAGTTACGTTCAACTAAATGCGTGACTAAATTATTTATCCTCCGCCATGGAAGCAGGTGATTCACACA

CAACTTGCTGCACACATTGCTCTCAAACCTTTCCTATAAATATCCGTAGCAGGGGCTGCGATGATACAC

AACGCATTTAATCAAACTACTTTGATTACTTTCTGTGGGTTCTACTTTCTTTGAATAGTCAGTTCTGCT

GTTTTTAGAAGATTTATGAGAATGGCCAAAATTCAGGTATCAAACGGGAAC

SEQ ID NO. 5
barnase mutant E73G (DNA)
ATGGCACAGGTTATCAACACGTTTGACGGGGTTGCGGATTATCTTCAGACATATCATAAGCTACCTGAT

AATTACATTACAAAATCAGAAGCACAAGCCCTCGGCTGGGTGGCATCAAAAGGGAACCTTGCAGACGTC

GCTCCGGGGAAAAGCATCGGCGGAGACATCTTCTCAAACAGGGAAGGCAAACTCCCGGGCAAAAGCGGA

CGAACATGGCGTGGAGCGGATATTAACTATACATCAGGCTTCAGAAATTCAGACCGGATTCTTTACTCA

AGCGACTGGCTGATTTACAAAACAACGGACCATTATCAGACCTTTACAAAAATCAGATAA

SEQ ID NO. 6
barnase mutant F106S (DNA)
ATGGCACAGGTTATCAACACGTTTGACGGGGTTGCGGATTATCTTCAGACATATCATAAGCTACCTGAT

AATTACATTACAAAATCAGAAGCACAAGCCCTCGGCTGGGTGGCATCAAAAGGGAACCTTGCAGACGTC

GCTCCGGGGAAAAGCATCGGCGGAGACATCTTCTCAAACAGGGAAGGCAAACTCCCGGGCAAAAGCGGA

CGAACATGGCGTGAAGCGGATATTAACTATACATCAGGCTTCAGAAATTCAGACCGGATTCTTTACTCA

AGCGACTGGCTGATTTACAAAACAACGGACCATTATCAGACCTCTACAAAAATCAGATAA

SEQ ID NO. 7
barnase mutant H102E (DNA)
ATGGCACAGGTTATCAACACGTTTGACGGGGTTGCGGATTATCTTCAGACATATCATAAGCTACCTGAT

AATTACATTACAAAATCAGAAGCACAAGCCCTCGGCTGGGTGGCATCAAAAGGGAACCTTGCAGACGTC

GCTCCGGGGAAAAGCATCGGCGGAGACATCTTCTCAAACAGGGAAGGCAAACTCCCGGGCAAAAGCGGA

CGAACATGGCGTGAAGCGGATATTAACTATACATCAGGCTTCAGAAATTCAGACCGGATTCTTTACTCA

AGCGACTGGCTGATTTACAAAACAACGGACGAGTATCAGACCTTTACAAAAATCAGATAA

SEQ ID NO. 8
barnase mutant K27A (DNA)
ATGGCACAGGTTATCAACACGTTTGACGGGGTTGCGGATTATCTTCAGACATATCATAAGCTACCTGAT

AATTACATTACAGCATCAGAAGCACAAGCCCTCGGCTGGGTGGCATCAAAAGGGAACCTTGCAGACGTC

GCTCCGGGGAAAAGCATCGGCGGAGACATCTTCTCAAACAGGGAAGGCAAACTCCCGGGCAAAAGCGGA

CGAACATGGCGTGAAGCGGATATTAACTATACATCAGGCTTCAGAAATTCAGACCGGATTCTTTACTCA

AGCGACTGGCTGATTTACAAAACAACGGACCATTATCAGACCTTTACAAAAATCAGATAA

SEQ ID NO. 9
barnase mutant E73G (AA)
MetAlaGlnValIleAsnThrPheAspGlyValAlaAspTyrLeuGlnThrTyrHisLysLeuProAsp AsnTyrIleThrLysSerGluAlaGlnAlaLeuGlyTrpValAlaSerLysGlyAsnLeuAlaAspVal AlaProGlyLysSerIleGlyGlyAspIlePheSerAsnArgGluGlyLysLeuProGlyLysSerGly -continued ArgThrTrpArgGlyAlaAspIleAsnTyrThrSerGlyPheArgAsnSerAspArgIleLeuTyrSer SerAspTrpLeuIleTyrLysThrThrAspHisTyrGlnThrPheThrLysIleArg SEQ ID NO. 10
barnase mutant F106S (AA)
MetAlaGlnValIleAsnThrPheAspGlyValAlaAspTyrLeuGlnThrTyrHisLysLeuProAsp AsnTyrIleThrLysSerGluAlaGlnAlaLeuGlyTrpValAlaSerLysGlyAsnLeuAlaAspVal AlaProGlyLysSerIleGlyGlyAspIlePheSerAsnArgGluGlyLysLeuProGlyLysSerGly ArgThrTrpArgGluAlaAspIleAsnTyrThrSerGlyPheArgAsnSerAspArgIleLeuTyrSer SerAspTrpLeuIleTyrLysThrThrAspHisTyrGlnThrSerThrLysIleArg SEQ ID NO. 11
barnase mutant H102E (AA)
MetAlaGlnValIleAsnThrPheAspGlyValAlaAspTyrLeuGlnThrTyrHisLysLeuProAsp AsnTyrIleThrLysSerGluAlaGlnAlaLeuGlyTrpValAlaSerLysGlyAsnLeuAlaAspVal AlaProGlyLysSerIleGlyGlyAspIlePheSerAsnArgGluGlyLysLeuProGlyLysSerGly ArgThrTrpArgGluAlaAspIleAsnTyrThrSerGlyPheArgAsnSerAspArgIleLeuTyrSer SerAspTrpLeuIleTyrLysThrThrAspGluTyrGlnThrPheThrLysIleArg SEQ ID NO. 12
barnase mutant K27A (AA)
MetAlaGlnValIleAsnThrPheAspGlyValAlaAspTyrLeuGlnThrTyrHisLysLeuProAsp AsnTyrIleThrAlaSerGluAlaGlnAlaLeuGlyTrpValAlaSerLysGlyAsnLeuAlaAspVal AlaProGlyLysSerIleGlyGlyAspIlePheSerAsnArgGluGlyLysLeuProGlyLysSerGly ArgThrTrpArgGluAlaAspIleAsnTyrThrSerGlyPheArgAsnSerAspArgIleLeuTyrSer SerAspTrpLeuIleTyrLysThrThrAspHisTyrGlnThrPheThrLysIleArg SEQ ID NO. 13
PrMC2::Barnase H102E::RNS2TER cassette
TCTCGAGTAAAACATAATTTTGGCAGTAAAAAGTGAATTCTATTGTTTTGAAAACAAAACAAAATACAG

GAAGCGTGATTGTGGGGTTGTTGTTGAACTTGCCCGGGCAAAAGAAGAATGATTAGCGGTAGAGGAGTT

AGTAGTTACGTTCAACTAAATGCGTGACTAAATTATTTATCCTCCGCCATGGAAGCAGGTGATTCACAC

ACAACTTGCTGCACACATTGCTCTCAAACCTTTCCTATAAATATCCGTAGCAGGGGCTGCGATGATACA

CAACGCATTTAATCAAACTACTTTGATTACTTTCTGTGGGTTCTACTTTCTTTGAATAGTCAGTTCTGC

TGTTTTTAGAAGATTTATGAGAATGGCCAAAATTCAGGTATCAAACGGGAACATGGCACAGGTTATCAA

CACGTTTGACGGGGTTGCGGATTATCTTCAGACATATCATAAGCTACCTGATAATTACATTACAAAATC

AGAAGCACAAGCCCTCGGCTGGGTGGCATCAAAAGGGAACCTTGCAGACGTCGCTCCGGGGAAAAGCAT

CGGCGGAGACATCTTCTCAAACAGGGAAGGCAAACTCCCGGGCAAAAGCGGACGAACATGGCGTGAAGC

GGATATTAACTATACATCAGGCTTCAGAAATTCAGACCGGATTCTTTACTCAAGCGACTGGCTGATTTA

CAAAACAACGGACGAGTATCAGACCTTTACAAAAATCAGATAACGAAAAAAACGGCTTCCTGCGGGAG

GCCGTTTTTTTCAGCTTTACATAAAGTGTGTAATAAATTTTTCTTCAAACTCTGATCGGTCAAGAGCTC

TTCTGAGAGACAATACATACATGTCTCTGATGTTGTAACTTTACTACCAAAACCTATAAAGATTGGCTT

ATTTCGTTCTATTGGATATGTATCATCATTACTGGTAAATCAAGTTTCTTTCTAATAATGTAGAAGATC

AGAAAATCCATAAGAAGATATCAACATTTGAGTTCTATGGTAAATTGAATTATATCAACTTAGTTGCAA

TGATTCATTCTTGACTGATGCATTGATGGCTTATCAAACCAGTTTACAAAATTCGATTAGATAGGGCCC

A

SEQ ID NO. 14
PrMC2::Barnase K27A::RNS2TER cassette
CTCGAGTAAAACATAATTTTGGCAGTAAAAAGTGAATTCTATTGTTTTGAAAACAAAACAAAATACAGG -continued

AAGCGTGATTGTGGGGTTGTTGTTGAACTTGCCCGGGCAAAAGAAGAATGATTAGCGGTAGAGGAGTTA

GTAGTTACGTTCAACTAAATGCGTGACTAAATTATTTATCCTCCGCCATGGAAGCAGGTGATTCACACA

CAACTTGCTGCACACATTGCTCTCAAACCTTTCCTATAAATATCCGTAGCAGGGGCTGCGATGATACAC

AACGCATTTAATCAAACTACTTTGATTACTTTCTGTGGGTTCTACTTTCTTTGAATAGTCAGTTCTGCT

GTTTTTAGAAGATTTATGAGAATGGCCAAAATTCAGGTATCAAACGGGAACATGGCACAGGTTATCAAC

ACGTTTGACGGGGTTGCGGATTATCTTCAGACATATCATAAGCTACCTGATAATTACATTACAGCATCA

GAAGCACAAGCCCTCGGCTGGGTGGCATCAAAAGGGAACCTTGCAGACGTCGCTCCGGGGAAAAGCATC

GGCGGAGACATCTTCTCAAACAGGGAAGGCAAACTCCCGGGCAAAAGCGGACGAACATGGCGTGAAGCG

GATATTAACTATACATCAGGCTTCAGAAATTCAGACCGGATTCTTTACTCAAGCGACTGGCTGATTTAC

AAAACAACGGACGAGTATCAGACCTTTACAAAAATCAGATAACGAAAAAAACGGCTTCCCTGCGGGAGG

CCGTTTTTTTCAGCTTTACATAAAGTGTGTAATAAATTTTTCTTCAAACTCTGATCGGTCAAGAGCTCT

TCTGAGAGACAATACATACATGTCTCTGATGTTGTAACTTTACTACCAAAACCTATAAAGATTGGCTTA

TTTCGTTCTATTGGATATGTATCATCATTACTGGTAAATCAAGTTTCTTTCTAATAATGTAGAAGATCA

GAAAATCCATAAGAAGATATCAACATTTGAGTTCTATGGTAAATTGAATTATATCAACTTAGTTGCAAT

GATTCATTCTTGACTGATGCATTGATGGCTTATCAAACCAGTTTACAAAATTCGATTAGATAGGGCCC

SEQ ID NO. 15
PrMC2::Barnase E73G::RNS2TER cassette
CTCGAGTAAAACATAATTTTGGCAGTAAAAAGTGAATTCTATTGTTTTGAAAACAAAACAAAATACAGG

AAGCGTGATTGTGGGGTTGTTGTTGAACTTGCCCGGGCAAAAGAAGAATGATTAGCGGTAGAGGAGTTA

GTAGTTACGTTCAACTAAATGCGTGACTAAATTATTTATCCTCCGCCATGGAAGCAGGTGATTCACACA

CAACTTGCTGCACACATTGCTCTCAAACCTTTCCTATAAATATCCGTAGCAGGGGCTGCGATGATACAC

AACGCATTTAATCAAACTACTTTGATTACTTTCTGTGGGTTCTACTTTCTTTGAATAGTCAGTTCTGCT

GTTTTTAGAAGATTTATGAGAATGGCCAAAATTCAGGTATCAAACGGGAACATGGCACAGGTTATCAAC

ACGTTTGACGGGGTTGCGGATTATCTTCAGACATATCATAAGCTACCTGATAATTACATTACAAAATCA

GAAGCACAAGCCCTCGGCTGGGTGGCATCAAAAGGGAACCTTGCAGACGTCGCTCCGGGGAAAAGCATC

GGCGGAGACATCTTCTCAAACAGGGAAGGCAAACTCCCGGGCAAAAGCGGACGAACATGGCGTGGAGCG

GATATTAACTATACATCAGGCTTCAGAAATTCAGACCGGATTCTTTACTCAAGCGACTGGCTGATTTAC

AAAACAACGGACGAGTATCAGACCTTTACAAAAATCAGATAACGAAAAAAACGGCTTCCCTGCGGGAGG

CCGTTTTTTTCAGCTTTACATAAAGTGTGTAATAAATTTTTCTTCAAACTCTGATCGGTCAAGAGCTCT

TCTGAGAGACAATACATACATGTCTCTGATGTTGTAACTTTACTACCAAAACCTATAAAGATTGGCTTA

TTTCGTTCTATTGGATATGTATCATCATTACTGGTAAATCAAGTTTCTTTCTAATAATGTAGAAGATCA

GAAAATCCATAAGAAGATATCAACATTTGAGTTCTATGGTAAATTGAATTATATCAACTTAGTTGCAAT

GATTCATTCTTGACTGATGCATTGATGGCTTATCAAACCAGTTTACAAAATTCGATTAGATAGGGCCC

SEQ ID NO. 16
PrMC2.400-3 promoter
TAAAACATAATTTTGGCAGTAAAAAGTGAATTCTATTGTTTTGAAAACAAAACAAAATACAGGAAGCGT

GATTGTGGGGTTGTTGTTGAACTTGCCCGGGCAAAAGAAGAATGATTAGCGGTAGAGGAGTTAGTAGTT

ACGTTCAACTAAATGCGTGACTAAATTATTTATCCTCCGCCATGGAAGCAGGTGATTCACACACAACTT

GCTGCACACATTGCTCTCAAACCTTTCCTATAAATATCCGTAGCAGGGGCTGCGATGATACACAACGCA

TTTAATCAAACTACTTTGATTACTTTCTGTGGGTTCTACTTTCTTTGAATAGTCAGTTCTGCTGTTTTT

AGAAGATTT

SEQ ID NO. 17
LPAG1d4
TTCATTCATCCCAAAACCTAAATTTATCCTCTCCATTACTATTACCTACACCTATACCTAGTAAATATG

TCCTGCCTTGTAACTCCTCCACTGCCTGCACACGTCTTAGTCAATCCATCTGCCTTCAAATAGGCATTA

TTTTGTTCTTTCCCCTCCGACTGAAAGGCTATCGACCGACCGACCGCTCATCTTCTTCTTCTGCGCAAT

TTTTTCTGCTGGATCATCATCATTACCATCATCGCCATCCCCACCATCATCATCATGATGGTATCTCTA

TCTCTCCCTGGCAATCGATTGTAGAGGAAAGGAAGAGGGAAGGGGCATATGTATTGATCAACCTACCCG

AAAAAACAATCTGATCAGCCCTGCTAATCTTGCTTATAAATCTCTTATCCACTGTTCAATCATTCAGGT

TTCTTCCCACTTCCAAGCAAAGGCGCCCGGATTGGCCGTGTTCTTAGATTTTCAGGTACTTAAATGGAC

AATATTCCCCACCTGAAGCCGTTCTGAAAAAGATTTGTTTGTAGAAACAAACGATTGTAATATTTGCTT

AAGTTGAGCTTAAGGGGTTTGGTACCTAACTTGCCTTGTGGTTATTTGTTTCTCAGAACTCGGGCTGCG

TCCAACTGTAGGAACGAACCAGCACAAGGGGTTGCAGCTTTTGCTGTTGCTGTTGCGCCCATTGCTTTT

GGACTGGTATTAGTAGTTGCAGCTTTGTTTTGCATACGCTGTGAGGATCTGTGCGCGGAAATTTTGTGT

ACAAATC

For the sequences denoted as SEQ ID NOs. 18-26 see FIGS. 1-9 and 13.

---

What is claimed is:

1. A method for obtaining wood pulp, comprising
   (a) introducing into a plant cell of a woody plant a construct comprising (i) a promoter having the sequence of any one of SEQ ID NOs. 4 or 16 operably linked to (ii) a desired nucleic acid that comprises the sequence of SEQ ID NO. 7 or which comprises a nucleotide sequence that encodes the amino acid sequence of SEQ ID NO. 11;
   (b) culturing said transformed plant cell under conditions that promote growth of a plant; and
   (c) obtaining wood pulp from said plant.

2. A construct, comprising (i) the sequence of either SEQ ID NOs. 4 or 16 operably linked to the sequence of SEQ ID NO: 7, or (ii) the sequence depicted in SEQ ID NO. 24.

3. A transgenic plant, comprising the construct of claim 2.

4. A transgenic plant, comprising a construct that comprises a polynucleotide selected from any one of SEQ ID NO: 4 or 16 operably linked to a desired nucleic acid that comprises the sequence of SEQ ID NO. 7 or which encodes the amino acid sequence of SEQ ID NO. 11.

5. A method for producing a transgenic plant, comprising
   (a) transforming a plant cell with a construct that comprises at least one polynucleotide having the sequence of any one of SEQ ID NOs. 4 or 16 operably linked to a desired nucleic acid, wherein said polynucleotide regulates the activity of said desired nucleic acid that has the sequence of SEQ ID NO. 7 or which encodes the amino acid sequence of SEQ ID NO. 11;
   (b) culturing said transformed plant cell under conditions that promote growth of a plant, wherein said plant is a transgenic plant that exhibits a phenotype that is different from a plant of the same species that does not contain said construct.

6. A construct comprising a polynucleotide selected from any one of SEQ ID NO. 4 or 16 operably linked to a desired nucleic acid that comprises the sequence of SEQ ID NO. 7 which encodes SEQ ID NO. 11, wherein said polynucleotide regulates the expression of said desired nucleic acid in a plant cell transformed with the construct.

7. A hybrid progeny plant transformed with a construct comprising the sequence of SEQ ID NO. 24.

8. The hybrid progeny plant of claim 7, wherein the hybrid progeny plant is obtained from the cross of pitch *Pinus rigida* with loblolly pine *P. taeda*.

9. A construct, comprising *Pinus radiata* male cone (PrMC) promoter operably linked to a desired nucleic acid, wherein the PrMC promoter regulates the expression of the desired nucleic acid that encodes an H102E barnase mutant in a plant cell transformed with the construct and wherein the H102E barnase mutant is capable of disrupting reproductive development of at least one of a male reproductive structure in a plant.

10. The construct of claim 9 wherein the nucleic acid encoding the H102E barnase mutant comprises the sequence of SEQ ID NO. 7.

11. The construct of claim 9, wherein the desired nucleic acid encodes the protein of SEQ ID NO. 11.

12. The construct of claim 9, wherein the PrMC promoter/H102E barnase mutant construct comprises the sequence of SEQ ID NO. 24.

13. A method for producing a transgenic plant, comprising
(a) transforming a plant cell with a construct that comprises
   (i) a functional promoter having the sequence of SEQ ID NO. 4 or SEQ ID NO. 16 operably linked to (ii) an H102E mutant barnase-encoding polynucleotide; and
(b) culturing the transformed plant cell under conditions that promote growth of a plant, wherein said plant is a transgenic plant that exhibits a phenotype that is different from a plant of the same species that has not been transformed with the construct.

14. A method for producing a transgenic plant, comprising
(a) transforming a plant cell with a construct that comprises
   (i) a functional PrMC promoter operably linked to (ii) a polynucleotide that comprises the sequence of SEQ ID NO. 7; and
(b) culturing the transformed plant cell under conditions that promote growth of a plant, wherein said plant is a transgenic plant that exhibits a phenotype that is different from a plant of the same species that has not been transformed with the construct.

15. A method for producing a transgenic plant, comprising
(a) transforming a plant cell with a construct that comprises the sequence of SEQ ID NO. 24; and
(b) culturing the transformed plant cell under conditions that promote growth of a plant, wherein said plant is a transgenic plant that exhibits a phenotype that is different from a plant of the same species that has not been transformed with the construct.

* * * * *

SEQUENCE LISTING

<160> NUMBER OF SEQ ID NOS: 52

<210> SEQ ID NO 1
<211> LENGTH: 1395
<212> TYPE: DNA
<213> ORGANISM: Pinus taeda

<400> SEQUENCE: 1

```
cagcaaatat gatttagatt atgacctaga aataagcata gcattaaagc atatacaaaa      60
caagcggtga tatactctga ctgccactgt acttgaggaa aggtagtgga ctctgctcag     120
gtacattagt ttggtaaggt tggcttggct tctgggtaat atgagaagta aagaagtaaa     180
aggtatttga ctctagtcaa gtacattgga ttgccttcgt cggggcttgg atggcttggg     240
ttcgtgtgag aagccaacaa tttataaaaa aatatattga aaaaaaaaaa aatcgtctaa     300
gtgttggaag tgaaaacggt gggacataaa tatacacaga agagtacttt aacaatgcgc     360
aaccaaggca gattcacaac ttgatttctg gacctcgaat acgagataat ggtggtaaga     420
aataaaggaa gagtggagtg catttgaaaa tgaatggaga gcgcacaaaa tggaggacga     480
ataaatgaaa tataatgcaa gagtgcattt ccctattatt tccagaaatg tatatgtggg     540
gtcggcattc acatgggcgt cgcattcagg gggtgtcata gcggtccttt gattgcagtg     600
tgggagttgc aacatgtacc aacaaattca ttcatcccaa aacctaaatt tatcctctcc     660
attactatta cctacaccta tacctagtaa atatgtcctg ccttgtaact cctccactgc     720
ctgcacacgt cttagtcaat ccatctgcct tcaaataggc attattttgt tctttcccct     780
ccgactgaaa ggctatcgac cgaccgaccg ctcatcttct tcttctgcgc aattttttct     840
gctggatcat catcattacc atcatcgcca tccccaccat catcatcatg atggtatctc     900
tatctctccc tggcaatcga ttgtagagga aggaagagg aaggggcat atgtattgat     960
caacctaccc gaaaaaacaa tctgatcagc cctgctaatc ttgcttataa atctcttatc    1020
cactgttcaa tcattcaggt ttcttcccac ttccaagcaa aggcgcccgg attggccgtg    1080
```

```
ttcttagatt ttcaggtact taaatggaca atattcccca cctgaagccg ttctgaaaaa    1140
gatttgtttg tagaaacaaa cgattgtaat atttgcttaa gttgagctta aggggtttgg    1200
tacctaactt gccttgtggt tatttgtttc tcagaactcg ggctgcgtcc aactgtagga    1260
acgaaccagc acaaggggtt gcagcttttg ctgttgctgt tgcgcccatt gcttttggac    1320
tggtattagt agttgcagct ttgttttgca tacgctgtga ggatctgtgc gcggaaattt    1380
tgtgtacaaa tcatg                                                    1395

<210> SEQ ID NO 2
<211> LENGTH: 1385
<212> TYPE: DNA
<213> ORGANISM: Pinus taeda

<400> SEQUENCE: 2
cagcaaatat gatttagatt atgacctaga ataagcata gcattaaagc atatacataa    60
caagcggtga tatactctga ctgccactgt acttgatgaa aggtagtgga ctctgctcag    120
gtacattagt ttggtaaggt tggcttggct tctgggtaat atgagaagta aagaagtaaa    180
aggtatttga ctctagtcaa gtacattgga ttgcctttgt cggggcttgg atggcttggg    240
ttcgtgtgag aagccaacaa tttataataa aaataaaata aaaatcgaa gtgttggaag    300 tgaaaacggt ggggcataaa tatacacaga agagtacttt aacaatgcgc aaccaaggca    360
gattcacaac ttgatttctg gacctcgaat acgagataat ggtggtaaga aataaaggaa    420
gagtggagtg catttgaaaa tgaatggaga gcgcacaaaa tggaggacga ataaatgaaa    480
tataatgcaa gagtgcattt ccctattatt tccagaaatg tatatgtggg gtcggcattc    540
acatgggcgt cgcattcagg gggtgtcata gcggtccttt gattgcagtg tgggagttgc    600
aacatgtacc aacaaattca ttcatcccaa aacctaaatt tatcctctcc attactatta    660
cctacaccta tacctagtaa atatgtcctg ccttgtaact cctccactgc ctgcacacgt    720
cttagtcaat ccatctgcct tcaaataggc attattttgt tctttcccct ccgactgaaa    780
ggctatcgac cgaccgaccg ctcatcttct tcttctgcgc aattttttct gctggatcat    840
catcattacc atcatcgcca tccccaccat catcatcatg atggtatctc tatctctccc    900
tggcaatcga ttgtagagga aaggaagagg gaaggggcat atgtattgat caacctaccc    960
gaaaaaacaa tctgatcagc cctgctaatc ttgcttataa atctcttatc cactgttcaa    1020
tcattcaggt ttcttcccac tttcaagcaa aggcgcccgg attggccgtg ttcttagatt    1080
ttcaggtact taaatggaca atattcccca cctgaagccg ttctgaaaaa gatttgtttg    1140
tagaaacaaa cgattgtaat atttgcttaa gttgagctta aggggtttgg tacctaactt    1200
gccttgtggt tatttgtttc tcagaactcg ggctgcgtcc aactgtagga acgaaccagc    1260
acaaggggtt gcagcttttg ctgttgctgt tgcgcccatt gcttttggac tggtattagt    1320
agttgcagct ttgttttgca tacgctgtga ggatctgtgc gcggaaattt tgtgtacaaa    1380
tcatg                                                              1385

<210> SEQ ID NO 3
<211> LENGTH: 4172
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3
```

```
gatagggtca aatcgaccac ttgcacagtt aagtgattct aatacgaaac cttaaaagca      60
aacatcggtt cttttgagtc agaagaaatg caacttaatg tgacacatga tgtgaagaaa     120
aaacaaaagt aatataagaa aagggaacaa ttaaatagtt aataaaatat ttccttaaag     180
ttgtaacaaa taagaatca ttttatgaaa caatatgaac cctaaataaa ttaaaattcc     240
tctgaaacct taaatttatc gagctagtga ttggctgcca actgccatgc tggcaaaatt     300
agagtgacat gattggtctg aacatgtcta gggtttcaga catgtgacat gtgtcaacaa     360
cccattaaca cattgggtat aaatccaata gacatttgat agtattaaaa ttgtaaccat     420
tggattaaat ttaaacgtga tggatgtaac taaatgactt gtccgagtaa catcacaacg     480
ttccatactt tccttatttg aatataatt aaatttacca tttattcttt tttcttgagt     540
ttcctgtata tgtacttgta catagatata tatgcacaaa tacgtattac aatgacatat     600
tatagacttt gatgtctgaa ctctcaacct tctcgatgga gagatcatga ccgtagattt     660
ttttggatcg tagaaggcag accaaactct taaactattg gatccggact aaaaatctca     720
cttTccctctc agtacccata tgagagaga aatgataaa aatccctaac attattctct     780
ctctagaaaa aaaagatac ttcaaaaaga agagaaatt gcataaatct atctacacca     840
aagatgttga agcaattcca atgctatact tctatgccaa atctatttat tcagtgatca     900
ttaatctttt tacttccaag aaatatgaac aatttagtat ccttataatt tttgtctcta     960
tatatgtaat atgaacattg ggtattgacc aaatgagaaa tctaatatta aatggtcaaa    1020
agtagtaata tgatgacatt tttgaattta taaataggtt acaaattaat tcattatgac    1080
ataaaacctt cttgtcagaa gtcaagaact gaaactaaca aactttata ataaattagt    1140
aaaaatacaa atgaaaaata aaagaaata atatctgagt gatgacgtga tcaaagattc    1200
tttaacaaag acaacaaatc ttacagaccc aaaacctaat cttgcgctca attccaacct    1260
ctgaaaaaac ctcaaaaatc ttataaaaga aaataaataa agaaacgaaa ctctgatttc    1320
gtagagtacc catcggatat ataaaaagaa attagtaggt aaatgaagac taattttgat    1380
tgactgattt aatttgaagt cgttgttagc ttttcttgtt ttggacatga gaattatata    1440
tttcaggaca tgagagttga caactgtaaa cgattaagaa aattgatctt ttaatttttca    1500
aacaccattt aatcttgaca tgttttatgt tttggtggag aagaaagtaa tcacgtggga    1560
ctctctacta ataagtattt ggaaattgcg tgtcgaatta gagattacta gtttgagtaa    1620
tgtagttcga aatgagatta gttattttta atttaaaaa gagtaatttt aaggaataac    1680
aaaaaagagt ccccataagc taatttgtct taattaccte cttgtttcat tgactatttg    1740
aaatcttgaa aattcagttg aaatttcaaa tctatgtttc ttttgaccac ttctaaacta    1800
atcttagctc atatataatt ttccaaaact acaaaaataa cactaacatt taacattctc    1860
aagagaaaac aaaacaaaa acttagataa ccatctaaat tgtcctacat gtacgtataa    1920
gttccattat tttctatcac tcatataagt taaaatttca tgaaaactca aaaatctagc    1980
tagtttcacc ttattcactc tcacttacca tcacatgtgt ttgtatcaaa tatatgatat    2040
gatataattc atgagagaga aagagagcta gagataagaa aggaaagtaa gagaaagaag    2100
agaagaaaaa gagagacaca gacattaaca acaatggagg atggatgatc acaaaacaga    2160
agatatgacc tcatagtcct tccttactct ctccccaatt tgtttcccaa aacttacttt    2220
tatagtcata aaaatcaagt ttttacctat tacaacacca gatctataaa tatatctaaa    2280
tcttcaagta cttgttagta aggaaaatag aaagatataa gatttattta ttattataat    2340
aacagaaatg agtgaagaaa gaacacccaa caaagtgaat cttagttcta caaaactgaa    2400
```

-continued

```
tctaaaactc cacattagaa aaaccctga tggtttctta tttcttttca tttattatct      2460
aactctcact cagatctcct ttaactttgt accatttccc tcacttcata tatctatata      2520
taacaaactc tctcttttta tttaagtctt aagggaaaat taatatacac atgaagaaca      2580
agaaattaga tctacaaaat tgttacaaaa accccgaag taaataaaat aaacatatca       2640
aacaaatatt cccactaatg ttagtgtgtt tatatatata tgtgtgtgga atatgaagga      2700
aaaaagtgaa aataatcct acccataaga gcattcaaga agaagctcga ggtcgacggt       2760
atcgataagc ttaaactcga cagcaaatat gatttagatt atgacctaga ataagcata      2820 gcattaaagc atatacataa caagcggtga tatactctga ctgccactgt acttgaggaa     2880
aggtagtgga ctctgctcag gtacattagt ttggtaaggt tggcttggct tctgggtaat    2940
atgagaagta aagaagtaaa aggtatttga ctctagtcaa gtacattgga ttgcctttgt    3000
cggggcttgg atggcttggg ttcgtgtgag aagccaacaa tttataagaa atatataaaa    3060 taaaaataa aaaatttaa gtgttggaag tgaaaacggt ggggcagaaa tatacacaga      3120
agagtacttt aacaatgcgc aaccaaggca gattcacaac ttgatttctg gacctcgaat    3180
acgagataat ggtggtaaga aataaaggaa gagtggagcg catttgaaaa tgaatggaga   3240
gcgcacaaaa tggaggacga ataaatgaaa tataatgcaa gggtgcattt ccctattatt    3300
tccagaaatg tatatgtggg gtcggcattc tcatgggcgt cgcattcagg gggtgtcata   3360
gcggtccttt gattgcagtg tgggagttgc aacatgtacc aacaaatcca ttcatcccaa   3420
aacctaaatt tatcctctcc attactatta cctacaccta tacctagtaa atatgtcctg   3480
ccttgtaact cctccactgc ctgcacacgt cttagtcaat ccatctgcct tcaaataggc   3540
attattttgt tctttcccct ccgactgaaa ggctatcgac cgaccgaccg ctcatcttct   3600
tcttctgcgc aattttttct gctggatcat catcattacc atcatcgcca tccccaccat    3660
catcatcatg atggtatctc tatctctccc tggcaatcga ttgtagagga aggaagagg    3720 gaagggcat atgtattgat caacctaccc gaaaaaacaa tctgatcagc cctgctaatc    3780
ttgcttataa atctcttatc cactgttcaa tcattcaggt ttcttcccac tttcaagcaa   3840
aggcgcccgg attggccgtg ttcttagatt ttcaggtact taaatggaca atattcccca   3900
cctgaagccg ttctgaaaaa gatttgtttg tagaaacaaa cgattgtaat atttgcttaa   3960
gttgagctta aggggtttgg tacctaactt gccttgtggt tatttgtttc tcagaactcg    4020
ggctgcgtcc aactgtagga acgaaccagc acaaggggtt gcagcttttg ctgttgctgt    4080
tgcgcccatt gcttttggac tggtattagt agttgcagct ttgttttgca tacgctgtga    4140
ggatctgtgc gcggaaattt tgtgtacaaa tc                                  4172
```

<210> SEQ ID NO 4
<211> LENGTH: 396
<212> TYPE: DNA
<213> ORGANISM: Pinus radiata

<400> SEQUENCE: 4

```
ctcgagtaaa acataatttt ggcagtaaaa agtgaattct attgttttga aaacaaaaca     60
aaatacagga agcgtgattg tggggttgtt gttgaacttg cccgggcaaa agaagaatga    120
ttagcggtag aggagttagt agttacgttc aactaaatgc gtgactaaat tatttatcct    180
ccgccatgga agcaggtgat tcacacacaa cttgctgcac acattgctct caaacctttc    240
ctataaatat ccgtagcagg ggctgcgatg atacacaacg catttaatca aactactttg    300
```

```
attactttct gtgggttcta ctttctttga atagtcagtt ctgctgtttt tagaagattt    360
atgagaatgg ccaaaattca ggtatcaaac gggaac                              396

<210> SEQ ID NO 5
<211> LENGTH: 336
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 5
atggcacagg ttatcaacac gtttgacggg gttgcggatt atcttcagac atatcataag     60
ctacctgata attacattac aaaatcagaa gcacaagccc tcggctgggt ggcatcaaaa    120
gggaaccttg cagacgtcgc tccggggaaa agcatcggcg agacatctt ctcaaacagg    180 gaaggcaaac tcccgggcaa aagcggacga acatggcgtg gagcggatat taactataca    240
tcaggcttca gaaattcaga ccggattctt tactcaagcg actggctgat ttacaaaaca    300
acggaccatt atcagacctt tacaaaaatc agataa                              336

<210> SEQ ID NO 6
<211> LENGTH: 336
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 6
atggcacagg ttatcaacac gtttgacggg gttgcggatt atcttcagac atatcataag     60
ctacctgata attacattac aaaatcagaa gcacaagccc tcggctgggt ggcatcaaaa    120
gggaaccttg cagacgtcgc tccggggaaa agcatcggcg agacatctt ctcaaacagg    180 gaaggcaaac tcccgggcaa aagcggacga acatggcgtg aagcggatat taactataca    240
tcaggcttca gaaattcaga ccggattctt tactcaagcg actggctgat ttacaaaaca    300
acggaccatt atcagacctc tacaaaaatc agataa                              336

<210> SEQ ID NO 7
<211> LENGTH: 336
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
atggcacagg ttatcaacac gtttgacggg gttgcggatt atcttcagac atatcataag     60
ctacctgata attacattac aaaatcagaa gcacaagccc tcggctgggt ggcatcaaaa    120
gggaaccttg cagacgtcgc tccggggaaa agcatcggcg agacatctt ctcaaacagg    180 gaaggcaaac tcccgggcaa aagcggacga acatggcgtg aagcggatat taactataca    240
tcaggcttca gaaattcaga ccggattctt tactcaagcg actggctgat ttacaaaaca    300
acggacgagt atcagacctt tacaaaaatc agataa                              336

<210> SEQ ID NO 8
<211> LENGTH: 336
<212> TYPE: DNA
<213> ORGANISM: Artificial Sequence
<220> FEATURE:
```

-continued

```
<223> OTHER INFORMATION: Description of Artificial Sequence: Synthetic
      construct

<400> SEQUENCE: 8
atggcacagg ttatcaacac gtttgacggg gttgcggatt atcttcagac atatcataag      60
ctacctgata attacattac agcatcagaa gcacaagccc tcggctgggt ggcatcaaaa     120
gggaaccttg cagacgtcgc tccggggaaa agcatcggcg agacatcttc tcaaacagg      180 gaaggcaaac tcccgggcaa aagcggacga acatggcgtg aagcggatat taactataca     240
tcaggcttca gaaattcaga ccggattctt tactcaagcg actggctgat ttacaaaaca     300
acggaccatt atcagacctt tacaaaaatc agataa                               336

<210> SEQ ID NO 9
<211> LENGTH: 111
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 9
```

Met Ala Gln Val Ile Asn Thr Phe Asp Gly Val Ala Asp Tyr Leu Gln
 1               5                  10                  15

Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
    50                  55                  60

Pro Gly Lys Ser Gly Arg Thr Trp Arg Gly Ala Asp Ile Asn Tyr Thr
65                  70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Phe Thr Lys Ile Arg
            100                 105                 110

```
<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10
```

Met Ala Gln Val Ile Asn Thr Phe Asp Gly Val Ala Asp Tyr Leu Gln
 1               5                  10                  15

Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
    50                  55                  60

Pro Gly Lys Ser Gly Arg Thr Trp Arg Glu Ala Asp Ile Asn Tyr Thr
65                  70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Ser Thr Lys Ile Arg

-continued

```
              100                 105                 110
```

<210> SEQ ID NO 11
<211> LENGTH: 111
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

Met Ala Gln Val Ile Asn Thr Phe Asp Gly Val Ala Asp Tyr Leu Gln
 1               5                  10                  15

Thr Tyr His Lys Leu Pro Asp Asn Tyr Ile Thr Lys Ser Glu Ala Gln
             20                  25                  30

Ala Leu Gly Trp Val Ala Ser Lys Gly Asn Leu Ala Asp Val Ala Pro
         35                  40                  45

Gly Lys Ser Ile Gly Gly Asp Ile Phe Ser Asn Arg Glu Gly Lys Leu
     50                  55                  60

Pro Gly Lys Ser Gly Arg Thr Trp Arg Glu Ala Asp Ile Asn Tyr Thr
 65                  70                  75                  80

Ser Gly Phe Arg Asn Ser Asp Arg Ile Leu Tyr Ser Ser Asp Trp Leu
                 85                  90                  95

Ile Tyr Lys Thr Thr Asp Glu Tyr Gln Thr Phe Thr Lys Ile Arg
             100                 105                 110

<210> SEQ ID NO 12
<211> LENGTH: 111
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Met Ala Gln Val Ile Asn Thr Phe Asp Gly Val Ala Asp Tyr Leu Gln
 1               5                  10                  15

Thr Tyr His Lys Leu Pro Asp Asn Tyr Ile Thr Ala Ser Glu Ala Gln
             20                  25                  30

Ala Leu Gly Trp Val Ala Ser Lys Gly Asn Leu Ala Asp Val Ala Pro
         35                  40                  45

Gly Lys Ser Ile Gly Gly Asp Ile Phe Ser Asn Arg Glu Gly Lys Leu
     50                  55                  60

Pro Gly Lys Ser Gly Arg Thr Trp Arg Glu Ala Asp Ile Asn Tyr Thr
 65                  70                  75                  80

Ser Gly Phe Arg Asn Ser Asp Arg Ile Leu Tyr Ser Ser Asp Trp Leu
                 85                  90                  95

Ile Tyr Lys Thr Thr Asp His Tyr Gln Thr Phe Thr Lys Ile Arg
             100                 105                 110

<210> SEQ ID NO 13
<211> LENGTH: 1105
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 13
tctcgagtaa aacataattt tggcagtaaa aagtgaattc tattgttttg aaaacaaaac      60
```

```
aaaatacagg aagcgtgatt gtggggttgt tgttgaactt gcccgggcaa aagaagaatg      120
attagcggta gaggagttag tagttacgtt caactaaatg cgtgactaaa ttatttatcc      180
tccgccatgg aagcaggtga ttcacacaca acttgctgca cacattgctc tcaaacccttt    240 cctataaata tccgtagcag gggctgcgat gatacacaac gcatttaatc aaactactttt   300 gattactttc tgtgggttct actttctttg aatagtcagt tctgctgttt ttagaagatt     360
tatgagaatg gccaaaattc aggtatcaaa cgggaacatg gcacaggtta tcaacacgtt    420
tgacggggtt gcggattatc ttcagacata tcataagcta cctgataatt acattacaaa    480
atcagaagca caagccctcg gctgggtggc atcaaaaggg aaccttgcag acgtcgctcc    540
ggggaaaagc atcggcggag acatcttctc aaacagggaa ggcaaactcc cgggcaaaag    600
cggacgaaca tggcgtgaag cggatattaa ctatacatca ggcttcagaa attcagaccg    660
gattctttac tcaagcgact ggctgattta caaaacaacg gacgagtatc agacctttac    720
aaaaatcaga taacgaaaaa aacggcttcc ctgcgggagg ccgttttttt cagctttaca    780
taaagtgtgt aataaatttt tcttcaaact ctgatcggtc aagagctctt ctgagagaca    840
atacatacat gtctctgatg ttgtaacttt actaccaaaa cctataaaga ttggcttatt    900
tcgttctatt ggatatgtat catcattact ggtaaatcaa gtttctttct aataatgtag    960
aagatcagaa aatccataag aagatatcaa catttgagtt ctatggtaaa ttgaattata   1020
tcaacttagt tgcaatgatt cattcttgac tgatgcattg atggcttatc aaaccagttt   1080
acaaaattcg attagatagg gccca                                          1105
```

<210> SEQ ID NO 14
<211> LENGTH: 1103
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 14

```
ctcgagtaaa acataatttt ggcagtaaaa agtgaattct attgtttttga aaacaaaaca      60 aaatacagga agcgtgattg tggggttgtt gttgaacttg cccgggcaaa agaagaatga    120
ttagcggtag aggagttagt agttacgttc aactaaatgc gtgactaaat tatttatcct    180
ccgccatgga agcaggtgat tcacacacaa cttgctgcac acattgctct caaacccttc    240
ctataaatat ccgtagcagg ggctgcgatg atacacaacg catttaatca aactactttg    300
attactttct gtgggttcta ctttctttga atagtcagtt ctgctgtttt tagaagattt    360
atgagaatgg ccaaaattca ggtatcaaac gggaacatgg cacaggttat caacacgttt   420
gacggggttg cggattatct tcagacatat cataagctac ctgataatta cattacagca    480
tcagaagcac aagccctcgg ctgggtggca tcaaaaggga accttgcaga cgtcgctccg    540
gggaaaagca tcggcggaga catcttctca aacagggaag gcaaactccc gggcaaaagc    600
ggacgaacat ggcgtgaagc ggatattaac tatacatcag gcttcagaaa ttcagaccgg    660
attctttact caagcgactg gctgatttac aaaacaacgg acgagtatca gacctttaca    720
aaaatcagat aacgaaaaaa acggcttccc tgcgggaggc cgttttttttc agctttacat    780 aaagtgtgta ataaatttt cttcaaactc tgatcggtca agagctcttc tgagagacaa    840
tacatacatg tctctgatgt tgtaacttta ctaccaaaac ctataaagat tggcttattt    900
cgttctattg gatatgtatc atcattactg gtaaatcaag tttctttcta ataatgtaga    960
```

-continued

```
agatcagaaa atccataaga agatatcaac atttgagttc tatggtaaat tgaattatat    1020
caacttagtt gcaatgattc attcttgact gatgcattga tggcttatca aaccagttta    1080
caaaattcga ttagataggg ccc                                           1103
```

<210> SEQ ID NO 15
<211> LENGTH: 1103
<212> TYPE: DNA
<213> ORGANISM: Artificial Sequence
<220> FEATURE:
<223> OTHER INFORMATION: Description of Artificial Sequence: Synthetic
       construct

<400> SEQUENCE: 15

```
ctcgagtaaa acataatttt ggcagtaaaa agtgaattct attgttttga aaacaaaaca     60
aaatacagga agcgtgattg tggggttgtt gttgaacttg cccgggcaaa agaagaatga    120
ttagcggtag aggagttagt agttacgttc aactaaatgc gtgactaaat tatttatcct    180
ccgccatgga agcaggtgat tcacacacaa cttgctgcac acattgctct caaacctttc    240
ctataaatat ccgtagcagg ggctgcgatg atacacaacg catttaatca aactactttg    300
attactttct gtgggttcta ctttctttga atagtcagtt ctgctgtttt tagaagattt    360
atgagaatgg ccaaaattca ggtatcaaac gggaacatgg cacaggttat caacacgttt    420
gacggggttg cggattatct tcagacatat cataagctac ctgataatta cattacaaaa    480
tcagaagcac aagccctcgg ctgggtggca tcaaaggga accttgcaga cgtcgctccg    540
gggaaaagca tcggcggaga catcttctca aacagggaag gcaaactccc gggcaaaagc    600
ggacgaacat ggcgtggagc ggatattaac tatacatcag gcttcagaaa ttcagaccgg    660
attctttact caagcgactg gctgattac aaaacaacgg acgagtatca gacctttaca    720
aaaatcagat aacgaaaaaa acggcttccc tgcgggaggc cgttttttc agctttacat    780 aaagtgtgta ataatttttt cttcaaactc tgatcggtca agagctcttc tgagagacaa    840
tacatacatg tctctgatgt tgtaacttta ctaccaaaac ctataaagat tggcttattt    900
cgttctattg gatatgtatc atcattactg gtaaatcaag tttctttcta ataatgtaga    960
agatcagaaa atccataaga agatatcaac atttgagttc tatggtaaat tgaattatat   1020
caacttagtt gcaatgattc attcttgact gatgcattga tggcttatca aaccagttta   1080
caaaattcga ttagataggg ccc                                          1103
```

<210> SEQ ID NO 16
<211> LENGTH: 354
<212> TYPE: DNA
<213> ORGANISM: Pinus radiata

<400> SEQUENCE: 16

```
taaaacataa ttttggcagt aaaaagtgaa ttctattgtt ttgaaaacaa aacaaaatac     60
aggaagcgtg attgtggggt tgttgttgaa cttgcccggg caaagaagaa atgattagcg    120
gtagaggagt tagtagttac gttcaactaa atgcgtgact aaattattta tcctccgcca    180
tggaagcagg tgattcacac acaacttgct gcacacattg ctctcaaacc tttcctataa    240
atatccgtag caggggctgc gatgatacac aacgcattta atcaaactac tttgattact    300
ttctgtgggt tctactttct tgaatagtc agttctgctg tttttagaag attt          354
```

<210> SEQ ID NO 17
<211> LENGTH: 766
<212> TYPE: DNA

<213> ORGANISM: Artificial Sequence
<220> FEATURE:
<223> OTHER INFORMATION: Description of Artificial Sequence: Synthetic
      construct

<400> SEQUENCE: 17

```
ttcattcatc ccaaaaccta aatttatcct ctccattact attacctaca cctataccta      60
gtaaatatgt cctgccttgt aactcctcca ctgcctgcac acgtcttagt caatccatct     120
gccttcaaat aggcattatt ttgttctttc ccctccgact gaaaggctat cgaccgaccg     180
accgctcatc ttcttcttct gcgcaatttt ttctgctgga tcatcatcat taccatcatc     240
gccatcccca ccatcatcat catgatggta tctctatctc tccctggcaa tcgattgtag     300
aggaaaggaa gagggaaggg gcatatgtat tgatcaacct acccgaaaaa acaatctgat     360
cagccctgct aatcttgctt ataaatctct tatccactgt tcaatcattc aggtttcttc     420
ccacttccaa gcaaaggcgc ccggattggc cgtgttctta gattttcagg tacttaaatg     480
gacaatattc cccacctgaa gccgttctga aaaagatttg tttgtagaaa caaacgattg     540
taatatttgc ttaagttgag cttaaggggt ttggtaccta acttgccttg tggttatttg     600
tttctcagaa ctcgggctgc gtccaactgt aggaacgaac cagcacaagg ggttgcagct     660
tttgctgttg ctgttgcgcc cattgctttt ggactggtat tagtagttgc agctttgttt     720
tgcatacgct gtgaggatct gtgcgcggaa attttgtgta caaatc                   766
```

<210> SEQ ID NO 18
<211> LENGTH: 8006
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 18

```
cgccggcgtt gtggatacct cgcggaaaac ttggccctca ctgacagatg aggggcggac      60
gttgacactt gaggggccga ctcacccggc gcggcgttga cagatgaggg gcaggctcga     120
tttcggccgg cgacgtggag ctggccagcc tcgcaaatcg gcgaaaacgc ctgattttac     180
gcgagtttcc cacagatgat gtggacaagc ctggggataa gtgccctgcg gtattgacac     240
ttgaggggcg cgactactga cagatgaggg gcgcgatcct tgacacttga ggggcagagt     300
gctgacagat gaggggcgca cctattgaca tttgaggggc tgtccacagg cagaaaatcc     360
agcatttgca agggtttccg cccgtttttc ggccaccgct aacctgtctt ttaacctgct     420
tttaaaccaa tatttataaa ccttgttttt aaccagggct gcgccctgtg cgcgtgaccg     480
cgcacgccga agggggggtgc cccccttcct cgaaccctcc cggcccgcta acgcgggcct     540
cccatccccc caggggctgc gcccctcggc cgcgaacggc ctcacccaa aaatggcagc     600
gctggcagtc cataattgtg gtccaatttg cagccgtccg agacaggagg acatcgtcca     660
gctgaaaccg gggcagaatc cggccatttc tgaagagaaa aatggtaaac tgatagaata     720
aaatcataag aaaggagccg cacatgaaaa aagcagtcat taacgggaa caaatcagaa     780
gtatcagcga cctccaccag acattgaaaa aggagcttgc ccttccggaa tactacggtg     840
aaaacctgga cgctttatgg gattgtctga ccggatgggt ggagtacccg ctcgttttgg     900
aatggaggca gtttgaacaa agcaagcagc tgactgaaaa tggcgccgag agtgtgcttc     960
aggttttccg tgaagcgaaa gcggaaggct gcgacatcac catcatactt tcttaatacg    1020
atcaatggga gaggaacaat atggaaacac aaaccacaat tgtggtttca aaatcggctc    1080
```

-continued

```
cgtcgatact atgttatacg ccaactttga aaacaacttt gaaaaagctg ttttctggta    1140
tttaaggttt tagaatgcaa ggaacagtga attggagttc gtcttgttat aattagcttc    1200
ttggggtatc tttaaatact gtagaaaaga ggaaggaaat aataaatggc taaaatgaga    1260
atatcaccgg aattgaaaaa actgatcgaa aaataccgct gcgtaaaaga tacggaagga    1320
atgtctcctg ctaaggtata taagctggtg ggagaaaatg aaaacctata tttaaaaatg    1380
acggacagcc ggtataaagg gaccacctat gatgtggaac gggaaaagga catgatgcta    1440
tggctggaag gaaagctgcc tgttccaaag gtcctgcact ttgaacggca tgatggctgg    1500
agcaatctgc tcatgagtga ggccgatggc gtccttgct cggaagagta tgaagatgaa    1560
caaagccctg aaaagattat cgagctgtat gcggagtgca tcaggctctt tcactccatc    1620
gacatatcgg attgtcccta tacgaatagc ttagacagcc gcttagccga attggattac    1680
ttactgaata cgatctggc cgatgtggat tgcgaaaact gggaagaaga cactccattt    1740
aaagatccgc gcgagctgta tgattttta aagacggaaa agcccgaaga ggaacttgtc    1800
ttttcccacg gcgacctggg agacagcaac atctttgtga agatggcaa agtaagtggc    1860 tttattgatc ttgggagaag cggcagggcg acaagtggt atgacattgc cttctgcgtc    1920
cggtcgatca ggggagatat cggggaagaa cagtatgtcg agctatttt tgacttactg    1980 gggatcaagc ctgattggga gaaaataaaa tattatattt tactggatga attgttttag    2040
tacctagatg tggcgcaacg atgccggcga caagcaggag cgcaccgact tcttccgcat    2100
caagtgtttt ggctctcagg ccgaggccca cggcaagtat ttgggcaagg ggtcgctggt    2160
attcgtgcag gcaagattc ggaataccaa gtacgagaag gacggccaga cggtctacgg    2220
gaccgacttc attgccgata aggtggatta tctggacacc aaggcaccag gcgggtcaaa    2280
tcaggaataa gggcacattg ccccggcgtg agtcgggca atcccgcaag gagggtgaat    2340
gaatcggacg tttgaccgga aggcatacag gcaagaactg atcgacgcgg ggttttccgc    2400
cgaggatgcc gaaaccatcg caagccgcac cgtcatgcgt gcgccccgcg aaaccttcca    2460
gtccgtcggc tcgatggtcc agcaagctac ggccaagatc gagcgcgaca gcgtgcaact    2520 ggctcccct gccctgcccg cgccatcggc cgccgtggag cgttcgcgtc gtctcgaaca    2580
ggaggcggca ggtttggcga agtcgatgac catcgcacg cgaggaacta tgacgaccaa    2640
gaagcgaaaa accgccggcg aggacctggc aaaacaggtc agcgaggcca agcaggccgc    2700
gttgctgaaa cacacgaagc agcagatcaa ggaaatgcag ctttccttgt tcgatattgc    2760
gccgtggccg gacacgatgc gagcgatgcc aaacgacacg gcccgctctg ccctgttcac    2820
cacgcgcaac aagaaaatcc gcgcgcgagg gctgcaaaac aaggtcattt tccacgtcaa    2880
caaggacgtg aagatcacct acaccggcgt cgagctgcgg gccgacgatg acgaactggt    2940
gtggcagcag gtgttggagt acgcgaagcg caccccctatc ggcagccga tcaccttcac    3000 gttctacgag ctttgccagg acctgggctg gtcgatcaat ggccggtatt acacgaaggc    3060
cgaggaatgc ctgtcgcgcc tacaggcgac ggcgatgggc ttcacgtccg accgcgttgg    3120
gcacctggaa tcggtgtcgc tgctgcaccg cttccgcgtc ctggaccgtg gcaagaaaac    3180
gtcccgttgc caggtcctga tcgacgagga aatcgtcgtg ctgtttgctg gcgaccacta    3240
cacgaaattc atatgggaga agtaccgcaa gctgtcgccg acggcccgac ggatgttcga    3300
ctatttcagc tcgcaccggg agccgtaccc gctcaagctg gaaaccttcc gcctcatgtg    3360
cggatcggat tccacccgcg tgaagaagtg gcgcgagcag gtcggcgaag cctgcgaaga    3420
```

```
gttgcgaggc agcggcctgg tggaacacgc ctgggtcaat gatgacctgg tgcattgcaa    3480
acgctagggc cttgtggggt cagttccggc tgggggttca gcagccagcg ctttactggc    3540
atttcaggaa caagcgggca ctgctcgacg cacttgcttc gctcagtatc gctcgggacg    3600 cacgcgcgc tctacgaact gccgatagac aactgtcacg gttaagcgag aaatgaataa     3660
gaaggctgat aattcggatc tctgcgaggg agatgatatt tgatcacagg cagcaacgct    3720
ctgtcatcgt tacaatcaac atgctaccct ccgcgagatc atccgtgttt caacccggc     3780 agcttagttg ccgttcttcc gaatagcatc ggtaacatga gcaaagtctg ccgccttaca    3840
acggctctcc cgctgacgcc gtcccggact gatgggctgc ctgtatcgag tggtgatttt    3900
gtgccgagct gccggtcggg gagctgttgg ctggctggtg gcaggatata ttgtggtgta    3960
aacaaattga cgcttagaca acttaataac acattgcgga cgtttttaat gtactggggt    4020
ggttttcctt ttcaccagtg agacgggcaa cagctgattg cccttcaccg cctggccctg    4080
agagagttgc agcaagcggt ccacgctggt ttgccccagc aggcgaaaat cctgtttgat    4140
ggtggttccg aaatcggcaa aatcccttat aaatcaaaag aatagcccga atagggttg     4200 agtgttgttc cagtttggaa caagagtcca ctattaaaga acgtggactc caacgtcaaa    4260
gggcgaaaaa ccgtctatca gggcgatggc ccacggccgc tctagaacta gtggatcccc    4320
cctacgtgcg atcagtaac atagatgaca ccgcgcgcga taatttatcc tagtttgcgc     4380
gctatatttt gttttctatc gcgtattaaa tgtataattg cgggactcta atcataaaaa    4440
cccatctcat aaataacgtc atgcattaca tgttaattat tacatgctta acgtaattca    4500
acagaaatta tatgataatc atcgcaagac cggcaacagg attcaatctt aagaaacttt    4560
attgccaaat gtttgaacga tccctcagaa gaactcgtca agaaggcgat agaaggcgat    4620
gcgctgcgaa tcgggagcgg cgataccgta aagcacgagg aagcggtcag cccattcgcc    4680
gccaagctct tcagcaatat cacgggtagc caacgctatg tcctgatagc ggtccgccac    4740
acccagccgg ccacagtcga tgaatccaga aaagcggcca ttttccacca tgatattcgg    4800
caagcaggca tcgccatggg tcacgacgag atcctcgccg tcgggcatgc gcgccttgag    4860
cctggcgaac agttcggctg gcgcgagccc ctgatgctct tcgtccagat catcctgatc    4920
gacaagaccg gcttccatcc gagtacgtgc tcgctcgatg cgatgtttcg cttggtggtc    4980
gaatgggcag gtagccggat caagcgtatg cagccgccgc attgcatcag ccatgatgga    5040
tactttctcg gcaggagcaa ggtgagatga caggagatcc tgccccggca cttcgcccaa    5100
tagcagccag tcccttcccg cttcagtgac aacgtcgagc acagctgcgc aaggaacgcc    5160
cgtcgtggcc agccacgata gccgcgctgc ctcgtcctgg agttcattca gggcaccgga    5220
caggtcggtc ttgacaaaaa gaaccgggcg cccctgcgct gacagccgga acacggcggc    5280
atcagagcag ccgattgtct gttgtgccca gtcatagccg aatagcctct ccacccaagc    5340
ggccggagaa cctgcgtgca atccatcttg ttcaatcatc tgttaatcag aaaaactcag    5400
attaatcgac aaattcgatc gcacaaacta gaaactaaca ccagatctag atagaaatca    5460
caaatcgaag agtaattatt cgacaaaact caaattattt gaacaaatcg gatgatattt    5520
atgaaaccct aatcgagaat taagatgata tctaacgatc aaacccagaa atcgtcttc     5580 gatctaagat taacagaatc taaaccaaag aacatatacg aaattgggat cgaacgaaaa    5640
caaaatcgaa gattttgaga gaataaggaa cacagaaatt taccttgatc acggtagaga    5700
gaattgagag aaagttttta agattttgag aaattgaaat ctgaattgtg aagaagaaga    5760
gctctttggg tattgtttta tagaagaaga agaagaaaag acgaggacga ctaggtcacg    5820
```

```
agaaagctaa ggcggtgaag caatagctaa taataaaatg acacgtgtat tgagcgttgt    5880
ttacacgcaa agttgttttt ggctaattgc cttattttta ggttgaggaa aagtatttgt    5940
gctttgagtt gataaacacg actcgtgtgt gccggctgca accactttga cgccgtttat    6000
tactgactcg tcgacaacca caatttctaa cggtcgtcat aagatccagc cgttgagatt    6060
taacgatcgt tacgatttat attttttag cattatcgtt ttatttttta aatatacggt     6120
ggagctgaaa attggcaata attgaaccgt gggtcccact gcattgaagc gtatttcgta    6180
ttttctagaa ttcttcgtgc tttatttctt ttcctttttg ttttttttg ccatttatct     6240 aatgcaagtg ggcttataaa atcagtgaat ttcttggaaa agtaacttct ttatcgtata    6300
acatattgtg aaattatcca tttcttttaa ttttttagtg ttattggata ttttgtatg     6360 attattgatt tgcataggat aatgactttt gtatcaagtt ggtgaacaag tctcgttaaa    6420
aaaggcaagt ggtttggtga ctcgatttat tcttgttatt taattcatat atcaatggat    6480
cttatttggg gcctggtcca tatttaacac tcgtgttcag tccaatgacc aataatattt    6540
tttcattaat aacaatgtaa caagaatgat acacaaaaca ttctttgaat aagttcgcta    6600
tgaagaaggg aacttatccg gtcctagatc atcagttcat acaaacctcc atagagttca    6660
acatcttaaa caaggatatc ctgatccgtt gacggcgcgc caagcggccg catttaaatg    6720
ggccctatct aatcgaattt tgtaaactgg tttgataagc catcaatgca tcagtcaaga    6780
atgaatcatt gcaactaagt tgatataatt caatttacca tagaactcaa atgttgatat    6840
cttcttatgg atttttctgat cttctacatt attagaaaga aacttgattt accagtaatg    6900
atgatacata tccaatagaa cgaaataagc caatctttat aggttttggt agtaaagtta    6960
caacatcaga gacatgtatg tattgtctct cagaagagct cttgaccgat cagagtttga    7020
agaaaaattt attacacact ttatgtaaag ctgaaaaaaa cggcctcccg cagggaagcc    7080 gttttttcg ttatctgatt tttgtaaagg tctgatactc gtccgttgtt ttgtaaatca     7140
gccagtcgct tgagtaaaga atccggtctg aatttctgaa gcctgatgta tagttaatat    7200
ccgcttcacg ccatgttcgt ccgcttttgc ccgggagttt gccttccctg tttgagaaga    7260
tgtctccgcc gatgcttttc cccggagcga cgtctgcaag gttcccttt gatgccaccc      7320 agccgagggc ttgtgcttct gattttgtaa tgtaattatc aggtagctta tgatatgtct    7380
gaagataatc cgcaacccg tcaaacgtgt tgataacctg tgccatgttc ccgtttgata      7440
cctgaatttt ggccattctc ataaatcttc taaaaacagc agaactgact attcaaagaa    7500
agtagaaccc acagaaagta atcaaagtag tttgattaaa tgcgttgtgt atcatcgcag    7560
cccctgctac ggatatttat aggaaaggtt tgagagcaat gtgtgcagca agttgtgtgt    7620
gaatcacctg cttccatggc ggaggataaa taatttagtc acgcatttag ttgaacgtaa    7680
ctactaactc ctctaccgct aatcattctt cttttgcccg ggcaagttca acaacaaccc    7740
cacaatcacg cttcctgtat tttgttttgt tttcaaaaca atagaattca cttttactg     7800 ccaaaattat gttttactcg agagcccggg ctcctgcagg taccttaatt aaaagtttaa    7860
actatcagtg tttgacagga tatattggcg ggtaaaccta agagaaaaga gcgtttatta    7920
gaataatcgg atatttaaaa gggcgtgaaa aggtttatcc gttcgtccat ttgtatgtgc    7980
atgccaacca cagggttccc cagatc                                          8006
```

<210> SEQ ID NO 19
<211> LENGTH: 13001
<212> TYPE: DNA

<213> ORGANISM: Artificial Sequence
<220> FEATURE:
<223> OTHER INFORMATION: Description of Artificial Sequence: Synthetic vector sequence

<400> SEQUENCE: 19

```
gtttacccgc caatatatcc tgtcaaacac tgatagttta aacttttaat taaggtacct      60
gcaggagccc gggctgcagg aattcgatat caagcttgat agggtcaaat cgaccacttg     120
cacagttaag tgattctaat acgaaacctt aaaagcaaac atcggttctt ttgagtcaga     180
agaaatgcaa cttaatgtga cacatgatgt gaagaaaaaa caaagtaat ataagaaaag      240
ggaacaatta aatagttaat aaaatatttc cttaaagttg taacaaataa agaatcattt     300
tatgaaacaa tatgaaccct aaataaatta aaattcctct gaaaccttaa atttatcgag     360
ctagtgattg gctgccaact gccatgctgg caaaattaga gtgacatgat tggtctgaac     420
atgtctaggg tttcagacat gtgacatgtg tcaacaaccc attaacacat tgggtataaa     480
tccaatagac atttgatagt attaaaattg taaccattgg attaaattta aacgtgatgg     540
atgtaactaa atgacttgtc cgagtaacat cacaacgttc catactttcc ttatttggaa     600
tataattaaa tttaccatt attcttttt cttgagtttc ctgtatatgt acttgtacat       660
agatatatat gcacaaatac gtattacaat gacatattat agactttgat gtctgaactc     720
tcaaccttct cgatggagag atcatgaccg tagatttttt tggatcgtag aaggcagacc     780
aaactcttaa actattggat ccgtactaaa aatctcactt tcctctcagt acccataatg     840
agagagaaaa tgataaaaat ccctaacatt attctctctc tagaaaaaaa aagatacttc     900
aaaaagaaag agaaattgca taaatctatc tacaccaaag atgttgaagc aattccaatg     960
ctatacttct atgccaaatc tatttattca gtgatcatta atcttttac ttccaagaaa    1020
tatgaacaat ttagtatcct tataattttt gtctctatat atgtaatatg aacattgggt    1080
attgaccaaa tgagaaatct aatattaaat ggtcaaaagt agtaatatga tgacattttt    1140
gaatttataa ataggttaca aattaattca ttatgacata aaaccttctt gtcagaagtc    1200
aagaactgaa actaacaaaa ctttataata aattagtaaa aatacaaatg aaaaataaaa    1260
agaaataata tctgagtgat gacgtgatca agattctttt aacaaagaca acaaatctta    1320
cagacccaaa acctaatctt gcgctcaatt ccaacctctg aaaaaacctc aaaaatctta    1380
taaagaaaaa taaataaaga aacgaaactc tgatttcgta gagtacccat cggatatata    1440
aaaagaaatt agtaggtaaa tgaagactaa ttttgattga ctgatttaat ttgaagtcgt    1500
tgttagcttt tcttgttttg gacatgagaa ttatatattt caggacatga gagttgacaa    1560
ctgtaaacga ttaagaaaat tgatctttta attttcaaac accatttaat cttgacatgt    1620
tttatgtttt ggtggagaag aaagtaatca cgtgggactc tctactaata agtatttgga    1680
aattgcgtgt cgaattagag attactagtt tgagtaatgt agttcgaaat gagattagtt    1740
attttttaatt ttaaaagag taattttaag gaataacaaa aaagagtccc cataagctaa    1800
tttgtcttaa ttacctccctt gtttcattga ctatttgaaa tcttgaaaat tcagttgaaa    1860
tttcaaatct atgtttcttt tgaccacttc taaactaatc ttagctcata tataattttc    1920
caaaactaca aaataacac taacatttaa cattctcaag agaaaacaaa acaaaaact     1980
tagataacca tctaaattgt cctacatgta cgtataagtt ccattatttt ctatcactca    2040
tataagttaa aatttcatga aaactcaaaa atctagctag tttcaccttta ttcactctca    2100
cttaccatca catgtgtttg tatcaaatat atgatatgat ataattcatg agagagaaag    2160
```

```
agagctagag ataagaaagg aaagtaagag aaagaagaga agaaaaagag agacacagac    2220
attaacaaca atggaggatg gatgatcaca aaacagaaga tatgacctca tagtccttcc    2280
ttactctctc cccaatttgt ttcccaaaac ttacttttat agtcataaaa atcaagtttt    2340
tacctattac aacaccagat ctataaatat atctaaatct tcaagtactt gttagtaagg    2400
aaaatagaaa gatataagat tttattatta ttataataac agaaatgagt gaagaaagaa    2460
cacccaacaa agtgaatctt agttctacaa aactgaatct aaaactccac attagaaaaa    2520
accctgatgg tttcttattt cttttcattt attatctaac tctcactcag atctccttta    2580
actttgtacc atttccctca cttcatatat ctatatataa caaactctct cttttattt     2640 aagtcttaag ggaaaattaa tatacacatg aagacaagaa attagatcta caaaattgtt    2700 acaaaaccc ccgaagtaaa taaaataaac atatcaaaca aatattccca ctaatgttag     2760
tgtgtttata tatatatgtg tgtggaatat gaaggaaaaa agtgaaaaat aatcctaccc    2820
ataagagcat tcaagaagaa gctcgagggt atcgataagc ttaaactcga cagcaaatat    2880
gatttagatt atgacctaga aataagcata gcattaaagc atatacataa caagcggtga    2940
tatactctga ctgccactgt acttgaggaa aggtagtgga ctctgctcag gtacattagt    3000
ttggtaaggt tggcttggct tctgggtaat atgagaagta aagaagtaaa aggtatttga    3060
ctctagtcaa gtacattgga ttgcctttgt cggggcttgg atggcttggg ttcgtgtgag    3120
aagccaacaa tttataagaa atatataaaa taaaaaataa aaaaatttaa gtgttggaag    3180
tgaaaacggt ggggcagaaa tatacacaga agagtacttt aacaatgcgc aaccaaggca    3240
gattcacaac ttgatttctg gacctcgaat acgagataat ggtggtaaga aataaaggaa    3300
gagtggagcg catttgaaaa tgaatggaga gcgcacaaaa tggaggacga ataaatgaaa    3360
tataatgcaa gggtgcattt ccctattatt tccagaaatg tatatgtggg gtcggcattc    3420
tcatgggcgt cgcattcagg gggtgtcata gcggtccttt gattgcagtg tgggagttgc    3480
aacatgtacc aacaaatcca ttcatcccaa aacctaaatt tatcctctcc attactatta    3540
cctacaccta tacctagtaa atatgtcctg ccttgtaact cctccactgc ctgcacacgt    3600
cttagtcaat ccatctgcct tcaaataggc attattttgt tctttcccct ccgactgaaa    3660
ggctatcgac cgaccgaccg ctcatcttct tcttctgcgc aatttttct gctggatcat     3720 catcattacc atcatcgcca tccccaccat catcatcatg atggtatctc tatctctccc    3780
tggcaatcga ttgtagagga aaggaagagg gaagggcat atgtattgat caacctaccc    3840
gaaaaaacaa tctgatcagc cctgctaatc ttgcttataa atctcttatc cactgttcaa    3900
tcattcaggt ttcttcccac tttcaagcaa aggcgcccgg attggccgtg ttcttagatt    3960
ttcaggtact taaatggaca atattcccca cctgaagccg ttctgaaaaa gatttgtttg    4020
tagaaacaaa cgattgtaat atttgcttaa gttgagctta aggggtttgg tacctaactt    4080
gccttgtggt tatttgtttc tcagaactcg ggctgcgtcc aactgtagga acgaaccagc    4140 acaagggggtt gcagcttttg ctgttgctgt tgcgcccatt gcttttggac tggtattagt    4200
agttgcagct ttgttttgca tacgctgtga ggatctgtgc gcggaaattt tgtgtacaaa    4260
tcatgttacg tcctgtagaa accccaaccc gtgaaatcaa aaaactcgac ggcctgtggg    4320
cattcagtct ggatcgcgaa aactgtgaa ttggtcagcg ttggtgggaa agcgcgttac      4380
aagaaagccg ggcaattgct gtgccaggca gttttaacga tcagttcgcc gatgcagata    4440
ttcgtaatta tgcgggcaac gtctggtatc agcgcgaagt ctttataccg aaaggttggg    4500
caggccagcg tatcgtgctg cgtttcgatg cggtcactca ttacggcaaa gtgtgggtca    4560
```

-continued

```
ataatcagga agtgatggag catcagggcg gctatacgcc atttgaagcc gatgtcacgc    4620
cgtatgttat tgccgggaaa agtgtacgta agtttctgct tctacctttg atatatatat    4680
aataattatc attaattagt agtaatataa tatttcaaat attttttttca aaataaaaga    4740 atgtagtata tagcaattgc ttttctgtag tttataagtg tgtatatttt aatttataac    4800
ctttctaata tatgaccaaa atttgttgat gtgcaggtat caccgtttgt gtgaacaacg    4860
aactgaactg gcagactatc ccgccgggaa tggtgattac cgacgaaaac ggcaagaaaa    4920
agcggtctta cttccatgat ttctttaact atgccggaat ccatcgcagc gtaatgctct    4980
acaccacgcc gaacacctgg gtggacgata tcaccgtggt gacgcatgtc gcgcaagact    5040
gtaaccacgc gtctgttgac tggcaggtgg tggccaatgg tgatgtcagc gttgaactgc    5100
gtgatgcgga tcaacaggtg gttgcaactg gacaaggcac tagcgggact ttgcaagtgg    5160
tgaatccgca cctctggcaa ccgggtgaag gttatctcta tgaactgtgc gtcacagcca    5220
aaagccagac agagtgtgat atctacccgc ttcgcgtcgg catccggtca gtggcagtga    5280
agggcgaaca gttcctgatt aaccacaaac cgttctactt tactggcttt ggtcgtcatg    5340
aagatgcgga cttgcgtggc aaaggattcg ataacgtgct gatggtgcac gaccacgcat    5400
taatggactg gattggggcc aactcctacc gtacctcgca ttacccttac gctgaagaga    5460
tgctcgactg ggcagatgaa catggcatcg tggtgattga tgaaactgct gctgtcggct    5520
ttaacctctc tttaggcatt ggtttcgaag cgggcaacaa gccgaaagaa ctgtacagcg    5580
aagaggcagt caacggggaa actcagcaag cgcacttaca ggcgattaaa gagctgatag    5640
cgcgtgacaa aaaccaccca agcgtggtga tgtggagtat tgccaacgaa ccggataccc    5700
gtccgcaagg tgcacgggaa tatttcgcgc cactggcgga agcaacgcgt aaactcgacc    5760
cgacgcgtcc gatcacctgc gtcaatgtaa tgttctgcga cgctcacacc gataccatca    5820
gcgatctctt tgatgtgctg tgcctgaacc gttattacgg atggtatgtc caaagcggcg    5880
atttggaaac ggcagagaag gtactggaaa agaacttct ggcctggcag gagaaactgc    5940
atcagccgat tatcatcacc gaatacggcg tggatacgtt agccgggctg cactcaatgt    6000
acaccgacat gtggagtgaa gagtatcagt gtgcatggct ggatatgtat caccgcgtct    6060
ttgatcgcgt cagcgccgtc gtcggtgaac aggtatggaa tttcgccgat tttgcgacct    6120
cgcaaggcat attgcgcgtt ggcggtaaca agaaagggat cttcactcgc gaccgcaaac    6180
cgaagtcggc ggctttcctg ctgcaaaaac gctggactgg catgaacttc ggtgaaaaac    6240
cgcagcaggg aggcaaacaa tgaatcaaca actctcctgg cgcaccatcg tcggctacag    6300
cctcgggaat tgctaccgga gagagagctc gaatttcccc gatcgttcaa acatttggca    6360
ataaagtttc ttaagattga atcctgttgc cggtcttgcg atgattatca tataatttct    6420
gttgaattac gttaagcatg taataattaa catgtaatgc atgacgttat ttatgagatg    6480
ggtttttatg attagagtcc cgcaattata catttaatac gcgatagaaa acaaaatata    6540
gcgcgcaaac taggataaat tatcgcgcgc ggtgtcatct atgttactag atcgggaatt    6600
cctgcagccc gggggatcca ctagttctag agcggccgct tggcgcgccg tcaacggatc    6660
aggatatcct tgtttaagat gttgaactct atggaggttt gtatgaactg atgatctagg    6720
accggataag ttcccttctt catagcgaac ttattcaaag aatgttttgt gtatcattct    6780
tgttacattg ttattaatga aaaaatatta ttggtcattg gactgaacac gagtgttaaa    6840
tatggaccag gccccaaata agatccattg atatatgaat taaataacaa gaataaatcg    6900
```

```
agtcaccaaa ccacttgcct tttttaacga gacttgttca ccaacttgat acaaaagtca   6960
ttatcctatg caaatcaata atcatacaaa aatatccaat aacactaaaa aattaaaaga   7020
aatggataat ttcacaatat gttatacgat aaagaagtta cttttccaag aaattcactg   7080
attttataag cccacttgca ttagataaat ggcaaaaaaa aacaaaaagg aaaagaaata   7140
aagcacgaag aattctagaa aatacgaaat acgcttcaat gcagtgggac ccacggttca   7200
attattgcca attttcagct ccaccgtata tttaaaaaat aaaacgataa tgctaaaaaa   7260
atataaatcg taacgatcgt taaatctcaa cggctggatc ttatgacgac cgttagaaat   7320
tgtggttgag tcagtaataa acggcgtcaa agtggttgca gccggcacac acgagtcgtg   7380
tttatcaact caaagcacaa atacttttcc tcaacctaaa aataaggcaa ttagccaaaa   7440
acaactttgc gtgtaaacaa cgctcaatac acgtgtcatt ttattattag ctattgcttc   7500
accgccttag ctttctcgtg acctagtcgt cctcgtcttt tcttcttctt cttctataaa   7560
acaataccca aagagctctt cttcttcaca attcagattt caatttctca aaatcttaaa   7620
aactttctct caattctctc taccgtgatc aaggtaaatt tctgtgttcc ttattctctc   7680
aaaatcttcg attttgtttt cgttcgatcc caatttcgta tatgttcttt ggtttagatt   7740
ctgttaatct tagatcgaag acgattttct gggtttgatc gttagatatc atcttaattc   7800
tcgattaggg tttcataaat atcatccgat ttgttcaaat aatttgagtt ttgtcgaata   7860
attactcttc gatttgtgat ttctatctag atctggtgtt agtttctagt ttgtgcgatc   7920
gaatttgtcg attaatctga gtttttctga ttaacagatg attgaacaag atggattgca   7980
cgcaggttct ccggccgctt gggtggagag gctattcggc tatgactggg cacaacagac   8040
aatcggctgc tctgatgccg ccgtgttccg gctgtcagcg caggggcgcc cggttctttt   8100
tgtcaagacc gacctgtccg gtgccctgaa tgaactccag gacgaggcag cgcggctatc   8160
gtggctggcc acgacgggcg ttccttgcgc agctgtgctc gacgttgtca ctgaagcggg   8220
aagggactgg ctgctattgg gcgaagtgcc ggggcaggat ctcctgtcat ctcaccttgc   8280
tcctgccgag aaagtatcca tcatggctga tgcaatgcgg cggctgcata cgcttgatcc   8340
ggctacctgc ccattcgacc accaagcgaa acatcgcatc gagcgagcac gtactcggat   8400
ggaagccggt cttgtcgatc aggatgatct ggacgaagag catcaggggc tcgcgccagc   8460
cgaactgttc gccaggctca aggcgcgcat gcccgacggc gaggatctcg tcgtgaccca   8520
tggcgatgcc tgcttgccga atatcatggt ggaaaatggc cgcttttctg gattcatcga   8580
ctgtggccgg ctgggtgtgg cggaccgcta tcaggacata gcgttggcta cccgtgatat   8640
tgctgaagag cttggcggcg aatgggctga ccgcttcctc gtgctttacg gtatcgccgc   8700
tcccgattcg cagcgcatcg ccttctatcg ccttcttgac gagttcttct gagggatcgt   8760
tcaaacattt ggcaataaag tttcttaaga ttgaatcctg ttgccggtct tgcgatgatt   8820
atcatataat ttctgttgaa ttacgttaag catgtaataa ttaacatgta atgcatgacg   8880
ttatttatga gatgggtttt tatgattaga gtcccgcaat tatacattta atacgcgata   8940
gaaaacaaaa tatagcgcgc aaactaggat aaattatcgc gcgcggtgtc atctatgtta   9000
ctagatcgca cgtaggggg atccactagt tctagagcgg ccgtgggcca tcgccctgat   9060
agacggtttt tcgccctttg acgttggagt ccacgttctt taatagtgga ctcttgttcc   9120
aaactggaac aacactcaac cctatctcgg gctattcttt tgatttataa gggattttgc   9180
cgatttcgga accaccatca aacaggattt tcgcctgctg gggcaaacca gcgtggaccg   9240
cttgctgcaa ctctctcagg gccaggcggt gaagggcaat cagctgttgc ccgtctcact   9300
```

```
ggtgaaaaga aaaaccaccc cagtacatta aaaacgtccg caatgtgtta ttaagttgtc   9360
taagcgtcaa tttgtttaca ccacaatata tcctgccacc agccagccaa cagctccccg   9420
accggcagct cggcacaaaa tcaccactcg atacaggcag cccatcagtc cgggacggcg   9480
tcagcgggag agccgttgta aggcggcaga ctttgctcat gttaccgatg ctattcggaa   9540
gaacggcaac taagctgccg ggtttgaaac acggatgatc tcgcggaggg tagcatgttg   9600
attgtaacga tgacagagcg ttgctgcctg tgatcaaata tcatctccct cgcagagatc   9660
cgaattatca gccttcttat tcatttctcg cttaaccgtg acagttgtct atcggcagtt   9720
cgtagagcgc gccgtgcgtc ccgagcgata ctgagcgaag caagtgcgtc gagcagtgcc   9780
cgcttgttcc tgaaatgcca gtaaagcgct ggctgctgaa cccccagccg gaactgaccc   9840
cacaaggccc tagcgtttgc aatgcaccag gtcatcattg acccaggcgt gttccaccag   9900
gccgctgcct cgcaactctt cgcaggcttc gccgacctgc tcgcgccact tcttcacgcg   9960
ggtggaatcc gatccgcaca tgaggcggaa ggtttccagc ttgagcgggt acggctcccg  10020
gtgcgagctg aaatagtcga acatccgtcg ggccgtcggc gacagcttgc ggtacttctc  10080
ccatatgaat ttcgtgtagt ggtcgccagc aaacagcacg acgatttcct cgtcgatcag  10140
gacctggcaa cgggacgttt tcttgccacg gtccaggacg cggaagcggt gcagcagcga  10200
caccgattcc aggtgcccaa cgcggtcgga cgtgaagccc atcgccgtcg cctgtaggcg  10260
cgacaggcat cctcggcct tcgtgtaata ccggccattg atcgaccagc ccaggtcctg  10320
gcaaagctcg tagaacgtga aggtgatcgg ctcgccgata ggggtgcgct tcgcgtactc  10380
caacacctgc tgccacacca gttcgtcatc gtcggcccgc agctcgacgc cggtgtaggt  10440
gatcttcacg tccttgttga cgtggaaaat gaccttgttt gcagcgcct cgcgcgggat  10500
tttcttgttg cgcgtggtga acagggcaga gcgggccgtg tcgtttggca tcgctcgcat  10560
cgtgtccggc cacggcgcaa tatcgaacaa ggaaagctgc atttccttga tctgctgctt  10620
cgtgtgtttc agcaacgcgg cctgcttggc ctcgctgacc tgttttgcca ggtcctcgcc  10680
ggcggttttt cgcttcttgg tcgtcatagt tcctcgcgtg tcgatggtca tcgacttcgc  10740
caaacctgcc gcctcctgtt cgagacgacg cgaacgctcc acggcggccg atggcgcggg  10800
cagggcaggg ggagccagtt gcacgctgtc gcgctcgatc ttggccgtag cttgctggac  10860
catcgagccg acggactgga aggtttcgcg gggcgcacgc atgacggtgc ggcttgcgat  10920
ggtttcggca tcctcggcgg aaaacccggc gtcgatcagt tcttgcctgt atgccttccg  10980
gtcaaacgtc cgattcattc accctccttg cgggattgcc ccgactcacg ccggggcaat  11040
gtgcccttat tcctgatttg acccgcctgg tgccttggtg tccagataat ccaccttatc  11100
ggcaatgaag tcggtcccgt agaccgtctg gccgtccttc tcgtacttgg tattccgaat  11160
cttgccctgc acgaatacca gcgacccctt gcccaaatac ttgccgtggg cctcggcctg  11220
agagccaaaa cacttgatgc ggaagaagtc ggtgcgctcc tgcttgtcgc cggcatcgtt  11280
gcgccacatc taggtactaa acaattcat ccagtaaaat ataatatttt attttctccc  11340
aatcaggctt gatccccagt aagtcaaaaa atagctcgac atactgttct tccccgatat  11400
cctccctgat cgaccggacg cagaaggcaa tgtcatacca cttgtccgcc ctgccgcttc  11460
tcccaagatc aataaagcca cttactttgc catctttcac aaagatgttg ctgtctccca  11520
ggtcgccgtg ggaaaagaca agttcctctt cgggcttttc cgtctttaaa aaatcataca  11580
gctcgcgcgg atctttaaat ggagtgtctt cttcccagtt ttcgcaatcc acatcggcca  11640
```

```
gatcgttatt cagtaagtaa tccaattcgg ctaagcggct gtctaagcta ttcgtatagg    11700
gacaatccga tatgtcgatg gagtgaaaga gcctgatgca ctccgcatac agctcgataa    11760
tcttttcagg gctttgttca tcttcatact cttccgagca aaggacgcca tcggcctcac    11820
tcatgagcag attgctccag ccatcatgcc gttcaaagtg caggaccttt ggaacaggca    11880
gctttccttc cagccatagc atcatgtcct tttcccgttc cacatcatag gtggtccctt    11940
tataccggct gtccgtcatt tttaaatata ggttttcatt ttctcccacc agcttatata    12000
ccttagcagg agacattcct tccgtatctt ttacgcagcg gtattttccg atcagttttt    12060
tcaattccgg tgatattctc attttagcca tttattattt ccttcctctt ttctacagta    12120
tttaaagata ccccaagaag ctaattataa caagacgaac tccaattcac tgttccttgc    12180
attctaaaac cttaaatacc agaaaacagc ttttcaaag ttgttttcaa agttggcgta    12240
taacatagta tcgacggagc cgattttgaa accacaatta tggactgcca gcgctgccat    12300
ttttggggtg aggccgttcg cggccgaggg gcgcagcccc tggggggatg ggaggcccgc    12360
gttagcgggc cggagggtt cgagaagggg gggcaccccc cttcggcgtg cgcggtcacg    12420
cgcacagggc gcagccctgg ttaaaaacaa ggtttataaa tattggttta aaagcaggtt    12480
aaaagacagg ttagcggtgg ccgaaaaacg ggcggaaacc cttgcaaatg ctggatttc    12540 tgcctgtgga cagcccctca aatgtcaata ggtgcgcccc tcatctgtca gcactctgcc    12600
cctcaagtgt caaggatcgc gcccctcatc tgtcagtagt cgcgcccctc aagtgtcaat    12660
accgcagggc acttatcccc aggcttgtcc acatcatctg tgggaaactc gcgtaaaatc    12720
aggcgttttc gccgatttgc gaggctggcc agctccacgt cgccggccga atcgagcct    12780 gccctcatc tgtcaacgcc gcgccgggtg agtcggcccc tcaagtgtca acgtccgccc    12840
ctcatctgtc agtgagggcc aagttttccg cgaggtatcc acaacgccgg cggatctggg    12900
gaaccctgtg gttggcatgc acatacaaat ggacgaacgg ataaaccttt tcacgccctt    12960
ttaaatatcc gattattcta ataaacgctc ttttctctta g                         13001
```

<210> SEQ ID NO 20
<211> LENGTH: 8534
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 20

```
gtttacccgc caatatatcc tgtcaaacac tgatagttta aacttttaat taaggtacct     60
gcaggagccc gggctctcga ggtcgacggt atcgataagc ttaaactcga cagcaaatat    120
gatttagatt atgacctaga aataagcata gcattaaagc atatacataa caagcggtga    180
tatactctga ctgccactgt acttgaggaa aggtagtgga ctctgctcag gtacattagt    240
ttggtaaggt tggcttggct tctgggtaat atgagaagta aagaagtaaa aggtatttga    300
ctctagtcaa gtacattgga ttgcctttgt cggggcttgg atggcttggg ttcgtgtgag    360
aagccaacaa tttataagaa atatataaaa taaaaaataa aaaaatttaa gtgttggaag    420
tgaaaacggt ggggcagaaa tatacacaga agagtacttt aacaatgcgc aaccaaggca    480
gattcacaac ttgattctg gacctcgaat acgagataat ggtggtaaga aataaaggaa    540
gagtggagcg catttgaaaa tgaatggaga gcgcacaaaa tggaggacga ataaatgaaa    600
tataatgcaa gggtgcattt ccctattatt tccagaaatg tatatgtggg gtcggcattc    660
```

-continued

```
tcatgggcgt cgcattcagg gggtgtcata gcggtccttt gattgcagtg tgggagttgc    720
aacatgtacc aacaaatcca ttcatcccaa aacctaaatt tatcctctcc attactatta    780
cctacaccta tacctagtaa atatgtcctg ccttgtaact cctccactgc ctgcacacgt    840
cttagtcaat ccatctgcct tcaaataggc attattttgt tctttcccct ccgactgaaa    900
ggctatcgac cgaccgaccg ctcatcttct tcttctgcgc aattttttct gctggatcat    960
catcattacc atcatcgcca tccccaccat catcatcatg atggtatctc tatctctccc   1020
tggcaatcga ttgtagagga aaggaagagg gaaggggcat atgtattgat caacctaccc   1080
gaaaaaacaa tctgatcagc cctgctaatc ttgcttataa atctcttatc cactgttcaa   1140
tcattcaggt ttcttcccac tttcaagcaa aggcgcccgg attggccgtg ttcttagatt   1200
ttcaggtact taaatggaca atattcccca cctgaagccg ttctgaaaaa gatttgtttg   1260
tagaaacaaa cgattgtaat atttgcttaa gttgagctta aggggtttgg tacctaactt   1320
gccttgtggt tatttgtttc tcagaactcg ggctgcgtcc aactgtagga acgaaccagc   1380
acaaggggtt gcagcttttg ctgttgctgt tgcgcccatt gcttttggac tggtattagt   1440
agttgcagct ttgttttgca tacgctgtga ggatctgtgc gcggaaattt tgtgtacaaa   1500
tcatggcaca ggttatcaac acgtttgacg gggttgcgga ttatcttcag acatatcata   1560
agctacctga taattacatt acaaaatcag aagcacaagc cctcggctgg gtggcatcaa   1620
aagggaacct tgcagacgtc gctccgggga aaagcatcgg cggagacatc ttctcaaaca   1680
gggaaggcaa actcccgggc aaaagcggac gaacatggcg tgaagcggat attaactata   1740
catcaggctt cagaaattca gaccggattc tttactcaag cgactggctg atttacaaaa   1800
caacggacca ttatcagacc tctacaaaaa tcagataacg aaaaaaacgg cttccctgcg   1860
ggaggccgtt ttttcagct ttacataaag tgtgtaataa attttctc aaactctgat   1920 cggtcaattg cactttgagc tcgaatttcc ccgatcgttc aaacatttgg caataaagtt   1980
tcttaagatt gaatcctgtt gccggtcttg cgatgattat catataattt ctgttgaatt   2040
acgttaagca tgtaataatt aacatgtaat gcatgacgtt atttatgaga tgggtttta   2100 tgattagagt cccgcaatta tacatttaat acgcgataga aaacaaaata tagcgcgcaa   2160
actaggataa attatcgcgc gcggtgtcat ctatgttact agatcgggaa ggcgcgccgc   2220
ggccgcaaca ctgatagttt aaactgaagg cgggaaacga caatctgatc atgagcggag   2280
aattaaggga gtcacgttat gaccccgcc gatgacgcgg gacaagccgt tttacgtttg   2340
gaactgacag aaccgcaacg ttgaaggagc cactcagccg cgggtttctg gagtttaatg   2400
agctaagcac atacgtcaga aaccattatt gcgcgttcaa aagtcgccta aggtcactat   2460
cagctagcaa atatttcttg tcaaaaatgc tccactgacg ttccataaat tcccctcggt   2520
atccaattag agtctcatat tcactctcaa tccaaataat ctgcaccgga tctggatcgt   2580
ttcgcatgat tgaacaagat ggattgcacg caggttctcc ggccgcttgg gtggagaggc   2640
tattcggcta tgactgggca caacagacaa tcggctgctc tgatgccgcc gtgttccggc   2700
tgtcagcgca ggggcgcccg gttcttttg tcaagaccga cctgtccggt gccctgaatg   2760
aactgcagga cgaggcagcg cggctatcgt ggctggccac gacgggcgtt ccttgcgcag   2820
ctgtgctcga cgttgtcact gaagcgggaa gggactggct gctattgggc gaagtgccgg   2880
ggcaggatct cctgtcatct caccttgctc ctgccgagaa agtatccatc atggctgatg   2940
caatgcggcg gctgcatacg cttgatccgg ctacctgccc attcgaccac caagcgaaac   3000
atcgcatcga gcgagcacgt actcggatgg aagccggtct tgtcgatcag gatgatctgg   3060
```

```
acgaagagca tcagggctc gcgccagccg aactgttcgc caggctcaag gcgcgcatgc    3120
ccgacggcga tgatctcgtc gtgacccatg gcgatgcctg cttgccgaat atcatggtgg    3180
aaaatggccg cttttctgga ttcatcgact gtggccggct gggtgtggcg gaccgctatc    3240
aggacatagc gttggctacc cgtgatattg ctgaagagct tggcggcgaa tgggctgacc    3300
gcttcctcgt gctttacggt atcgccgctc ccgattcgca gcgcatcgcc ttctatcgcc    3360
ttcttgacga gttcttctga gcgggactct ggggttcgaa atgaccgacc aagcgacgcc    3420
caacctgcca tcacgagatt tcgattccac cgccgccttc tatgaaaggt tgggcttcgg    3480
aatcgttttc cgggacgccg gctggatgat cctccagcgc ggggatctca tgctggagtt    3540
cttcgcccac gggatctctg cggaacaggc ggtcgaaggt gccgatatca ttacgacagc    3600
aacggccgac aagcacaacg ccacgatcct gagcgacaat atgatcgggc ccggcgtcca    3660
catcaacggc gtcggcggcg actgcccagg caagaccgag atgcaccgcg atatcttgct    3720
gcgttcggat attttcgtgg agttcccgcc acagacccgg atgatccccg atcgttcaaa    3780
catttggcaa taaagtttct taagattgaa tcctgttgcc ggtcttgcga tgattatcat    3840
ataatttctg ttgaattacg ttaagcatgt aataattaac atgtaatgca tgacgttatt    3900
tatgagatgg gttttatga ttagagtccc gcaattatac atttaatacg cgatagaaaa    3960
caaaatatag cgcgcaaact aggataaatt atcgcgcgcg gtgtcatcta tgttactaga    4020
tcgggcctcc tgtcaatgct ggcggcggct ctggtggtgg ttctggtgga tccactagtt    4080
ctagagcggc cgtgggccat cgccctgata gacggttttt cgcccttga cgttggagtc    4140 cacgttcttt aatagtggac tcttgttcca aactggaaca acactcaacc ctatctcggg    4200
ctattctttt gatttataag ggattttgcc gatttcggaa ccaccatcaa acaggatttt    4260
cgcctgctgg gcaaaccag cgtggaccgc ttgctgcaac tctctcaggg ccaggcggtg    4320
aagggcaatc agctgttgcc cgtctcactg gtgaaaagaa aaaccacccc agtacattaa    4380
aaacgtccgc aatgtgttat taagttgtct aagcgtcaat ttgtttacac cacaatatat    4440
cctgccacca gccagccaac agctccccga ccggcagctc ggcacaaaat caccactcga    4500
tacaggcagc ccatcagtcc gggacggcgt cagcgggaga gccgttgtaa ggcggcagac    4560
tttgctcatg ttaccgatgc tattcggaag aacggcaact aagctgccgg gtttgaaaca    4620
cggatgatct cgcggagggt agcatgttga ttgtaacgat gacagagcgt tgctgcctgt    4680
gatcaaatat catctcccct gcagagatcc gaattatcag ccttcttatt catttctcgc    4740
ttaaccgtga cagttgtcta tcggcagttc gtagagcgcg ccgtgcgtcc cgagcgatac    4800
tgagcgaagc aagtgcgtcg agcagtgccc gcttgttcct gaaatgccag taaagcgctg    4860
gctgctgaac ccccagccgg aactgacccc acaaggccct agcgtttgca atgcaccagg    4920
tcatcattga cccaggcgtg ttccaccagg ccgctgcctc gcaactcttc gcaggcttcg    4980
ccgacctgct cgcgccactt cttcacgcgg gtggaatccg atccgcacat gaggcggaag    5040
gtttccagct tgagcgggta cggctcccgg tgcgagctga atagtcgaa catccgtcgg    5100 gccgtcggcg acagcttgcg gtacttctcc catatgaatt tcgtgtagtg gtcgccagca    5160
aacagcacga cgatttcctc gtcgatcagg acctggcaac gggacgtttt cttgccacgg    5220
tccaggacgc ggaagcggtg cagcagcgac accgattcca ggtgcccaac gcggtcggac    5280
gtgaagccca tcgccgtcgc ctgtaggcgc gacaggcatt cctcggcctt cgtgtaatac    5340
cggccattga tcgaccagcc caggtcctgg caaagctcgt agaacgtgaa ggtgatcggc    5400
```

```
tcgccgatag gggtgcgctt cgcgtactcc aacacctgct gccacaccag ttcgtcatcg    5460
tcggcccgca gctcgacgcc ggtgtaggtg atcttcacgt ccttgttgac gtggaaaatg    5520
accttgtttt gcagcgcctc gcgcgggatt ttcttgttgc gcgtggtgaa cagggcagag    5580
cgggccgtgt cgtttggcat cgctcgcatc gtgtccggcc acggcgcaat atcgaacaag    5640
gaaagctgca tttccttgat ctgctgcttc gtgtgtttca gcaacgcggc ctgcttggcc    5700
tcgctgacct gttttgccag gtcctcgccg gcggtttttc gcttcttggt cgtcatagtt    5760
cctcgcgtgt cgatggtcat cgacttcgcc aaacctgccg cctcctgttc gagacgacgc    5820
gaacgctcca cggcggccga tggcgcgggc agggcagggg gagccagttg cacgctgtcg    5880
cgctcgatct tggccgtagc ttgctggacc atcgagccga cggactggaa ggtttcgcgg    5940
ggcgcacgca tgacggtgcg gcttgcgatg gtttcggcat cctcggcgga aaaccccgcg    6000
tcgatcagtt cttgcctgta tgccttccgg tcaaacgtcc gattcattca ccctccttgc    6060
gggattgccc cgactcacgc cggggcaatg tgcccttatt cctgatttga cccgcctggt    6120
gccttggtgt ccagataatc caccttatcg gcaatgaagt cggtcccgta gaccgtctgg    6180
ccgtccttct cgtacttggt attccgaatc ttgccctgca cgaataccag cgacccgttg    6240
cccaaatact gccgtgggc ctcggcctga gagccaaaac acttgatgcg gaagaagtcg    6300
gtgcgctcct gcttgtcgcc ggcatcgttg cgccacatct aggtactaaa acaattcatc    6360
cagtaaaata taatatttta ttttctccca atcaggcttg atccccagta agtcaaaaaa    6420
tagctcgaca tactgttctt ccccgatatc ctccctgatc gaccggacgc agaaggcaat    6480
gtcataccac ttgtccgccc tgccgcttct cccaagatca ataaagccac ttactttgcc    6540
atctttcaca aagatgttgc tgtctcccag gtcgccgtgg aaaagacaa gttcctcttc     6600 gggcttttcc gtctttaaaa aatcatacag ctcgcgcgga tctttaaatg gagtgtcttc    6660
ttcccagttt tcgcaatcca catcggccag atcgttattc agtaagtaat ccaattcggc    6720
taagcggctg tctaagctat tcgtataggg acaatccgat atgtcgatgg agtgaaagag    6780
cctgatgcac tccgcataca gctcgataat cttttcaggg cttttgttcat cttcatactc    6840 ttccgagcaa aggacgccat cggcctcact catgagcaga ttgctccagc catcatgccg    6900
ttcaaagtgc aggaccttg gaacaggcag ctttccttcc agccatagca tcatgtcctt     6960
ttcccgttcc acatcatagg tggtcccttt ataccggctg tccgtcattt ttaaatatag    7020
gttttcattt tctcccacca gcttatatac cttagcagga gacattcctt ccgtatcttt    7080
tacgcagcgg tattttttcga tcagttttttt caattccggt gatattctca ttttagccat    7140
ttattatttc cttcctcttt tctacagtat ttaaagatac cccaagaagc taattataac    7200
aagacgaact ccaattcact gttccttgca ttctaaaacc ttaaatacca gaaacagct     7260 ttttcaaagt tgtttcaaa gttggcgtat aacatagtat cgacggagcc gattttgaaa    7320
ccacaattat gggagagacc ataatgtggt ccaatttgca gcagccgtcc gagacaggag    7380
gacatcgtcc agctgaaacc ggggcagaat ccggccattt ctgaagagaa aaatggtaaa    7440
ctgatagaat aaaatcataa gaaggagcc gcacatgaaa aaagcagtca ttaacgggga    7500
acaaatcaga agtatcagcg acctccacca gacattgaaa aaggagcttg cccttccgga    7560
atactacggt gaaaacctgg acgctttatg ggattgtctg accggatggg tggagtaccc    7620
gctcgttttg gaatggaggc agtttgaaca aagcaagcag ctgactgaaa atggcgccga    7680
gagtgtgctt caggttttcc gtgaagcgaa agcggaaggc tgcgcatca ccatcatact     7740 ttcttaatac gatcaatggg agatgaacaa tatggaaaca caaaccacaa ttatgtctct    7800
```

```
cagcccacaa ttatggactg ccagcgctgc cattttttggg gtgaggccgt tcgcggccga   7860
ggggcgcagc ccctgggggg atgggaggcc cgcgttagcg ggccgggagg gttcgagaag   7920 gggggggcacc ccccttcggc gtgcgcggtc acgcgcacag ggcgcagccc tggttaaaaa   7980
caaggtttat aaatattggt ttaaaagcag gttaaaagac aggttagcgg tggccgaaaa   8040
acgggcggaa acccttgcaa atgctggatt ttctgcctgt ggacagcccc tcaaatgtca   8100
ataggtgcgc ccctcatctg tcagcactct gcccctcaag tgtcaaggat cgcgcccctc   8160
atctgtcagt agtcgcgccc ctcaagtgtc aataccgcag ggcacttatc cccaggcttg   8220
tccacatcat ctgtgggaaa ctcgcgtaaa atcaggcgtt ttcgccgatt tgcgaggctg   8280
gccagctcca cgtcgccggc cgaaatcgag cctgcccctc atctgtcaac gccgcgccgg   8340
gtgagtcggc ccctcaagtg tcaacgtccg cccctcatct gtcagtgagg gccaagtttt   8400
ccgcgaggta tccacaacgc cggcggatct ggggaaccct gtggttggca tgcacataca   8460
aatggacgaa cggataaacc ttttcacgcc cttttaaata tccgattatt ctaataaacg   8520
ctcttttctc ttag                                                   8534

<210> SEQ ID NO 21
<211> LENGTH: 11300
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 21
gtttacccgc caatatatcc tgtcaaacac tgatagttta aacttttaat taaggtacct     60
gcaggagccc gggctgcagg aattcgatat caagcttgat agggtcaaat cgaccacttg    120
cacagttaag tgattctaat acgaaacctt aaaagcaaac atcggttctt ttgagtcaga    180
agaaatgcaa cttaatgtga cacatgatgt gaagaaaaaa caaaagtaat ataagaaaag    240
ggaacaatta aatagttaat aaaatatttc cttaaagttg taacaaataa agaatcattt    300
tatgaaacaa tatgaaccct aaataaatta aaattcctct gaaaccttaa atttatcgag    360
ctagtgattg gctgccaact gccatgctgg caaaattaga gtgacatgat tggtctgaac    420
atgtctaggg tttcagacat gtgacatgtg tcaacaaccc attaacacat tgggtataaa    480
tccaatagac atttgatagt attaaaattg taaccattgg attaaattta aacgtgatgg    540
atgtaactaa atgacttgtc cgagtaacat cacaacgttc catactttcc ttatttggaa    600
tataattaaa tttaccattt attctttttt cttgagtttc ctgtatatgt acttgtacat    660
agatatatat gcacaaatac gtattacaat gacatattat agactttgat gtctgaactc    720
tcaaccttct cgatggagag atcatgaccg tagatttttt tggatcgtag aaggcagacc    780
aaactcttaa actattggat ccgtactaaa atctcactt tcctctcagt acccataatg    840
agagagaaaa tgataaaaat ccctaacatt attctctctc tagaaaaaaa aagatacttc    900
aaaaagaaag agaaattgca taaatctatc tacaccaaag atgttgaagc aattccaatg    960
ctatacttct atgccaaatc tatttattca gtgatcatta atcttttac ttccaagaaa   1020 tatgaacaat ttagtatcct tataattttt gtctctatat atgtaatatg aacattgggt   1080
attgaccaaa tgagaaatct aatattaaat ggtcaaaagt agtaatatga tgacattttt   1140
gaatttataa ataggttaca aattaattca ttatgacata aaaccttctt gtcagaagtc   1200
aagaactgaa actaacaaaa ctttataata aattagtaaa aatacaaatg aaaaataaaa   1260
```

```
agaaataata tctgagtgat gacgtgatca aagattcttt aacaaagaca acaaatctta    1320
cagacccaaa acctaatctt gcgctcaatt ccaacctctg aaaaaacctc aaaaatctta    1380
taaaagaaaa taaataaaga aacgaaactc tgatttcgta gagtacccat cggatatata    1440
aaaagaaatt agtaggtaaa tgaagactaa ttttgattga ctgatttaat ttgaagtcgt    1500
tgttagcttt tcttgttttg gacatgagaa ttatatattt caggacatga gagttgacaa    1560
ctgtaaacga ttaagaaaat tgatctttta attttcaaac accatttaat cttgacatgt    1620
tttatgtttt ggtggagaag aaagtaatca cgtgggactc tctactaata agtatttgga    1680
aattgcgtgt cgaattagag attactagtt tgagtaatgt agttcgaaat gagattagtt    1740 attttaatt ttaaaagag taattttaag gaataacaaa aaagagtccc cataagctaa    1800
tttgtcttaa ttacctcctt gtttcattga ctatttgaaa tcttgaaaat tcagttgaaa    1860
tttcaaatct atgtttcttt tgaccacttc taaactaatc ttagctcata tataattttc    1920
caaaactaca aaataacac taacatttaa cattctcaag agaaaacaaa acaaaaact     1980 tagataacca tctaaattgt cctacatgta cgtataagtt ccattatttt ctatcactca    2040
tataagttaa aatttcatga aaactcaaaa atctagctag tttcaccta ttcactctca     2100 cttaccatca catgtgtttg tatcaaatat atgatatgat ataattcatg agagagaaag    2160
agagctagag ataagaaagg aaagtaagag aaagaagaga agaaaagag agacacagac     2220 attaacaaca atggaggatg gatgatcaca aaacagaaga tatgacctca tagtccttcc    2280
ttactctctc cccaatttgt ttcccaaaac ttacttttat agtcataaaa atcaagtttt    2340
tacctattac aacaccagat ctataaatat atctaaatct tcaagtactt gttagtaagg    2400
aaaatagaaa gatataagat tttattatta ttataataac agaaatgagt gaagaaagaa    2460
cacccaacaa agtgaatctt agttctacaa aactgaatct aaaactccac attagaaaaa    2520
accctgatgg tttcttattt cttttcattt attatctaac tctcactcag atctccttta    2580
actttgtacc atttccctca cttcatatat ctatatataa caaactctct cttttattt     2640 aagtcttaag ggaaaattaa tatacacatg aagacaagaa attagatcta caaaattgtt    2700
acaaaacccc ccgaagtaaa taaaataaac atatcaaaca atattccca ctaatgttag      2760 tgtgtttata tatatatgtg tgtggaatat gaaggaaaaa agtgaaaaat aatcctaccc    2820
ataagagcat tcaagaagaa gctcgaggtc gacggtatcg ataagcttaa actcgacagc    2880
aaatatgatt tagattatga cctagaaata agcatagcat taaagcatat acataacaag    2940
cggtgatata ctctgactgc cactgtactt gaggaaaggt agtggactct gctcaggtac    3000
attagtttgg taaggttggc ttggcttctg ggtaatatga gaagtaaaga agtaaaaggt    3060
atttgactct agtcaagtac attggattgc ctttgtcggg gcttggatgg cttgggttcg    3120
tgtgagaagc caacaattta taagaaatat ataaaataaa aataaaaaa atttaagtgt     3180 tggaagtgaa aacggtgggg cagaaatata cacagaagag tactttaaca atgcgcaacc    3240
aaggcagatt cacaacttga tttctggacc tcgaatacga gataatggtg gtaagaaata    3300
aaggaagagt ggagcgcatt tgaaaatgaa tggagagcgc acaaaatgga ggacgaataa    3360
atgaaatata atgcaagggt gcatttccct attatttcca gaaatgtata tgtgggtcg     3420 gcattctcat gggcgtcgca ttcaggggt gtcatagcgg tcctttgatt gcagtgtggg     3480
agttgcaaca tgtaccaaca aatccattca tcccaaaacc taaatttatc ctctccatta    3540
ctattaccta cacctatacc tagtaaatat gtcctgcctt gtaactcctc cactgcctgc    3600
```

```
acacgtctta gtcaatccat ctgccttcaa ataggcatta ttttgttctt tcccctccga   3660
ctgaaaggct atcgaccgac cgaccgctca tcttcttctt ctgcgcaatt ttttctgctg   3720
gatcatcatc attaccatca tcgccatccc caccatcatc atcatgatgg tatctctatc   3780
tctccctggc aatcgattgt agaggaaagg aagagggaag gggcatatgt attgatcaac   3840
ctacccgaaa aaacaatctg atcagccctg ctaatcttgc ttataaatct cttatccact   3900
gttcaatcat tcaggtttct tcccactttc aagcaaaggc gcccggattg gccgtgttct   3960
tagattttca ggtacttaaa tggacaatat tccccacctg aagccgttct gaaaaagatt   4020
tgtttgtaga aacaaacgat tgtaatattt gcttaagttg agcttaaggg gtttggtacc   4080
taacttgcct tgtggttatt tgtttctcag aactcgggct gcgtccaact gtaggaacga   4140
accagcacaa ggggttgcag cttttgctgt tgctgttgcg cccattgctt ttggactggt   4200
attagtagtt gcagctttgt tttgcatacg ctgtgaggat ctgtgcgcgg aaattttgtg   4260
tacaaatcat ggcacaggtt atcaacacgt ttgacggggt tgcggattat cttcagacat   4320
atcataagct acctgataat tacattacaa aatcagaagc acaagccctc ggctgggtgg   4380
catcaaaagg gaaccttgca gacgtcgctc cggggaaaag catcggcgga gacatcttct   4440
caaacaggga aggcaaactc ccgggcaaaa gcggacgaac atggcgtgaa gcggatatta   4500
actatacatc aggcttcaga aattcagacc ggattcttta ctcaagcgac tggctgattt   4560
acaaaacaac ggaccattat cagacctcta caaaaatcag ataacgaaaa aaacggcttc   4620
cctgcgggag gccgtttttt tcagctttac ataaagtgtg taataaattt ttcttcaaac   4680
tctgatcggt caattgcact ttgagctcga atttccccga tcgttcaaac atttggcaat   4740
aaagtttctt aagattgaat cctgttgccg gtcttgcgat gattatcata taatttctgt   4800
tgaattacgt taagcatgta ataattaaca tgtaatgcat gacgttattt atgagatggg   4860
tttttatgat tagagtcccg caattataca tttaatacgc gatagaaaac aaaatatagc   4920
gcgcaaacta ggataaatta tcgcgcgcgg tgtcatctat gttactagat cgggaaggcg   4980
cgccgcggcc gcaacactga tagttttaaac tgaaggcggg aaacgacaat ctgatcatga   5040
gcggagaatt aagggagtca cgttatgacc cccgccgatg acgcgggaca agccgtttta   5100
cgtttggaac tgacagaacc gcaacgttga aggagccact cagccgcggg tttctggagt   5160
ttaatgagct aagcacatac gtcagaaacc attattgcgc gttcaaaagt cgcctaaggt   5220
cactatcagc tagcaaatat ttcttgtcaa aaatgctcca ctgacgttcc ataaattccc   5280
ctcggtatcc aattagagtc tcatattcac tctcaatcca ataatctgc accggatctg    5340
gatcgtttcg catgattgaa caagatggat tgcacgcagg ttctccggcc gcttgggtgg   5400
agaggctatt cggctatgac tgggcacaac agacaatcgg ctgctctgat gccgccgtgt   5460
tccggctgtc agcgcagggg cgcccggttc ttttgtcaa gaccgacctg tccggtgccc    5520
tgaatgaact gcaggacgag gcagcgcggc tatcgtggct ggccacgacg ggcgttcctt   5580
gcgcagctgt gctcgacgtt gtcactgaag cgggaaggga ctggctgcta ttgggcgaag   5640
tgccggggca ggatctcctg tcatctcacc ttgctcctgc cgagaaagta tccatcatgg   5700
ctgatgcaat gcggcggctg catacgcttg atccggctac ctgcccattc gaccaccaag   5760
cgaaacatcg catcgagcga gcacgtactc ggatggaagc cggtcttgtc gatcaggatg   5820
atctggacga agagcatcag gggctcgcgc cagccgaact gttcgccagg ctcaaggcgc   5880
gcatgcccga cggcgatgat ctcgtcgtga cccatggcga tgcctgcttg ccgaatatca   5940
tggtggaaaa tggccgcttt tctggattca tcgactgtgg ccggctgggt gtggcggacc   6000
```

```
gctatcagga catagcgttg gctacccgtg atattgctga agagcttggc ggcgaatggg    6060
ctgaccgctt cctcgtgctt tacggtatcg ccgctcccga ttcgcagcgc atcgccttct    6120
atcgccttct tgacgagttc ttctgagcgg gactctgggg ttcgaaatga ccgaccaagc    6180
gacgcccaac ctgccatcac gagatttcga ttccaccgcc gccttctatg aaaggttggg    6240
cttcggaatc gttttccggg acgccggctg gatgatcctc cagcgcgggg atctcatgct    6300
ggagttcttc gcccacggga tctctgcgga acaggcggtc gaaggtgccg atatcattac    6360
gacagcaacg gccgacaagc acaacgccac gatcctgagc gacaatatga tcgggcccgg    6420
cgtccacatc aacggcgtcg gcggcgactg cccaggcaag accgagatgc accgcgatat    6480
cttgctgcgt tcggatattt tcgtggagtt cccgccacag acccgatga tccccgatcg    6540
ttcaaacatt tggcaataaa gtttcttaag attgaatcct gttgccggtc ttgcgatgat    6600
tatcatataa tttctgttga attacgttaa gcatgtaata attaacatgt aatgcatgac    6660
gttatttatg agatgggttt ttatgattag agtcccgcaa ttatacattt aatacgcgat    6720
agaaaacaaa atatagcgcg caaactagga taaattatcg cgcgcggtgt catctatgtt    6780
actagatcgg gcctcctgtc aatgctggcg gcggctctgg tggtggttct ggtggatcca    6840
ctagttctag agcggccgtg ggccatcgcc ctgatagacg ttttttcgcc ctttgacgtt    6900
ggagtccacg ttctttaata gtggactctt gttccaaact ggaacaacac tcaaccctat    6960
ctcgggctat tcttttgatt tataagggat tttgccgatt tcggaaccac catcaaacag    7020
gattttcgcc tgctggggca aaccagcgtg gaccgcttgc tgcaactctc tcagggccag    7080
gcggtgaagg gcaatcagct gttgcccgtc tcactggtga aagaaaaac cacccccagta    7140
cattaaaaac gtccgcaatg tgttattaag ttgtctaagc gtcaatttgt ttacaccaca    7200
atatatcctg ccaccagcca gccaacagct ccccgaccgg cagctcggca caaaatcacc    7260
actcgataca ggcagcccat cagtccggga cggcgtcagc gggagagccg ttgtaaggcg    7320
gcagactttg ctcatgttac cgatgctatt cggaagaacg gcaactaagc tgccgggttt    7380
gaaacacgga tgatctcgcg gagggtagca tgttgattgt aacgatgaca gagcgttgct    7440
gcctgtgatc aaatatcatc tccctcgcag agatccgaat tatcagcctt cttattcatt    7500
tctcgcttaa ccgtgacagt tgtctatcgg cagttcgtag agcgcgccgt gcgtcccgag    7560
cgatactgag cgaagcaagt gcgtcgagca gtgcccgctt gttcctgaaa tgccagtaaa    7620
gcgctggctg ctgaaccccc agccggaact gaccccacaa ggcccagcg tttgcaatgc    7680
accaggtcat cattgaccca ggcgtgttcc accaggccgc tgcctcgcaa ctcttcgcag    7740
gcttcgccga cctgctcgcg ccacttcttc acgcgggtgg aatccgatcc gcacatgagg    7800
cggaaggttt ccagcttgag cgggtacggc tcccggtgcg agctgaaata gtcgaacatc    7860
cgtcgggccg tcggcgacag cttgcggtac ttctcccata tgaatttcgt gtagtggtcg    7920
ccagcaaaca gcacgacgat ttcctcgtcg atcaggacct ggcaacggga cgttttcttg    7980
ccacggtcca ggacgcggaa gcggtgcagc agcgacaccg attccaggtg cccaacgcgg    8040
tcggacgtga agcccatcgc cgtcgcctgt aggcgcgaca ggcattcctc ggccttcgtg    8100
taataccggc cattgatcga ccagcccagg tcctggcaaa gctcgtagaa cgtgaaggtg    8160
atcggctcgc cgatagggt gcgcttcgcg tactccaaca cctgctgcca caccagttcg    8220
tcatcgtcgg cccgcagctc gacgccggta taggtgatct tcacgtcctt gttgacgtgg    8280
aaaatgacct tgttttgcag cgcctcgcgc gggattttct tgttgcgcgt ggtgaacagg    8340
```

```
gcagagcggg ccgtgtcgtt tggcatcgct cgcatcgtgt ccggccacgg cgcaatatcg    8400
aacaaggaaa gctgcatttc cttgatctgc tgcttcgtgt gtttcagcaa cgcggcctgc    8460
ttggcctcgc tgacctgttt tgccaggtcc tcgccggcgg ttttttcgct tcttggtcgtc   8520
atagttcctc gcgtgtcgat ggtcatcgac ttcgccaaac ctgccgcctc ctgttcgaga    8580
cgacgcgaac gctccacggc ggccgatggc gcgggcaggg caggggagc cagttgcacg     8640
ctgtcgcgct cgatcttggc cgtagcttgc tggaccatcg agccgacgga ctggaaggtt    8700
tcgcggggcg cacgcatgac ggtgcggctt gcgatggttt cggcatcctc ggcggaaaac    8760
cccgcgtcga tcagttcttg cctgtatgcc ttccggtcaa acgtccgatt cattcaccct    8820
ccttgcggga ttgccccgac tcacgccggg gcaatgtgcc cttattcctg atttgacccg    8880
cctggtgcct tggtgtccag ataatccacc ttatcggcaa tgaagtcggt cccgtagacc    8940
gtctggccgt ccttctcgta cttggtattc cgaatcttgc cctgcacgaa taccagcgac    9000
cccttgccca aatacttgcc gtgggcctcg gcctgagagc caaaacactt gatgcggaag    9060
aagtcggtgc gctcctgctt gtcgccggca tcgttgcgcc acatctaggt actaaaacaa    9120
ttcatccagt aaaatataat atttttatttt ctcccaatca ggcttgatcc ccagtaagtc   9180
aaaaaatagc tcgacatact gttcttcccc gatatcctcc ctgatcgacc ggacgcagaa    9240
ggcaatgtca taccacttgt ccgccctgcc gcttctccca agatcaataa agccacttac    9300
tttgccatct ttcacaaaga tgttgctgtc tcccaggtcg ccgtgggaaa agacaagttc    9360
ctcttcgggc ttttccgtct ttaaaaaatc atacagctcg cgcggatctt taaatggagt    9420
gtcttcttcc cagttttcgc aatccacatc ggccagatcg ttattcagta agtaatccaa    9480
ttcggctaag cggctgtcta agctattcgt ataggggacaa tccgatatgt cgatggagtg   9540
aaagagcctg atgcactccg catacagctc gataatcttt tcagggcttt gttcatcttc    9600
atactcttcc gagcaaagga cgccatcggc ctcactcatg agcagattgc tccagccatc    9660
atgccgttca aagtgcagga cctttggaac aggcagcttt ccttccagcc atagcatcat    9720
gtccttttcc cgttccacat cataggtggt ccctttatac cggctgtccg tcattttttaa   9780
ataggtttt tcattttctc ccaccagctt atataccta gcaggagaca ttccttccgt      9840
atcttttacg cagcggtatt tttcgatcag ttttttcaat tccggtgata ttctcatttt    9900
agccatttat tatttccttc ctcttttcta cagtatttaa agatacccca agaagctaat    9960
tataacaaga cgaactccaa ttcactgttc cttgcattct aaaaccttaa ataccagaaa   10020
acagcttttt caaagttgtt ttcaaagttg gcgtataaca tagtatcgac ggagccgatt  10080
ttgaaaccac aattatggga gagaccataa tgtggtccaa tttgcagcag ccgtccgaga  10140
caggaggaca tcgtccagct gaaaccgggg cagaatccgg ccatttctga agagaaaaat  10200
ggtaaactga tagaataaaa tcataagaaa ggagccgcac atgaaaaaag cagtcattaa  10260
cggggaacaa atcagaagta tcagcgacct ccaccagaca ttgaaaaagg agcttgccct  10320
tccggaatac tacggtgaaa acctggacgc tttatgggat tgtctgaccg gatgggtgga  10380
gtacccgctc gttttggaat ggaggcagtt tgaacaaagc aagcagctga ctgaaaatgg  10440
cgccgagagt gtgcttcagg ttttccgtga agcgaaagcg gaaggctgcg acatcaccat  10500
catactttct taatacgatc aatgggagat gaacaatatg gaaacacaaa ccacaattat  10560
gtctctcagc ccacaattat ggactgccag cgctgccatt tttggggtga ggccgttcgc  10620
ggccgagggg cgcagcccct gggggatgg gaggcccgcg ttagcggcc gggagggttc     10680
gagaaggggg ggcacccccc ttcggcgtgc gcggtcacgc gcacagggcg cagccctggt  10740
```

```
taaaaacaag gtttataaat attggtttaa aagcaggtta aaagacaggt tagcggtggc   10800
cgaaaaacgg gcggaaaccc ttgcaaatgc tggattttct gcctgtggac agcccctcaa   10860
atgtcaatag gtgcgcccct catctgtcag cactctgccc ctcaagtgtc aaggatcgcg   10920
cccctcatct gtcagtagtc gcgcccctca agtgtcaata ccgcagggca cttatcccca   10980
ggcttgtcca catcatctgt gggaaactcg cgtaaaatca ggcgttttcg ccgatttgcg   11040
aggctggcca gctccacgtc gccggccgaa atcgagcctg cccctcatct gtcaacgccg   11100
cgccgggtga gtcggcccct caagtgtcaa cgtccgcccc tcatctgtca gtagggcca    11160 agttttccgc gaggtatcca caacgccggc ggatctgggg aaccctgtgg ttggcatgca   11220
catacaaatg gacgaacgga taaaccttt cacgcccttt taaatatccg attattctaa   11280
taaacgctct tttctcttag                                              11300

<210> SEQ ID NO 22
<211> LENGTH: 12631
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 22
ggccgcattt gggctcctgc aggtaccta attaaaagtt taaactatca gtgtttgaca     60
ggatatattg gcgggtaaac ctaagagaaa agagcgttta ttagaataat cggatattta    120
aaagggcgtg aaaaggttta tccgttcgtc catttgtatg tgcatgccaa ccacagggtt    180
ccccagatcc gccggcgttg tggataccctc gcggaaaact tggccctcac tgacagatga    240
ggggcggacg ttgacacttg aggggccgac tcacccggcg cggcgttgac agatgagggg    300
caggctcgat ttcggccggc gacgtggagc tggccagcct cgcaaatcgg cgaaaacgcc    360
tgattttacg cgagtttccc acagatgatg tggacaagcc tggggataag tgccctgcgg    420
tattgacact tgaggggcgc gactactgac agatgagggg cgcgatcctt gacacttgag    480
gggcagagtg ctgacagatg aggggcgcac ctattgacat ttgaggggct gtccacaggc    540
agaaaatcca gcatttgcaa gggtttccgc ccgttttcg gccaccgcta acctgtcttt    600
taacctgctt ttaaaccaat atttataaac cttgttttta accagggctg cgccctgtgc    660
gcgtgaccgc gcacgccgaa ggggggtgcc ccccttctc gaaccctccc ggcccgctaa     720
cgcgggcctc ccatcccccc aggggctgcg ccctcggcc gcgaacggcc tcaccccaaa    780
aatggcagcg ctggcagtcc ataattgtgg tccaatttgc agccgtccga cacaggagga    840
catcgtccag ctgaaaccgg ggcagaatcc ggccattttct gaagagaaaa atggtaaact    900
gatagaataa aatcataaga aaggagccgc acatgaaaaa agcagtcatt aacgggaac     960 aaatcagaag tatcagcgac ctccaccaga cattgaaaaa ggagcttgcc cttccggaat   1020
actacggtga aacctggac gctttatggg attgtctgac cggatgggtg gagtacccgc   1080
tcgttttgga atgaggcag tttgaacaaa gcaagcagct gactgaaaat ggcgccgaga   1140
gtgtgcttca ggttttccgt gaagcgaaag cggaaggctg cgacatcacc atcatacttt   1200
cttaatacga tcaatgggag atgaacaata tggaaacaca aaccacaatt gtggtttcaa   1260
aatcggctcc gtcgatacta tgttatacgc caactttgaa aacaactttg aaaaagctgt   1320
tttctggtat ttaaggtttt agaatgcaag gaacagtgaa ttggagttcg tcttgttata   1380
attagcttct tgggggtatct ttaaatactg tagaaaagag gaaggaaata ataaatggct   1440
```

-continued

```
aaaatgagaa tatcaccgga attgaaaaaa ctgatcgaaa aataccgctg cgtaaaagat    1500
acggaaggaa tgtctcctgc taaggtatat aagctggtgg gagaaaatga aaacctatat    1560
ttaaaaatga cggacagccg gtataaaggg accacctatg atgtggaacg ggaaaaggac    1620
atgatgctat ggctggaagg aaagctgcct gttccaaagg tcctgcactt tgaacggcat    1680
gatggctgga gcaatctgct catgagtgag gccgatggcg tcctttgctc ggaagagtat    1740
gaagatgaac aaagccctga aaagattatc gagctgtatg cggagtgcat caggctcttt    1800
cactccatcg acatatcgga ttgtccctat acgaatagct tagacagccg cttagccgaa    1860
ttggattact tactgaataa cgatctggcc gatgtggatt gcgaaaactg ggaagaagac    1920
actccattta aagatccgcg cgagctgtat gatttttaa agacggaaaa gcccgaagag    1980
gaacttgtct tttcccacgg cgacctggga gacagcaaca tctttgtgaa agatggcaaa    2040
gtaagtggct ttattgatct tgggagaagc ggcagggcgg acaagtggta tgacattgcc    2100
ttctgcgtcc ggtcgatcag ggaggatatc ggggaagaac agtatgtcga gctattttt    2160 gacttactgg ggatcaagcc tgattgggag aaaataaaat attatatttt actggatgaa    2220
ttgttttagt acctagatgt ggcgcaacga tgccggcgac aagcaggagc gcaccgactt    2280
cttccgcatc aagtgttttg gctctcaggc cgaggcccac ggcaagtatt tgggcaaggg    2340
gtcgctggta ttcgtgcagg gcaagattcg gaataccaag tacgagaagg acggccagac    2400
ggtctacggg accgacttca ttgccgataa ggtggattat ctggacacca aggcaccagg    2460
cgggtcaaat caggaataag ggcacattgc cccggcgtga gtcggggcaa tcccgcaagg    2520
agggtgaatg aatcggacgt ttgaccggaa ggcatacagg caagaactga tcgacgcggg    2580
gttttccgcc gaggatgccg aaaccatcgc aagccgcacc gtcatgcgtg cgccccgcga    2640
aaccttccag tccgtcggct cgatggtcca gcaagctacg gccaagatcg agcgcgacag    2700
cgtgcaactg gctcccctg ccctgccgc gccatcggcc gccgtggagc gttcgcgtcg    2760
tctcgaacag gaggcggcag gtttggcgaa gtcgatgacc atcgacacgc gaggaactat    2820
gacgaccaag aagcgaaaaa ccgccggcga ggacctggca aaacaggtca gcgaggccaa    2880
gcaggccgcg ttgctgaaac acacgaagca gcagatcaag gaaatgcagc tttccttgtt    2940
cgatattgcg ccgtggccgg acacgatgcg agcgatgcca acgacacgg cccgctctgc    3000 cctgttcacc acgcgcaaca agaaaatccc gcgcgaggcg ctgcaaaaca aggtcatttt    3060
ccacgtcaac aaggacgtga agatcaccta caccggcgtc gagctgcggg ccgacgatga    3120
cgaactggtg tggcagcagg tgttggagta cgcgaagcgc accctatcg gcgagccgat    3180 caccttcacg ttctacgagc tttgccagga cctgggctgg tcgatcaatg gccggtatta    3240
cacgaaggcc gaggaatgcc tgtcgcgcct acaggcgacg gcgatgggct tcacgtccga    3300
ccgcgttggg cacctggaat cggtgtcgct gctgcaccgc ttccgcgtcc tggaccgtgg    3360
caagaaaacg tcccgttgcc aggtcctgat cgacgaggaa atcgtcgtgc tgtttgctgg    3420
cgaccactac acgaaattca tatgggagaa gtaccgcaag ctgtcgccga cggcccgacg    3480
gatgttcgac tatttcagct cgcaccggga gccgtacccg ctcaagctgg aaaccttccg    3540
cctcatgtgc ggatcggatt ccacccgcgt gaagaagtgg cgcgagcagg tcggcgaagc    3600
ctgcgaagag ttgcgaggca gcggcctggt ggaacacgcc tgggtcaatg atgacctggt    3660
gcattgcaaa cgctagggcc ttgtggggtc agttccggct gggggttcag cagccagcgc    3720
tttactggca tttcaggaac aagcgggcac tgctcgacgc acttgcttcg ctcagtatcg    3780
```

```
ctcgggacgc acggcgcgct ctacgaactg ccgatagaca actgtcacgg ttaagcgaga   3840
aatgaataag aaggctgata attcggatct ctgcgaggga gatgatattt gatccggtgt   3900
gaaataccgc acagatgcgt aaggagaaaa taccgcatca ggcgctcttc cgcttcctcg   3960
ctcactgact cgctgcgctc ggtcgttcgg ctgcggcgag cggtatcagc tcactcaaag   4020
gcggtaatac ggttatccac agaatcaggg gataacgcag gaaagaacat gtgagcaaaa   4080
ggccagcaaa aggccaggaa ccgtaaaaag gccgcgttgc tggcgttttt ccataggctc   4140
cgcccccctg acgagcatca caaaaatcga cgctcaagtc agaggtggcg aaacccgaca   4200
ggactataaa gataccaggc gtttccccct ggaagctccc tcgtgcgctc tcctgttccg   4260
accctgccgc ttaccggata cctgtccgcc tttctccctt cgggaagcgt ggcgctttct   4320
catagctcac gctgtaggta tctcagttcg gtgtaggtcg ttcgctccaa gctgggctgt   4380
gtgcacgaac cccccgttca gcccgaccgc tgcgccttat ccggtaacta tcgtcttgag   4440
tccaacccgg taagacacga cttatcgcca ctggcagcag ccactggtaa caggattagc   4500
agagcgaggt atgtaggcgg tgctacagag ttcttgaagt ggtggcctaa ctacggctac   4560
actagaagga cagtatttgg tatctgcgct ctgctgaagc cagttacctt cggaaaaaga   4620
gttggtagct cttgatccgg caaacaaacc accgctggta gcggtggttt ttttgtttgc   4680
aagcagcaga ttacgcgcag aaaaaaagga tcaagaag atcctttgat cttttctacg   4740
gggtctgacg ctcagtggaa cgaaaactca cgttaaggga ttttggtcat gagattatca   4800
aaaaggatct tcacctagat ccttttaaat taaaaatgaa gttttaaatc aatctaaagt   4860
atatatgagt aaacttggtc tgacagttac caatgcttca tcagtgaggc tgatcacagg   4920
cagcaacgct ctgtcatcgt tacaatcaac atgctaccct ccgcgagatc atccgtgttt   4980
caaacccggc agcttagttg ccgttcttcc gaatagcatc ggtaacatga gcaaagtctg   5040
ccgccttaca acggctctcc cgctgacgcc gtcccggact gatgggctgc ctgtatcgag   5100
tggtgatttt gtgccgagct gccggtcggg gagctgttgg ctggctggtg gcaggatata   5160
ttgtggtgta aacaaattga cgcttagaca acttaataac acaccgcggt ctagaactag   5220
tggatccccc ctacgtgcga tctagtaaca tagatgacac cgcgcgcgat aatttatcct   5280
agtttgcgcg ctatattttg ttttctatcg cgtattaaat gtataattgc gggactctaa   5340
tcataaaaac ccatctcata ataacgtca tgcattacat gttaattatt acatgcttaa   5400
cgtaattcaa cagaaattat atgataatca tcgcaagacc ggcaacagga ttcaatctta   5460
agaaacttta ttgccaaatg tttgaacgat ccctcagaag aactcgtcaa gaaggcgata   5520
gaaggcgatg cgctgcgaat cgggagcggc gataccgtaa agcacgagga agcggtcagc   5580
ccattcgccg ccaagctctt cagcaatatc acgggtagcc aacgctatgt cctgatagcg   5640
gtccgccaca cccagccggc cacagtcgat gaatccagaa aagcggccat tttccaccat   5700
gatattcggc aagcaggcat cgccatgggt cacgacgaga tcctcgccgt cgggcatgcg   5760
cgccttgagc ctggcgaaca gttcggctgg cgcgagcccc tgatgctctt cgtccagatc   5820
atcctgatcg acaagaccgg cttccatccg agtacgtgct cgctcgatgc gatgtttcgc   5880
ttggtggtcg aatgggcagg tagccggatc aagcgtatgc agccgccgca ttgcatcagc   5940
catgatggat actttctcgg caggagcaag gtgagatgac aggagatcct gccccggcac   6000
ttcgcccaat agcagccagt cccttcccgc ttcagtgaca acgtcgagca cagctgcgca   6060
aggaacgccc gtcgtggcca gccacgatag ccgcgctgcc tcgtcctgga gttcattcag   6120
ggcaccggac aggtcggtct tgacaaaaag aaccgggcgc ccctgcgctg acagccggaa   6180
```

```
cacggcggca tcagagcagc cgattgtctg ttgtgcccag tcatagccga atagcctctc   6240
cacccaagcg gccggagaac ctgcgtgcaa tccatcttgt tcaatcatct gttaatcaga   6300
aaaactcaga ttaatcgaca aattcgatcg cacaaactag aaactaacac cagatctaga   6360
tagaaatcac aaatcgaaga gtaattattc gacaaaactc aaattatttg aacaaatcgg   6420
atgatattta tgaaaccta atcgagaatt aagatgatat ctaacgatca aacccagaaa   6480
atcgtcttcg atctaagatt aacagaatct aaaccaaaga acatatacga aattgggatc   6540
gaacgaaaac aaaatcgaag attttgagag aataaggaac acagaaattt accttgatca   6600
cggtagagag aattgagaga aagttttaa gattttgaga aattgaaatc tgaattgtga   6660
agaagaagag ctctttgggt attgttttat agaagaagaa gaagaaaaga cgaggacgac   6720
taggtcacga gaaagctaag gcggtgaagc aatagctaat aataaaatga cacgtgtatt   6780
gagcgttgtt tacacgcaaa gttgttttg gctaattgcc ttattttag gttgaggaaa   6840 agtatttgtg ctttgagttg ataaacacga ctcgtgtgtg ccggctgcaa ccactttgac   6900
gccgtttatt actgactcgt cgacaaccac aatttctaac ggtcgtcata agatccagcc   6960
gttgagattt aacgatcgtt acgatttata tttttttagc attatcgttt tattttttaa   7020
atatacggtg gagctgaaaa ttggcaataa ttgaaccgtg ggtcccactg cattgaagcg   7080
tatttcgtat tttctagaat tcttcgtgct ttattcttt tccttttgt tttttttgc   7140 catttatcta atgcaagtgg gcttataaaa tcagtgaatt tcttggaaaa gtaacttctt   7200
tatcgtataa catattgtga aattatccat ttctttaat tttttagtgt tattggatat   7260
ttttgtatga ttattgattt gcataggata atgacttttg tatcaagttg gtgaacaagt   7320
ctcgttaaaa aaggcaagtg gtttggtgac tcgatttat cttgttattt aattcatata   7380
tcaatggatc ttatttgggg cctggtccat atttaacact cgtgttcagt ccaatgacca   7440
ataatatttt tcattaata acaatgtaac aagaatgata cacaaaacat tctttgaata   7500
agttcgctat gaagaaggga acttatccgg tcctagatca tcagttcata caaacctcca   7560
tagagttcaa catcttaaac aaggatatcc tgatccgttg acggcgcgcc aagcggggcc   7620
gcatttaaat gggccctatc taatcgaatt ttgtaaactg gtttgataag ccatcaatgc   7680
atcagtcaag aatgaatcat tgcaactaag ttgatataat tcaatttacc atagaactca   7740
aatgttgata tcttcttatg gattttctga tcttctacat tattagaaag aaacttgatt   7800
taccagtaat gatgatacat atccaataga acgaaataag ccaatcttta taggttttgg   7860
tagtaaagtt acaacatcag agacatgtat gtattgtctc tcagaagagc tcttgaccga   7920
tcagagtttg aagaaaaatt tattacacac tttatgtaaa gctgaaaaaa acggcctccc   7980
gcagggaagc cgttttttc gttatctgat ttttgtaaag gtctgatact cgtccgttgt   8040
tttgtaaatc agccagtcgc ttgagtaaag aatccggtct gaatttctga agcctgatgt   8100
atagttaata tccgcttcac gccatgttcg tccgcttttg cccgggagtt tgccttccct   8160
gtttgagaag atgtctccgc cgatgctttt ccccggagcg acgtctgcaa ggttcccttt   8220
tgatgccacc cagccgaggg cttgtgcttc tgattttgta atgtaattat caggtagctt   8280
atgatatgtc tgaagataat ccgcaacccc gtcaaacgtg ttgataacct gtgccatgtt   8340
cccgtttgat acctgaattt tggccattct cataaatctt ctaaaaacag cagaactgac   8400
tattcaaaga aagtagaacc cacagaaagt aatcaaagta gtttgattaa atgcgttgtg   8460
tatcatcgca gccctgcta cggatattta taggaaaggt ttgagagcaa tgtgtgcagc   8520
```

```
aagttgtgtg tgaatcacct gcttccatgg cggaggataa ataatttagt cacgcattta    8580
gttgaacgta actactaact cctctaccgc taatcattct tcttttgccc gggcaagttc    8640
aacaacaacc ccacaatcac gcttcctgta ttttgttttg ttttcaaaac aatagaattc    8700 acttttact gccaaaatta tgttttactc gagagcccaa atgcggccgc ggccgggtgg    8760
tgacatttat tcataaattc atctcaaaac aagaaggatt tacaaaaata aagaaaaca    8820 aaattttcat ctttaacata attataattg tgttcacaaa attcaaactt aaacccttaa    8880
tataaagaat ttcttttcaac aatacacttt aatcacaact tcttcaatca caacctcctc    8940
caacaaaatt aaaatagatt aataaataaa taaacttaac tatttaaaaa aaatatttat    9000
acaaaattta ttaaaacttc aaaataaaca aacttttttat acaaaattca tcaaaacttt    9060
aaaataaagc taaacactga aaatgtgagt acatttaaaa ggacgctgat cacaaaaatt    9120
ttgaaaacat aaacaaactt gaaactctac cttttaagaa tgagtttgtc gtctcattaa    9180
ctcattagtt ttatagttcg aatccaatta acgtatcttt tattttatgg aataagggtg    9240
ttttaataag tgattttggg attttttttag taatttatttt gtgatatgtt atggagtttt    9300
taaaaatata tatatatata tatatttttg ggttgagttt acttaaaatt tggaaaaggt    9360
tggtaagaac tataaattga gttgtgaatg agtgttttat ggattttttta agatgttaaa    9420 tttatatatg taattaaaat tttattttga ataacaaaaa ttataattgg ataaaaaatt    9480
gttttgttaa atttagagta aaaatttcaa aatctaaaat aattaaacac tattattttt    9540
aaaaaatttg ttggtaaatt ttatcttata tttagttaaa atttagaaaa aattaattttt    9600 aaattaataa acttttgaag tcaaatattc caaatatttt ccaaatatt aaatctatt    9660 tgcattcaaa atacaattta aataataaaa cttcatggaa tagattaacc aatttgtata    9720
aaaaccaaaa atctcaaata aaatttaaat tacaaaacat tatcaacatt atgatttcaa    9780
gaaagacaat aaccagtttc caataaaata aaaaaacctca tggcccgtaa ttaagatctc    9840
attaattaat tcttattttt taattttttt acatagaaaa tatctttata tcgtatccaa    9900
gaaatataga atgttctcgt ccagggacta ttaatctcca aacaagtttc aaaatcatta    9960
cattaaagct catcatgtca tttgtggatt ggaaattata ttgtataaga gaaatataga   10020
atgttctcgt ctagggacta ttaatttcca aacaaatttc aaaatcatta cattaaagct   10080
catcatgtca tttgtggatt ggaaattaga caaaaaaaat cccaaatatt tctctcaatc   10140
tcccaaaata tagttcgaac tccatatttt tggaaattga gaattttttt acccaataat   10200
atattttttt atacatttta gagattttcc agacatattt gctctgggat ttattggaat   10260
gaaggtttga gttataaaact ttcagtaatc caagtatctt cggttttttga agatactaaa   10320 tccattatat aataaaaaca cattttaaac accaatttaa tgggatttca gatttgtatc   10380
ccatgctatt ggctaaggca tttttctat tgtaatctaa ccaattctaa tttccaccct   10440
ggtgtgaact gactgacaaa tgcggtccga aaacagcgaa tgaaatgtct gggtgatcgg   10500
tcaaacaagc ggtgggcgag agagcgcggg tgttggccta gccgggatgg gggtaggtag   10560
acggcgtatt accggcgagt tgtccgaatg gagttttcgg ggtaggtagt aacgtagacg   10620
tcaatggaaa aagtcataat ctccgtcaaa aatccaaccg ctccttcaca tcgcagagtt   10680
ggtggccacg ggaccctcca cccactcact cgatcgcctg ccgtggttgc ccattattca   10740
accatacgcc acttgactct tcaccaacaa ttccaggccg gctttctata caatgtactg   10800
cacaggaaaa tccaatataa aaagccggcc tctgcttcct tctcagtagc ccccagctca   10860
ttcaattctt cccactgcag gctacatttg tcagacacgt tttccgccat ttttcgcctg   10920
```

```
tttctgcgga gaatttgatc aggttcggat tgggattgaa tcaattgaaa ggtttttatt   10980
ttcagtattt cgatcgccgg atcccccggg ctgcaggaat tgggctgcag atcgatattt   11040
gatttcacat gctattgtaa tgtatttatt gtttcaattc cgaattagac aaagtgctta   11100
aagctctctt ttcggatttt ttttttcatt aatgtataat aattgcggac attacaatat   11160
actgtacaac gtgatttgag cttgatgaat tacaagattg gaagaacttc gaagacaaaa   11220
aaaaaatcga tctgcaggaa ttcgtccagc agtaattcgg taccoctgat cagcactgct   11280 gccaagaatg taagttttta tttctttat atgttcaaac agttttataa agtactataa   11340 gctttttta gccaaaagaa atatcttaag ttttagtaac caataaagaa ttattgcggc   11400
ctccttattt aattatagta catatgtcat agtagatgtt ttttttatta ttattatttt   11460 ttatttttt atagttttt acaaattcga cttggagacc ttatgatttg gaagatactc   11520
catttaattt tatgagttgt gtttgaaaac atattttaag actaaacacg tagagaacat   11580
tcttaacaaa tttgtaaata aataaattta actctattct ctaggattta aatattatag   11640
gtatatatat aattttctaa taagtttata tcgagtcact catacgagtt gtgtagaaag   11700
ttaatcacgg gtaccaattt taaattaaaa ataagaataa ttatatgatc ttaaatttat   11760
acaactctga taaagattg ggctttgaca tctttgaaga aaactagatt tagtaatatt   11820
ctgattaaat tgggttcaca ctttgtagtg ggcacacttt ccgggttcga aatcgaaatc   11880
tggaagctta tcgatctcga ggggcccact agtatcgatc tcgaggggcc cactagtatc   11940
gatcgatttt ttttttgtct tcgaagttct tccaatcttg taattcatca agctcaaatc   12000
acgttgtaca gtatattgta atgtccgcaa ttattataca ttaatgaaaa aaaaaatccg   12060
aaaagagagc tttaagcact ttgtctaatt cggaattgaa acaataaata cattacaata   12120
gcatgtgaaa tcaaatatcg atccgatggg tgttatttgt ggataataaa ttcgggtgat   12180
gttcagtgtt tgtcgtattt ctcacgaata aattgtgttt atgtatgtgt tagtgttgtt   12240
tgtctgtttc agaccctctt atgttatatt tttcttttcg tcggtcagtt gaagccaata   12300
ctggtgtcct ggccggcact gcaataccat ttcgtttaat ataaagactc tgttatccgt   12360
gagctcgaat ttccccgatc gttcaaacat ttggcaataa agtttcttaa gattgaatcc   12420
tgttgccggt cttgcgatga ttatcatata atttctgttg aattacgtta agcatgtaat   12480
aattaacatg taatgcatga cgttattta gagatgggtt tttatgatta gagtcccgca   12540
attatacatt taatacgcga tagaaaacaa aatatagcgc gcaaactagg ataaattatc   12600
gcgcgcggtg tcatctatgt tactagatcg c                                  12631
```

<210> SEQ ID NO 23
<211> LENGTH: 16396
<212> TYPE: DNA
<213> ORGANISM: Artificial Sequence
<220> FEATURE:
<223> OTHER INFORMATION: Description of Artificial Sequence: Synthetic vector sequence

<400> SEQUENCE: 23

```
ggccgcattt gggctcctgc aggtacctta attaaaagtt taaactatca gtgtttgaca    60
ggatatattg gcgggtaaac ctaagagaaa agagcgttta ttagaataat cggatattta   120
aaagggcgtg aaaaggttta tccgttcgtc catttgtatg tgcatgccaa ccacagggtt   180
ccccagatcc gccggcgttg tggataccctc gcggaaaact tggccctcac tgacagatga   240
ggggcggacg ttgacacttg aggggccgac tcacccggcg cggcgttgac agatgagggg   300
```

```
caggctcgat tccggccggc gacgtggagc tggccagcct cgcaaatcgg cgaaaacgcc    360
tgattttacg cgagtttccc acagatgatg tggacaagcc tggggataag tgccctgcgg    420
tattgacact tgaggggcgc gactactgac agatgagggg cgcgatcctt gacacttgag    480
gggcagagtg ctgacagatg aggggcgcac ctattgacat ttgagggget gtccacaggc    540
agaaaatcca gcatttgcaa gggtttccgc ccgttttttcg gccaccgcta acctgtcttt    600
taacctgctt ttaaaccaat atttataaac cttgttttta accagggctg cgccctgtgc    660
gcgtgaccgc gcacgccgaa gggggtgcc cccccttctc gaaccctccc ggcccgctaa    720
cgcgggcctc ccatcccccc aggggctgcg cccctcggcc gcgaacggcc tcaccccaaa    780
aatggcagcg ctggcagtcc ataattgtgg tccaatttgc agccgtccga gacaggagga    840
catcgtccag ctgaaaccgg ggcagaatcc ggccatttct gaagagaaaa atggtaaact    900
gatagaataa aatcataaga aaggagccgc acatgaaaaa agcagtcatt aacggggaac    960
aaatcagaag tatcagcgac ctccaccaga cattgaaaaa ggagcttgcc cttccggaat   1020
actacggtga aaacctggac gctttatggg attgtctgac cggatgggtg gagtacccgc   1080
tcgttttgga atggaggcag tttgaacaaa gcaagcagct gactgaaaat ggcgccgaga   1140
gtgtgcttca ggttttccgt gaagcgaaag cggaaggctg cgacatcacc atcatacttt   1200
cttaatacga tcaatgggag atgaacaata tggaaacaca accacaatt gtggtttcaa   1260
aatcggctcc gtcgatacta tgttatacgc caactttgaa acaactttg aaaaagctgt   1320
tttctggtat ttaaggtttt agaatgcaag gaacagtgaa ttggagttcg tcttgttata   1380
attagcttct tggggtatct ttaaatactg tagaaaagag gaaggaaata ataaatggct   1440
aaaatgagaa tatcaccgga attgaaaaaa ctgatcgaaa aataccgctg cgtaaaagat   1500
acggaaggaa tgtctcctgc taaggtatat aagctggtgg gagaaaatga aaacctatat   1560
ttaaaatga cggacagccg gtataaaggg accacctatg atgtgaacg ggaaaaggac   1620
atgatgctat ggctggaagg aaagctgcct gttccaaagg tcctgcactt gaacggcat   1680
gatggctgga gcaatctgct catgagtgag gccgatggcg tcctttgctc ggaagagtat   1740
gaagatgaac aaagccctga aaagattatc gagctgtatg cggagtgcat caggctcttt   1800
cactccatcg acatatcgga ttgtccctat acgaatagct tagacagccg cttagccgaa   1860
ttggattact tactgaataa cgatctggcc gatgtggatt gcgaaaactg ggaagaagac   1920
actccattta aagatccgcg cgagctgtat gattttttaa agacggaaaa gcccgaagag   1980
gaacttgtct tttcccacgg cgacctggga gacagcaaca tctttgtgaa agatggcaaa   2040
gtaagtggct ttattgatct tgggagaagc ggcagggcgg acaagtggta tgacattgcc   2100
ttctgcgtcc ggtcgatcag ggaggatatc ggggaagaac agtatgtcga gctattttt   2160
gacttactgg ggatcaagcc tgattgggag aaaataaaat attatatttt actggatgaa   2220
ttgtttttagt acctagatgt ggcgcaacga tgccggcgac aagcaggagc gcaccgactt   2280
cttccgcatc aagtgttttg gctctcaggc cgaggcccac ggcaagtatt tgggcaaggg   2340
gtcgctggta ttcgtgcagg gcaagattcg gaataccaag tacgagaagg acggccagac   2400
ggtctacggg accgacttca ttgccgataa ggtggattat ctggcaccca aggcaccagg   2460
cgggtcaaat caggaataag ggcacattgc cccggcgtga gtcggggcaa tcccgcaagg   2520
agggtgaatg aatcggacgt ttgaccggaa ggcatacagg caagaactga tcgacgcggg   2580
gttttccgcc gaggatgccg aaaccatcgc aagccgcacc gtcatgcgtg cgccccgcga   2640
```

```
aaccttccag tccgtcggct cgatggtcca gcaagctacg gccaagatcg agcgcgacag   2700
cgtgcaactg gctccccctg ccctgcccgc gccatcggcc gccgtggagc gttcgcgtcg   2760
tctcgaacag gaggcggcag gtttggcgaa gtcgatgacc atcgacacgc gaggaactat   2820
gacgaccaag aagcgaaaaa ccgccggcga ggacctggca aaacaggtca gcgaggccaa   2880
gcaggccgcg ttgctgaaac acacgaagca gcagatcaag gaaatgcagc tttccttgtt   2940
cgatattgcg ccgtggccgg acacgatgcg agcgatgcca acgacacgg cccgctctgc    3000 cctgttcacc acgcgcaaca agaaaatccc gcgcgaggcg ctgcaaaaca aggtcatttt   3060
ccacgtcaac aaggacgtga agatcaccta caccggcgtc gagctgcggg ccgacgatga   3120
cgaactggtg tggcagcagg tgttggagta cgcgaagcgc acccctatcg gcgagccgat   3180
caccttcacg ttctacgagc tttgccagga cctgggctgg tcgatcaatg ccggtatta    3240 cacgaaggcc gaggaatgcc tgtcgcgcct acaggcgacg gcgatgggct tcacgtccga   3300
ccgcgttggg cacctggaat cggtgtcgct gctgcaccgc ttccgcgtcc tggaccgtgg   3360
caagaaaacg tcccgttgcc aggtcctgat cgacgaggaa atcgtcgtgc tgtttgctgg   3420
cgaccactac acgaaattca tatgggagaa gtaccgcaag ctgtcgccga cggcccgacg   3480
gatgttcgac tatttcagct cgcaccggga gccgtacccg ctcaagctgg aaaccttccg   3540
cctcatgtgc ggatcggatt ccacccgcgt gaagaagtgg cgcgagcagg tcggcgaagc   3600
ctgcgaagag ttgcgaggca gcggcctggt ggaacacgcc tgggtcaatg atgacctggt   3660
gcattgcaaa cgctagggcc ttgtggggtc agttccggct gggggttcag cagccagcgc   3720
tttactggca tttcaggaac aagcgggcac tgctcgacgc acttgcttcg ctcagtatcg   3780
ctcgggacgc acgcgcgct ctacgaactg ccgatagaca actgtcacgg ttaagcgaga    3840
aatgaataag aaggctgata attcggatct ctgcgaggga gatgatattt gatccggtgt   3900
gaaataccgc acagatgcgt aaggagaaaa taccgcatca ggcgctcttc cgcttcctcg   3960
ctcactgact cgctgcgctc ggtcgttcgg ctgcggcgag cggtatcagc tcactcaaag   4020
gcggtaatac ggttatccac agaatcaggg ataacgcag gaaagaacat gtgagcaaaa    4080
ggccagcaaa aggccaggaa ccgtaaaaag gccgcgttgc tggcgttttt ccataggctc   4140
cgcccccctg acgagcatca aaaaatcga cgctcaagtc agaggtggcg aaacccgaca    4200
ggactataaa gataccaggc gtttccccct ggaagctccc tcgtgcgctc tcctgttccg   4260
accctgccgc ttaccggata cctgtccgcc tttctccctt cgggaagcgt ggcgctttct   4320
catagctcac gctgtaggta tctcagttcg gtgtaggtcg ttcgctccaa gctgggctgt   4380
gtgcacgaac cccccgttca gcccgaccgc tgcgccttat ccggtaacta tcgtcttgag   4440
tccaacccgg taagacacga cttatcgcca ctggcagcag ccactggtaa caggattagc   4500
agagcgaggt atgtaggcgg tgctacagag ttcttgaagt ggtggcctaa ctacggctac   4560
actagaagga cagtatttgg tatctgcgct ctgctgaagc cagttacctt cggaaaaaga   4620
gttggtagct cttgatccgg caaacaaacc accgctggta gcggtggttt tttgtttgc    4680 aagcagcaga ttacgcgcag aaaaaaagga tcaagaag atccttttgat cttttctacg    4740 gggtctgacg ctcagtggaa cgaaaactca cgttaaggga ttttggtcat gagattatca   4800
aaaaggatct tcacctagat ccttttaaat taaaaatgaa gttttaaatc aatctaaagt   4860
atatatgagt aaacttggtc tgacagttac caatgcttca tcagtgaggc tgatcacagg   4920
cagcaacgct ctgtcatcgt tacaatcaac atgctaccct ccgcgagatc atccgtgttt   4980
caaacccggc agcttagttg ccgttcttcc gaatagcatc ggtaacatga gcaaagtctg   5040
```

```
ccgccttaca acggctctcc cgctgacgcc gtcccggact gatgggctgc ctgtatcgag    5100
tggtgatttt gtgccgagct gccggtcggg gagctgttgg ctggctggtg gcaggatata    5160
ttgtggtgta aacaaattga cgcttagaca acttaataac acaccgcggt ctagaactag    5220
tggatccccc ctacgtgcga tctagtaaca tagatgacac cgcgcgcgat aatttatcct    5280
agtttgcgcg ctatattttg ttttctatcg cgtattaaat gtataattgc gggactctaa    5340
tcataaaaac ccatctcata ataacgtca tgcattacat gttaattatt acatgcttaa    5400
cgtaattcaa cagaaattat atgataatca tcgcaagacc ggcaacagga ttcaatctta    5460
agaaacttta ttgccaaatg tttgaacgat ccctcagaag aactcgtcaa gaaggcgata    5520
gaaggcgatg cgctgcgaat cgggagcggc gataccgtaa agcacgagga agcggtcagc    5580
ccattcgccg ccaagctctt cagcaatatc acgggtagcc aacgctatgt cctgatagcg    5640
gtccgccaca cccagccggc cacagtcgat gaatccagaa aagcggccat tttccaccat    5700
gatattcggc aagcaggcat cgccatgggt cacgacgaga tcctcgccgt cgggcatgcg    5760
cgccttgagc ctggcgaaca gttcggctgg cgcgagcccc tgatgctctt cgtccagatc    5820
atcctgatcg acaagaccgg cttccatccg agtacgtgct cgctcgatgc gatgtttcgc    5880
ttggtggtcg aatgggcagg tagccggatc aagcgtatgc agccgccgca ttgcatcagc    5940
catgatggat actttctcgg caggagcaag gtgagatgac aggagatcct gccccggcac    6000
ttcgcccaat agcagccagt cccttcccgc ttcagtgaca acgtcgagca cagctgcgca    6060
aggaacgccc gtcgtggcca gccacgatag ccgcgctgcc tcgtcctgga gttcattcag    6120
ggcaccggac aggtcggtct tgacaaaaag aaccgggcgc ccctgcgctg acagccggaa    6180
cacggcggca tcagagcagc cgattgtctg ttgtgcccag tcatagccga atagcctctc    6240
cacccaagcg gccggagaac ctgcgtgcaa tccatcttgt tcaatcatct gttaatcaga    6300
aaaactcaga ttaatcgaca aattcgatcg cacaaactag aaactaacac cagatctaga    6360
tagaaatcac aaatcgaaga gtaattattc gacaaaactc aaattatttg aacaaatcgg    6420
atgatattta tgaaaccta atcgagaatt aagatgatat ctaacgatca aacccagaaa    6480
atcgtcttcg atctaagatt aacagaatct aaaccaaaga acatatacga aattgggatc    6540
gaacgaaaac aaaatcgaag attttgagag aataaggaac acagaaattt accttgatca    6600
cggtagagag aattgagaga aagttttaa gattttgaga aattgaaatc tgaattgtga    6660
agaagaagag ctctttgggt attgttttat agaagaagaa gaagaaaaga cgaggacgac    6720
taggtcacga gaaagctaag gcggtgaagc aatagctaat aataaaatga cacgtgtatt    6780
gagcgttgtt tacacgcaaa gttgtttttg gctaattgcc ttatttttag gttgaggaaa    6840
agtatttgtg ctttgagttg ataaacacga ctcgtgtgtg ccggctgcaa ccactttgac    6900
gccgtttatt actgactcgt cgacaaccac aatttctaac ggtcgtcata agatccagcc    6960
gttgagattt aacgatcgtt acgatttata tttttttagc attatcgttt tatttttaa    7020
atatacggtg gagctgaaaa ttggcaataa ttgaaccgtg gtcccactg cattgaagcg    7080
tatttcgtat tttctagaat tcttcgtgct ttatttcttt tccttttgt ttttttgc      7140
catttatcta atgcaagtgg gcttataaaa tcagtgaatt tcttggaaaa gtaacttctt    7200
tatcgtataa catattgtga aattatccat ttcttttaat ttttagtgt tattggatat    7260
ttttgtatga ttattgattt gcataggata atgacttttg tatcaagttg gtgaacaagt    7320
ctcgttaaaa aaggcaagtg gtttggtgac tcgatttatt cttgttattt aattcatata    7380
```

```
tcaatggatc ttatttgggg cctggtccat atttaacact cgtgttcagt ccaatgacca    7440
ataatatttt ttcattaata acaatgtaac aagaatgata cacaaaacat tctttgaata    7500
agttcgctat gaagaaggga acttatccgg tcctagatca tcagttcata caaacctcca    7560
tagagttcaa catcttaaac aaggatatcc tgatccgttg acggcgcgcc ttcccgatct    7620
agtaacatag atgacaccgc gcgcgataat ttatcctagt ttgcgcgcta tattttgttt    7680
tctatcgcgt attaaatgta taattgcggg actctaatca taaaaaccca tctcataaat    7740
aacgtcatgc attacatgtt aattattaca tgcttaacgt aattcaacag aaattatatg    7800
ataatcatcg caagaccggc aacaggattc aatcttaaga aactttattg ccaaatgttt    7860
gaacgatcgg ggaaattcga gctcaaagtg caattgaccg atcagagttt gaagaaaaat    7920
ttattacaca ctttatgtaa agctgaaaaa aacggcctcc cgcagggaag ccgttttttt    7980
cgttatctga tttttgtaaa ggtctgataa tggtccgttg ttttgtaaat cagccagtcg    8040
cttgagtaaa gaatccggtc tgaatttctg aagcctgatg tatagttaat atccgctcca    8100
cgccatgttc gtccgctttt gcccgggagt ttgccttccc tgtttgagaa gatgtctccg    8160
ccgatgcttt tccccggagc gacgtctgca aggttccctt ttgatgccac ccagccgagg    8220
gcttgtgctt ctgattttgt aatgtaatta tcaggtagct tatgatatgt ctgaagataa    8280
tccgcaaccc cgtcaaacgt gttgataacc tgtgccatga tttgtacaca aaatttccgc    8340
gcacagatcc tcacagcgta tgcaaaacaa agctgcaact actaatacca gtccaaaagc    8400
aatgggcgca acagcaacag caaaagctgc aaccccttgt gctggttcgt tcctacagtt    8460
ggacgcagcc cgagttctga gaaacaaata accacaaggc aagttaggta ccaaacccct    8520
taagctcaac ttaagcaaat attacaatcg tttgtttcta caaacaaatc tttttcagaa    8580
cggcttcagg tggggaatat tgtccattta agtacctgaa aatctaagaa cacggccaat    8640
ccgggcgcct ttgcttgaaa gtgggaagaa acctgaatga ttgaacagtg ataagagat    8700 ttataagcaa gattagcagg gctgatcaga ttgttttttc gggtaggttg atcaatacat    8760 atgcccttc cctcttcctt tcctctacaa tcgattgcca gggagagata gagataccat    8820
catgatgatg atggtgggga tggcgatgat ggtaatgatg atgatccagc agaaaaaatt    8880
gcgcagaaga agaagatgag cggtcggtcg gtcgatagcc tttcagtcgg aggggaaaga    8940
acaaaataat gcctatttga aggcagatgg attgactaag acgtgtgcag gcagtggagg    9000
agttacaagg caggacatat ttactaggta taggtgtagg taatagtaat ggagaggata    9060
aatttaggtt ttgggatgaa tggatttgtt ggtacatgtt gcaactccca cactgcaatc    9120
aaaggaccgc tatgacaccc cctgaatgcg acgccatga gaatgccgac cccacatata    9180
catttctgga ataataggg aaatgcaccc ttgcattata tttcatttat tcgtcctcca    9240
ttttgtgcgc tctccattca ttttcaaatg cgctccactc ttcctttatt tcttaccacc    9300
attatctcgt attcgaggtc cagaaatcaa gttgtgaatc tgccttggtt gcgcattgtt    9360
aaagtactct tctgtgtata tttctgcccc accgttttca cttccaacac ttaaattttt    9420
ttatttttta ttttatatat ttcttataaa ttgttggctt ctcacacgaa cccaagccat    9480
ccaagccccg acaaaggcaa tccaatgtac ttgactagag tcaaatacct tttacttctt    9540
tacttctcat attacccaga agccaagcca accttaccaa actaatgtac ctgagcagag    9600
tccactacct ttcctcaagt acagtggcag tcagagtata tcaccgcttg ttatgtatat    9660
gctttaatgc tatgcttatt tctaggtcat aatctaaatc atatttgctg tcgagtttaa    9720
gcttatcgat accgtcgacc tcgagcttct tcttgaatgc tcttatgggt aggattattt    9780
```

-continued

```
ttcactttttt tccttcatat tccacacaca tatatatata aacacactaa cattagtggg    9840
aatatttgtt tgatatgttt attttattta cttcggggggt ttttgtaaca attttgtaga    9900
tctaatttct tgttcttcat gtgtatatta attttccctt aagacttaaa taaaaagaga    9960
gagtttgtta tatatagata tatgaagtga gggaaatggt acaaagttaa aggagatctg   10020
agtgagagtt agataataaa tgaaaagaaa taagaaacca tcagggtttt ttctaatgtg   10080
gagttttaga ttcagttttg tagaactaag attcactttg ttgggtgttc tttcttcact   10140
catttctgtt attataataa taataaaatc ttatatcttt ctattttcct tactaacaag   10200
tacttgaaga tttagatata tttatagatc tggtgttgta ataggtaaaa acttgatttt   10260
tatgactata aaagtaagtt ttgggaaaca aattggggag agagtaagga aggactatga   10320
ggtcatatct tctgttttgt gatcatccat cctccattgt tgttaatgtc tgtgtctctc   10380
tttttcttct cttctttctc ttactttcct ttcttatctc tagctctctt tctctctcat   10440
gaattatatc atatcatata tttgatacaa acacatgtga tggtaagtga gagtgaataa   10500
ggtgaaacta gctagatttt tgagttttca tgaaatttta acttatatga gtgatagaaa   10560
ataatggaac ttatacgtac atgtaggaca atttagatgg ttatctaagt ttttgttttt   10620
gttttctctt gagaatgtta aatgttagtg ttattttgt agttttggaa aattatatat   10680
gagctaagat tagtttagaa gtggtcaaaa gaaacataga tttgaaattt caactgaatt   10740
ttcaagattt caaatagtca atgaaacaag gaggtaatta agacaaatta gcttatgggg   10800
actctttttt gttattcctt aaaattactc ttttaaaat taaaaataac taatctcatt   10860
tcgaactaca ttactcaaac tagtaatctc taattcgaca cgcaatttcc aaatacttat   10920
tagtagagag tcccacgtga ttactttctt ctccaccaaa acataaaaca tgtcaagatt   10980
aaatggtgtt tgaaaattaa aagatcaatt ttcttaatcg tttacagttg tcaactctca   11040
tgtcctgaaa tatataattc tcatgtccaa aacaagaaaa gctaacaacg acttcaaatt   11100
aaatcagtca atcaaaatta gtcttcattt acctactaat ttcttttat atatccgatg   11160
ggtactctac gaaatcagag tttcgtttct ttatttattt tctttataa gatttttgag   11220
gttttttcag aggttggaat tgagcgcaag attaggtttt gggtctgtaa gatttgttgt   11280
ctttgttaaa gaatctttga tcacgtcatc actcagatat tatttcttt tatttttcat   11340
ttgtattttt actaatttat tataaagttt tgttagtttc agttcttgac ttctgacaag   11400
aaggttttat gtcataatga attaatttgt aacctattta taaattcaaa aatgtcatca   11460
tattactact tttgaccatt taatattaga tttctcattt ggtcaatacc caatgttcat   11520
attacatata tagagacaaa aattataagg atactaaatt gttcatattt cttggaagta   11580
aaaagattaa tgatcactga ataaatagat ttggcataga agtatagcat tggaattgct   11640
tcaacatctt tggtgtagat agatttatgc aatttctctt tctttttgaa gtatcttttt   11700
ttttctagag agagaataat gttagggatt tttatcattt tctctctcat tatgggtact   11760
gagaggaaag tgagattttt agtacggatc caatagtttta agagtttggt ctgccttcta   11820
cgatccaaaa aaatctacgg tcatgatctc tccatcgaga aggttgagag ttcagacatc   11880
aaagtctata atatgtcatt gtaatacgta tttgtgcata tatatctatg tacaagtaca   11940
tatacaggaa actcaagaaa aaagaataaa tggtaaattt aattatattc caaataagga   12000
aagtatggaa cgttgtgatg ttactcggac aagtcattta gttacatcca tcacgttaa    12060
atttaatcca atggttacaa ttttaatact atcaaatgtc tattggattt atacccaatg   12120
```

```
tgttaatggg ttgttgacac atgtcacatg tctgaaaccc tagacatgtt cagaccaatc    12180
atgtcactct aattttgcca gcatggcagt tggcagccaa tcactagctc gataaattta    12240
aggtttcaga ggaattttaa tttatttagg gttcatattg tttcataaaa tgattcttta    12300
tttgttacaa ctttaaggaa atattttatt aactatttaa ttgttccctt ttcttatatt    12360
acttttgttt tttcttcaca tcatgtgtca cattaagttg catttcttct gactcaaaag    12420
aaccgatgtt tgcttttaag gtttcgtatt agaatcactt aactgtgcaa gtggtcgatt    12480
tgaccctatc aagcttgata tcgaattgcg gccgcggccg ggtggtgaca tttattcata    12540
aattcatctc aaaacaagaa ggattacaa aaataaaaga aaacaaaatt ttcatcttta    12600
acataattat aattgtgttc acaaaattca aacttaaacc cttaatataa agaatttctt    12660
tcaacaatac actttaatca caacttcttc aatcacaacc tcctccaaca aaattaaaat    12720
agattaataa ataaataaac ttaactattt aaaaaaaaat attatacaaa atttattaaa    12780
acttcaaaat aaacaaactt tttatacaaa attcatcaaa actttaaaat aaagctaaac    12840
actgaaaatg tgagtacatt taaaaggacg ctgatcacaa aaattttgaa aacataaaca    12900
aacttgaaac tctaccttt aagaatgagt ttgtcgtctc attaactcat tagttttata    12960
gttcgaatcc aattaacgta tctttattt tatggaataa gggtgtttta ataagtgatt    13020
ttgggatttt tttagtaatt tatttgtgat atgttatgga gttttaaaa atatatatat    13080 atatatatat ttttggggtg agtttactta aaatttggaa aaggttggta agaactataa    13140
attgagttgt gaatgagtgt tttatggatt ttttaagatg ttaaatttat atatgtaatt    13200 aaaatttat tttgaataac aaaaattata attggataaa aaattgtttt gttaaattta    13260
gagtaaaaat ttcaaaatct aaaataatta aacactatta tttttaaaaa atttgttggt    13320 aaatttatc ttatatttag ttaaaattta gaaaaaatta attttaaatt aataaacttt    13380
tgaagtcaaa tattccaaat attttccaaa atattaaatc tattttgcat tcaaaataca    13440
atttaaataa taaaacttca tggaatagat taaccaattt gtataaaaac caaaaatctc    13500
aaataaaatt taaattacaa aacattatca acattatgat ttcaagaaag acaataacca    13560
gtttccaata aaataaaaaa cctcatggcc cgtaattaag atctcattaa ttaattctta    13620
ttttttaatt tttttacata gaaaatatct ttatatcgta tccaagaaat atagaatgtt    13680
ctcgtccagg gactattaat ctccaaacaa gtttcaaaat cattacatta aagctcatca    13740
tgtcatttgt ggattggaaa ttatattgta taagagaaat atagaatgtt ctcgtctagg    13800
gactattaat ttccaaacaa atttcaaaat cattacatta aagctcatca tgtcatttgt    13860
ggattggaaa ttagacaaaa aaaatcccaa atatttctct caatctccca aaatatagtt    13920
cgaactccat attttggaa attgagaatt ttttacccca ataatatatt ttttatatca    13980
ttttagagat tttccagaca tatttgctct gggatttatt ggaatgaagg tttgagttat    14040
aaactttcag taatccaagt atcttcggtt tttgaagata ctaaatccat tatataataa    14100
aaacacattt taaacaccaa tttaatggga tttcagattt gtatcccatg ctattggcta    14160 aggcatttt cttattgtaa tctaaccaat tctaatttcc accctggtgt gaactgactg    14220
acaaatgcgg tccgaaaaca gcgaatgaaa tgtctgggtg atcggtcaaa caagcggtgg    14280
gcgagagagc gcgggtgttg gcctagccgg gatgggggta ggtagacggc gtattaccgg    14340
cgagttgtcc gaatggagtt tcggggtag gtagtaacgt agacgtcaat ggaaaaagtc    14400
ataatctccg tcaaaaatcc aaccgctcct tcacatcgca gagttggtgg ccacgggacc    14460
ctccacccac tcactcgatc gcctgccgtg gttgcccatt attcaaccat acgccacttg    14520
```

```
actcttcacc aacaattcca ggccggcttt ctatacaatg tactgcacag gaaaatccaa    14580
tataaaaagc cggcctctgc ttccttctca gtagccccca gctcattcaa ttcttcccac    14640
tgcaggctac atttgtcaga cacgttttcc gccatttttc gcctgtttct gcggagaatt    14700
tgatcaggtt cggattggga ttgaatcaat tgaaaggttt ttattttcag tatttcgatc    14760
gccggatccc ccgggctgca ggaattgggc tgcagatcga tatttgattt cacatgctat    14820
tgtaatgtat ttattgtttc aattccgaat tagacaaagt gcttaaagct ctcttttcgg    14880
attttttttt tcattaatgt ataataattg cggacattac aatatactgt acaacgtgat    14940
ttgagcttga tgaattacaa gattggaaga acttcgaaga caaaaaaaaa atcgatctgc    15000
aggaattcgt ccagcagtaa ttcggtaccc ctgatcagca ctgctgccaa gaatgtaagt    15060
ttttatttct tttatatgtt caaacagttt tataaagtac tataagcttt ttttagccaa    15120
aagaaatatc ttaagttta gtaaccaata aagaattatt gcggcctcct tatttaatta    15180
tagtacatat gtcatagtag atgtttttt tattattatt atttttatt ttttatagt    15240 tttttacaaa ttcgacttgg agaccttatg atttggaaga tactccattt aattttatga    15300
gttgtgtttg aaaacatatt ttaagactaa acacgtagag aacattctta acaaatttgt    15360
aaataaataa atttaactct attctctagg atttaaatat tataggtata tatataattt    15420
tctaataagt ttatatcgag tcactcatac gagttgtgta gaaagttaat cacgggtacc    15480
aattttaaat taaaaataag aataattata tgatcttaaa tttatacaac tctgataaaa    15540
gattgggctt tgacatcttt gaagaaaact agatttagta atattctgat taaattgggt    15600
tcacactttg tagtgggcac actttccggg ttcgaaatcg aaatctggaa gcttatcgat    15660
ctcgaggggc ccactagtat cgatctcgag gggcccacta gtatcgatcg attttttttt    15720
tgtcttcgaa gttcttccaa tcttgtaatt catcaagctc aaatcacgtt gtacagtata    15780
ttgtaatgtc cgcaattatt atacattaat gaaaaaaaaa atccgaaaag agagctttaa    15840
gcactttgtc taattcggaa ttgaaacaat aaatacatta caatagcatg tgaaatcaaa    15900
tatcgatccg atgggtgtta tttgtggata ataaattcgg gtgatgttca gtgtttgtcg    15960
tatttctcac gaataaattg tgtttatgta tgtgttagtg ttgtttgtct gtttcagacc    16020
ctcttatgtt atatttttct tttcgtcggt cagttgaagc caatactggt gtcctggccg    16080
gcactgcaat accatttcgt ttaatataaa gactctgtta tccgtgagct cgaatttccc    16140
cgatcgttca aacatttggc aataaagttt cttaagattg aatcctgttg ccggtcttgc    16200
gatgattatc atataatttc tgttgaatta cgttaagcat gtaataatta acatgtaatg    16260
catgacgtta tttatgagat gggttttat gattagagtc ccgcaattat acatttaata    16320
cgcgatagaa aacaaaatat agcgcgcaaa ctaggataaa ttatcgcgcg cggtgtcatc    16380
tatgttacta gatcgc                                                    16396
```

<210> SEQ ID NO 24
<211> LENGTH: 7970
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 24

```
cgccggcgtt gtggatacct cgcggaaaac ttggccctca ctgacagatg agggggcggac    60 gttgacactt gaggggccga ctcacccggc gcggcgttga cagatgaggg gcaggctcga    120
```

-continued

```
tttcggccgg cgacgtggag ctggccagcc tcgcaaatcg gcgaaaacgc ctgattttac     180
gcgagtttcc cacagatgat gtggacaagc ctggggataa gtgccctgcg gtattgacac     240
ttgaggggcg cgactactga cagatgaggg gcgcgatcct tgacacttga ggggcagagt     300
gctgacagat gaggggcgca cctattgaca tttgaggggc tgtccacagg cagaaaatcc     360
agcatttgca agggtttccg cccgttttc ggccaccgct aacctgtctt ttaacctgct      420
tttaaaccaa tatttataaa ccttgttttt aaccagggct gcgccctgtg cgcgtgaccg     480
cgcacgccga aggggggtgc cccccttct cgaaccctcc cggcccgcta acgcgggcct      540
cccatccccc caggggctgc gcccctcggc cgcgaacggc ctcaccccaa aaatggcagc     600
gctggcagtc cataattgtg gtccaatttg cagccgtccg agacaggagg acatcgtcca     660
gctgaaaccg gggcagaatc cggccatttc tgaagagaaa aatggtaaac tgatagaata     720
aaatcataag aaaggagccg cacatgaaaa aagcagtcat taacggggaa caaatcagaa     780
gtatcagcga cctccaccag acattgaaaa aggagcttgc ccttccggaa tactacggtg     840
aaaacctgga cgctttatgg gattgtctga ccggatgggt ggagtacccg ctcgttttgg     900
aatggaggca gtttgaacaa agcaagcagc tgactgaaaa tggcgccgag agtgtgcttc     960
aggttttccg tgaagcgaaa gcggaaggct gcgacatcac catcatactt tcttaatacg    1020
atcaatggga gaggaacaat atggaaacac aaaccacaat tgtggtttca aaatcggctc    1080
cgtcgatact atgttatacg ccaactttga aaacaacttt gaaaaagctg ttttctggta    1140
tttaaggttt tagaatgcaa ggaacagtga attggagttc gtcttgttat aattagcttc    1200
ttggggtatc tttaaatact gtagaaaaga ggaaggaaat aataaatggc taaaatgaga    1260
atatcaccgg aattgaaaaa actgatcgaa aaataccgct gcgtaaaaga tacgaaagga    1320
atgtctcctg ctaaggtata taagctggtg ggagaaaatg aaaacctata tttaaaaatg    1380
acggacagcc ggtataaagg gaccacctat gatgtggaac gggaaaagga catgatgcta    1440
tggctggaag gaaagctgcc tgttccaaag gtcctgcact ttgaacggca tgatggctgg    1500
agcaatctgc tcatgagtga ggccgatggc gtcctttgct cggaagagta tgaagatgaa    1560
caaagccctg aaaagattat cgagctgtat gcggagtgca tcaggctctt tcactccatc    1620
gacatatcgg attgtcccta tacgaatagc ttagacagcc gcttagccga attggattac    1680
ttactgaata acgatctggc cgatgtggat tgcgaaaact gggaagaaga cactccattt    1740
aaagatccgc gcgagctgta tgattttta aagacgaaa agcccgaaga ggaacttgtc     1800
ttttcccacg gcgacctggg agacagcaac atctttgtga agatggcaa agtaagtggc     1860
tttattgatc ttgggagaag cggcagggcg acaagtggt atgacattgc cttctgcgtc     1920
cggtcgatca gggaggatat cggggaagaa cagtatgtcg agctatttt tgacttactg    1980
gggatcaagc ctgattggga gaaaataaaa tattatattt tactggatga attgttttag    2040
tacctagatg tggcgcaacg atgccggcga caagcaggag cgcaccgact tcttccgcat    2100
caagtgtttt ggctctcagg ccgaggccca cggcaagtat ttgggcaagg gtcgctggt    2160
attcgtgcag ggcaagattc ggaataccaa gtacgagaag gacggccaga cggtctacgg    2220
gaccgacttc attgccgata aggtggatta tctggacacc aaggcaccag gcgggtcaaa    2280
tcaggaataa gggcacattg ccccggcgtg agtcgggca atcccgcaag gagggtgaat      2340
gaatcggacg tttgaccgga aggcatacag gcaagaactg atcgacgcgg gttttccgc     2400
cgaggatgcc gaaaccatcg caagccgcac cgtcatgcgt gcgccccgcg aaaccttcca    2460
```

```
gtccgtcggc tcgatggtcc agcaagctac ggccaagatc gagcgcgaca gcgtgcaact    2520
ggctccccct gccctgcccg cgccatcggc cgccgtggag cgttcgcgtc gtctcgaaca    2580
ggaggcggca ggtttggcga agtcgatgac catcgacacg cgaggaacta tgacgaccaa    2640
gaagcgaaaa accgccggcg aggacctggc aaaacaggtc agcgaggcca agcaggccgc    2700
gttgctgaaa cacacgaagc agcagatcaa ggaaatgcag ctttccttgt tcgatattgc    2760
gccgtggccg gacacgatgc gagcgatgcc aaacgacacg gcccgctctg ccctgttcac    2820
cacgcgcaac aagaaaatcc gcgcgaggc gctgcaaaac aaggtcattt tccacgtcaa    2880
caaggacgtg aagatcacct acaccggcgt cgagctgcgg gccgacgatg acgaactggt    2940
gtggcagcag gtgttggagt acgcgaagcg caccccatc ggcgagccga tcaccttcac    3000
gttctacgag ctttgccagg acctgggctg gtcgatcaat ggccggtatt acacgaaggc    3060
cgaggaatgc ctgtcgcgcc tacaggcgac ggcgatgggc ttcacgtccg accgcgttgg    3120
gcacctggaa tcggtgtcgc tgctgcaccg cttccgcgtc ctggaccgtg caagaaaaac    3180
gtcccgttgc caggtcctga tcgacgagga atcgtcgtg ctgtttgctg cgaccacta    3240
cacgaaattc atatgggaga agtaccgcaa gctgtcgccg acggcccgac ggatgttcga    3300
ctatttcagc tcgcaccggg agccgtaccc gctcaagctg gaaaccttcc gcctcatgtg    3360
cggatcggat tccacccgcg tgaagaagtg gcgcgagcag gtcggcgaag cctgcgaaga    3420
gttgcgaggc agcggcctgg tggaacacgc ctgggtcaat gatgacctgg tgcattgcaa    3480
acgctagggc cttgtggggt cagttccggc tgggggttca gcagccagcg ctttactggc    3540
atttcaggaa caagcgggca ctgctcgacg cacttgcttc gctcagtatc gctcgggacg    3600
cacggcgcgc tctacgaact gccgatagac aactgtcacg gttaagcgag aaatgaataa    3660
gaaggctgat aattcggatc tctgcgaggg agatgatatt tgatcacagg cagcaacgct    3720
ctgtcatcgt tacaatcaac atgctaccct ccgcgagatc atccgtgttt caaacccggc    3780
agcttagttg ccgttcttcc gaatagcatc ggtaacatga gcaaagtctg ccgccttaca    3840
acggctctcc cgctgacgcc gtcccggact gatgggctgc ctgtatcgag tggtgatttt    3900
gtgccgagct gccggtcggg gagctgttgg ctggctggtg gcaggatata ttgtggtgta    3960
aacaaattga cgcttagaca acttaataac acattgcgga cgttttaat gtactggggt    4020
ggttttctt ttcaccagtg agacgggcaa cagctgattg cccttcaccg cctggccctg    4080
agagagttgc agcaagcggt ccacgctggt ttgccccagc aggcgaaaat cctgtttgat    4140
ggtggttccg aaatcggcaa aatcccttat aaatcaaaag aatagcccga gatagggttg    4200
agtgttgttc cagtttggaa caagagtcca ctattaaaga acgtggactc caacgtcaaa    4260
gggcgaaaaa ccgtctatca gggcgatggc ccacggccgc tctagaacta gtggatcccc    4320
cctacgtgcg atctagtaac atagatgaca ccgcgcgcga taatttatcc tagtttgcgc    4380
gctatatttt gttttctatc gcgtattaaa tgtataattg cgggactcta atcataaaaa    4440
cccatctcat aaataacgtc atgcattaca tgttaattat tacatgctta acgtaattca    4500
acagaaatta tatgataatc atcgcaagac cggcaacagg attcaatctt aagaaacttt    4560
attgccaaat gtttgaacga tccctcagaa gaactcgtca agaaggcgat agaaggcgat    4620
gcgctgcgaa tcgggagcgg cgataccgta agcacgagg aagcggtcag cccattcgcc    4680
gccaagctct tcagcaatat cacgggtagc caacgctatg tcctgatagc ggtccgccac    4740
acccagccgg ccacagtcga tgaatccaga aaagcggcca ttttccacca tgatattcgg    4800
caagcaggca tcgccatggg tcacgacgag atcctcgccg tcgggcatgc gcgccttgag    4860
```

-continued

```
cctggcgaac agttcggctg gcgcgagccc ctgatgctct tcgtccagat catcctgatc    4920
gacaagaccg gcttccatcc gagtacgtgc tcgctcgatg cgatgtttcg cttggtggtc    4980
gaatgggcag gtagccggat caagcgtatg cagccgccgc attgcatcag ccatgatgga    5040
tactttctcg gcaggagcaa ggtgagatga caggagatcc tgccccggca cttcgcccaa    5100
tagcagccag tcccttcccg cttcagtgac aacgtcgagc acagctgcgc aaggaacgcc    5160
cgtcgtggcc agccacgata gccgcgctgc ctcgtcctgg agttcattca gggcaccgga    5220
caggtcggtc ttgacaaaaa gaaccgggcg cccctgcgct gacagccgga acacggcggc    5280
atcagagcag ccgattgtct gttgtgccca gtcatagccg aatagcctct ccacccaagc    5340
ggccggagaa cctgcgtgca atccatcttg ttcaatcatc tgttaatcag aaaaactcag    5400
attaatcgac aaattcgatc gcacaaacta gaaactaaca ccagatctag atagaaatca    5460
caaatcgaag agtaattatt cgacaaaact caaattattt gaacaaatcg gatgatattt    5520
atgaaaccct aatcgagaat taagatgata tctaacgatc aaacccagaa aatcgtcttc    5580
gatctaagat taacagaatc taaaccaaag aacatatacg aaattgggat cgaacgaaaa    5640
caaaatcgaa gattttgaga gaataaggaa cacagaaatt taccttgatc acggtagaga    5700
gaattgagag aaagttttta agattttgag aaattgaaat ctgaattgtg aagaagaaga    5760
gctctttggg tattgtttta tagaagaaga agaagaaaag acgaggacga ctaggtcacg    5820
agaaagctaa ggcggtgaag caatagctaa taataaaatg cacgtgtat tgagcgttgt     5880
ttacacgcaa agttgttttt ggctaattgc cttatttta ggttgaggaa aagtatttgt      5940
gctttgagtt gataaacacg actcgtgtgt gccggctgca accactttga cgccgtttat    6000
tactgactcg tcgacaacca caatttctaa cggtcgtcat aagatccagc cgttgagatt    6060
taacgatcgt tacgatttat attttttag cattatcgtt ttattttta aatatacggt        6120
ggagctgaaa attggcaata attgaaccgt gggtcccact gcattgaagc gtatttcgta    6180
ttttctagaa ttcttcgtgc tttatttctt ttccttttg ttttttttg ccatttatct        6240
aatgcaagtg ggcttataaa atcagtgaat ttccttggaaa agtaacttct ttatcgtata    6300
acatattgtg aaattatcca tttcttttaa ttttttagtg ttattggata tttttgtatg    6360
attattgatt tgcataggat aatgacttt gtatcaagtt ggtgaacaag tctcgttaaa     6420
aaaggcaagt ggtttggtga ctcgatttat tcttgttatt taattcatat atcaatggat    6480
cttatttggg gcctggtcca tatttaacac tcgtgttcag tccaatgacc aataatattt    6540
tttcattaat aacaatgtaa caagaatgat acacaaaaca ttctttgaat aagttcgcta    6600
tgaagagggg aacttatccg gtcctagatc atcagttcat acaaacctcc atagagttca    6660
acatcttaaa caaggatatc ctgatccgtt gacggcgcgc caagcggccg catttaaatg    6720
ggccctatct aatcgaattt tgtaaactgg tttgataagc catcaatgca tcagtcaaga    6780
atgaatcatt gcaactaagt tgatataatt caatttacca tagaactcaa atgttgatat    6840
cttcttatgg attttctgat cttctacatt attagaaaga aacttgatttt accagtaatg    6900
atgatacata tccaatagaa cgaaataagc caatctttat aggttttggt agtaaagtta    6960
caacatcaga gacatgtatg tattgtctct cagaagagct cttgaccgat cagagtttga    7020
agaaaaattt attacacact ttatgtaaag ctgaaaaaaa cggcctcccg cagggaagcc    7080
gtttttttcg ttatctgatt tttgtaaagg tctgatactc gtccgttgtt ttgtaaatca    7140
gccagtcgct tgagtaaaga atccggtctg aatttctgaa gcctgatgta tagttaatat    7200
```

```
ccgcttcacg ccatgttcgt ccgcttttgc ccgggagttt gccttccctg tttgagaaga    7260
tgtctccgcc gatgcttttc cccggagcga cgtctgcaag gttccctttt gatgccaccc    7320
agccgagggc ttgtgcttct gattttgtaa tgtaattatc aggtagctta tgatatgtct    7380
gaagataatc cgcaaccccg tcaaacgtgt tgataacctg tgccataaat cttctaaaaa    7440
cagcagaact gactattcaa agaaagtaga acccacagaa agtaatcaaa gtagtttgat    7500
taaatgcgtt gtgtatcatc gcagcccctg ctacggatat ttataggaaa ggtttgagag    7560
caatgtgtgc agcaagttgt gtgtgaatca cctgcttcca tggcggagga taaataattt    7620
agtcacgcat ttagttgaac gtaactacta actcctctac cgctaatcat tcttcttttg    7680
cccgggcaag ttcaacaaca accccacaat cacgcttcct gtattttgtt ttgttttcaa    7740
aacaatagaa ttcactttt  actgccaaaa ttatgtttta ctcgagagcc cgggctcctg    7800
caggtacctt aattaaaagt ttaaactatc agtgtttgac aggatatatt ggcgggtaaa    7860
cctaagagaa aagagcgttt attagaataa tcggatattt aaaagggcgt gaaaaggttt    7920
atccgttcgt ccatttgtat gtgcatgcca accacagggt tccccagatc              7970
```

```
<210> SEQ ID NO 25
<211> LENGTH: 10312
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 25
```

```
gtttacccgc caatatatcc tgtcaaacac tgatagttta aacttttaat taaggtacct      60
gcaggagccc gggctctcga gcagcaaata tgatttagat tatgacctag aaataagcat     120
agcattaaag catatacaaa acaagcggtg atatactctg actgccactg tacttgagga     180
aaggtagtgg actctgctca ggtacattag tttggtaagg ttggcttggc ttctgggtaa     240
tatgagaagt aaagaagtaa aaggtatttg actctagtca agtacattgg attgccttcg     300
tcggggcttg gatggcttgg gttcgtgtga gaagccaaca atttataaaa aaatatattg     360
aaaaaaaaaa aaatcgtcta agtgttggaa gtgaaaacgg tgggacataa atatacacag     420
aagagtactt taacaatgcg caaccaaggc agattcacaa cttgatttct ggacctcgaa     480
tacgagataa tggtggtaag aaataaagga agagtggagt gcatttgaaa atgaatggag     540
agcgcacaaa atggaggacg aataaatgaa atataatgca agagtgcatt tccctattat     600
ttccagaaat gtatatgtgg ggtcggcatt cacatgggcg tcgcattcag ggggtgtcat     660
agcggtcctt tgattgcagt gtgggagttg caacatgtac caacaaattc attcatccca     720
aaacctaaat ttatcctctc cattactatt acctacacct atacctagta aatatgtcct     780
gccttgtaac tcctccactg cctgcacacg tcttagtcaa tccatctgcc ttcaaatagg     840
cattattttg ttcttttcccc tccgactgaa aggctatcga ccgaccgacc gctcatcttc     900
ttcttctgcg caatttttc tgctggatca tcatcattac catcatcgcc atccccacca     960
tcatcatcat gatggtatct ctatctctcc ctggcaatcg attgtagagg aaaggaagag    1020
ggaaggggca tatgtattga tcaacctacc cgaaaaaaca atctgatcag ccctgctaat    1080
cttgcttata aatctcttat ccactgttca atcattcagg tttcttccca cttccaagca    1140
aaggcgcccg gattggccgt gttcttagat tttcaggtac ttaaatggac aatattcccc    1200
acctgaagcc gttctgaaaa agatttgttt gtagaaacaa acgattgtaa tatttgctta    1260
```

```
agttgagctt aaggggtttg gtacctaact tgccttgtgg ttatttgttt ctcagaactc    1320
gggctgcgtc caactgtagg aacgaaccag cacaagggggg tgcagctttt gctgttgctg   1380
ttgcgcccat tgcttttgga ctggtattag tagttgcagc tttgttttgc atacgctgtg    1440
aggatctgtg cgcggaaatt ttgtgtacaa atcatggcac aggttatcaa cacgtttgac    1500
ggggttgcgg attatcttca gacatatcat aagctacctg ataattacat tacaaaatca    1560
gaagcacaag ccctcggctg ggtggcatca aagggaacc ttgcagacgt cgctccgggg     1620
aaaagcatcg gcggagacat cttctcaaac agggaaggca aactcccggg caaaagcgga    1680
cgaacatggc gtggagcgga tattaactat acatcaggct tcagaaattc agaccggatt    1740 cttttactcaa gcgactggct gatttacaaa acaacggacc attatcagac ctttacaaaa    1800
atcagataac gaaaaaaacg gcttccctgc gggaggccgt tttttcagc tttacataaa     1860 gtgtgtaata aattttttctt caaactctga tcggtcaatt gcactttgag ctcgaatttc    1920
cccgatcgtt caaacatttg gcaataaagt ttcttaagat tgaatcctgt tgccggtctt    1980
gcgatgatta tcatataatt tctgttgaat tacgttaagc atgtaataat taacatgtaa    2040
tgcatgacgt tatttatgag atgggttttt atgattagag tcccgcaatt atacatttaa    2100
tacgcgatag aaaacaaaat atagcgcgca aactaggata aattatcgcg cgcggtgtca    2160
tctatgttac tagatcggga aggcgcgccg cggccgcttg gcgcgccgtc aacggatcag    2220
gatatccttg tttaagatgt tgaactctat ggaggtttgt atgaactgat gatctaggac    2280
cggataagtc cccttcttca tagcgaactt attcaaagaa tgttttgtgt atcattcttg     2340
ttacattgtt attaatgaaa aaatattatt ggtcattgga ctgaacacga gtgttaaata    2400
tggaccaggc cccaaataag atccattgat atatgaatta ataacaaga ataaatcgag      2460 tcaccaaacc acttgccttt tttaacgaga cttgttcacc aacttgatac aaaagtcatt    2520
atcctatgca aatcaataat catacaaaaa tatccaataa cactaaaaaa ttaaaagaaa    2580
tggataattt cacaatatgt tatacgataa agaagttact tttccaagaa attcactgat    2640
tttataagcc cacttgcatt agataaatgg caaaaaaaaa caaaaaggaa aagaaataaa    2700
gcacgaagaa ttctagaaaa tacgaaatac gcttcaatgc agtgggaccc acggttcaat    2760
tattgccaat tttcagctcc accgtatatt taaaaaataa aacgataatg ctaaaaaaat    2820
ataaatcgta acgatcgtta aatctcaacg gctggatctt atgacgaccg ttagaaattg    2880
tggttgtcga cgagtcagta ataaacggcg tcaaagtggt tgcagccggc acacacgagt    2940
cgtgtttatc aactcaaagc acaaatactt ttcctcaacc taaaaataag gcaattagcc    3000
aaaaacaact ttgcgtgtaa acaacgctca atacacgtgt cattttatta ttagctattg    3060
cttcaccgcc ttagctttct cgtgacctag tcgtcctcgt ctttttcttct tcttcttcta   3120 taaaacaata cccaaagagc tcttcttctt cacaattcag atttcaattt ctcaaaatct    3180
taaaaacttt ctctcaattc tctctaccgt gatcaaggta aatttctgtg ttccttattc    3240
tctcaaaatc ttcgattttg ttttcgttcg atcccaattt cgtatatgtt ctttggttta    3300
gattctgtta atcttagatc gaagacgatt ttctgggttt gatcgttaga tatcatctta    3360
attctcgatt agggtttcat aaatatcatc cgatttgttc aaataatttg agttttgtcg    3420
aataattact cttcgatttg tgatttctat ctagatctgg tgttagtttc tagtttgtgc    3480
gatcgaattt gtcgattaat ctgagttttt ctgattaaca gatgattgaa caagatggat    3540
tgcacgcagg ttctccggcc gcttgggtgg agaggctatt cggctatgac tgggcacaac    3600
agacaatcgg ctgctctgat gccgccgtgt tccggctgtc agcgcagggg cgcccggttc    3660
```

-continued

```
tttttgtcaa gaccgacctg tccggtgccc tgaatgaact ccaggacgag gcagcgcggc    3720
tatcgtggct ggccacgacg ggcgttcctt gcgcagctgt gctcgacgtt gtcactgaag    3780
cgggaaggga ctggctgcta ttgggcgaag tgccggggca ggatctcctg tcatctcacc    3840
ttgctcctgc cgagaaagta tccatcatgg ctgatgcaat gcggcggctg catacgcttg    3900
atccggctac ctgcccattc gaccaccaag cgaaacatcg catcgagcga gcacgtactc    3960
ggatggaagc cggtcttgtc gatcaggatg atctggacga agagcatcag gggctcgcgc    4020
cagccgaact gttcgccagg ctcaaggcgc gcatgcccga cggcgaggat ctcgtcgtga    4080
cccatggcga tgcctgcttg ccgaatatca tggtggaaaa tggccgcttt tctggattca    4140
tcgactgtgg ccggctgggt gtggcggacc gctatcagga catagcgttg gctacccgtg    4200
atattgctga agagcttggc ggcgaatggg ctgaccgctt cctcgtgctt tacggtatcg    4260
ccgctcccga ttcgcagcgc atcgccttct atcgccttct tgacgagttc ttctgagaat    4320
tcagctttcg ttcgtatcat cggtttcgac aacgttcgtc aagttcaatg catcagtttc    4380
attgcgcaca caccagaatc ctactgagtt cgagtattat ggcattggga aaactgtttt    4440
tcttgtacca tttgttgtgc ttgtaattta ctgtgttttt tattcggttt tcgctatcga    4500
actgtgaaat ggaaatggat ggagaagagt taatgaatga tatggtcctt ttgttcattc    4560
tcaaattaat attatttgtt ttttctctta tttgttgtgt gttgaatttg aaattataag    4620
agatatgcaa acatttttgtt ttgagtaaaa atgtgtcaaa tcgtggcctc taatgaccga    4680
agttaatatg aggagtaaaa cacttgtagt tgtaccatta tgcttattca ctaggcaaca    4740
aatatatttt cagacctaga aaagctgcaa atgttactga atacaagtat gtcctcttgt    4800
gttttagaca tttatgaact ttcctttatg taattttcca gaatccttgt cagattctaa    4860
tcattgcttt ataattatag ttatactcat ggatttgtag ttgagtatga aaatattttt    4920
taatgcattt tatgacttgc caattgattg acaacgcaag cttttcattc atcccaaaac    4980
ctaaatttat cctctccatt actattacct acacctatac ctagtaaata tgtcctgcct    5040
tgtaactcct ccactgcctg cacacgtctt agtcaatcca tctgccttca ataggcatt     5100 attttgttct ttcccctccg actgaaaggc tatcgaccga ccgaccgctc atcttcttct    5160
tctgcgcaat ttttctgct ggatcatcat cattaccatc atcgccatcc ccaccatcat     5220
catcatgatg gtatctctat ctctccctgg caatcgattg tagaggaaag gaagagggaa    5280
ggggcatatg tattgatcaa cctacccgaa aaaacaatct gatcagccct gctaatcttg    5340
cttataaatc tcttatccac tgttcaatca ttcaggtttc ttcccacttc caagcaaagg    5400
cgcccggatt ggccgtgttc ttagattttc aggtacttaa atggacaata ttccccacct    5460
gaagccgttc tgaaaagat ttgtttgtag aaacaaacga ttgtaatatt tgcttaagtt     5520
gagcttaagg ggtttggtac ctaacttgcc ttgtggttat ttgtttctca gaactcgggc    5580
tgcgtccaac tgtaggaacg aaccagcaca aggggttgca gcttttgctg ttgctgttgc    5640
gcccattgct tttggactgg tattagtagt tgcagctttg ttttgcatac gctgtgagga    5700
tctgtgcgcg gaaattttgt gtacaaatca tgaaaaagc agtcattaac ggggaacaaa     5760
tcagaagtat cagcgacctc caccagacat tgaaaaagga gcttgccctt ccggaatact    5820
acggtgaaaa cctggacgct ttatgggatt gtctgaccgg atgggtggag tacccgctcg    5880
ttttggaatg gaggcagttt gaacaaagca agcagctgac tgaaaatggc gccgagagtg    5940
tgcttcaggt tttccgtgaa gcgaaagcgg aaggctgcga catcaccatc atactttctt    6000
```

```
aatacgatca atgggagatg aacaatatgg aaacacaaac cacaattatg tctctcagcg   6060
agctcgaatt tccccgatcg ttcaaacatt tggcaataaa gtttcttaag attgaatcct   6120
gttgccggtc ttgcgatgat tatcatataa tttctgttga attacgttaa gcatgtaata   6180
attaacatgt aatgcatgac gttatttatg agatgggttt ttatgattag agtcccgcaa   6240
ttatacattt aatacgcgat agaaaacaaa atatagcgcg caaactagga taaattatcg   6300
cgcgcggtgt catctatgtt actagatcgg ggatccacta gttctagagc ggcgtgggcc   6360
atcgccctga tagacggttt ttcgcccttt gacgttggag tccacgttct ttaatagtgg   6420
actcttgttc caaactggaa caacactcaa ccctatctcg ggctattctt ttgatttata   6480
agggattttg ccgatttcgg aaccaccatc aaacaggatt ttcgcctgct ggggcaaacc   6540
agcgtggacc gcttgctgca actctctcag gccaggcgg tgaagggcaa tcagctgttg    6600
cccgtctcac tggtgaaaag aaaaaccacc ccagtacatt aaaaacgtcc gcaatgtgtt   6660
attaagttgt ctaagcgtca atttgtttac accacaatat atcctgccac cagccagcca   6720
acagctcccc gaccggcagc tcggcacaaa atcaccactc gatacaggca gcccatcagt   6780
ccgggacggc gtcagcggga gagccgttgt aaggcggcag actttgctca tgttaccgat   6840
gctattcgga agaacggcaa ctaagctgcc gggtttgaaa cacggatgat ctcgcggagg   6900
gtagcatgtt gattgtaacg atgacagagc gttgctgcct gtgatcaaat atcatctccc   6960
tcgcagagat ccgaattatc agccttctta ttcatttctc gcttaaccgt gacagttgtc   7020
tatcggcagt tcgtagagcg cgccgtgcgt cccgagcgat actgagcgaa gcaagtgcgt   7080
cgagcagtgc ccgcttgttc ctgaaatgcc agtaaagcgc tggctgctga accccagcc    7140 ggaactgacc ccacaaggcc ctagcgtttg caatgcacca ggtcatcatt gacccaggcg   7200
tgttccacca ggccgctgcc tcgcaactct tcgcaggctt cgccgacctg ctcgcgccac   7260
ttcttcacgc gggtggaatc cgatccgcac atgaggcgga aggtttccag cttgagcggg   7320
tacggctccc ggtgcgagct gaaatagtcg aacatccgtc gggccgtcgg cgacagcttg   7380
cggtacttct cccatatgaa tttcgtgtag tggtcgccag caaacagcac gacgatttcc   7440
tcgtcgatca ggacctggca acgggacgtt ttcttgccac ggtccaggac gcggaagcgg   7500
tgcagcagcg acaccgattc caggtgccca acgcggtcgg acgtgaagcc catcgccgtc   7560
gcctgtaggc gcgacaggca ttcctcggcc ttcgtgtaat accggccatt gatcgaccag   7620
cccaggtcct ggcaaagctc gtagaacgtg aaggtgatcg gctcgccgat aggggtgcgc   7680
ttcgcgtact ccaacacctg ctgccacacc agttcgtcat cgtcggcccg cagctcgacg   7740
ccggtgtagg tgatcttcac gtccttgttg acgtggaaaa tgaccttgtt ttgcagcgcc   7800
tcgcgcggga ttttcttgtt gcgcgtggtg aacagggcag agcgggccgt gtcgtttggc   7860
atcgctcgca tcgtgtccgg ccacggcgca atatcgaaca aggaaagctg catttccttg   7920
atctgctgct tcgtgtgttt cagcaacgcg gcctgcttgg cctcgctgac ctgttttgcc   7980
aggtcctcgc cggcggtttt tcgcttcttg gtcgtcatag ttcctcgcgt gtcgatggtc   8040
atcgacttcg ccaaacctgc cgcctcctgt tcgagacgac gcgaacgctc cacggcggcc   8100
gatggcgcgg gcagggcagg gggagccagt tgcacgctgt cgcgctcgat cttggccgta   8160
gcttgctgga ccatcgagcc gacggactgg aaggtttcgc ggggcgcacg catgacggtg   8220
cggcttgcga tggtttcggc atcctcggcg gaaaacccg cgtcgatcag ttcttgcctg    8280
tatgccttcc ggtcaaacgt ccgattcatt caccctcctt gcgggattgc cccgactcac   8340
gccggggcaa tgtgccctta ttcctgattt gacccgcctg gtgccttggt gtccagataa   8400
```

```
tccaccttat cggcaatgaa gtcggtcccg tagaccgtct ggccgtcctt ctcgtacttg    8460
gtattccgaa tcttgccctg cacgaatacc agcgacccct tgcccaaata cttgccgtgg    8520
gcctcggcct gagagccaaa acacttgatg cggaagaagt cggtgcgctc ctgcttgtcg    8580
ccggcatcgt tgcgccacat ctaggtacta aaacaattca tccagtaaaa tataatattt    8640
tattttctcc caatcaggct tgatccccag taagtcaaaa aatagctcga catactgttc    8700
ttccccgata tcctccctga tcgaccggac gcagaaggca atgtcatacc acttgtccgc    8760
cctgccgctt ctcccaagat caataaagcc acttactttg ccatctttca caaagatgtt    8820
gctgtctccc aggtcgccgt gggaaaagac aagttcctct tcgggctttt ccgtctttaa    8880
aaaatcatac agctcgcgcg gatctttaaa tggagtgtct tcttcccagt tttcgcaatc    8940
cacatcggcc agatcgttat tcagtaagta atccaattcg gctaagcggc tgtctaagct    9000
attcgtatag ggacaatccg atatgtcgat ggagtgaaag agcctgatgc actccgcata    9060
cagctcgata atcttttcag ggctttgttc atcttcatac tcttccgagc aaaggacgcc    9120
atcggcctca ctcatgagca gattgctcca gccatcatgc cgttcaaagt gcaggacctt    9180
tggaacaggc agctttcctt ccagccatag catcatgtcc ttttcccgtt ccacatcata    9240
ggtggtccct ttataccggc tgtccgtcat ttttaaatat aggttttcat tttctcccac    9300
cagcttatat accttagcag gagacattcc ttccgtatct tttacgcagc ggtattttc     9360 gatcagtttt ttcaattccg gtgatattct cattttagcc atttattatt tccttcctct    9420
tttctacagt atttaaagat accccaagaa gctaattata acaagacgaa ctccaattca    9480
ctgttccttg cattctaaaa ccttaaatac cagaaaacag ctttttcaaa gttgttttca    9540
aagttggcgt ataacatagt atcgacggag ccgattttga aaccacaatt atggactgcc    9600
agcgctgcca ttttttggggt gaggccgttc gcggccgagg ggcgcagccc ctgggggggat    9660 gggaggcccg cgttagcggg ccgggagggt tcgagaaggg ggggcacccc ccttcggcgt    9720
gcgcggtcac gcgcacaggg cgcagccctg gttaaaaaca aggtttataa atattggttt    9780
aaaagcaggt taaagacag gttagcggtg gccgaaaaac gggcggaaac ccttgcaaat    9840
gctggatttt ctgcctgtgg acagcccctc aaatgtcaat aggtgcgccc tcatctgtc    9900 agcactctgc ccctcaagtg tcaaggatcg cgccctcat ctgtcagtag tcgcgcccct    9960
caagtgtcaa taccgcaggg cacttatccc caggcttgtc cacatcatct gtgggaaact   10020
cgcgtaaaat caggcgtttt cgccgatttg cgaggctggc cagctccacg tcgccggccg   10080
aaatcgagcc tgcccctcat ctgtcaacgc cgcgccgggt gagtcggccc ctcaagtgtc   10140
aacgtccgcc cctcatctgt cagtgagggc caagttttcc gcgaggtatc cacaacgccg   10200
gcggatctgg ggaaccctgt ggttggcatg cacatacaaa tggacgaacg gataaacctt   10260
ttcacgcccc tttaaatatc cgattattct aataaacgct cttttctctt ag          10312
```

<210> SEQ ID NO 26
<211> LENGTH: 10312
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 26

```
gtttaccccgc caatatatcc tgtcaaacac tgatagttta aacttttaat taaggtacct      60
gcaggagccc gggctctcga gcagcaaata tgatttagat tatgacctag aaataagcat     120
```

```
agcattaaag catatacaaa acaagcggtg atatactctg actgccactg tacttgagga      180
aaggtagtgg actctgctca ggtacattag tttggtaagg ttggcttggc ttctgggtaa      240
tatgagaagt aaagaagtaa aaggtatttg actctagtca agtacattgg attgccttcg      300
tcggggcttg gatggcttgg gttcgtgtga gaagccaaca atttataaaa aaatatattg      360
aaaaaaaaaa aaatcgtcta agtgttggaa gtgaaaacgg tgggacataa atatacacag      420
aagagtactt taacaatgcg caaccaaggc agattcacaa cttgatttct ggacctcgaa      480
tacgagataa tggtggtaag aaataaagga agagtggagt gcatttgaaa atgaatggag      540
agcgcacaaa atggaggacg aataaatgaa atataatgca agagtgcatt tccctattat      600
ttccagaaat gtatatgtgg ggtcggcatt cacatgggcg tcgcattcag ggggtgtcat      660
agcggtcctt tgattgcagt gtgggagttg caacatgtac caacaaattc attcatccca      720
aaacctaaat ttatcctctc cattactatt acctacacct atacctagta aatatgtcct      780
gccttgtaac tcctccactg cctgcacacg tcttagtcaa tccatctgcc ttcaaatagg      840
cattattttg ttcttteccc tccgactgaa aggctatcga ccgaccgacc gctcatcttc      900
ttcttctgcg caattttttc tgctggatca tcatcattac catcatcgcc atccccacca      960
tcatcatcat gatggtatct ctatctctcc ctggcaatcg attgtagagg aaaggaagag     1020
ggaaggggca tatgtattga tcaacctacc cgaaaaaaca atctgatcag ccctgctaat     1080
cttgcttata aatctcttat ccactgttca atcattcagg tttcttccca cttccaagca     1140
aaggcgcccg gattggccgt gttcttagat tttcaggtac ttaaatggac aatattcccc     1200
acctgaagcc gttctgaaaa agatttgttt gtagaaacaa acgattgtaa tatttgctta     1260
agttgagctt aaggggtttg gtacctaact tgccttgtgg ttatttgttt ctcagaactc     1320
gggctgcgtc caactgtagg aacgaaccag cacaaggggt tgcagctttt gctgttgctg     1380
ttgcgcccat tgcttttgga ctggtattag tagttgcagc tttgtttttgc atacgctgtg     1440 aggatctgtg cgcggaaatt ttgtgtacaa atcatggcac aggttatcaa cacgtttgac     1500
ggggttgcgg attatcttca gacatatcat aagctacctg ataattacat tacaaaatca     1560
gaagcacaag ccctcggctg ggtggcatca aagggaacc ttgcagacgt cgctccgggg      1620
aaaagcatcg gcggagacat cttctcaaac agggaaggca aactcccggg caaaagcgga     1680
cgaacatggc gtgaagcgga tattaactat acatcaggct tcagaaattc agaccggatt     1740
ctttactcaa gcgactggct gatttacaaa acaacggacc attatcagac ctctacaaaa     1800
atcagataac gaaaaaaacg gcttccctgc gggaggccgt ttttttcagc tttacataaa     1860
gtgtgtaata aatttttctt caaactctga tcggtcaatt gcactttgag ctcgaatttc     1920
cccgatcgtt caaacatttg gcaataaagt ttcttaagat tgaatcctgt tgccggtctt     1980
gcgatgatta tcatataatt tctgttgaat tacgttaagc atgtaataat taacatgtaa     2040
tgcatgacgt tatttatgag atgggttttt atgattagag tcccgcaatt atacatttaa     2100
tacgcgatag aaaacaaaat atagcgcgca aactaggata aattatcgcg cgcggtgtca     2160
tctatgttac tagatcggga aggcgcgccg cggccgcttg gcgcgccgtc aacggatcag     2220
gatatccttg tttaagatgt tgaactctat ggaggtttgt atgaactgat gatctaggac     2280
cggataagtt cccttcttca tagcgaactt attcaaagaa tgttttgtgt atcattcttg     2340
ttacattgtt attaatgaaa aaatattatt ggtcattgga ctgaacacga gtgttaaata     2400
tggaccaggc cccaaataag atccattgat atatgaatta ataacaaga ataaatcgag      2460
```

```
tcaccaaacc acttgccttt tttaacgaga cttgttcacc aacttgatac aaaagtcatt    2520
atcctatgca aatcaataat catacaaaaa tatccaataa cactaaaaaa ttaaaagaaa    2580
tggataattt cacaatatgt tatacgataa agaagttact tttccaagaa attcactgat    2640
tttataagcc cacttgcatt agataaatgg caaaaaaaaa caaaaaggaa aagaaataaa    2700
gcacgaagaa ttctagaaaa tacgaaatac gcttcaatgc agtgggaccc acggttcaat    2760
tattgccaat tttcagctcc accgtatatt taaaaaataa aacgataatg ctaaaaaaat    2820
ataaatcgta acgatcgtta aatctcaacg gctggatctt atgacgaccg ttagaaattg    2880
tggttgtcga cgagtcagta ataaacggcg tcaaagtggg tgcagccggc acacacgagt    2940
cgtgtttatc aactcaaagc acaaatactt ttcctcaacc taaaaataag gcaattagcc    3000
aaaaacaact ttgcgtgtaa acaacgctca atacacgtgt cattttatta ttagctattg    3060
cttcaccgcc ttagctttct cgtgacctag tcgtcctcgt cttttcttct tcttcttcta    3120
taaaacaata cccaaagagc tcttcttctt cacaattcag atttcaattt ctcaaaatct    3180
taaaaacttt ctctcaattc tctctaccgt gatcaaggta aatttctgtg ttccttattc    3240
tctcaaaatc ttcgattttg ttttcgttcg atcccaattt cgtatatgtt ctttggttta    3300
gattctgtta atcttagatc gaagacgatt ttctgggttt gatcgttaga tatcatctta    3360
attctcgatt agggtttcat aaatatcatc cgatttgttc aaataatttg agttttgtcg    3420
aataattact cttcgatttg tgatttctat ctagatctgg tgttagtttc tagtttgtgc    3480
gatcgaattt gtcgattaat ctgagttttt ctgattaaca gatgattgaa caagatggat    3540
tgcacgcagg ttctccggcc gcttgggtgg agaggctatt cggctatgac tgggcacaac    3600
agacaatcgg ctgctctgat gccgccgtgt tccggctgtc agcgcagggg cgcccggttc    3660
tttttgtcaa gaccgacctg tccggtgccc tgaatgaact ccaggacgag gcagcgcggc    3720
tatcgtggct ggccacgacg ggcgttcctt gcgcagctgt gctcgacgtt gtcactgaag    3780
cgggaaggga ctggctgcta ttgggcgaag tgccggggca ggatctcctg tcatctcacc    3840
ttgctcctgc cgagaaagta tccatcatgg ctgatgcaat gcggcggctg catacgcttg    3900
atccggctac ctgcccattc gaccaccaag cgaaacatcg catcgagcga gcacgtactc    3960
ggatggaagc cggtcttgtc gatcaggatg atctggacga agagcatcag gggctcgcgc    4020
cagccgaact gttcgccagg ctcaaggcgc gcatgcccga cggcgaggat ctcgtcgtga    4080
cccatggcga tgcctgcttg ccgaatatca tggtggaaaa tggccgcttt tctggattca    4140
tcgactgtgg ccggctgggt gtggcggacc gctatcagga catagcgttg gctacccgtg    4200
atattgctga agagcttggc ggcgaatggg ctgaccgctt cctcgtgctt tacggtatcg    4260
ccgctcccga ttcgcagcgc atcgccttct atcgccttct tgacgagttc ttctgagaat    4320 tcagcttttcg ttcgtatcat cggtttcgac aacgttcgtc aagttcaatg catcagtttc    4380
attgcgcaca caccagaatc ctactgagtt cgagtattat ggcattggga aaactgtttt    4440
tcttgtacca tttgttgtgc ttgtaattta ctgtgttttt tattcggttt tcgctatcga    4500
actgtgaaat ggaaatggat ggagaagagt taatgaatga tatggtcctt ttgttcattc    4560
tcaaattaat attatttgtt ttttctctta tttgttgtgt gttgaatttg aaattataag    4620
agatatgcaa acattttgtt ttgagtaaaa atgtgtcaaa tcgtggcctc taatgaccga    4680
agttaatatg aggagtaaaa cacttgtagt tgtaccatta tgcttattca ctaggcaaca    4740
aatatatttt cagacctaga aaagctgcaa atgttactga atacaagtat gtcctcttgt    4800
gttttagaca tttatgaact ttcctttatg taattttcca gaatccttgt cagattctaa    4860
```

```
tcattgcttt ataattatag ttatactcat ggatttgtag ttgagtatga aaatatttt       4920 taatgcattt tatgacttgc caattgattg acaacgcaag cttttcattc atcccaaaac     4980
ctaaatttat cctctccatt actattacct acacctatac ctagtaaata tgtcctgcct     5040
tgtaactcct ccactgcctg cacacgtctt agtcaatcca tctgccttca aataggcatt     5100
attttgttct ttcccctccg actgaaaggc tatcgaccga ccgaccgctc atcttcttct     5160
tctgcgcaat tttttctgct ggatcatcat cattaccatc atcgccatcc ccaccatcat     5220
catcatgatg gtatctctat ctctccctgg caatcgattg tagaggaaag gaagagggaa     5280
ggggcatatg tattgatcaa cctacccgaa aaaacaatct gatcagccct gctaatcttg     5340
cttataaatc tcttatccac tgttcaatca ttcaggtttc ttcccacttc caagcaaagg     5400
cgcccggatt ggccgtgttc ttagattttc aggtacttaa atggacaata ttccccacct     5460
gaagccgttc tgaaaaagat tgtttgtag aaacaaacga ttgtaatatt tgcttaagtt      5520
gagcttaagg ggtttggtac ctaacttgcc ttgtggttat ttgtttctca gaactcgggc     5580
tgcgtccaac tgtaggaacg aaccagcaca aggggttgca gcttttgctg ttgctgttgc     5640
gcccattgct tttggactgg tattagtagt tgcagctttg ttttgcatac gctgtgagga     5700
tctgtgcgcg gaaattttgt gtacaaatca tgaaaaagc agtcattaac ggggaacaaa      5760
tcagaagtat cagcgacctc caccagacat tgaaaagga gcttgccctt ccggaatact      5820
acggtgaaaa cctggacgct ttatgggatt gtctgaccgg atgggtggag tacccgctcg     5880
ttttggaatg gaggcagttt gaacaaagca agcagctgac tgaaaatggc gccgagagtg     5940
tgcttcaggt tttccgtgaa gcgaaagcgg aaggctgcga catcaccatc atactttctt     6000
aatacgatca atgggagatg aacaatatgg aaacacaaac cacaattatg tctctcagcg     6060
agctcgaatt tccccgatcg ttcaaacatt tggcaataaa gtttcttaag attgaatcct     6120
gttgccggtc ttgcgatgat tatcatataa tttctgttga attacgttaa gcatgtaata     6180
attaacatgt aatgcatgac gttatttatg agatgggttt ttatgattag agtcccgcaa     6240
ttatacattt aatacgcgat agaaaacaaa atatagcgcg caaactagga taaattatcg     6300
cgcgcggtgt catctatgtt actagatcgg ggatccacta gttctagagc ggcgtgggcc     6360
atcgccctga tagacggttt ttcgcccttt gacgttggag tccacgttct ttaatagtgg     6420
actcttgttc caaactggaa caacactcaa ccctatctcg ggctattctt ttgatttata     6480
agggattttg ccgatttcgg aaccaccatc aaacaggatt ttcgcctgct ggggcaaacc     6540
agcgtggacc gcttgctgca actctctcag gccaggcgg tgaagggcaa tcagctgttg      6600
cccgtctcac tggtgaaaag aaaaaccacc ccagtacatt aaaaacgtcc gcaatgtgtt     6660
attaagttgt ctaagcgtca atttgtttac accacaatat atcctgccac cagccagcca     6720
acagctcccc gaccggcagc tcggcacaaa atcaccactc gatacaggca gcccatcagt     6780
ccgggacggc gtcagcggga gagccgttgt aaggcggcag actttgctca tgttaccgat     6840
gctattcgga agaacggcaa ctaagctgcc gggtttgaaa cacgatgat ctcgcggagg      6900 gtagcatgtt gattgtaacg atgacagagc gttgctgcct gtgatcaaat atcatctccc     6960
tcgcagagat ccgaattatc agccttctta ttcatttctc gcttaaccgt gacagttgtc     7020
tatcggcagt tcgtagagcg cgccgtgcgt cccgagcgat actgagcgaa gcaagtgcgt     7080
cgagcagtgc ccgcttgttc ctgaaatgcc agtaaagcgc tggctgctga accccccagcc    7140 ggaactgacc ccacaaggcc ctagcgtttg caatgcacca ggtcatcatt gacccaggcg     7200
```

```
tgttccacca ggccgctgcc tcgcaactct tcgcaggctt cgccgacctg ctcgcgccac   7260
ttcttcacgc gggtggaatc cgatccgcac atgaggcgga aggtttccag cttgagcggg   7320
tacggctccc ggtgcgagct gaaatagtcg aacatccgtc gggccgtcgg cgacagcttg   7380
cggtacttct cccatatgaa tttcgtgtag tggtcgccag caaacagcac gacgatttcc   7440
tcgtcgatca ggacctggca acgggacgtt ttcttgccac ggtccaggac gcggaagcgg   7500
tgcagcagcg acaccgattc caggtgccca acgcggtcgg acgtgaagcc catcgccgtc   7560
gcctgtaggc gcgacaggca ttcctcggcc ttcgtgtaat accggccatt gatcgaccag   7620
cccaggtcct ggcaaagctc gtagaacgtg aaggtgatcg gctcgccgat aggggtgcgc   7680
ttcgcgtact ccaacacctg ctgccacacc agttcgtcat cgtcggcccg cagctcgacg   7740
ccggtgtagg tgatcttcac gtccttgttg acgtggaaaa tgaccttgtt ttgcagcgcc   7800
tcgcgcggga ttttcttgtt gcgcgtggtg aacagggcag agcgggccgt gtcgtttggc   7860
atcgctcgca tcgtgtccgg ccacggcgca atatcgaaca aggaaagctg catttccttg   7920
atctgctgct tcgtgtgttt cagcaacgcg gcctgcttgg cctcgctgac ctgttttgcc   7980
aggtcctcgc cggcggtttt tcgcttcttg gtcgtcatag ttcctcgcgt gtcgatggtc   8040
atcgacttcg ccaaacctgc cgcctcctgt tcgagacgac gcgaacgctc cacggcggcc   8100 gatgcgcgg gcagggcagg gggagccagt tgcacgctgt cgcgctcgat cttggccgta   8160
gcttgctgga ccatcgagcc gacggactgg aaggtttcgc ggggcgcacg catgacggtg   8220
cggcttgcga tggtttcggc atcctcggcg gaaaaccccg cgtcgatcag ttcttgcctg   8280
tatgccttcc ggtcaaacgt ccgattcatt caccctcctt gcgggattgc cccgactcac   8340
gccggggcaa tgtgccctta ttcctgattt gacccgcctg gtgccttggt gtccagataa   8400
tccaccttat cggcaatgaa gtcggtcccg tagaccgtct ggccgtcctt tcgtacttg   8460 gtattccgaa tcttgccctg cacgaatacc agcgaccct tgcccaaata cttgccgtgg   8520
gcctcggcct gagagccaaa acacttgatg cggaagaagt cggtgcgctc ctgcttgtcg   8580
ccggcatcgt tgcgccacat ctaggtacta aaacaattca tccagtaaaa tataatattt   8640
tattttctcc caatcaggct tgatccccag taagtcaaaa aatagctcga catactgttc   8700
ttccccgata tcctccctga tcgaccggac gcagaaggca atgtcatacc acttgtccgc   8760
cctgccgctt ctcccaagat caataaagcc acttactttg ccatctttca caaagatgtt   8820
gctgtctccc aggtcgccgt gggaaaagac aagttcctct tcgggctttt ccgtctttaa   8880
aaaatcatac agctcgcgcg gatctttaaa tggagtgtct tcttcccagt tttcgcaatc   8940
cacatcggcc agatcgttat tcagtaagta atccaattcg gctaagcggc tgtctaagct   9000
attcgtatag ggacaatccg atatgtcgat ggagtgaaag agcctgatgc actccgcata   9060
cagctcgata atcttttcag ggctttgttc atcttcatac tcttccgagc aaaggacgcc   9120
atcggcctca ctcatgagca gattgctcca gccatcatgc cgttcaaagt gcaggacctt   9180
tggaacaggc agctttcctt ccagccatag catcatgtcc ttttcccgtt ccacatcata   9240
ggtggtccct ttataccggc tgtccgtcat ttttaaatat aggttttcat tttctcccac   9300
cagcttatat accttagcag gagacattcc ttccgtatct tttacgcagc ggtatttttc   9360
gatcagtttt ttcaattccg gtgatattct cattttagcc atttattatt tccttcctct   9420
tttctacagt atttaaagat accccaagaa gctaattata acaagacgaa ctccaattca   9480
ctgttccttg cattctaaaa ccttaaatac cagaaaacag cttttcaaa gttgttttca   9540 aagttggcgt ataacatagt atcgacggag ccgatttga aaccacaatt atggactgcc   9600
```

-continued

```
agcgctgcca tttttggggt gaggccgttc gcggccgagg ggcgcagccc ctgggggat    9660 gggaggcccg cgttagcggg ccgggagggt tcgagaaggg ggggcacccc ccttcggcgt   9720
gcgcggtcac gcgcacaggg cgcagccctg gttaaaaaca aggtttataa atattggttt   9780
aaaagcaggt taaaagacag gttagcggtg gccgaaaaac gggcggaaac ccttgcaaat   9840
gctggatttt ctgcctgtgg acagcccctc aaatgtcaat aggtgcgccc ctcatctgtc   9900
agcactctgc ccctcaagtg tcaaggatcg cgcccctcat ctgtcagtag tcgcgcccct   9960
caagtgtcaa taccgcaggg cacttatccc caggcttgtc cacatcatct gtgggaaact  10020
cgcgtaaaat caggcgtttt cgccgatttg cgaggctggc cagctccacg tcgccggccg  10080
aaatcgagcc tgcccctcat ctgtcaacgc cgcgccgggt gagtcggccc ctcaagtgtc  10140
aacgtccgcc cctcatctgt cagtgagggc caagttttcc gcgaggtatc cacaacgccg  10200
gcggatctgg ggaaccctgt ggttggcatg cacatacaaa tggacgaacg gataaacctt  10260
ttcacgccct tttaaatatc cgattattct aataaacgct cttttctctt ag          10312
```

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtttggtac ctaacttgcc                                                20

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgtgttgata acctgtgcca tgatttgtac acaaaatttc cg                       42

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cggaaatttt gtgtacaaat catggcacag gttatcaaca cg                       42

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggttctcgag tttcacgtta actggctag                                      29

<210> SEQ ID NO 31

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgacaaccat ggcacaggtt atcaacacgt ttgac                              35

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaagtgcaat tgaccgatca gagtttgaag                                    30

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tttcacaacc tccacacact t                                             21

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtaaaggtct gatactcgtc cgttg                                         25

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaagaagagc tcttgaccga tcagagtttg aag                                33

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgcttctgat gctgtaatgt aattatcag                                     29

<210> SEQ ID NO 37
<211> LENGTH: 28
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aattacatta cagcatcaga agcacaag                                            28

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaagaactcg agtaaaacat aattttggca gtaaaaagtg a                             41

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
catgttcccg tttgatacct gaattttg                                            28

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cataaatctt ctaaaaacag cagaactgac                                          30

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gagagaggat ccggtgtgaa ataccgcaca g                                        31

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gagagatgat cagcctcact gattaagcat tggtaactg                                39

<210> SEQ ID NO 43
<211> LENGTH: 16
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 43
aatgcggccg cagaga                                                    16

<210> SEQ ID NO 44
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tctctgcggc cgc                                                       13

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gaagaaagcc gaaataaaga gg                                             22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ttgaacgtat agtcgccgat ag                                             22

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aaggagatat aacaatgatt gaacaagatg gattgc                              36

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tcagaagaac tcgtcaagaa gg                                             22

<210> SEQ ID NO 49
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 49
cgaaaacggc aagaaaaagc ag                                                    22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acgaccaaag ccagtaaagt ag                                                    22

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aatgggaagc ctgagtttac a                                                     21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggccagcatg ttttcctcca g                                                     21
```